US005180418A

United States Patent [19]

Pissiotas et al.

[11] Patent Number: 5,180,418

[45] Date of Patent: Jan. 19, 1993

[54] HERBICIDALLY ACTIVE THIADIAZABICYCLONONANES AND NONENES

[75] Inventors: Georg Pissiotas, Lörrach, Fed. Rep. of Germany; Hans Moser, Magden, Switzerland; Hans-Georg Brunner, Lausen, Switzerland; Eginhard Steiner, Füllinsdorf, Switzerland

[73] Assignee: Ciba-Geigy Corporation, Ardsley, N.Y.

[21] Appl. No.: 732,988

[22] Filed: Jul. 19, 1991

[30] Foreign Application Priority Data

Jul. 23, 1990 [CH] Switzerland ........................ 2439/90

[51] Int. Cl.[5] .................... A01N 43/82; C07D 513/04

[52] U.S. Cl. .................................... 504/193; 504/177; 504/178; 504/179; 504/180; 504/283; 504/236; 504/225; 504/221; 504/249; 504/219; 504/246; 504/287; 504/248; 504/286; 504/223; 504/273; 504/220; 540/545; 544/60; 544/61; 544/94; 544/117; 544/127; 544/130; 544/141; 544/144; 544/224; 544/229; 544/235; 544/236; 544/360; 544/362; 544/372; 544/373; 546/121; 546/200; 546/208; 546/219; 546/220; 548/262.4; 548/491; 548/546; 548/547; 558/17; 558/396; 560/16; 562/431; 562/868; 564/74; 564/123; 564/189; 564/190; 564/191

[58] Field of Search ................ 544/229, 235, 61, 117; 71/88, 90

[56] References Cited

U.S. PATENT DOCUMENTS

| | | | |
|---|---|---|---|
| 4,684,397 | 8/1987 | Nagano et al. | 71/96 |
| 4,789,394 | 12/1988 | Böhner | 71/76 |
| 4,801,408 | 1/1989 | Nagano et al. | 562/431 |
| 4,885,023 | 12/1989 | Yamaguchi et al. | 544/235 |
| 5,039,331 | 8/1991 | Satow et al. | 71/90 |
| 5,049,181 | 9/1991 | Pissiotas | 71/90 |
| 5,061,310 | 10/1991 | Ooms | 71/88 |
| 5,069,711 | 12/1991 | Fischer | 71/92 |

FOREIGN PATENT DOCUMENTS

| | | |
|---|---|---|
| 585372 | 1/1987 | Australia . |
| 0126419 | 11/1984 | European Pat. Off. . |
| 0238711 | 9/1987 | European Pat. Off. . |
| 0288960 | 11/1988 | European Pat. Off. . |
| 0304920 | 3/1989 | European Pat. Off. . |
| 0312064 | 4/1989 | European Pat. Off. . |

*Primary Examiner*—Mukund J. Shah
*Assistant Examiner*—E. Bernhardt
*Attorney, Agent, or Firm*—Kevin T. Mansfield; Edward McC. Roberts

[57] ABSTRACT

Cycloalkanecarboxylic acid derivatives of formula I

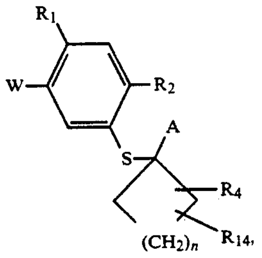

(I)

wherein W is

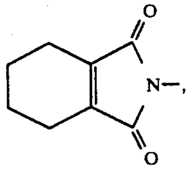

(W1)

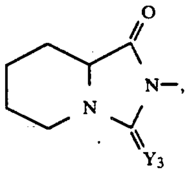

(W2)

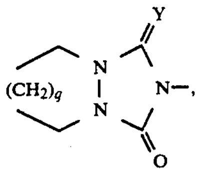

(W3)

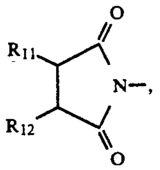

(W4)

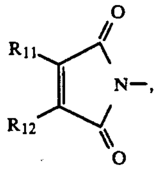

(W5)

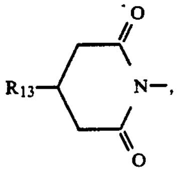

(W6)

(Abstract continued on next page.)

-continued

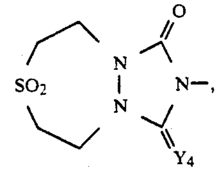

(W₇)

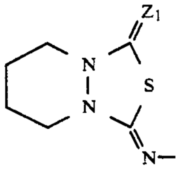

(W₈)

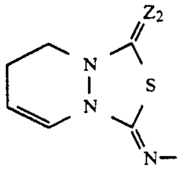

or (W₉)

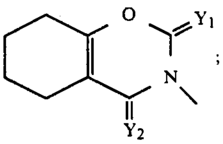

;

(W₁₀)

and A is CO—$R_3$ or CN; $R_1$ is hydrogen or fluorine; $R_2$ is halogen or cyano; $R_3$ is chlorine, X—$R_5$, amino, $C_1$-$C_4$alkylamino, d-$C_1$-$C_4$alkylamino, $C_2$-$C_4$haloalkylamino, di-$C_2$-$C_4$haloalkylamino, $C_1$-$C_4$hydroxyalkylamino, di-$C_1$-$C_4$hydroxyalkylamino, $C_3$-$C_4$alkenylamino, diallylamino, —N-pyrrolidino, —N-piperidino, —N-morpholino, —N-thiomorpholino, —N-piperidazino, the group —O—N═C—($R_9$)$R_{10}$ or the group —N—$R_6$($OR_6$); each of $R_4$ and $R_{14}$, independently of the other, is hydrogen, fluorine, chlorine, bromine, $C_1$-$C_4$alkyl or trifluoromethyl; $R_5$ is hydrogen, $C_1$-$C_{10}$alkyl, $C_1$-$C_4$alkoxy-$C_1$-$C_4$alkyl, halo-$C_1$-$C_8$alkyl, $C_1$-$C_{10}$alkylthio-$C_1$-$C_4$alkyl, di-$C_1$-$C_4$alkylamino-$C_1$-$C_4$alkyl, cyano-$C_1$-$C_8$alkyl, $C_3$-$C_8$alkenyl, halo-$C_3$-$C_8$alkenyl, $C_3$-$C_8$alkynyl, $C_3$-$C_7$cycloalkyl, $C_3$-$C_7$cycloalkyl-$C_1$-$C_4$alkyl or halo-$C_3$-$C_7$cycloalkyl, or benzyl which is unsubstituted or substituted at the phenyl ring by up to three identical or different substituents selected from halogen, $C_1$-$C_4$alkyl, halo-$C_1$-$C_4$alkyl, halo-$C_1$-$C_4$alkoxy or $C_1$-$C_4$alkoxy, or is an alkali metal ion, an alkaline earth metal ion or an ammonium ion, the group —[$CHR_6$—$(CH_2)_m$]—$COOR_7$, or the group [$CHR_6$—$(CH_2)_t$—$Si(R_8)_3$]; $R_6$ is hydrogen or $C_1$-$C_4$alkyl; $R_7$ is hydrogen, $C_1$-$C_6$alkyl, $C_3$-$C_8$alkenyl, $C_3$-$C_8$alkynyl, $C_1$-$C_8$alkoxy-$C_2$-$C_8$alkyl, $C_1$-$C_8$alkylthio-$C_2$-$C_8$ alkyl or $C_3$-$C_7$cycloalkyl; $R_8$ is $C_1$-$C_4$alkyl; $R_9$ is $C_1$-$C_4$alkyl; $R_{10}$ is $C_1$-$C_4$alkyl or phenyl; or $R_9$ and $R_{10}$, together with the carbon atom to which they are bonded, form a cyclohexane ring; $R_{11}$ is $C_1$-$C_8$alkyl; $R_{12}$ is hydrogen or $C_1$-$C_8$alkyl; $R_{13}$ is hydrogen, $C_1$-$C_6$alkyl, $C_3$-$C_7$cycloalkyl, $C_1$-$C_4$alkoxy-$C_1$-$C_4$alkyl, $C_1$-$C_4$alkylthio-$C_1$-$C_4$alkyl, halo-$C_1$-$C_7$alkyl, $C_3$-$C_7$alkenyl or $C_3$-$C_7$alkynyl; X, Y, $Y_1$, $Y_2$, $Y_3$, $Y_4$, $Z_1$ and $Z_2$ are each independently oxygen or sulfur; n is 0, 1, 2, 3 or 4; m is 0, 1, 2, 3 or 4; q is 1 or 2; and t is 0, 1, 2, 3 or 4, have good pre- and post-emergence selective herbicidal and growth regulating properties.

20 Claims, No Drawings

HERBICIDALLY ACTIVE THIADIAZABICYCLONONANES AND NONENES

The present invention relates to novel herbicidally active and plant growth regulating cycloalkanecarboxylic acid derivatives, to processes for their preparation, to compositions comprising them as active ingredients, and to their use for controlling weeds, especially selectively in crops of useful plants, or for regulating and inhibiting plant growth.

S-Phenylthioglycolic acid derivatives having herbicidal activity are known from European Patent Applications Nos. 0 238 711 and 0 304 920 and from U.S. Pat. Nos. 4,885,023, 4,684,397 and 4,801,408. However, the compounds disclosed therein are not always able to satisfy requirements as regards potency and selectivity. There is therefore a need for compounds having better activity and greater selectivity.

Novel cycloalkanecarboxylic acid derivatives having improved herbicidal and plant growth regulating activity have now been found.

The cycloalkanecarboxylic acid derivatives according to the invention have the formula I

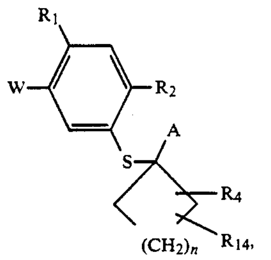

(I)

wherein W is

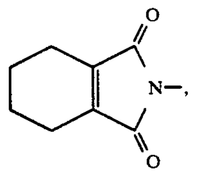

($W_1$)

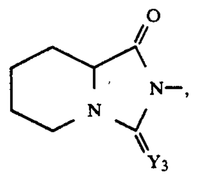

($W_2$)

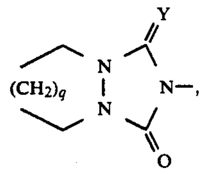

($W_3$)

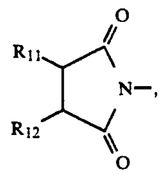

($W_4$)

-continued

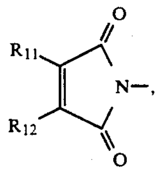

($W_5$)

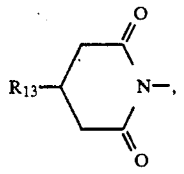

($W_6$)

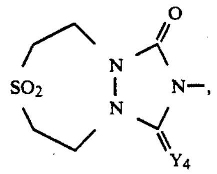

($W_7$)

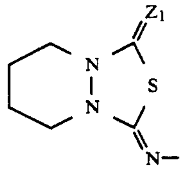

($W_8$)

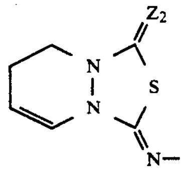

($W_9$)

or

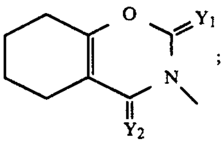

($W_{10}$)

;

and

A is CO—$R_3$ or CN;

$R_1$ is hydrogen or fluorine;

$R_2$ is halogen or cyano;

$R_3$ is chlorine, X—$R_5$, amino, $C_1$-$C_4$alkylamino, di-$C_1$-$C_4$alkylamino, $C_2$-$C_4$haloalkylamino, di-$C_2$-$C_4$-haloalkylamino, $C_1$-$C_4$hydroxyalkylamino, di-$C_1$-$C_4$-hydroxyalkylamino, $C_3$-$C_4$alkenylamino, diallylamino, —N-pyrrolidino, —N-piperidino, —N-morpholino, —N-thiomorpholino, —N-piperidazino, the group —O—N=C—($R_9$)$R_{10}$ or the group —N—$R_6$(O$R_6$); each of $R_4$ and $R_{14}$, independently of the other, is hydrogen, fluorine, chlorine, bromine, $C_1$-$C_4$alkyl or trifluoromethyl;

$R_5$ is hydrogen, $C_1$-$C_{10}$alkyl, $C_1$-$C_4$alkoxy-$C_1$-$C_4$alkyl, halo-$C_1$-$C_8$alkyl, $C_1$-$C_{10}$-alkylthio-$C_1$-$C_4$alkyl, di-$C_1$-$C_4$alkylamino-$C_1$-$C_4$alkyl, cyano-$C_1$-$C_8$alkyl, $C_3$-$C_8$alkenyl, halo-$C_3$-$C_8$alkenyl, $C_3$-$C_8$alkynyl, $C_3$-$C_7$cycloalkyl, $C_3$-$C_7$cycloalkyl-$C_1$-$C_4$alkyl or halo-$C_3$-$C_7$cycloalkyl, or benzyl which is unsubstituted or substituted at the phenyl ring by up to three identical or different substituents selected from halogen, $C_1$-$C_4$alkyl, halo-$C_1$-$C_4$alkyl, halo-$C_1$-$C_4$alkoxy or $C_1$-$C_4$alkoxy, or is an alkali metal ion, an alkaline earth metal ion or an ammonium ion, the group $-[CHR_6-(CH_2)_m]-COOR_7$, or the group $[CHR_6-(CH_2)_t-Si(R_8)_3]$;

$R_6$ is hydrogen or $C_1$–$C_4$alkyl;

$R_7$ is hydrogen, $C_1$–$C_6$alkyl, $C_3$–$C_8$alkenyl, $C_3$–$C_8$alkynyl, $C_1$–$C_8$alkoxy-$C_2$–$C_8$alkyl, $C_1$–$C_8$alkylthio-$C_2$–$C_8$alkyl or $C_3$–$C_7$cycloalkyl;

$R_8$ is $C_1$–$C_4$alkyl;

$R_9$ is $C_1$–$C_4$alkyl;

$R_{10}$ is $C_1$–$C_4$alkyl or phenyl;

or $R_9$ and $R_{10}$, together with the carbon atom to which they are bonded, form a cyclohexane ring;

$R_{11}$ is $C_1$–$C_8$alkyl;

$R_{12}$ is hydrogen or $C_1$–$C_8$alkyl;

$R_{13}$ is hydrogen, $C_1$–$C_6$alkyl, $C_3$–$C_7$cycloalkyl, $C_1$–$C_4$alkoxy-$C_1$–$C_4$alkyl, $C_1$–$C_4$alkylthio-$C_1$–$C_4$alkyl, halo-$C_1$–$C_7$alkyl, $C_3$–$C_7$alkenyl or $C_3$–$C_7$alkynyl;

X is oxygen or sulfur;

Y is oxygen or sulfur;

$Y_1$ is oxygen or sulfur;

$Y_2$ is oxygen or sulfur;

$Y_3$ is oxygen or sulfur;

$Y_4$ is oxygen or sulfur;

$Z_1$ is oxygen or sulfur;

$Z_2$ is oxygen or sulfur;

n is 0, 1, 2, 3 or 4;

m is 0, 1, 2, 3 or 4;

q is 1 or 2; and t is 0, 1, 2, 3 or 4, including the salts and complexes with acids, bases or complexing agents, as well as the possible stereoisomers which are in the form of enantiomers or diastereoisomers or of mixtures thereof.

In the definitions used in this description, the generic terms given and the individual meanings of the substituents obtainable by combining individual subsidiary terms include, for example, the following individual substituents, but this list does not constitute a limitation of the invention.

In the above definitions, halogen is to be understood as being fluorine, chlorine, bromine and iodine, preferably fluorine, chlorine and bromine, and especially chlorine and bromine in the case of $R_2$.

Alkyl is, for example, methyl, ethyl, isopropyl, n-propyl, n-butyl, isobutyl, sec-butyl, tert-butyl and the various isomeric pentyl, hexyl, heptyl, octyl, nonyl and decyl radicals.

Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl and 2,2,2-trichloroethyl; preferably trichloromethyl, difluorochloromethyl, trifluoromethyl and dichlorofluoromethyl.

Alkoxy is, for example, methoxy, ethoxy, propoxy, isopropoxy, n-butoxy, isobutoxy, sec-butoxy and tert-butoxy; preferably methoxy and ethoxy, Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy and 2,2,2-trichloroethoxy; preferably difluoromethoxy, 2-chloroethoxy and trifluoromethoxy.

Alkylthio is, for example, methylthio, ethylthio, propylthio, isopropylthio, n-butylthio, isobutylthio, sec-butylthio, tert-butylthio or the isomeric pentylthios, preferably methylthio and ethylthio.

Alkenyl is to be understood as being straight-chain or branched alkenyl, for example vinyl, allyl, methallyl, 1-methylvinyl, but-2-en-1-yl, 3-pentenyl, 2-hexenyl or 3-heptenyl. Alkenyl radicals having a chain length of 2 or 3 carbon atoms are preferred.

The alkynyl radicals occurring in the definitions of the substituents may be straight-chained or branched, for example ethynyl, propargyl, 3-butynyl, 1-methylpropargyl, 2-pentynyl or 2-hexynyl. Ethynyl and propargyl are preferred.

Within the context of the present invention, the alkenyl and alkynyl groups bonded to oxygen or nitrogen are as a rule bonded via a saturated carbon atom.

Cycloalkyl is, for example, cyclopropyl, dimethylcyclopropyl, cyclobutyl, cyclopentyl, methylcyclopentyl, cyclohexyl or cycloheptyl, but preferably cyclopropyl, cyclopentyl or cyclohexyl.

Alkoxycarbonyl is, for example: methoxycarbonyl, ethoxycarbonyl, n-propoxycarbonyl, isopropoxycarbonyl and n-butoxycarbonyl, preferably methoxycarbonyl and ethoxycarbonyl.

Alkoxyalkyl is, for example: methoxymethyl, ethoxymethyl, propoxymethyl, methoxyethyl, ethoxyethyl, propoxyethyl, methoxypropyl, ethoxypropyl or propoxypropyl.

Alkylthioalkyl is, for example: methylthiomethyl, ethylthiomethyl, methylthioethyl, ethylthioethyl or isopropylthioethyl.

Alkylaminoalkyl is, for example: methylaminoethyl, dimethylaminoethyl, ethylaminoethyl or diethylaminoethyl.

Cyanoalkyl is, for example: cyanomethyl, cyanoethyl or cyanopropyl.

When $R_4$ and $R_{14}$ are simultaneously other than hydrogen and n is one, $R_4$ and $R_{14}$ are preferably bonded to the same carbon atom.

Halocycloalkyl is, for example: 2,2-dichlorocyclopropyl or pentachlorocyclohexyl.

Alkylsulfonyl is, for example: methylsulfonyl, ethylsulfonyl, propylsulfonyl or butylsulfonyl. Preference is given to methylsulfonyl and ethylsulfonyl.

Cycloalkoxycarbonyl is, for example: cyclopentyloxycarbonyl or cyclohexyloxycarbonyl.

Phenyl by itself and as part of a substituent such as phenoxy, phenylthio, phenoxycarbonyl, phenylaminocarbonyl, benzyl or benzoyl, may generally be unsubstituted or substituted by further substituents. The substituents may be in the ortho-, meta- and/or para-positions. Preferred positions for substituents are the ortho- and para-positions relative to the ring-linkage site. Preferred substituents are halogen atoms.

In the further substituents that are made up of a plurality of basic elements, the individual elements have the meanings illustrated above by examples. In these cases also, the lists do not constitute a limitation of the invention: they are of an illustrative nature.

Of the compounds of formula I, preference is given to those wherein W is $W_1$, $W_2$, $W_3$, $W_6$, $W_8$ or $W_9$; $R_{14}$ is preferably hydrogen.

Within the scope of formula I, preference is also given to those compounds wherein $R_1$ is fluorine and $R_2$ is chlorine.

In an especially prominent group of compounds of formula I, A is $CO-R_3$ and $R_3$ is preferably $X-R_5$. Of that group, preference is given to those compounds wherein $R_5$ is $C_1$–$C_{10}$alkyl, especially $C_1$–$C_4$alkyl. Very especially good biological activity is exhibited by those compounds of that group wherein W is $W_8$ or $W_9$. In the compounds of that group that are given very special preference, $R_4$ is hydrogen and X is oxygen, and n is preferably 1.

There may be mentioned as prominent individual compounds within the scope of formula I:

1-[2-chloro-4-fluoro-5-(1,2,3,4,5,6-hexahydro-1,3-dioxo-isoindolyl)-phenylthio]-cyclopropanecarboxylic acid methyl ester;

9-[4-chloro-2-fluoro-5-(1-methoxycarbonylcyclobutyl-thio)-phenylimino]-8-thia-1,6-diazabicyclo[4.3.0]nonan-7-one;

9-[4-chloro-2-fluoro-5-(1-methoxycarbonylcyclo-propylthio)-phenylimino]-8-thia-1,6-diazabicyclo[4.3.0]nonan-7-one; and 1-[4-chloro-2-fluoro-5-(1-methoxycarbonylcyclobutyl)-phenylthio]-4-trifluoromethylpiperidine-2,6-dione.

The compounds of formula I wherein W is $W_1$, $W_4$, $W_5$ or $W_6$ can be prepared by reacting the respective anhydrides of the radicals $W_1$ (tetrahydrophthalic anhydride), $W_4$ (maleic anhydride), $W_5$ (succinic anhydride) and $W_6$ (glutaric anhydride) with amines of formula III

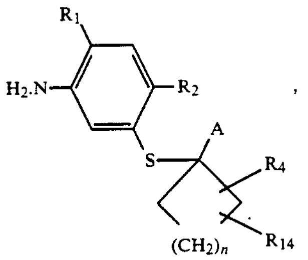
(III)

wherein A, $R_1$, $R_2$, $R_4$, $R_{14}$ and n are as defined for formula I. For example, compounds of formula I wherein W is $W_6$ can be prepared by reacting a glutaric anhydride of formula II, wherein $R_{13}$ is as defined for formula I, with amines of formula III, wherein A, $R_1$, $R_2$, $R_4$ and n are as defined for formula I, to form a glutaric acid monoanilide of formula IV, and then cyclising the resulting monoamide of formula IV with a condensation agent to form a cycloalkanecarboxylic acid derivative of formula I.

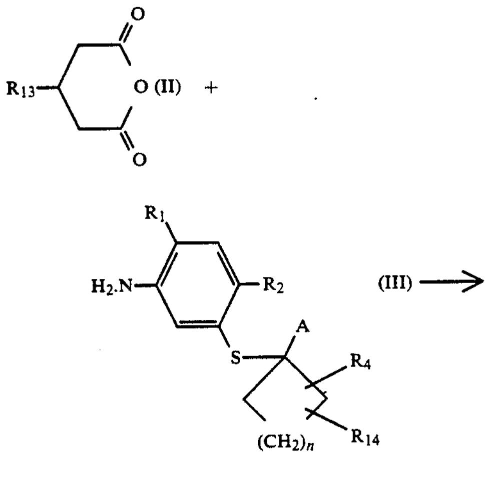
(II) +

(III)

-continued

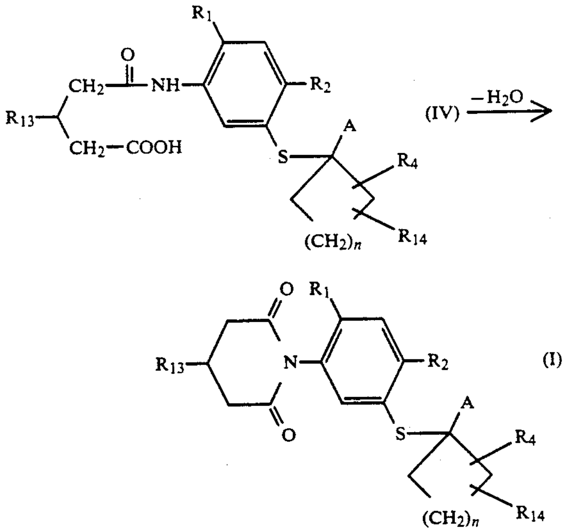
(IV)

$-H_2O$ (I)

The above reaction is advantageously carried out in an inert organic solvent. The reaction temperature is generally from room temperature to the boiling temperature of the reaction mixture, and the reaction mixture is preferably heated to reflux. The condensation reaction can be accelerated by the addition of condensation catalysts and removal of the elements of water that form. The same effect is achieved by adding agents that remove the elements of water, for example sulfuric acid. Suitable solvents are, especially, higher-boiling hydrocarbons, lower alkanecarboxylic acids and their esters and amides, higher-boiling ketones and ethers. Examples of suitable solvents are: benzene, toluene, xylene, dimethylformamide, dimethylacetamide, acetic acid, ethyl acetate, diisopropyl ether, ethylene glycol dimethyl ether, tetrahydrofuran or 2-butanone.

Suitable catalysts are, for example: p-toluenesulfonic acid, benzoic acid, 4-dimethylaminopyridine, sulfuric acid, hydrogen chloride or naphthalenesulfonic acid. The compounds of formula I wherein W is $W_1$, $W_4$ or $W_5$ can be prepared analogously.

The compounds of formula II and the corresponding anhydrides of the radicals $W_1$, $W_4$ and $W_5$ and the compounds of formula IV are known or can be prepared analogously to known methods.

Various methods for the synthesis of anhydrides of formula II and of the anhydrides of the radicals $W_1$, $W_4$ and $W_5$ are described in the literature.

For example, the reaction sequence shown in Scheme 1, which is based on very simple, generally available synthesis building blocks (aldehyde and cyanoacetic acid ester), is suitable for the preparation of the compounds of formula II:

Scheme 1

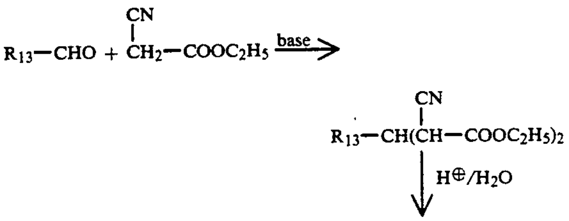

-continued

Scheme 1

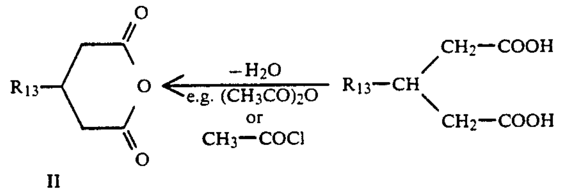

II

The process according to Scheme 1 is described in detail inter alia in the following literature references: J. Chem. Soc. 117 (1920) 1465; J. Chem. Soc. 123 (1923), 3131; J. Chem. Soc. 1952, 4785; Rec. Trav. Chim. Pays-Bas 84 (1965), 1183 and J. Ind. Chem. Soc. 13 (1936), 322.

Another variant of the process for the preparation of the glutaric anhydrides of formula II is based on a malonic ester synthesis and is summarised in Scheme 2:

Scheme 2

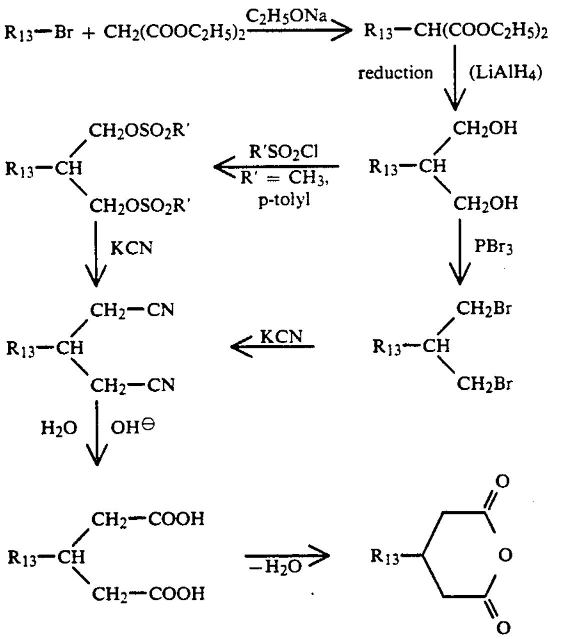

II

The anhydrides of the radicals $W_1$, $W_4$ and $W_5$ can be prepared analogously. The process outlined in Scheme 2 is known inter alia from the following literature references: Chem. Soc. Perkin Trans. I, 1978, 1636; J. Am. Chem. Soc. 95 (1973), 7437; Org. Prep. Proc. Int. 7, (1975), 283.

The anilines of formula III are novel and were developed specifically for the synthesis of the compounds of formula I. The present invention therefore relates also to these.

They can be prepared, for example, according to methods known per se by a) reduction of the corresponding nitro compounds by means of catalytic processes (for example $H_2/Pd/C$, or $H_2/Pt$) or b) reaction of a thiophenol of formula V with a compound of formula VI in the presence of a base in accordance with the following Scheme:

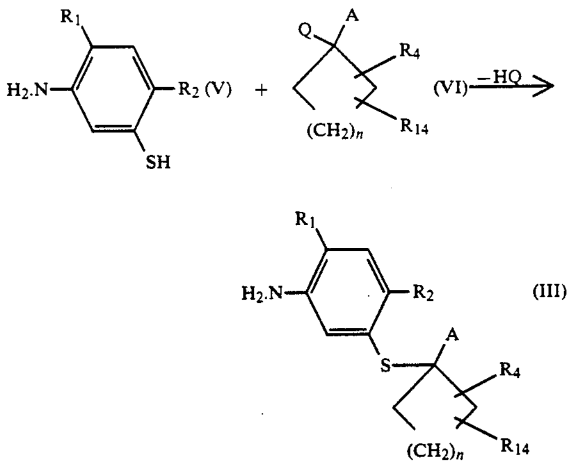

In the above reaction scheme, Q is a group that can be replaced under the reaction conditions, for example halogen, preferably chlorine, bromine or iodine, or a phenylsulfonyl radical that is, if desired, alkylated or halogenated in the phenyl nucleus, or a radical of the formula

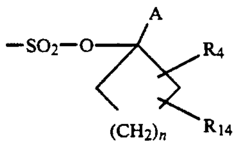

wherein the substituents A, $R_1$, $R_2$, $R_4$ and $R_{14}$ are as defined for formula I and n is 1, 2, 3 or 4.

The thiophenols of formula V are known from EP-A 0 259 265. The compounds of formula VI are known or can be prepared by analogy with known methods (see, for example, J. Org. Chem. 54, 6096-6100 (1989)).

The compounds of formula III can also be prepared by reacting a thiophenol of formula V

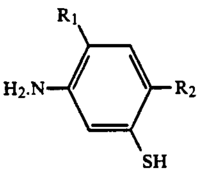

(V)

wherein $R_1$ and $R_2$ are as defined for formula I, in the presence of a base, with a compound of formula XXI $$X_1—C(R_{14}R_4)—(CH_2)_p—CH(A)—X_2 \quad (XXI)$$

wherein each of $X_1$ and $X_2$, independently of the other, is chlorine or bromine, A and $R_4$ are as defined for formula I and p is 1, 2, 3, 4 or 5, either a) when A is CN:

to form a compound of formula XXIII (XXIII)

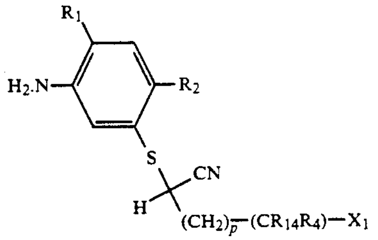

which is then cyclised in the presence of a base to form the compound of formula III wherein A is CN, or b) when A is COOH:

to form a compound of formula XXIIIa (XXIIIa)

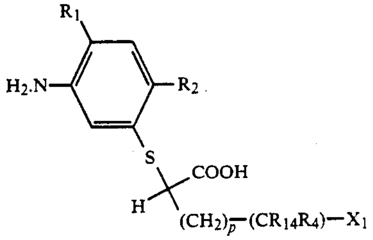

which is converted by methods known per se, in the presence of a base, into the compound of formula XXIIIb (XXIIIb)

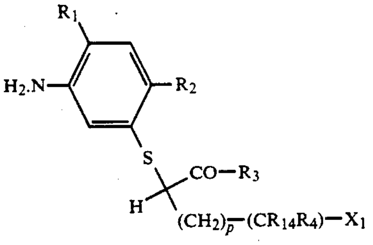

which is then cyclised in the presence of a base to form the compound of formula III wherein A is CO—$R_3$. The position of the substituents $R_4$ and $R_{14}$ in the alkylene chain of the compound of formula XXI can vary and depends on the desired substitution position of $R_4$ and $R_{14}$ on the cycloalkane ring of the compounds of formula III.

The compounds of formula III wherein A is CN can also be prepared by cyclising a compound of formula Va (Va)

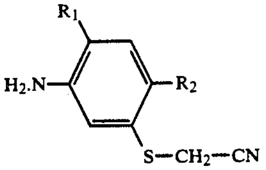

wherein $R_1$ and $R_2$ are as defined for formula V, in the presence of a base, with a compound of formula XXIa $X_1—C(R_{14}R_4)—(CH_2)_p—CH_2—X_2$ (XXIa)

wherein $X_1$, $X_2$, p, $R_{14}$ and $R_4$ are as defined for formula XXI. In the case of the compound of formula XXIa, the position of the substituents $R_4$ and $R_{14}$ in the alkylene chain depends on the desired substitution position of $R_4$ and $R_{14}$ on the cycloalkane ring of the compounds of formula III. Such reactions are described, for example, in Tetrahedron Letters 23, 2391-2394 (1972).

A further variant of the method for preparing compounds of formula III wherein A is CN comprises reacting compounds of formula III wherein A is COCl with ammonia to form the corresponding acetamide which can be converted into the desired nitrile by removing the elements of water (for example by the action of phosphorus pentoxide). Such reactions are known and are familiar to a person skilled in the art.

In formula XXI, $X_1$ and $X_2$ are preferably chlorine. Suitable bases for these reactions are oxides, hydrides, hydroxides, carbonates, carboxylic acid salts or alcoholates of an alkali or alkaline earth metal, trialkylamines or pyridine bases. The following bases have proved to be especially suitable: sodium methoxide, sodium ethoxide, sodium hydroxide, potassium hydroxide, sodium carbonate and potassium carbonate. Examples of solvents suitable for these reactions are compounds from the group of the open-chained or cyclic ethers, such as dioxane, tetrahydrofuran, diethyl ether, diisopropyl ether, dimethoxymethane or 1,2-dimethoxyethane, from the group of the alcohols, such as methanol, ethanol or isopropanol or from the group of the ketones, such as acetone, methyl ethyl ketone or methyl isobutyl ketone. The reactions are generally carried out at temperatures of from room temperature to the boiling temperature of the solvent.

The compounds of formula I wherein W is $W_2$ and $Y_3$ is oxygen are prepared by condensing an isocyanate of formula VIIb (VIIb)

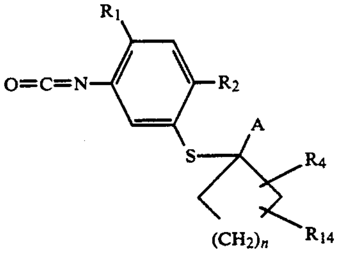

wherein $R_1$, $R_2$, $R_4$, $R_{14}$, A and n are as defined for formula I, in an organic solvent in the presence of a base at a temperature of from 0° to +150° C., with a 2-carboxypiperidine of formula XXIV (XXIV)

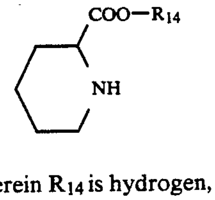

wherein $R_{14}$ is hydrogen, $C_1$-$C_6$alkyl or benzyl, to form the compound of formula XXV (XXV)

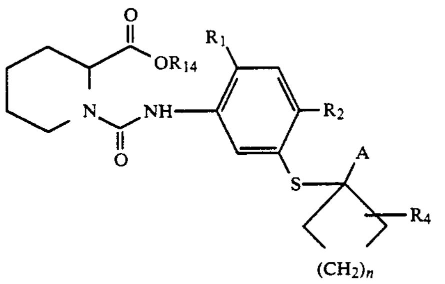

which is then cyclised under acidic conditions at a temperature of from +50° to +150° C. to form the compound of formula I. Such reactions are described, for example, in EP-A 0 211 805.

The compounds of formula I wherein W is $W_2$ and $Y_3$ is sulfur are prepared by condensing an isothiocyanate of formula VIIa (VIIa)

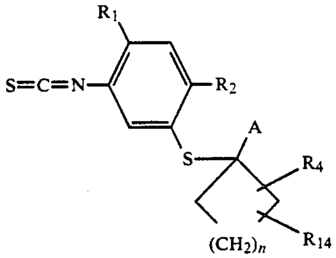

wherein $R_1$, $R_2$, $R_4$, $R_{14}$, A and n are as defined for formula I, in an organic solvent in the presence of a base at a temperature of from 0° to +150° C. with a 2-carboxypiperidine of formula XXIV (XXIV)

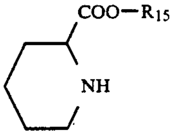

wherein $R_{15}$ is hydrogen, $C_1$-$C_6$alkyl or benzyl, to form the compound of formula XXVa (XXVa)

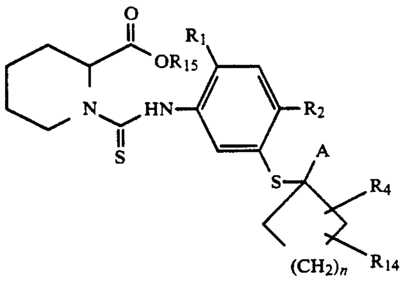

which is then cyclised under acidic conditions at a temperature of from +50° to +150° C. to form the compound of formula I. Such reactions are likewise described in EP-A 0 211 805.

The compounds of formula I wherein W is $W_3$ and Y is sulfur can be prepared by condensing an isocyanate of formula VIIb (VIIb)

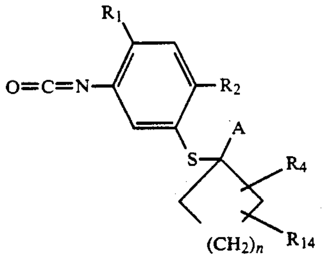

wherein $R_1$, $R_2$, $R_4$, $R_{14}$, A and n are as defined for formula I, in an organic solvent in the presence of a base at a temperature of from 0° to +150° C. with a compound of formula XXVI (XXVI)

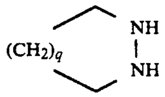

wherein q is as defined for formula I, and then reacting the resulting compound of formula XXVII (XXVII)

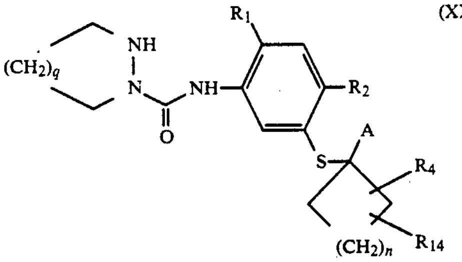

in the presence of an inorganic base at a temperature of from 0° to +150° C. with thiophosgene. Such reactions are described, for example, in EP-A 0 211 805.

The compounds of formula I wherein W is $W_3$ and Y is oxygen can be prepared by condensing an isocyanate of formula VIIb (VIIb)

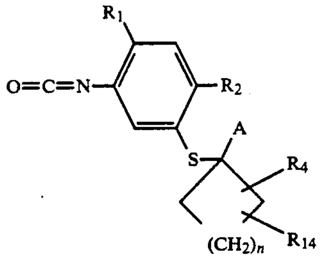

wherein $R_1$, $R_2$, $R_4$, $R_{14}$, A and n are as defined for formula I, in an organic solvent in the presence of a base at a temperature of from 0° to +150° C. with a compound of formula XXVI (XXVI)

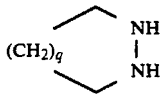

wherein q is as defined for formula I, then reacting the resulting compound of formula XXVII

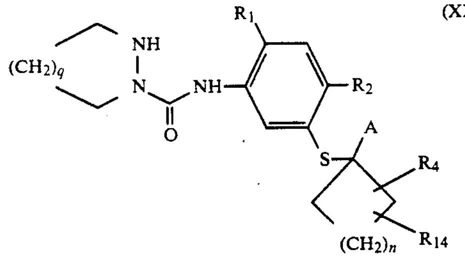

(XXVII)

in the presence of a base at a temperature of from 0° to +150° C. with a chlorocarbonic acid ester of formula XXVIII

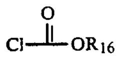

XXVIII wherein $R_{16}$ is $C_1$-$C_6$alkyl or benzyl, to form a compound of formula XXIX

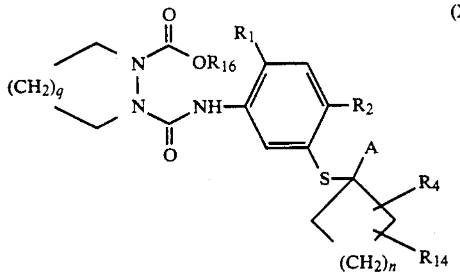

(XXIX)

which is cyclised in an inert solvent in the presence of a base at a temperature of from +50° to +180° C. to form the compound of formula I. Such reactions are likewise described in EP-A 0 211 805.

The compounds of formula I wherein W is $W_3$ and Y is sulfur can also be prepared from the compounds of formula I wherein W is $W_3$ and Y is oxygen by heating the latter compounds with a reagent capable of introducing the thioxo group. Such reagents are, for example, phosphorus pentafluoride or Lawesson's reagent (2,4-bis-(4-methoxyphenyl)-1,3-dithia-2,4-diphosphetan-2,4-disulfide). Such reactions are known and their execution is familiar to a person skilled in the art.

The compounds of formula I in which W is $W_7$ and $Y_4$ is oxygen are prepared by reacting an isocyanate of formula VIIb

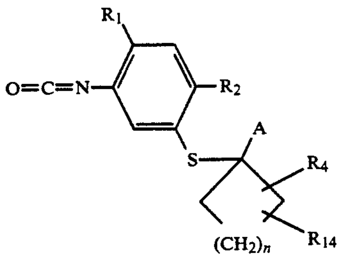

(VIIb)

wherein the substituents A, $R_1$, $R_2$, $R_4$, $R_{14}$ and n are as defined for formula I, with a compound of formula XXX $H_2N$—NH—$COOR_{16}$ (XXX)

wherein $R_{16}$ is as defined above, to form the compound of formula XXXI

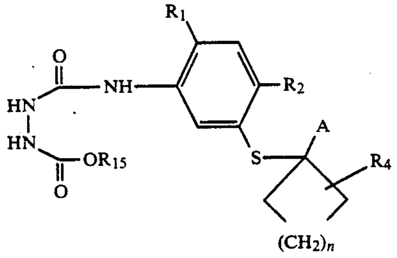

(XXXI)

which is cyclised in the presence of a base at a temperature of from +50° to +180° C. to form the compound of formula XXXII

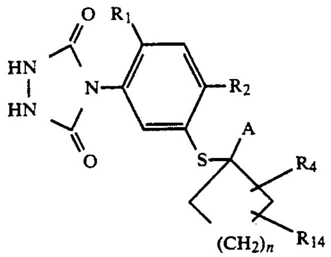

(XXXII)

which is reacted at a temperature of from 0° to +150° C. in the presence of a catalytic amount of a base with divinylsulfone $(CH_2{=}CH)_2SO_2$. Such reactions are described, for example, in EP-A 0 210 137.

The compounds of formula I wherein W is $W_7$ and $Y_4$ is sulfur are prepared by reacting an isothiocyanate of formula VIIa

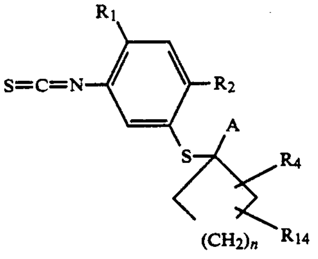

(VIIa)

wherein the substituents A, $R_1$, $R_2$, $R_4$, $R_{14}$ and n are as defined for formula I, with a compound of formula XXX $H_2n$—NH—$COOR_{16}$ (XXX)

wherein $R_{16}$ is as defined above, to form the compound of formula XXXIa (XXXIa)

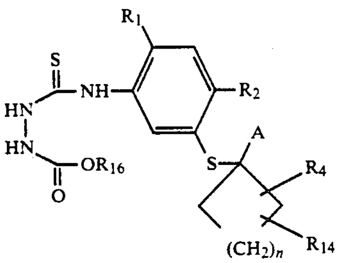

which is cyclised in the presence of a base at a temperature of from +50° to +180° C. to form the compound of formula XXXIIa (XXXIIa)

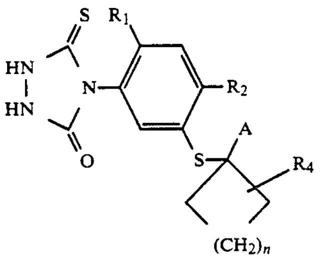

which is reacted at a temperature of from 0° to +150° C. in the presence of a catalytic amount of a base with divinylsulfone $(CH_2{=}CH)_2SO_2$. Such reactions are likewise described in EP-A 0 210 137.

The compounds of formula I wherein W is $W_8$ are prepared by converting an isothiocyanate of formula VIIa (VIIa)

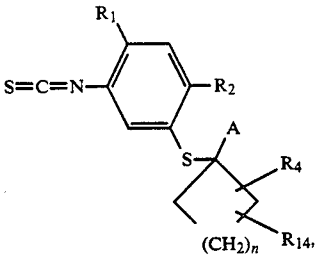

wherein the substituents A, $R_1$, $R_2$, $R_4$, $R_{14}$ and n are as defined for formula I, with a hexahydropyridazine of formula VIII (VIII)

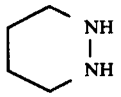

into the compound of formula IX (IX)

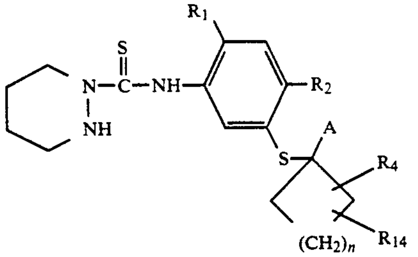

and then reacting the latter in the presence of a base with a compound of formula X $CZ_1Cl_2$ (X), wherein $Z_1$ is oxygen or sulfur.

The compounds of formula I wherein W is $W_9$ can be prepared by converting an isothiocyanate of formula VIIa (VIIa)

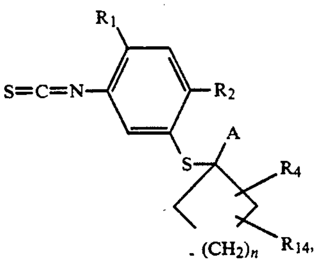

wherein the substituents A, $R_1$, $R_2$, $R_4$, $R_{14}$ and n are as defined for formula I, with a 1,4,5,6-tetrahydropyridazine of formula XI (XI)

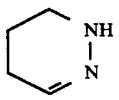

into the compound of formula XII (XII)

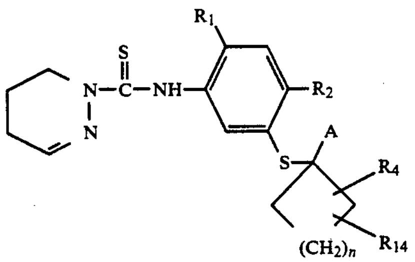

and then reacting the latter in the presence of a base with a compound of formula Xa $CZ_2Cl_2$ (Xa), wherein $Z_2$ is oxygen or sulfur.

The compounds of formula I wherein W is $W_9$ can also be prepared by hydrogenating a tetrahydropyridazin-3-one of formula XIII (XIII)

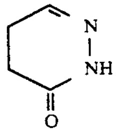

to form the hexahydropyridazin-3-one of formula XIV (XIV)

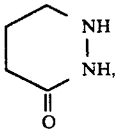

reacting the latter with an isothiocyanate of formula VIIa (VIIa)

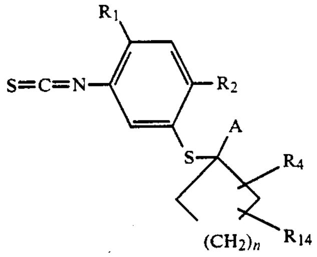

wherein the substituents A, $R_1$, $R_2$, $R_4$, $R_{14}$ and n are as defined for formula I, to form the compound of formula XVI (XVI)

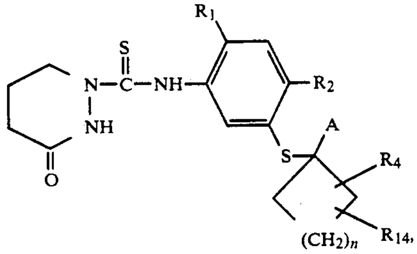

converting the latter with a compound of formula Xa $CZ_2Cl_2$ (Xa)

wherein $Z_2$ is oxygen or sulfur, or with $Cl_3(CO)_3Cl_3$ (triphosgene), into the compound of formula XVII (XVII)

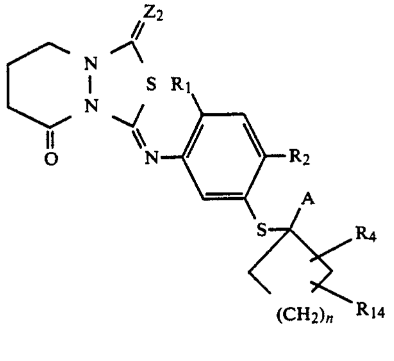

reacting the latter with sodium borohydride to form the compound of formula XVIII (XVIII)

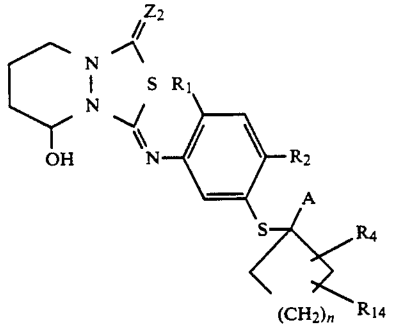

and then dehydrating the latter in the presence of an acid.

Compounds of formula I wherein W is $W_8$ can also be prepared by hydrogenating compounds of formula I wherein W is $W_9$. Such hydrogenation processes and the hydrogenation of the compound of formula XIII to form the compound of formula XIV are familiar to a person skilled in the art. They can be carried out, for example, with hydrogen in the presence of noble metal catalysts, such as platinum.

The reaction of the isothiocyanates of formula VIIa with the pyridazines of formulae VIII and XI and the pyridazin-3-ones of formula XIV is advantageously carried out in a solvent that is inert under the conditions of the reaction, at temperatures of from $-5°$ C. to the boiling temperature of the solvent, preferably from 0° to $+50°$ C., especially at room temperature. Examples of suitable solvents for this reaction are toluene, xylene, ethyl acetate or acetonitrile.

The reaction of the compound of formulae IX and XII with the compound of formula X and the reaction of the compound of formula XVI with the compound of formula X or with triphosgene is advantageously carried out in a solvent that is inert under the conditions of the reaction, at low temperatures, preferably at from 0° to $+50°$ C., especially at from 0° to $+15°$ C. Examples of suitable bases for this reaction are pyridine, triethylamine or N,N-dimethylaniline. Examples of suitable solvents are 1,2-dichloroethane, dichloromethane or toluene.

The reaction of the compound of formula XVII with sodium borohydride to form the compound of formula XVIII is advantageously carried out at temperatures of from room temperature to $+50°$ C., alcohols being preferred as solvents. The subsequent dehydration of the compound of formula XVIII is advantageously carried out in toluene at reflux temperature in the presence of p-toluenesulfonic acid, sulfuric acid or trifluoroacetic acid.

The pyridazines of formulae VIII and XI and the pyridazin-3-ones of formula XIV used as starting materials for the compounds of formula I according to the invention wherein W is $W_8$ or $W_9$ are known or can be prepared analogously to methods known from the literature. The preparation of such compounds is described, for example, in Coll. Czechoslov. Chem. Commun. 33, 2087 (1968), Khimiya Geterotsiklicheskikh Soedinenii, 4, (3), 530–535 (1968), Beilstein, E III/IV 23, p. 465 and EP-A 0 304 920.

The compounds of formula I wherein W is $W_{10}$ can be prepared by reacting a 2-hydroxycyclohex-1-enecarboxylic or -thiocarboxylic acid anilide of formula XIX

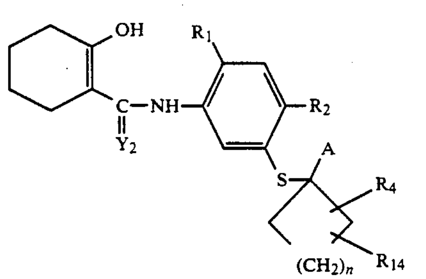
(XIX)

wherein A, $R_1$, $R_2$, $R_4$, $R_{14}$, $Y_2$ and n are as defined for formula I, with a reactive carbonic or thiocarbonic acid derivative of formula XX

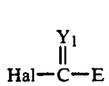
(XX)

wherein $Y_1$ is oxygen or sulfur, Hal is chlorine or bromine and E is chlorine, bromine or $C_1$-$C_4$alkoxy, ring closure to form the compound of formula I being effected.

The ring closure is effected in the presence of the equimolar amount of an organic or inorganic base in an inert solvent or diluent at a temperature of from room temperature to the boiling point of the reaction mixture.

Examples of suitable reactive carbonic acid esters and thiocarbonic acid esters are phosgene, thiophosgene, chloroformic acid ethyl ester and chloroformic acid methyl ester.

Suitable solvents and diluents are acetone, methyl ethyl ketone, dioxane or tetrahydrofuran, acetonitrile, toluene or chloroform.

The intermediates of formula XIX are novel compounds. They were developed specifically for the preparation of the compounds of formula I. The present invention therefore relates also to the intermediates of formula XIX. In order to prepare the compounds of formula XIX, for example morpholinocyclohexene is reacted with an isocyanate or isothiocyanate of formula VII and the resulting 2-morpholinocyclohex-1-enecarboxylic acid anilide or 2-morpholinocyclohex-1-ene-thiocarboxylic acid anilide of formula XXII is then hydrolysed in an aqueous acidic solution in accordance with the reaction scheme:

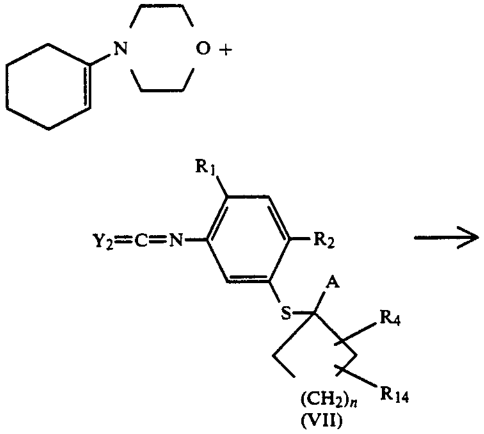
(VII)

-continued

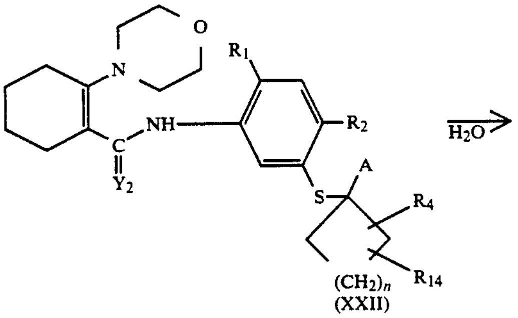

(XXII)

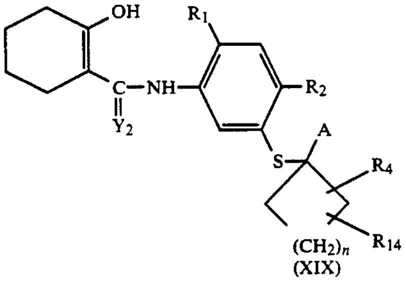
(XIX)

In the above formulae, the substituents are as defined for formula I.

1-Morpholinocyclohex-1-ene is known.

The isocyanates and isothiocyanates of formula VII are novel. Formula VII includes the isothiocyanates of formula VIIa and the isocyanates of formula VIIb. The compounds of formula VII were developed specifically for the preparation of the compounds of formula I and the present invention relates also to these. The isocyanates and isothiocyanates of formula VII are obtained in a manner known per se by reacting the corresponding amines of formula III

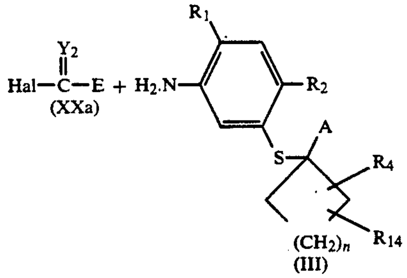
(XXa) (III)

with phosgene or thiophosgene or with a reactive carbonic acid ester or thiocarbonic acid ester of formula XXa. Such processes are described, for example, in EP-A 0 304 920.

In formula III, the substituents are as defined for formula I. In formula XXa, $Y_2$ is oxygen or sulfur, Hal is chlorine or bromine, and E is chlorine, bromine or $C_1$-$C_4$alkoxy.

The condensation of the isocyanate or isothiocyanate of formula VII with the 1-morpholinocyclohex-1-ene generally occurs spontaneously with the evolution of heat. It is advisable, however, for the reaction to be carried out in an absolute solvent, using freshly distilled 1-morpholinocyclohex-1-ene and with the exclusion of atmospheric oxygen, for example by expelling the air in the reaction vessel using nitrogen or a noble gas and heating the reaction mixture after the increase in temperature due to the exothermic reaction has subsided.

The processes described above can be carried out analogously to processes known from the literature. The reaction conditions preferred in those processes, such as temperature, molar ratios of the educts, reaction procedure, solvents, any necessary reagents, such as acids, bases, water-binding agents, and so on, are familiar to a person skilled in the art.

PREPARATION EXAMPLES

Example P1

Preparation of
1-(5-amino-2-chloro-4-fluorophenylthio)cyclobutanecarboxylic acid methyl ester

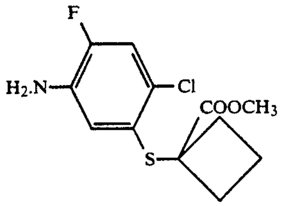

16.6 g of 5-amino-2-chloro-4-fluoro-phenylthiophenol are added to a solution, stirred at room temperature, of 4.7 g of sodium methoxide in 100 ml of methanol. After the dropwise addition of 16.6 g of 1-bromocyclobutanecarboxylic acid ethyl ester, the reaction mixture is heated slowly to boiling. When the reaction mixture has been maintained at reflux temperature for 6 hours, it is introduced into ice-water. The organic phase is then extracted with ether and dried over sodium sulfate. Concentration of the solution and chromatographic purification by silica gel chromatography yield 12 g of 1-(5-amino-2-chloro-4-fluoro-phenylthio)-cyclobutanecarboxylic acid methyl ester having a melting point of from +94° to +95° C.

Example P2

Preparation of
1-(2-chloro-4-fluoro-5-isothiocyanato-phenylthio)cyclobutanecarboxylic acid methyl ester

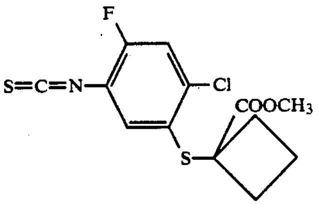

While stirring at a temperature of from +25° to +30° C., a solution of 12 g of 1-(5-amino-2-chloro-4-fluoro-phenylthio)-cyclobutanecarboxylic acid methyl ester obtained in accordance with Example P1 in 30 ml of ethylene chloride is added dropwise to a mixture of 12 g of calcium carbonate and 8 ml of thiophosgene in 40 ml of ethylene chloride and 40 ml of water. The reaction mixture is then stirred for 18 hours. After filtering off the resulting precipitate, the organic phase is dried over calcium chloride and then concentrated in vacuo, yielding 13.1 g of 2-(2-chloro-4-fluoro-5-isothiocyanato-phenylthio)-cyclobutanecarboxylic acid methyl ester in the form of an oil.

Example P3

Preparation of
1-[2-chloro-4-fluoro-5-(1-hexahydropyridazinyl-thiocarbonylamino)-phenylthio]-cyclobutanecarboxylic acid methyl ester

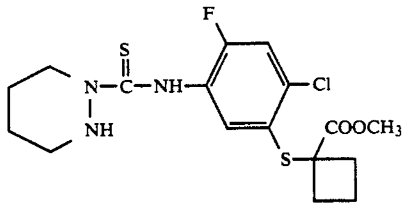

While stirring at room temperature, a solution of 13.1 g of 1-(2-chloro-4-fluoro-5-isothiocyanato-phenylthio)-cyclobutanecarboxylic acid methyl ester obtained in accordance with Example P2 in 200 ml of ethanol is added dropwise to a solution of 4 g of hexahydropyridazine in 30 ml of ethanol. After stirring for 3 hours at room temperature, the reaction mixture is concentrated by evaporation in vacuo, yielding 10.8 g of 1-[2-chloro-4-fluoro-5-(1-hexahydropyridazinyl-thiocarbonylamino)-phenylthio]-cyclobutanecarboxylic acid methyl ester having a melting point of from +112° to +113° C.

Example P4

Preparation of
9-[4-chloro-2-fluoro-5-(1-methoxycarbonyl-cyclobutylthio)phenylimino]-8-thia-1,6-diazabicyclo[4.3.0]nonan-7-one

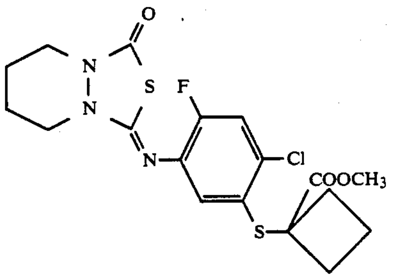

While stirring at a temperature of +10° C., 12.5 ml of a 20% solution of phosgene in toluene are added dropwise to a solution of 10.4 g of 1-[2-chloro-4-fluoro-5-(1-hexahydropyridazinyl-thiocarbonylamino)-phenylthio]-cyclobutanecarboxylic acid methyl ester and 10 ml of triethylamine in 100 ml of toluene. The reaction mixture is then stirred for 6 hours and then introduced into ice-water. The organic phase is then separated off and dried over sodium sulfate. Concentration by evaporation and subsequent chromatographic purification by means of silica gel chromatography yield 4.6 g of 9-[4-chloro-2-fluoro-5-(1-methoxycarbonyl-cyclobutylthio)-phenylimino]-8-thia-1,6-diazabicyclo[4.3.0]nonan-7one, $\eta_D^{22}$1.6010.

Example P5

Preparation of 1-[2-chloro-4-fluoro-5-(1,2,3,4,5,6-hexahydro-1,3-dioxo-isoindolyl)-phenylthio]-cyclobutanecarboxylic acid methyl ester

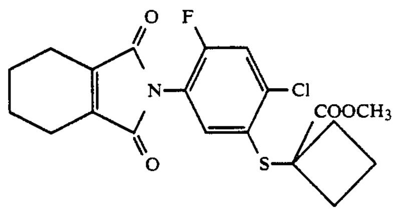

A mixture of 4.4 g of 1-(5-amino-2-chloro-4-fluoro-phenylthio)-cyclobutanecarboxylic acid methyl ester and 2.4 g of 3,4,5,6-tetrahydrophthalic anhydride in 60 ml of glacial acetic acid is heated under reflux for 5 hours while stirring. The reaction mixture is then introduced into ice-water and the resulting glutinous product is extracted with ethyl acetate. After drying the organic phase over sodium sulfate and concentrating by evaporation in vacuo, petroleum ether is added to the resulting residue and the substance solidifies. Filtering yields 4 g of 1-[2-chloro-4-fluoro-5-(1,2,3,4,5,6-hexahydro-1,3-dioxo-isoindolyl)-phenylthio]-cyclobutanecarboxylic acid methyl ester having a melting point of +98° C.

Example P6

Preparation of 2-(5-amino-2-chloro-4-fluoro-phenylthio)-4-chlorobutyric acid ethyl ester:

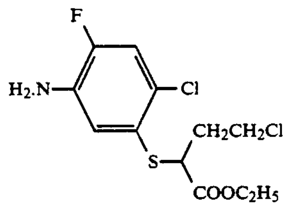

At room temperature, 16.2 g of 2,4-dichlorobutyric acid ethyl ester are added dropwise to a mixture of 14 g of 5-amino-2-chloro-4-fluoro-thiophenol and 12.7 g of potassium carbonate in 280 ml of methyl ethyl ketone (exothermic reaction). The reaction mixture is then heated under reflux for 18 hours. After cooling of the reaction mixture, the inorganic portion of the mixture is filtered off and washed with methyl ethyl ketone. Concentration of the organic solution by evaporation and chromatographic purification of the residue by silica gel chromatography yield 14.2 g of 2-(5-amino-2-chloro-4-fluorophenylthio)-4-chlorobutyric acid ethyl ester having a melting point of from +97° to +99° C.

Example P7

Preparation of 1-(5-amino-2-chloro-4-fluoro-phenylthio)-cyclopropanecarboxylic acid

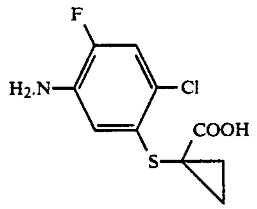

A solution of 2.4 g of potassium hydroxide in 50 ml of ethanol is added dropwise while stirring at a temperature of +5° C. to a solution of 14.2 g of 2-(5-amino-2-chloro-4-fluorophenylthio)-4-chlorobutyric acid ethyl ester in 25 ml of ethanol. After stirring for 18 hours, 0.9 g of potassium hydroxide is added a further 3 times, and the reaction mixture is stirred for 6 hours each time until the reaction is complete. The reaction mixture is then concentrated, water is added and extraction is carried out 3 times with ethyl acetate. The combined organic phases are dried over sodium sulfate and then concentrated by evaporation. Recrystallisation of the residue from ethyl acetate/n-hexane yields 8.4 g of 1-(5-amino-2-chloro-4-fluoro-phenylthio)-cyclopropanecarboxylic acid having a melting point of from +266° to +267° C.

Example P8

Preparation of 1-[2-chloro-4-fluoro-5-(1,2,3,4,5,6-hexahydro-1,3-dioxo-isoindolyl)-phenylthio]-cyclopropanecarboxylic acid

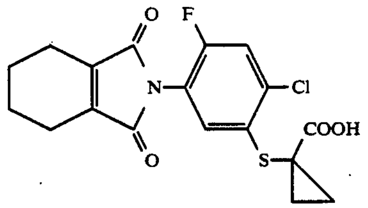

A mixture of 2.4 g of 1-(5-amino-2-chloro-4-fluoro-phenylthio)-cyclopropanecarboxylic acid, 1.5 g of 3,4,5,6-tetrahydrophthalic anhydride and 100 ml of glacial acetic acid is heated under reflux for 18 hours while stirring. The reaction mixture is then introduced into ice-water and the resulting product is extracted with ethyl acetate. Drying over sodium sulfate and concentration of the solution by evaporation yield 1.7 g of 1-[2-chloro-4-fluoro-5-(1,2,3,4,5,6-hexahydro-1,3-dioxo-isoindolyl)-phenylthio]-cyclopropanecarboxylic acid having a melting point of from +186° to +188° C.

Example P9

Preparation of 1-[2-chloro-4-fluoro-5-(1,2,3,4,5,6-hexahydro-1,3-dioxo-isoindolyl)-phenylthio]-cyclopropanecarboxylic acid chloride

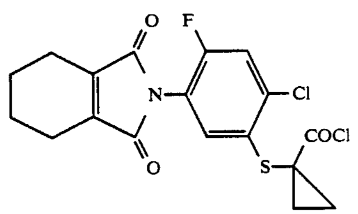

While stirring at room temperature, 3 ml of thionyl chloride are added to a solution of 1 g of 1-[2-chloro-4-fluoro-5-(1,2,3,4,5,6-hexahydro-1,3-dioxo-isoindolyl)-phenylthio]-cyclopropanecarboxylic acid and one drop of dimethylformamide in 40 ml of ethylene chloride and the reaction mixture is then heated under reflux for 3 hours. Concentration of the reaction mixture by evaporation yields 1 g of 1-[2-chloro-4-fluoro-5-(1,2,3,4,5,6-hexahydro-1,3-dioxo-isoindolyl)-phenylthio]-cyclopropanecarboxylic acid chloride in the form of an oil.

Example P10

Preparation of 1-[2-chloro-4-fluoro-5-(1,2,3,4,5,6-hexahydro-1,3-dioxo-isoindolyl)-phenylthio]-cyclopropanecarboxylic acid methyl ester

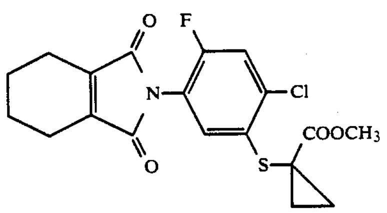

While stirring at room temperature, a solution of 1 g of 1-[2-chloro-4-fluoro-5-(1,2,3,4,5,6-hexahydro-1,3-dioxo-isoindolyl)-phenylthio]-cyclopropanecarboxylic acid chloride obtained in accordance with Example P9 in 10 ml of methyl acetate is added dropwise to a solution of 10 ml of methanol and 0.5 ml of triethylamine in 10 ml of methyl acetate. After stirring for 3 hours at room temperature, the resulting triethylamine hydrochloride is filtered off and the filtrate is concentrated by evaporation, yielding 0.9 g of 1-[2-chloro-4-fluoro-5-(1,2,3,4,5,6-hexahydro-1,3-dioxo-isoindolyl)-phenylthio]-cyclopropanecarboxylic acid methyl ester having a melting point of from +142° to +144° C.

Example P11

Preparation of N-[4-chloro-2-fluoro-5-(1-methoxycarbonyl-cyclobutylthio)-phenyl]-3-trifluoromethylglutaric acid monoamide

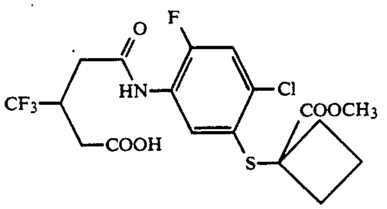

A mixture of 3.6 g of 3-trifluoromethylglutaric anhydride and 5.8 g of 1-(5-amino-2-chloro-4-fluoro-phenylthio)-cyclobutanecarboxylic acid methyl ester in 65 ml of benzene is heated under reflux for 3 hours while stirring. The resulting precipitate is then separated off, washed with diisopropyl ether and dried, yielding 7.9 g of N-[4-chloro-2-fluoro-5-(1-methoxycarbonyl-cyclobutylthio)-phenyl]-3-trifluoromethylglutaric acid monoamide having a melting point of from +165° to +167° C.

Example P12

Preparation of 1-[4-chloro-2-fluoro-5-(1-methoxycarbonyl-cyclobutyl)-phenylthio]-4-trifluoromethyl-piperidine-2,6-dione

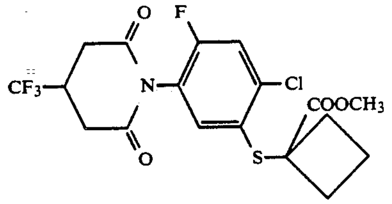

A mixture of 7.9 g of N-[4-chloro-2-fluoro-5-(1-methoxycarbonyl-cyclobutylthio)-phenyl]-3-trifluoromethylglutaric acid monoamide and 1.4 g of sodium acetate in 34 ml of acetic anhydride is stirred for 30 minutes at a temperature of +100° C. The reaction mixture is then concentrated by evaporation and a mixture of diethyl ether and ice-water is added to the residue. The ether phase is washed in succession with ice-water, 10% sodium hydrogen carbonate solution and saturated sodium chloride solution and then dried over sodium sulfate. The oil remaining after evaporation of the ether is recrystallised from n-hexane with the addition of a small amount of diisopropyl ether and then from methanol, yielding 5 g of 1-[4-chloro-2-fluoro-5-(1-methoxycarbonyl-cyclobutyl)-phenylthio]-4-trifluoromethylpiperidine-2,6-dione having a melting point of from +115° to +117° C.

Example P13

Preparation of 1-(5-amino-2-chloro-4-fluorophenylthio)-cyclopropanecarboxylic acid ethyl ester

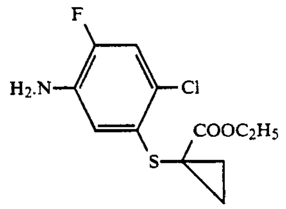

A mixture of 12.5 g of 2-(5-amino-2-chloro-4-fluorophenylthio)-4-chlorobutyric acid ethyl ester, 10.6 g of potassium carbonate and 0.7 g of tetrabutylammonium hydrogen sulfate in 14 ml of toluene is maintained at +80° C. for 40 hours. The solid portions of the reaction mixture are then filtered off and washed with acetone. Evaporation of the solvent and recrystallisation from n-hexane and a small amount of ethyl acetate yield 7.9 g of 1-(5-amino-2-chloro-4-fluoro-phenylthio)-cyclopropanecarboxylic acid ethyl ester having a melting point of from +96° to +97° C.

Example P14

Preparation of 2-(5-amino-2-chloro-4-fluorophenylthio)-4-bromobutyric acid methyl ester

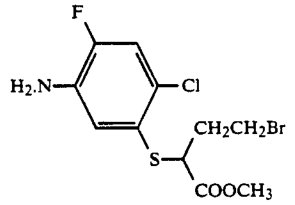

28.6 g of 2,4-dibromobutyric acid methyl ester are added dropwise at room temperature to a mixture of 17.8 g of 5-amino-2-chloro-4-fluoro-thiophenol and 15.2 g of potassium carbonate in 160 ml of methyl ethyl ketone (exothermic reaction). The reaction mixture is then heated under reflux for 2 hours. After cooling of the reaction mixture, the inorganic portion of the mixture is filtered off and washed with methyl ethyl ketone. Concentration of the organic solution by evaporation and chromatographic purification of the residue by means of silica gel chromatography yield 25.5 g of 2-(5-amino-2-chloro-4-fluoro-phenylthio)-4-bromobutyric acid methyl ester having a melting point of from +97° to +99° C.

Example P15

Preparation of 1-(5-amino-2-chloro-4-fluorophenylthio)-cyclopropanecarboxylic acid methyl ester

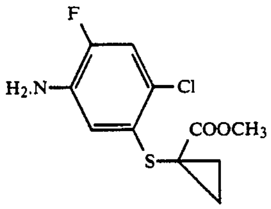

A mixture of 12.5 g of 2-(5-amino-2-chloro-4-fluorophenylthio)-4-bromobutyric acid methyl ester, 30.4 g of potassium carbonate and 1.7 g of tetrabutylammonium hydrogen sulfate in 38 ml of toluene is maintained at +80° C. for 40 hours. The solid portions of the reaction mixture are then filtered off and washed with acetone. Evaporation of the solvent yields 17 g of 1-(5-amino-2-chloro-4-fluorophenylthio)-cyclopropanecarboxylic acid methyl ester having a melting point of from +119° to +124° C.

Example P16

Preparation of 1-(5-amino-2-chloro-4-fluorophenylthio)-cyclopropanecarboxylic acid methyl ester A solution of 3.6 g of 1-(5-amino-2-chloro-4-fluorophenylthio)-cyclopropanecarboxylic acid and a few drops of sulfuric acid in 50 ml of methanol is heated under reflux until the starting material can no longer be detected. The methanol is then evaporated off, water and ethyl acetate are added to the residue and the organic phase is washed in succession with sodium hydrogen carbonate solution, water and saturated sodium chloride solution. Concentration and purification of the crude product by means of silica gel chromatography yield 5.7 g of 1-(5-amino-2-chloro-4-fluorophenylthio)-cyclopropanecarboxylic acid methyl ester having a melting point of from +119° to +121° C.

Example P17

Preparation of 1-(2-chloro-4-fluoro-5-isothiocyanato-phenylthio)-cyclopropanecarboxylic acid methyl ester

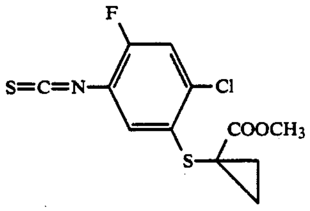

While stirring at room temperature, a solution of 5.5 g of 1-(5-amino-2-chloro-4-fluoro-phenylthio)-cyclopropanecarboxylic acid methyl ester in 20 ml of ethylene chloride is added dropwise to a mixture of 3 g of calcium carbonate, 2 ml of thiophosgene in 20 ml of ethylene chloride and 20 ml of water. After stirring for 4 hours at room temperature, the inorganic portion of the reaction mixture is filtered off and the organic phase is dried over calcium chloride and then concentrated by evaporation, yielding 6.3 g of 1-(2-chloro-4-fluoro-5-isothiocyanato-phenylthio)-cyclopropanecarboxylic acid methyl ester having a melting point of from +100° to +101° C.

Example P18

Preparation of 1-[2-chloro-4-fluoro-5-(1-hexahydropyridazinyl-thiocarbonylamino)-phenylthio]-cyclopropanecarboxylic acid methyl ester

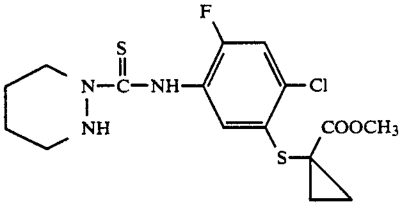

While stirring at room temperature, a solution of 6.3 g of 1-(2-chloro-4-fluoro-5-isothiocyanato-phenylthio)-cyclopropanecarboxylic acid methyl ester in 30 ml of ethanol is added dropwise to a solution of 2.2 g of hexahydropyridazine in 30 ml of ethanol. After stirring for 30 minutes at room temperature, the reaction mixture is concentrated by evaporation in vacuo, yielding 7.9 g of 1-[2-chloro-4-fluoro-5-(1-hexahydropyridazinyl-thiocarbonylamino)-phenylthio]-cyclopropanecarboxylic acid methyl ester having a melting point of from +156° to +157° C.

Example P19

Preparation of 9-[4-chloro-2-fluoro-5-(1-methoxycarbonyl-cyclopropylthio)-phenylimino]-8-thia-1,6-diazabicyclo[4.3.0-]nonan-7-one

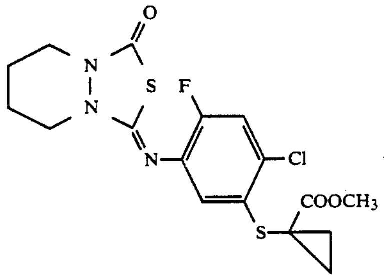

While stirring at a temperature of from 0° to +10° C., 5.7 ml of a 20% solution of phosgene in toluene are added dropwise to a solution of 3.7 g of 1-[2-chloro-4-fluoro-5-(1-hexahydropyridazinyl-thiocarbonylamino)-phenylthio]-cyclopropanecarboxylic acid methyl ester and 4.6 ml of triethylamine in 100 ml of toluene. The reaction mixture is then stirred for 4 hours and then introduced into ice-water. The organic phase is then separated off and dried over sodium sulfate. Concentration by evaporation and subsequent chromatographic purification by means of silica gel chromatography yield 3.7 g of 9-[4-chloro-2-fluoro-5-(1-methoxycarbonyl-cyclopropylthio)-phenylimino]-8-thia-1,6-diazabicyclo[4.3.0]nonan-7-one, having a melting point of +149° C.

The compounds of Tables 1 to 12 can be prepared analogously to the above Examples and the preparation methods mentioned in the description:

TABLE 1

Compounds of formula I wherein W = $W_1$ and $R_{14}$ = H

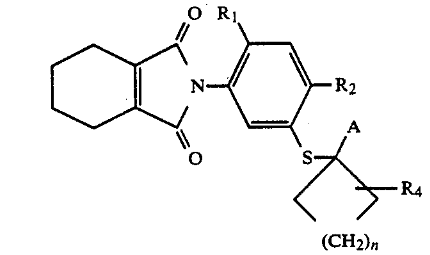

(I)

| Comp. No. | $R_1$ | $R_2$ | $R_3$ | $R_4$ | n | A | m.p. [°C.] |
|---|---|---|---|---|---|---|---|
| 1.001 | F | Cl | —Cl | H | 0 | —CO—$R_3$ | |
| 1.002 | F | Cl | —OH | H | 0 | —CO—$R_3$ | 186–188 |
| 1.003 | F | Cl | —$OCH_3$ | H | 0 | —CO—$R_3$ | 142 |
| 1.004 | F | Cl | —$OC_2H_5$ | H | 0 | —CO—$R_3$ | 85–86 |
| 1.005 | F | Cl | —$OC_3H_7$ | H | 0 | —CO—$R_3$ | |
| 1.006 | F | Cl | 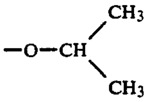 | H | 0 | —CO—$R_3$ | $n_D^{20}$ = 1.5368 |
| 1.007 | F | Cl | —$OC_4H_9$ | H | 0 | —CO—$R_3$ | |
| 1.008 | F | Cl | —O—$CH(CH_3)$—$C_2H_5$ | H | 0 | —CO—$R_3$ | |
| 1.009 | F | Cl | 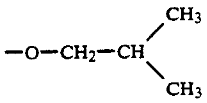 | H | 0 | —CO—$R_3$ | |

TABLE 1-continued

Compounds of formula I wherein W = $W_1$ and $R_{14}$ = H

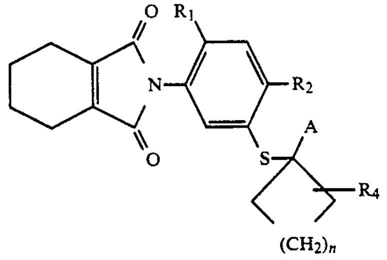

(I)

| Comp. No. | $R_1$ | $R_2$ | $R_3$ | $R_4$ | n | A | m.p. [°C.] |
|---|---|---|---|---|---|---|---|
| 1.010 | F | Cl | $-OC_5H_{11}$ | H | 0 | $-CO-R_3$ | |
| 1.011 | F | Cl | $-O-CH_2-CH_2-O-CH_3$ | H | 0 | $-CO-R_3$ | |
| 1.012 | F | Cl | $-O-CH_2-CH_2-O-C_2H_5$ | H | 0 | $-CO-R_3$ | |
| 1.013 | F | Cl | $-O-CH-(CH_3)-CH_2-O-CH_3$ | H | 0 | $-CO-R_3$ | |
| 1.014 | F | Cl | $-O-CH_2-CH_2-S-CH_3$ | H | 0 | $-CO-R_3$ | |
| 1.015 | F | Cl | $-O-CH(CH_3)-CH_2-S-CH_3$ | H | 0 | $-CO-R_3$ | |
| 1.016 | F | Cl | $-O-CH(CH_3)-CH_2-S-C_2H_5$ | H | 0 | $-CO-R_3$ | |
| 1.017 | F | Cl | $-O-CH(CH_3)-CH_2-S-C_3H_7$ | H | 0 | $-CO-R_3$ | |
| 1.018 | F | Cl | 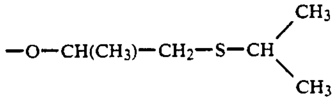 | H | 0 | $-CO-R_3$ | |
| 1.019 | F | Cl | $-O-CH(CH_3)-CH_2-S-C_4H_9$ | H | 0 | $-CO-R_3$ | |
| 1.020 | F | Cl | $-O-CH(CH_3)-CH_2-S-C_5H_{11}$ | H | 0 | $-CO-R_3$ | |
| 1.021 | F | Cl | 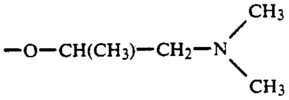 | H | 0 | $-CO-R_3$ | |
| 1.022 | F | Cl | 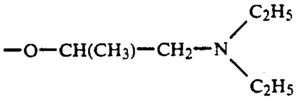 | H | 0 | $-CO-R_3$ | |
| 1.023 | F | Cl | $-NH_2$ | H | 0 | $-CO-R_3$ | |
| 1.024 | F | Cl | 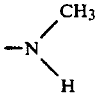 | H | 0 | $-CO-R_3$ | |
| 1.025 | F | Cl | 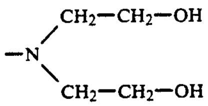 | H | 0 | $-CO-R_3$ | |
| 1.026 | F | Cl | $-NH-CH_2-CH=CH_2$ | H | 0 | $-CO-R_3$ | |
| 1.027 | F | Cl | $-N-(CH_2-CH=CH_2)_2$ | H | 0 | $-CO-R_3$ | |
| 1.028 | F | Cl | 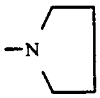 | H | 0 | $-CO-R_3$ | |
| 1.029 | F | Cl | 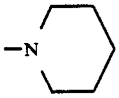 | H | 0 | $-CO-R_3$ | |
| 1.030 | F | Cl | 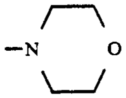 | H | 0 | $-CO-R_3$ | |

TABLE 1-continued
Compounds of formula I wherein W = $W_1$ and $R_{14}$ = H
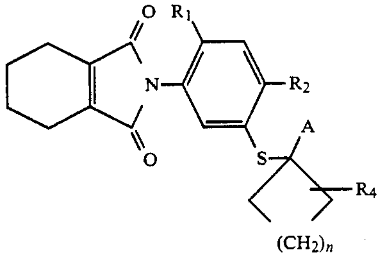
(I)
| Comp. No. | $R_1$ | $R_2$ | $R_3$ | $R_4$ | n | A | m.p. [°C.] |
|---|---|---|---|---|---|---|---|
| 1.031 | F | Cl | 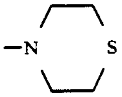 | H | 0 | $-CO-R_3$ | |
| 1.032 | F | Cl | 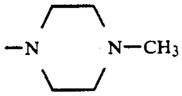 | H | 0 | $-CO-R_3$ | |
| 1.033 | F | Cl | 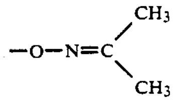 | H | 0 | $-CO-R_3$ | |
| 1.034 | F | Cl | $-O-CH_2-CH_2-Cl$ | H | 0 | $-CO-R_3$ | |
| 1.035 | F | Cl | $-O-CH_2-CN$ | H | 0 | $-CO-R_3$ | |
| 1.036 | F | Cl | 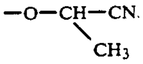 | H | 0 | $-CO-R_3$ | |
| 1.037 | F | Cl | $-O-CH_2-CH{=}CH_2$ | H | 0 | $-CO-R_3$ | |
| 1.038 | F | Cl | $-O-CH_2-CH{=}CHCl$ | H | 0 | $-CO-R_3$ | |
| 1.039 | F | Cl | 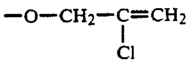 | H | 0 | $-CO-R_3$ | |
| 1.040 | F | Cl | $-O-CH_2{=}C{\equiv}CH$ | H | 0 | $-CO-R_3$ | |
| 1.041 | F | Cl | 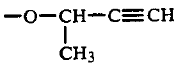 | H | 0 | $-CO-R_3$ | |
| 1.042 | F | Cl | 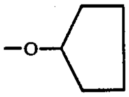 | H | 0 | $-CO-R_3$ | |
| 1.043 | F | Cl | 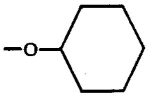 | H | 0 | $-CO-R_3$ | |
| 1.044 | F | Cl | 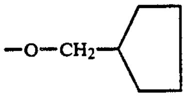 | H | 0 | $-CO-R_3$ | |
| 1.045 | F | Cl | 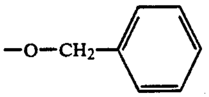 | H | 0 | $-CO-R_3$ | |

TABLE 1-continued

Compounds of formula I wherein W = $W_1$ and $R_{14}$ = H

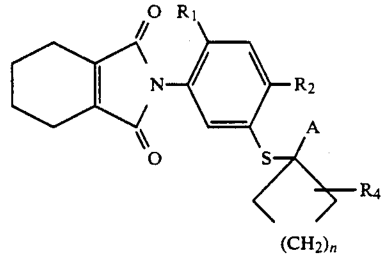

(I)

| Comp. No. | $R_1$ | $R_2$ | $R_3$ | $R_4$ | n | A | m.p. [°C.] |
|---|---|---|---|---|---|---|---|
| 1.046 | F | Cl | 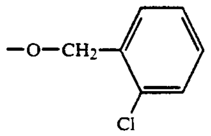 | H | 0 | $-CO-R_3$ | |
| 1.047 | F | Cl | 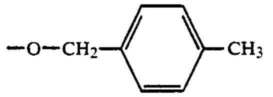 | H | 0 | $-CO-R_3$ | |
| 1.048 | F | Cl | $-S-CH_3$ | H | 0 | $-CO-R_3$ | |
| 1.049 | F | Cl | $-S-C_2H_5$ | H | 0 | $-CO-R_3$ | |
| 1.050 | F | Cl | $-S-C_3H_7$ | H | 0 | $-CO-R_3$ | |
| 1.051 | F | Cl | $-S-CH_2-CH=CH_2$ | H | 0 | $-CO-R_3$ | |
| 1.052 | F | Cl | $-S-CH_2-COOCH_3$ | H | 0 | $-CO-R_3$ | |
| 1.053 | F | Cl | $-S-CH_2-COOC_2H_5$ | H | 0 | $-CO-R_3$ | |
| 1.054 | F | Cl | $-S-CH_2-COOC_5H_{11}$ | H | 0 | $-CO-R_3$ | |
| 1.055 | F | Cl | $-S-CH(CH_3)-COOCH_3$ | H | 0 | $-CO-R_3$ | |
| 1.056 | F | Cl | $-S-(CH_3)-COOC_2H_5$ | H | 0 | $-CO-R_3$ | |
| 1.057 | F | Cl | $-S-CH(CH_3)-COOC_3H_7$ | H | 0 | $-CO-R_3$ | |
| 1.058 | F | Cl | $-S-CH_2-CH_2-COOCH_3$ | H | 0 | $-CO-R_3$ | |
| 1.059 | F | Cl | $-S-CH_2-COOCH_2-CH_2-O-CH_3$ | H | 0 | $-CO-R_3$ | |
| 1.060 | F | Cl | $-O-CH_2-COOCH_3$ | H | 0 | $-CO-R_3$ | |
| 1.061 | F | Cl | $-O-CH(CH_3)-COOCH_3$ | H | 0 | $-CO-R_3$ | |
| 1.062 | F | Cl | $-O-CH_2-COOC_5H_{11}$ | H | 0 | $-CO-R_3$ | |
| 1.063 | F | Cl | $-O-CH_2-CH_3-Si(CH_3)_3$ | H | 0 | $-CO-R_3$ | |
| 1.064 | F | Cl | $-ONa$ | H | 0 | $-CO-R_3$ | |
| 1.065 | F | Br | $-Cl$ | H | 0 | $-CO-R_3$ | |
| 1.066 | F | Br | $-OH$ | H | 0 | $-CO-R_3$ | |
| 1.067 | F | Br | $-OCH_3$ | H | 0 | $-CO-R_3$ | |
| 1.068 | F | Br | $-OC_2H_5$ | H | 0 | $-CO-R_3$ | |
| 1.069 | F | Br | $-OC_3H_7$ | H | 0 | $-CO-R_3$ | |
| 1.070 | F | Br | 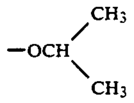 | H | 0 | $-CO-R_3$ | |
| 1.071 | F | Br | $-OC_4H_9$ | H | 0 | $-CO-R_3$ | |
| 1.072 | F | Br | $-OCH(CH_3)-CH_2-CH_3$ | H | 0 | $-CO-R_3$ | |
| 1.073 | F | Br | 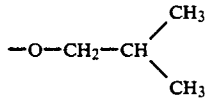 | H | 0 | $-CO-R_3$ | |
| 1.074 | F | Br | $-O-C_5H_{11}$ | H | 0 | $-CO-R_3$ | |
| 1.075 | F | Br | $-O-CH_2-CH_2-O-CH_3$ | H | 0 | $-CO-R_3$ | |
| 1.076 | F | Br | $-O-CH_2-CH_2-O-C_2H_5$ | H | 0 | $-CO-R_3$ | |
| 1.077 | F | Br | $-O-CH(CH_3)-CH_2-O-CH_3$ | H | 0 | $-CO-R_3$ | |
| 1.078 | F | Br | $-O-CH_2-CH_2-S-CH_3$ | H | 0 | $-CO-R_3$ | |
| 1.079 | F | Br | $-O-CH_2(CH_3)-S-CH_3$ | H | 0 | $-CO-R_3$ | |
| 1.080 | F | Br | $-O-CH-(CH_3)-S-C_2H_5$ | H | 0 | $-CO-R_3$ | |
| 1.081 | F | Br | $-O-CH(CH_3)-S-C_3H_7$ | H | 0 | $-CO-R_3$ | |
| 1.082 | F | Br | 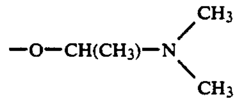 | H | 0 | $-CO-R_3$ | |

TABLE 1-continued

Compounds of formula I wherein W = $W_1$ and $R_{14}$ = H

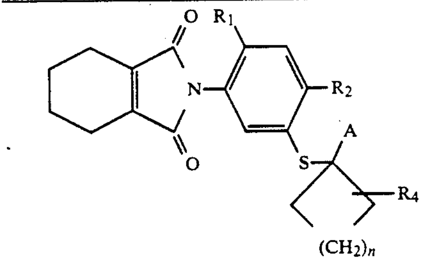

(I)

| Comp. No. | $R_1$ | $R_2$ | $R_3$ | $R_4$ | n | A | m.p. [°C.] |
|---|---|---|---|---|---|---|---|
| 1.083 | F | Br | $-NH_2$ | H | 0 | $-CO-R_3$ | |
| 1.084 | F | Br | 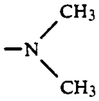 | H | 0 | $-CO-R_3$ | |
| 1.085 | F | Br | 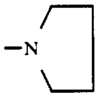 | H | 0 | $-CO-R_3$ | |
| 1.086 | F | Br | 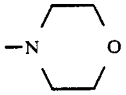 | H | 0 | $-CO-R_3$ | |
| 1.087 | F | Br | 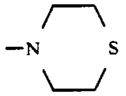 | H | 0 | $-CO-R_3$ | |
| 1.088 | F | Br | 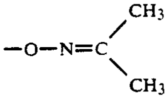 | H | 0 | $-CO-R_3$ | |
| 1.089 | F | Br | $-O-CH_2-CH_2-Cl$ | H | 0 | $-CO-R_3$ | |
| 1.090 | F | Br | $-O-CH_2-CN$ | H | 0 | $-CO-R_3$ | |
| 1.091 | F | Br | $-O-CH_2-CH=CH_2$ | H | 0 | $-CO-R_3$ | |
| 1.092 | F | Br | $-O-CH_2-C\equiv CH$ | H | 0 | $-CO-R_3$ | |
| 1.093 | F | Br | 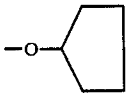 | H | 0 | $-CO-R_3$ | |
| 1.094 | F | Br | 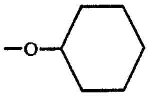 | H | 0 | $-CO-R_3$ | |
| 1.095 | F | Br | 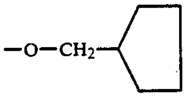 | H | 0 | $-CO-R_3$ | |
| 1.096 | F | Br | 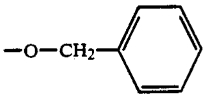 | H | 0 | $-CO-R_3$ | |
| 1.097 | F | Br | $-SCH_3$ | H | 0 | $-CO-R_3$ | |
| 1.098 | F | Br | $-S-CH_2-COOCH_3$ | H | 0 | $-CO-R_3$ | |
| 1.099 | F | Br | $-S-CH(CH_3)-COOCH_3$ | H | 0 | $-CO-R_3$ | |
| 1.100 | F | Br | $-O-CH_2-COOCH_3$ | H | 0 | $-CO-R_3$ | |
| 1.101 | F | Br | $-O-CH(CH_3)COOCH_3$ | H | 0 | $-CO-R_3$ | |

TABLE 1-continued

Compounds of formula I wherein W = $W_1$ and $R_{14}$ = H

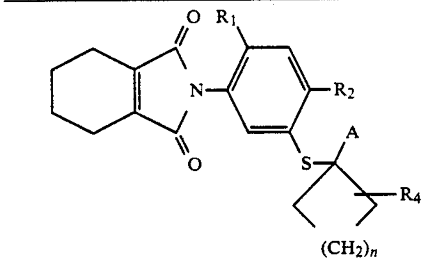

(I)

| Comp. No. | $R_1$ | $R_2$ | $R_3$ | $R_4$ | n | A | m.p. [°C.] |
|---|---|---|---|---|---|---|---|
| 1.102 | F | CN | —Cl | H | 0 | —CO—$R_3$ | |
| 1.103 | F | CN | —OH | H | 0 | —CO—$R_3$ | |
| 1.104 | F | CN | —$OCH_3$ | H | 0 | —CO—$R_3$ | |
| 1.105 | H | Cl | —Cl | H | 0 | —CO—$R_3$ | |
| 1.106 | H | Cl | —OH | H | 0 | —CO—$R_3$ | |
| 1.107 | H | Cl | —$OCH_3$ | H | 0 | —CO—$R_3$ | |
| 1.108 | H | Cl | —$OC_2H_5$ | H | 0 | —CO—$R_3$ | |
| 1.109 | H | Cl | 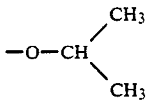 | H | 0 | —CO—$R_3$ | |
| 1.110 | H | Cl | —O—$CH_2$—$COOCH_3$ | H | 0 | —CO—$R_3$ | |
| 1.111 | H | Cl | —O—$CH(CH_3)COOCH_3$ | H | 0 | —CO—$R_3$ | |
| 1.112 | H | Cl | —S—$CH_2$—$COOCH_3$ | H | 0 | —CO—$R_3$ | |
| 1.113 | H | Cl | —S—$CH(CH_3)COOCH_3$ | H | 0 | —CO—$R_3$ | |
| 1.114 | H | Cl | 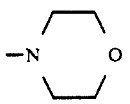 | H | 0 | —CO—$R_3$ | |
| 1.115 | F | Cl | —Cl | H | 1 | —CO—$R_3$ | |
| 1.116 | F | Cl | —OH | H | 1 | —CO—$R_3$ | |
| 1.117 | F | Cl | —$OCH_3$ | H | 1 | —CO—$R_3$ | 98 |
| 1.118 | F | Cl | —$OC_2H_5$ | H | 1 | —CO—$R_3$ | 122-123 |
| 1.119 | F | Cl | —$OC_3H_7$ | H | 1 | —CO—$R_3$ | |
| 1.120 | F | Cl | 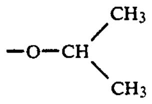 | H | 1 | —CO—$R_3$ | |
| 1.121 | F | Cl | —$OC_4H_9$ | H | 1 | —CO—$R_3$ | |
| 1.122 | F | Cl | —O—$CH(CH_3)$—$C_2H_5$ | H | 1 | —CO—$R_3$ | |
| 1.123 | F | Cl | 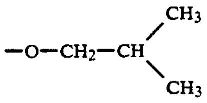 | H | 1 | —CO—$R_3$ | |
| 1.124 | F | Cl | —$OC_5H_{11}$ | H | 1 | —CO—$R_3$ | |
| 1.125 | F | Cl | —O—$CH_2$—$CH_2$—O—$CH_3$ | H | 1 | —CO—$R_3$ | |
| 1.126 | F | Cl | —O—$CH_2$—$CH_2$—O—$C_2H_5$ | H | 1 | —CO—$R_3$ | |
| 1.127 | F | Cl | —O—CH—$(CH_3)$—$CH_2$—O—$CH_3$ | H | 1 | —CO—$R_3$ | |
| 1.128 | F | Cl | —O—$CH_2$—$CH_2$—S—$CH_3$ | H | 1 | —CO—$R_3$ | |
| 1.129 | F | Cl | —O—$CH(CH_3)$—$CH_2$—S—$CH_3$ | H | 1 | —CO—$R_3$ | |
| 1.130 | F | Cl | —O—$CH(CH_3)$—$CH_2$—S—$C_2H_5$ | H | 1 | —CO—$R_3$ | |
| 1.131 | F | Cl | —O—$CH(CH_3)$—$CH_2$—S—$C_3H_7$ | H | 1 | —CO—$R_3$ | |
| 1.132 | F | Cl | 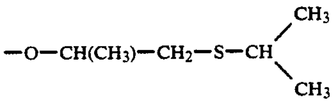 | H | 1 | —CO—$R_3$ | |
| 1.133 | F | Cl | —O—$CH(CH_3)$—$CH_2$—S—$C_4H_9$ | H | 1 | —CO—$R_3$ | |
| 1.134 | F | Cl | —O—$CH(CH_3)$—$CH_2$—S—$C_5H_{11}$ | H | 1 | —CO—$R_3$ | |

TABLE 1-continued
Compounds of formula I wherein W = $W_1$ and $R_{14}$ = H
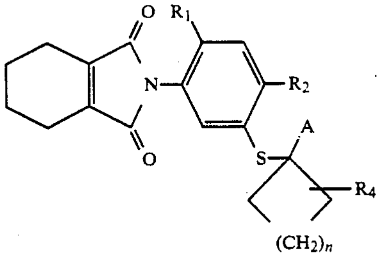
(I)
| Comp. No. | $R_1$ | $R_2$ | $R_3$ | $R_4$ | n | A | m.p. [°C.] |
|---|---|---|---|---|---|---|---|
| 1.135 | F | Cl | 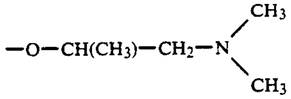 | H | 1 | $-CO-R_3$ | |
| 1.136 | F | Cl | 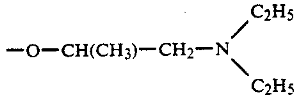 | H | 1 | $-CO-R_3$ | |
| 1.137 | F | Cl | $-NH_2$ | H | 1 | $-CO-R_3$ | |
| 1.138 | F | Cl | 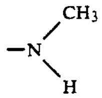 | H | 1 | $-CO-R_3$ | |
| 1.139 | F | Cl | 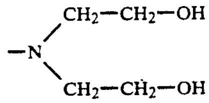 | H | 1 | $-CO-R_3$ | |
| 1.140 | F | Cl | $-NH-CH_2-CH=CH_2$ | H | 1 | $-CO-R_3$ | |
| 1.141 | F | Cl | $-N-(CH_2-CH=CH_2)_2$ | H | 1 | $-CO-R_3$ | |
| 1.142 | F | Cl | 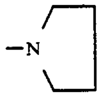 | H | 1 | $-CO-R_3$ | |
| 1.143 | F | Cl | 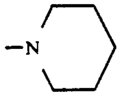 | H | 1 | $-CO-R_3$ | |
| 1.144 | F | Cl | 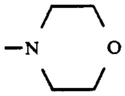 | H | 1 | $-CO-R_3$ | |
| 1.145 | F | Cl | 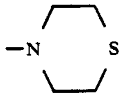 | H | 1 | $-CO-R_3$ | |
| 1.146 | F | Cl | 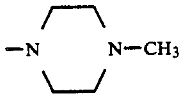 | H | 1 | $-CO-R_3$ | |
| 1.147 | F | Cl | 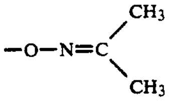 | H | 1 | $-CO-R_3$ | |
| 1.148 | F | Cl | $-O-CH_2-CH_2-Cl$ | H | 1 | $-CO-R_3$ | |
| 1.149 | F | Cl | $-O-CH_2-CN$ | H | 1 | $-CO-R_3$ | |

TABLE 1-continued

Compounds of formula I wherein W = $W_1$ and $R_{14}$ = H

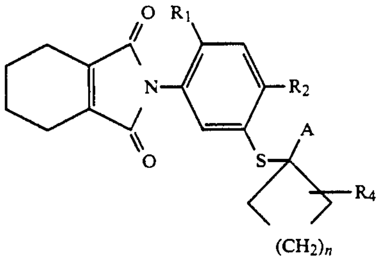

(I)

| Comp. No. | $R_1$ | $R_2$ | $R_3$ | $R_4$ | n | A | m.p. [°C.] |
|---|---|---|---|---|---|---|---|
| 1.150 | F | Cl | $-O-CH-CN$<br>$CH_3$ | H | 1 | $-CO-R_3$ | |
| 1.151 | F | Cl | $-O-CH_2-CH=CH_2$ | H | 1 | $-CO-R_3$ | |
| 1.152 | F | Cl | $-O-CH_2-CH=CHCl$ | H | 1 | $-CO-R_3$ | |
| 1.153 | F | Cl | $-O-CH_2-C=CH_2$<br>Cl | H | 1 | $-CO-R_3$ | |
| 1.154 | F | Cl | $-O-CH_2=C\equiv CH$ | H | 1 | $-CO-R_3$ | |
| 1.155 | F | Cl | $-O-CH-C\equiv CH$<br>$CH_3$ | H | 1 | $-CO-R_3$ | |
| 1.156 | F | Cl | 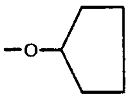 | H | 1 | $-CO-R_3$ | |
| 1.157 | F | Cl | 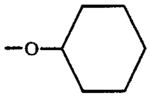 | H | 1 | $-CO-R_3$ | |
| 1.158 | F | Cl | 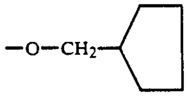 | H | 1 | $-CO-R_3$ | |
| 1.159 | F | Cl | 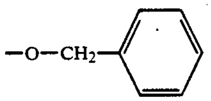 | H | 1 | $-CO-R_3$ | |
| 1.160 | F | Cl | 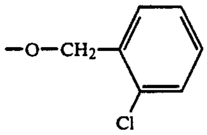 | H | 1 | $-CO-R_3$ | |
| 1.161 | F | Cl | 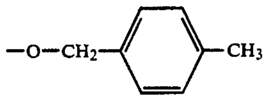 | H | 1 | $-CO-R_3$ | |
| 1.162 | F | Cl | $-S-CH_3$ | H | 1 | $-CO-R_3$ | |
| 1.163 | F | Cl | $-S-C_2H_5$ | H | 1 | $-CO-R_3$ | |
| 1.164 | F | Cl | $-S-C_3H_7$ | H | 1 | $-CO-R_3$ | |
| 1.165 | F | Cl | $-S-CH_2-CH=CH_2$ | H | 1 | $-CO-R_3$ | |
| 1.166 | F | Cl | $-S-CH_2-COOCH_3$ | H | 1 | $-CO-R_3$ | |
| 1.167 | F | Cl | $-S-CH_2-COOC_2H_5$ | H | 1 | $-CO-R_3$ | |
| 1.168 | F | Cl | $-S-CH_2-COOC_5H_{11}$ | H | 1 | $-CO-R_3$ | |
| 1.169 | F | Cl | $-S-CH(CH_3)-COOCH_3$ | H | 1 | $-CO-R_3$ | |
| 1.170 | F | Cl | $-S-(CH_3)-COOC_2H_5$ | H | 1 | $-CO-R_3$ | |
| 1.171 | F | Cl | $-S-CH(CH_3)-COOC_3H_7$ | H | 1 | $-CO-R_3$ | |

TABLE 1-continued

Compounds of formula I wherein W = $W_1$ and $R_{14}$ = H

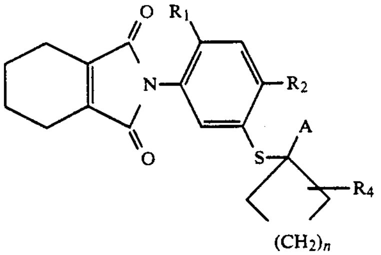

(I)

| Comp. No. | $R_1$ | $R_2$ | $R_3$ | $R_4$ | n | A | m.p. [°C.] |
|---|---|---|---|---|---|---|---|
| 1.172 | F | Cl | $-S-CH_2-CH_2-COOCH_3$ | H | 1 | $-CO-R_3$ | |
| 1.173 | F | Cl | $-S-CH_2-COOCH_2-CH_2-O-CH_3$ | H | 1 | $-CO-R_3$ | |
| 1.174 | F | Cl | $-O-CH_2-COOCH_3$ | H | 1 | $-CO-R_3$ | |
| 1.175 | F | Cl | $-O-CH(CH_3)-COOCH_3$ | H | 1 | $-CO-R_3$ | |
| 1.176 | F | Cl | $-O-CH_2-COOC_5H_{11}$ | H | 1 | $-CO-R_3$ | |
| 1.177 | F | Cl | $-O-CH_2-CH_3-Si(CH_3)_3$ | H | 1 | $-CO-R_3$ | |
| 1.178 | F | Cl | $-ONa$ | H | 1 | $-CO-R_3$ | |
| 1.179 | F | Br | $-Cl$ | H | 1 | $-CO-R_3$ | |
| 1.180 | F | Br | $-OH$ | H | 1 | $-CO-R_3$ | |
| 1.181 | F | Br | $-OCH_3$ | H | 1 | $-CO-R_3$ | |
| 1.182 | F | Br | $-OC_2H_5$ | H | 1 | $-CO-R_3$ | |
| 1.183 | F | Br | $-OC_3H_7$ | H | 1 | $-CO-R_3$ | |
| 1.184 | F | Br | 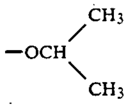 | H | 1 | $-CO-R_3$ | |
| 1.185 | F | Br | $-OC_4H_9$ | H | 1 | $-CO-R_3$ | |
| 1.186 | F | Br | $-OCH(CH_3)-CH_2-CH_3$ | H | 1 | $-CO-R_3$ | |
| 1.187 | F | Br | 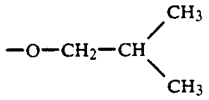 | H | 1 | $-CO-R_3$ | |
| 1.188 | F | Br | $-O-C_5H_{11}$ | H | 1 | $-CO-R_3$ | |
| 1.189 | F | Br | $-O-CH_2-CH_2-O-CH_3$ | H | 1 | $-CO-R_3$ | |
| 1.190 | F | Br | $-O-CH_2-CH_2-O-C_2H_5$ | H | 1 | $-CO-R_3$ | |
| 1.191 | F | Br | $-O-CH(CH_3)-CH_2-O-CH_3$ | H | 1 | $-CO-R_3$ | |
| 1.192 | F | Br | $-O-CH_2-CH_2-S-CH_3$ | H | 1 | $-OC-R_3$ | |
| 1.193 | F | Br | $-O-CH_2(CH_3)-S-CH_3$ | H | 1 | $-CO-R_3$ | |
| 1.194 | F | Br | $-O-CH-(CH_3)-S-C_2H_5$ | H | 1 | $-CO-R_3$ | |
| 1.195 | F | Br | $-O-CH(CH_3)-S-C_3H_7$ | H | 1 | $-CO-R_3$ | |
| 1.196 | F | Br | 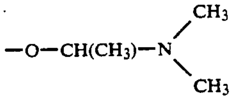 | H | 1 | $-CO-R_3$ | |
| 1.197 | F | Br | $-NH_2$ | H | 1 | $-CO-R_3$ | |
| 1.198 | F | Br | 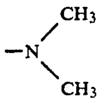 | H | 1 | $-CO-R_3$ | |
| 1.199 | F | Br | 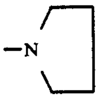 | H | 1 | $-CO-R_3$ | |
| 1.200 | F | Br | 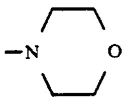 | H | 1 | $-CO-R_3$ | |

TABLE 1-continued

Compounds of formula I wherein W = $W_1$ and $R_{14}$ = H

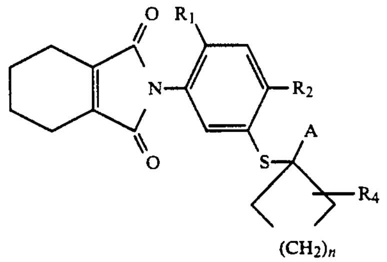

(I)

| Comp. No. | $R_1$ | $R_2$ | $R_3$ | $R_4$ | n | A | m.p. [°C.] |
|---|---|---|---|---|---|---|---|
| 1.201 | F | Br | 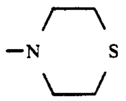 | H | 1 | $-CO-R_3$ | |
| 1.202 | F | Br | 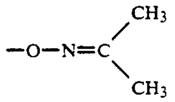 | H | 1 | $-CO-R_3$ | |
| 1.203 | F | Br | $-O-CH_2-CH_2-Cl$ | H | 1 | $-CO-R_3$ | |
| 1.204 | F | Br | $-O-CH_2-CN$ | H | 1 | $-CO-R_3$ | |
| 1.205 | F | Br | $-O-CH_2-CH=CH_2$ | H | 1 | $-CO-R_3$ | |
| 1.206 | F | Br | $-O-CH_2-C\equiv CH$ | H | 1 | $-CO-R_3$ | |
| 1.207 | F | Br | 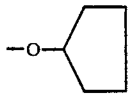 | H | 1 | $-CO-R_3$ | |
| 1.208 | F | Br | 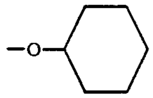 | H | 1 | $-CO-R_3$ | |
| 1.209 | F | Br | 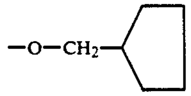 | H | 1 | $-CO-R_3$ | |
| 1.210 | F | Br | 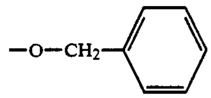 | H | 1 | $-CO-R_3$ | |
| 1.211 | F | Br | $-SCH_3$ | H | 1 | $-CO-R_3$ | |
| 1.212 | F | Br | $-S-CH_2-COOCH_3$ | H | 1 | $-CO-R_3$ | |
| 1.213 | F | Br | $-S-CH(CH_3)-COOCH_3$ | H | 1 | $-CO-R_3$ | |
| 1.214 | F | Br | $-O-CH_2-COOCH_3$ | H | 1 | $-CO-R_3$ | |
| 1.215 | F | Br | $-O-CH(CH_3)COOCH_3$ | H | 1 | $-CO-R_3$ | |
| 1.216 | F | CN | $-Cl$ | H | 1 | $-CO-R_3$ | |
| 1.217 | F | CN | $-OH$ | H | 1 | $-CO-R_3$ | |
| 1.218 | F | CN | $-OCH_3$ | H | 1 | $-CO-R_3$ | |
| 1.219 | H | Cl | $-Cl$ | H | 1 | $-CO-R_3$ | |
| 1.220 | H | Cl | $-OH$ | H | 1 | $-CO-R_3$ | |
| 1.221 | H | Cl | $-OCH_3$ | H | 1 | $-CO-R_3$ | |
| 1.222 | H | Cl | $-OC_2H_5$ | H | 1 | $-CO-R_3$ | |
| 1.223 | H | Cl | 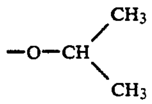 | H | 1 | $-CO-R_3$ | |
| 1.224 | H | Cl | $-O-CH_2-COOCH_3$ | H | 1 | $-CO-R_3$ | |
| 1.225 | H | Cl | $-O-CH(CH_3)COOCH_3$ | H | 1 | $-CO-R_3$ | |
| 1.226 | H | Cl | $-S-CH_2-COOCH_3$ | H | 1 | $-CO-R_3$ | |
| 1.227 | H | Cl | $-S-CH(CH_3)COOCH_3$ | H | 1 | $-CO-R_3$ | |

TABLE 1-continued

Compounds of formula I wherein W = $W_1$ and $R_{14}$ = H

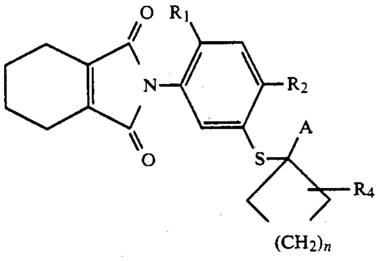

(I)

| Comp. No. | $R_1$ | $R_2$ | $R_3$ | $R_4$ | n | A | m.p. [°C.] |
|---|---|---|---|---|---|---|---|
| 1.228 | H | Cl | 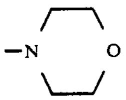 | H | 1 | $-CO-R_3$ | |
| 1.229 | F | Cl | Cl | H | 2 | $-CO-R_3$ | |
| 1.230 | F | Cl | OH | H | 2 | $-CO-R_3$ | |
| 1.231 | F | Cl | $OCH_3$ | H | 2 | $-CO-R_3$ | |
| 1.232 | F | Cl | $-OC_2H_5$ | H | 2 | $-CO-R_3$ | |
| 1.233 | F | Cl | 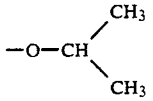 | H | 2 | $-CO-R_3$ | |
| 1.234 | F | Cl | $-O-CH_2-CH_2-O-CH_3$ | H | 2 | $-CO-R_3$ | |
| 1.235 | F | Cl | $-O-CH(CH_3)-CH_2-S-CH_3$ | H | 2 | $-CO-R_3$ | |
| 1.236 | F | Cl | $-O-CH_2-COOCH_3$ | H | 2 | $-CO-R_3$ | |
| 1.237 | F | Cl | $-S-CH_2-COOCH_3$ | H | 2 | $-CO-R_3$ | |
| 1.238 | F | Cl | $-CH_2-CH=CH_2$ | H | 2 | $-CO-R_3$ | |
| 1.239 | F | Cl | $-CH_2-C\equiv CH$ | H | 2 | $-CO-R_3$ | |
| 1.240 | F | Cl | Cl | H | 3 | $-CO-R_3$ | |
| 1.241 | F | Cl | OH | H | 3 | $-CO-R_3$ | |
| 1.242 | F | Cl | $OCH_3$ | H | 3 | $-CO-R_3$ | 102-103 |
| 1.243 | F | Cl | $OC_2H_5$ | H | 3 | $-CO-R_3$ | |
| 1.244 | F | Cl | 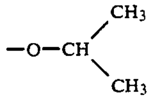 | H | 3 | $-CO-R_3$ | |
| 1.245 | F | Cl | $-O-CH_2-CH_2-O-CH$ | H | 3 | $-CO-R_3$ | |
| 1.246 | F | Cl | $-O-CH(CH_3)-CH_2-S-CH_3$ | H | 3 | $-CO-R_3$ | |
| 1.247 | F | Cl | $-O-CH_2-COOCH_3$ | H | 3 | $-CO-R_3$ | |
| 1.248 | F | Cl | $-S-CH_2-COOCH_3$ | H | 3 | $-CO-R_3$ | |
| 1.249 | F | Cl | $-O-CH_2-C\equiv CH$ | H | 3 | $-CO-R_3$ | |
| 1.250 | F | Cl | $-Cl$ | Cl | 0 | $-CO-R_3$ | |
| 1.251 | F | Cl | $-OH$ | Cl | 0 | $-CO-R_3$ | |
| 1.252 | F | Cl | $-OCH_3$ | Cl | 0 | $-CO-R_3$ | |
| 1.253 | F | Cl | $-OC_2H_5$ | Cl | 0 | $-CO-R_3$ | |
| 1.254 | F | Cl | 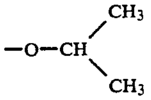 | Cl | 0 | $-CO-R_3$ | |
| 1.255 | F | Cl | $-O-CH_2-COOCH_3$ | Cl | 0 | $-CO-R_3$ | |
| 1.256 | F | Cl | $-S-CH_2-COOCH_3$ | Cl | 0 | $-CO-R_3$ | |
| 1.257 | F | Cl | $-OCH_3$ | Br | 0 | $-CO-R_3$ | |
| 1.258 | F | Cl | 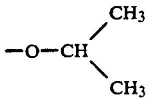 | Br | 0 | $-CO-R_3$ | |
| 1.259 | F | Cl | $-OCH_3$ | F | 0 | $-CO-R_3$ | |
| 1.260 | F | Cl | $-OCH_3$ | $CH_3$ | 0 | $-CO-R_3$ | |
| 1.261 | F | Cl | $-OC_2H_5$ | $CH_3$ | 0 | $-CO-R_3$ | |

TABLE 1-continued

Compounds of formula I wherein W = $W_1$ and $R_{14}$ = H (I)

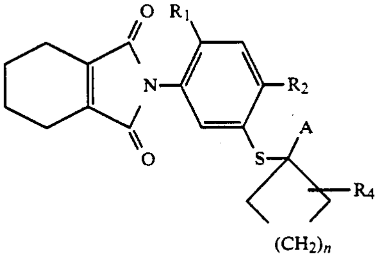

| Comp. No. | $R_1$ | $R_2$ | $R_3$ | $R_4$ | n | A | m.p. [°C.] |
|---|---|---|---|---|---|---|---|
| 1.262 | F | Cl | 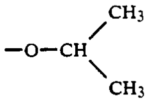 | $CH_3$ | 0 | $-CO-R_3$ | |
| 1.263 | F | Cl | $-O-CH_2-CH_2-O-CH_3$ | $CH_3$ | 0 | $-CO-R_3$ | |
| 1.264 | F | Cl | $-O-CH_2-COOCH_3$ | $CH_3$ | 0 | $-CO-R_3$ | |
| 1.265 | F | Cl | $-O-CH(CH_3)COOCH_3$ | $CH_3$ | 0 | $-CO-R_3$ | |
| 1.266 | F | Cl | $-S-CH_2-COOCH_3$ | $CH_3$ | 0 | $-CO-R_3$ | |
| 1.267 | F | Cl | $-OCH_3$ | $CF_3$ | 0 | $-CO-R_3$ | |
| 1.268 | F | Cl | $-OC_2H_5$ | $CF_3$ | 0 | $-CO-R_3$ | |
| 1.269 | F | Cl | 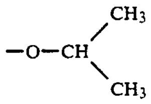 | $CF_3$ | 0 | $-CO-R_3$ | |
| 1.270 | F | Cl | $-O-CH_2-COOCH_3$ | $CF_3$ | 0 | $-CO-R_3$ | |
| 1.271 | F | Cl | $-S-CH_2-COOCH_3$ | $CF_3$ | 0 | $-CO-R_3$ | |
| 1.272 | F | Cl | — | H | 0 | $-CN$ | |
| 1.273 | F | Cl | — | H | 1 | $-CN$ | |
| 1.274 | F | Cl | — | H | 2 | $-CN$ | |
| 1.275 | F | Cl | — | H | 3 | $-CN$ | |
| 1.276 | F | Cl | — | H | 4 | $-CN$ | |

TABLE 2

Compounds of formula I wherein W is $W_2$, $Y_3$ is oxygen and $R_{14}$ is hydrogen:

(I)

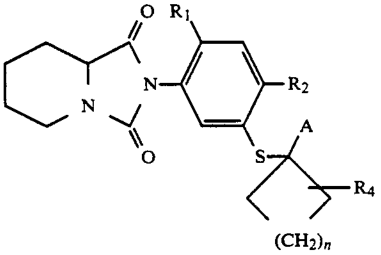

| Comp. No. | $R_1$ | $R_2$ | $R_3$ | $R_4$ | n | A | m.p. [°C.] |
|---|---|---|---|---|---|---|---|
| 2.001 | F | Cl | $-Cl$ | H | 0 | $-CO-R_3$ | |
| 2.002 | F | Cl | $-OH$ | H | 0 | $-CO-R_3$ | |
| 2.003 | F | Cl | $-OCH_3$ | H | 0 | $-CO-R_3$ | |
| 2.004 | F | Cl | $-OC_2H_5$ | H | 0 | $-CO-R_3$ | |
| 2.005 | F | Cl | $-OC_3H_7$ | H | 0 | $-CO-R_3$ | |
| 2.006 | F | Cl | 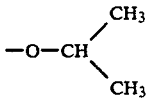 | H | 0 | $-CO-R_3$ | |
| 2.007 | F | Cl | $-OC_4H_9$ | H | 0 | $-CO-R_3$ | |
| 2.008 | F | Cl | $-O-CH(CH_3)-C_2H_5$ | H | 0 | $-CO-R_3$ | |
| 2.009 | F | Cl | 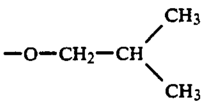 | H | 0 | $-CO-R_3$ | |

TABLE 2-continued

Compounds of formula I wherein W is $W_2$, $Y_3$ is oxygen and $R_{14}$ is hydrogen:

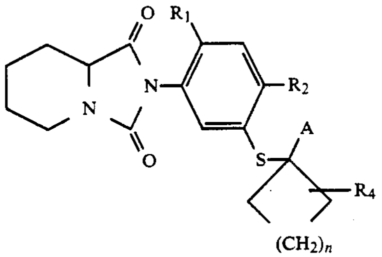

(I)

| Comp. No. | $R_1$ | $R_2$ | $R_3$ | $R_4$ | n | A | m.p. [°C.] |
|---|---|---|---|---|---|---|---|
| 2.010 | F | Cl | $-OC_5H_{11}$ | H | 0 | $-CO-R_3$ | |
| 2.011 | F | Cl | $-O-CH_2-CH_2-O-CH_3$ | H | 0 | $-CO-R_3$ | |
| 2.012 | F | Cl | $-O-CH_2-CH_2-O-C_2H_5$ | H | 0 | $-CO-R_3$ | |
| 2.013 | F | Cl | $-O-CH-(CH_3)-CH_2-O-CH_3$ | H | 0 | $-CO-R_3$ | |
| 2.014 | F | Cl | $-O-CH_2-CH_2-S-CH_3$ | H | 0 | $-CO-R_3$ | |
| 2.015 | F | Cl | $-O-CH(CH_3)-CH_2-S-CH_3$ | H | 0 | $-CO-R_3$ | |
| 2.016 | F | Cl | $-O-CH(CH_3)-CH_2-S-C_2H_5$ | H | 0 | $-CO-R_3$ | |
| 2.017 | F | Cl | $-O-CH(CH_3)-CH_2-S-C_3H_7$ | H | 0 | $-CO-R_3$ | |
| 2.018 | F | Cl | 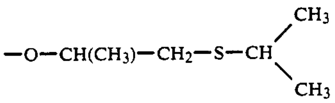 | H | 0 | $-CO-R_3$ | |
| 2.019 | F | Cl | $-O-CH(CH_3)-CH_2-S-C_4H_9$ | H | 0 | $-CO-R_3$ | |
| 2.020 | F | Cl | $-O-CH(CH_3)-CH_2-S-C_5H_{11}$ | H | 0 | $-CO-R_3$ | |
| 2.021 | F | Cl | 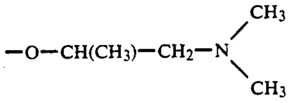 | H | 0 | $-CO-R_3$ | |
| 2.022 | F | Cl | 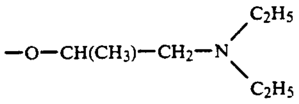 | H | 0 | $-CO-R_3$ | |
| 2.023 | F | Cl | $-NH_2$ | H | 0 | $-CO-R_3$ | |
| 2.024 | F | Cl | 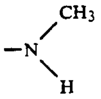 | H | 0 | $-CO-R_3$ | |
| 2.025 | F | Cl | 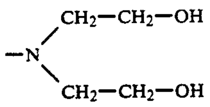 | H | 0 | $-CO-R_3$ | |
| 2.026 | F | Cl | $-NH-CH_2-CH=CH_2$ | H | 0 | $-CO-R_3$ | |
| 2.027 | F | Cl | $-N-(CH_2-CH=CH_2)_2$ | H | 0 | $-CO-R_3$ | |
| 2.028 | F | Cl | 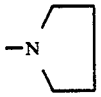 | H | 0 | $-CO-R_3$ | |
| 2.029 | F | Cl | 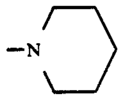 | H | 0 | $-CO-R_3$ | |
| 2.030 | F | Cl | 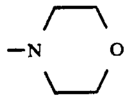 | H | 0 | $-CO-R_3$ | |

TABLE 2-continued
Compounds of formula I wherein W is $W_2$, $Y_3$ is oxygen and $R_{14}$ is hydrogen:
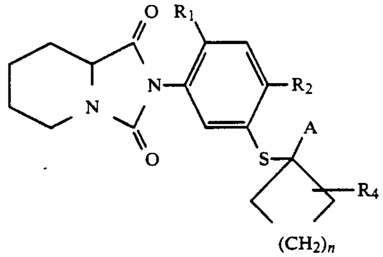
(I)
| Comp. No. | $R_1$ | $R_2$ | $R_3$ | $R_4$ | n | A | m.p. [°C.] |
|---|---|---|---|---|---|---|---|
| 2.031 | F | Cl | 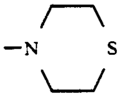 | H | 0 | $-CO-R_3$ | |
| 2.032 | F | Cl | 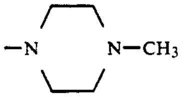 | H | 0 | $-CO-R_3$ | |
| 2.033 | F | Cl | 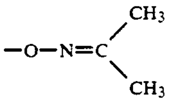 | H | 0 | $-CO-R_3$ | |
| 2.034 | F | Cl | $-O-CH_2-CH_2-Cl$ | H | 0 | $-CO-R_3$ | |
| 2.035 | F | Cl | $-O-CH_2-CN$ | H | 0 | $-CO-R_3$ | |
| 2.036 | F | Cl | 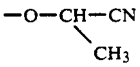 | H | 0 | $-CO-R_3$ | |
| 2.037 | F | Cl | $-O-CH_2-CH=CH_2$ | H | 0 | $-CO-R_3$ | |
| 2.038 | F | Cl | $-O-CH_2-CH=CHCl$ | H | 0 | $-CO-R_3$ | |
| 2.039 | F | Cl | 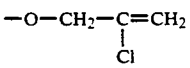 | H | 0 | $-CO-R_3$ | |
| 2.040 | F | Cl | $-O-CH_2=C\equiv CH$ | H | 0 | $-CO-R_3$ | |
| 2.041 | F | Cl | 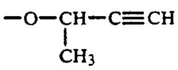 | H | 0 | $-CO-R_3$ | |
| 2.042 | F | Cl | 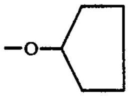 | H | 0 | $-CO-R_3$ | |
| 2.043 | F | Cl | 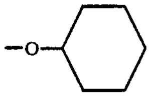 | H | 0 | $-CO-R_3$ | |
| 2.044 | F | Cl | 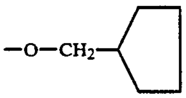 | H | 0 | $-CO-R_3$ | |
| 2.045 | F | Cl | 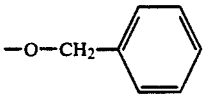 | H | 0 | $-CO-R_3$ | |

TABLE 2-continued

Compounds of formula I wherein W is $W_2$, $Y_3$ is oxygen and $R_{14}$ is hydrogen:

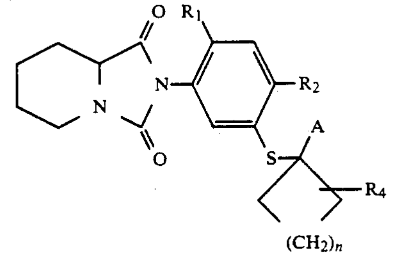

(I)

| Comp. No. | $R_1$ | $R_2$ | $R_3$ | $R_4$ | n | A | m.p. [°C.] |
|---|---|---|---|---|---|---|---|
| 2.046 | F | Cl | 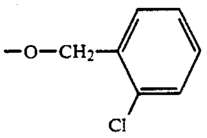 | H | 0 | $-CO-R_3$ | |
| 2.047 | F | Cl | 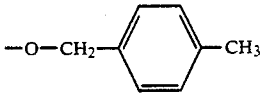 | H | 0 | $-CO-R_3$ | |
| 2.048 | F | Cl | $-S-CH_3$ | H | 0 | $-CO-R_3$ | |
| 2.049 | F | Cl | $-S-C_2H_5$ | H | 0 | $-CO-R_3$ | |
| 2.050 | F | Cl | $-S-C_3H_7$ | H | 0 | $-CO-R_3$ | |
| 2.051 | F | Cl | $-S-CH_2-CH=CH_2$ | H | 0 | $-CO-R_3$ | |
| 2.052 | F | Cl | $-S-CH_2-COOCH_3$ | H | 0 | $-CO-R_3$ | |
| 2.053 | F | Cl | $-S-CH_2-COOC_2H_5$ | H | 0 | $-CO-R_3$ | |
| 2.054 | F | Cl | $-S-CH_2-COOC_5H_{11}$ | H | 0 | $-CO-R_3$ | |
| 2.055 | F | Cl | $-S-CH(CH_3)-COOCH_3$ | H | 0 | $-CO-R_3$ | |
| 2.056 | F | Cl | $-S-(CH_3)-COOC_2H_5$ | H | 0 | $-CO-R_3$ | |
| 2.057 | F | Cl | $-S-CH(CH_3)-COOC_3H_7$ | H | 0 | $-CO-R_3$ | |
| 2.058 | F | Cl | $-S-CH_2-CH_2-COOCH_3$ | H | 0 | $-CO-R_3$ | |
| 2.059 | F | Cl | $-S-CH_2-COOCH_2-CH_2-O-CH_3$ | H | 0 | $-CO-R_3$ | |
| 2.060 | F | Cl | $-O-CH_2-COOCH_3$ | H | 0 | $-CO-R_3$ | |
| 2.061 | F | Cl | $-O-CH(CH_3)-COOCH_3$ | H | 0 | $-CO-R_3$ | |
| 2.062 | F | Cl | $-O-CH_2-COOC_5H_{11}$ | H | 0 | $-CO-R_3$ | |
| 2.063 | F | Cl | $-O-CH_2-CH_3-Si(CH_3)_3$ | H | 0 | $-CO-R_3$ | |
| 2.064 | F | Cl | $-ONa$ | H | 0 | $-CO-R_3$ | |
| 2.065 | F | Br | $-Cl$ | H | 0 | $-CO-R_3$ | |
| 2.066 | F | Br | $-OH$ | H | 0 | $-CO-R_3$ | |
| 2.067 | F | Br | $-OCH_3$ | H | 0 | $-CO-R_3$ | |
| 2.068 | F | Br | $-OC_2H_5$ | H | 0 | $-CO-R_3$ | |
| 2.069 | F | Br | $-OC_3H_7$ | H | 0 | $-CO-R_3$ | |
| 2.070 | F | Br | 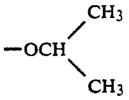 | H | 0 | $-CO-R_3$ | |
| 2.071 | F | Br | $-OC_4H_9$ | H | 0 | $-CO-R_3$ | |
| 2.072 | F | Br | $-OCH(CH_3)-CH_2-CH_3$ | H | 0 | $-CO-R_3$ | |
| 2.073 | F | Br | 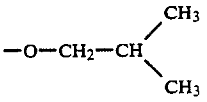 | H | 0 | $-CO-R_3$ | |
| 2.074 | F | Br | $-O-C_5H_{11}$ | H | 0 | $-CO-R_3$ | |
| 2.075 | F | Br | $-O-CH_2-CH_2-O-CH_3$ | H | 0 | $-CO-R_3$ | |
| 2.076 | F | Br | $-O-CH_2-CH_2-O-C_2H_5$ | H | 0 | $-CO-R_3$ | |
| 2.077 | F | Br | $-O-CH(CH_3)-CH_2-O-CH_3$ | H | 0 | $-CO-R_3$ | |
| 2.078 | F | Br | $-O-CH_2-CH_2-S-CH_3$ | H | 0 | $-CO-R_3$ | |
| 2.079 | F | Br | $-O-CH_2(CH_3)-S-CH_3$ | H | 0 | $-CO-R_3$ | |
| 2.080 | F | Br | $-O-CH-(CH_3)-S-C_2H_5$ | H | 0 | $-CO-R_3$ | |
| 2.081 | F | Br | $-O-CH(CH_3)-S-C_3H_7$ | H | 0 | $-CO-R_3$ | |
| 2.082 | F | Br | 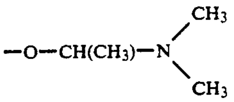 | H | 0 | $-CO-R_3$ | |

TABLE 2-continued

Compounds of formula I wherein W is $W_2$, $Y_3$ is oxygen and $R_{14}$ is hydrogen:

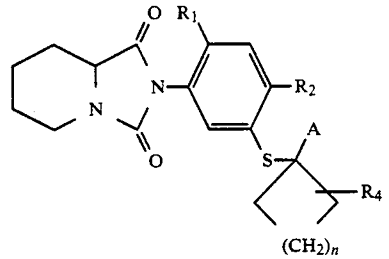

(I)

| Comp. No. | $R_1$ | $R_2$ | $R_3$ | $R_4$ | n | A | m.p. [°C.] |
|---|---|---|---|---|---|---|---|
| 2.083 | F | Br | $-NH_2$ | H | 0 | $-CO-R_3$ | |
| 2.084 | F | Br | 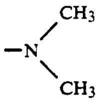 | H | 0 | $-CO-R_3$ | |
| 2.085 | F | Br | 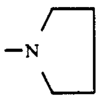 | H | 0 | $-CO-R_3$ | |
| 2.086 | F | Br | 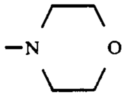 | H | 0 | $-CO-R_3$ | |
| 2.087 | F | Br | 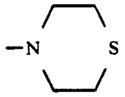 | H | 0 | $-CO-R_3$ | |
| 2.088 | F | Br | 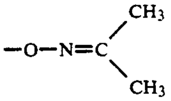 | H | 0 | $-CO-R_3$ | |
| 2.089 | F | Br | $-O-CH_2-CH_2-Cl$ | H | 0 | $-CO-R_3$ | |
| 2.090 | F | Br | $-O-CH_2-CN$ | H | 0 | $-CO-R_3$ | |
| 2.091 | F | Br | $-O-CH_2-CH{=}CH_2$ | H | 0 | $-CO-R_3$ | |
| 2.092 | F | Br | $-O-CH_2-C{\equiv}CH$ | H | 0 | $-CO-R_3$ | |
| 2.093 | F | Br | 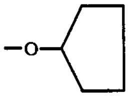 | H | 0 | $-CO-R_3$ | |
| 2.094 | F | Br | 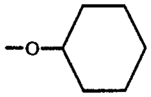 | H | 0 | $-CO-R_3$ | |
| 2.095 | F | Br | 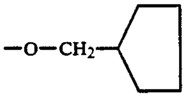 | H | 0 | $-CO-R_3$ | |
| 2.096 | F | Br | 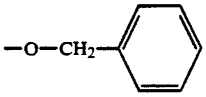 | H | 0 | $-CO-R_3$ | |
| 2.097 | F | Br | $-SCH_3$ | H | 0 | $-CO-R_3$ | |
| 2.098 | F | Br | $-S-CH_2-COOCH_3$ | H | 0 | $-CO-R_3$ | |
| 2.099 | F | Br | $-S-CH(CH_3)-COOCH_3$ | H | 0 | $-CO-R_3$ | |
| 2.100 | F | Br | $-O-CH_2-COOCH_3$ | H | 0 | $-CO-R_3$ | |
| 2.101 | F | Br | $-O-CH(CH_3)COOCH_3$ | H | 0 | $-CO-R_3$ | |

TABLE 2-continued

Compounds of formula I wherein W is $W_2$, $Y_3$ is oxygen and $R_{14}$ is hydrogen:

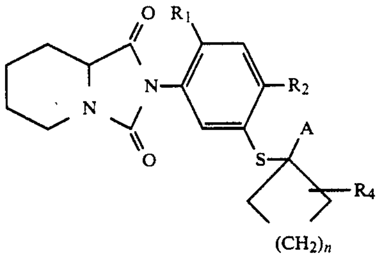

(I)

| Comp. No. | $R_1$ | $R_2$ | $R_3$ | $R_4$ | n | A | m.p. [°C.] |
|---|---|---|---|---|---|---|---|
| 2.102 | F | CN | —Cl | H | 0 | —CO—$R_3$ | |
| 2.103 | F | CN | —OH | H | 0 | —CO—$R_3$ | |
| 2.104 | F | CN | —$OCH_3$ | H | 0 | —CO—$R_3$ | |
| 2.105 | H | Cl | —Cl | H | 0 | —CO—$R_3$ | |
| 2.106 | H | Cl | —OH | H | 0 | —CO—$R_3$ | |
| 2.107 | H | Cl | —$OCH_3$ | H | 0 | —CO—$R_3$ | |
| 2.108 | H | Cl | —$OC_2H_5$ | H | 0 | —CO—$R_3$ | |
| 2.109 | H | Cl | 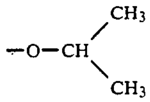 | H | 0 | —CO—$R_3$ | |
| 2.110 | H | Cl | —O—$CH_2$—$COOCH_3$ | H | 0 | —CO—$R_3$ | |
| 2.111 | H | Cl | —O—$CH(CH_3)COOCH_3$ | H | 0 | —CO—$R_3$ | |
| 2.112 | H | Cl | —S—$CH_2$—$COOCH_3$ | H | 0 | —CO—$R_3$ | |
| 2.113 | H | Cl | —S—$CH(CH_3)COOCH_3$ | H | 0 | —CO—$R_3$ | |
| 2.114 | H | Cl | 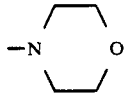 | H | 0 | —CO—$R_3$ | |
| 2.115 | F | Cl | —Cl | H | 1 | —CO—$R_3$ | |
| 2.116 | F | Cl | —OH | H | 1 | —CO—$R_3$ | |
| 2.117 | F | Cl | —$OCH_3$ | H | 1 | —CO—$R_3$ | 107-108 |
| 2.118 | F | Cl | —$OC_2H_5$ | H | 1 | —CO—$R_3$ | |
| 2.119 | F | Cl | —$OC_3H_7$ | H | 1 | —CO—$R_3$ | |
| 2.120 | F | Cl | 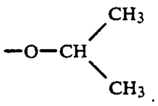 | H | 1 | —CO—$R_3$ | |
| 2.121 | F | Cl | —$OC_4H_9$ | H | 1 | —CO—$R_3$ | |
| 2.122 | F | Cl | —O—$CH(CH_3)$—$C_2H_5$ | H | 1 | —CO—$R_3$ | |
| 2.123 | F | Cl | 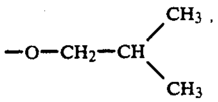 | H | 1 | —CO—$R_3$ | |
| 2.124 | F | Cl | —$OC_5H_{11}$ | H | 1 | —CO—$R_3$ | |
| 2.125 | F | Cl | —O—$CH_2$—$CH_2$—O—$CH_3$ | H | 1 | —CO—$R_3$ | |
| 2.126 | F | Cl | —O—$CH_2$—$CH_2$—O—$C_2H_5$ | H | 1 | —CO—$R_3$ | |
| 2.127 | F | Cl | —O—CH—$(CH_3)$—$CH_2$—O—$CH_3$ | H | 1 | —CO—$R_3$ | |
| 2.128 | F | Cl | —O—$CH_2$—$CH_2$—S—$CH_3$ | H | 1 | —CO—$R_3$ | |
| 2.129 | F | Cl | —O—$CH(CH_3)$—$CH_2$—S—$CH_3$ | H | 1 | —CO—$R_3$ | |
| 2.130 | F | Cl | —O—$CH(CH_3)$—$CH_2$—S—$C_2H_5$ | H | 1 | —CO—$R_3$ | |
| 2.131 | F | Cl | —O—$CH(CH_3)$—$CH_2$—S—$C_3H_7$ | H | 1 | —CO—$R_3$ | |
| 2.132 | F | Cl | 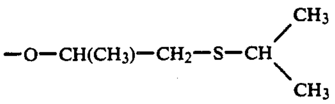 | H | 1 | —CO—$R_3$ | |
| 2.133 | F | Cl | —O—$CH(CH_3)$—$CH_2$—S—$C_4H_9$ | H | 1 | —CO—$R_3$ | |
| 2.134 | F | Cl | —O—$CH(CH_3)$—$CH_2$—S—$C_5H_{11}$ | H | 1 | —CO—$R_3$ | |

TABLE 2-continued
Compounds of formula I wherein W is $W_2$, $Y_3$ is oxygen and $R_{14}$ is hydrogen:
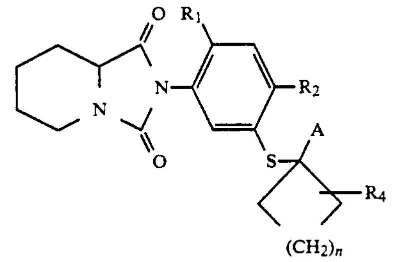
(I)
| Comp. No. | $R_1$ | $R_2$ | $R_3$ | $R_4$ | n | A | m.p. [°C.] |
|---|---|---|---|---|---|---|---|
| 2.135 | F | Cl | 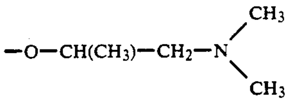 | H | 1 | $-CO-R_3$ | |
| 2.136 | F | Cl | 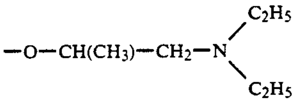 | H | 1 | $-CO-R_3$ | |
| 2.137 | F | Cl | $-NH_2$ | H | 1 | $-CO-R_3$ | |
| 2.138 | F | Cl | 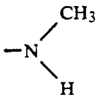 | H | 1 | $-CO-R_3$ | |
| 2.139 | F | Cl | 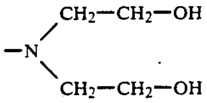 | H | 1 | $-CO-R_3$ | |
| 2.140 | F | Cl | $-NH-CH_2-CH=CH_2$ | H | 1 | $-CO-R_3$ | |
| 2.141 | F | Cl | $-N-(CH_2-CH=CH_2)_2$ | H | 1 | $-CO-R_3$ | |
| 2.142 | F | Cl | 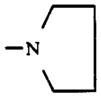 | H | 1 | $-CO-R_3$ | |
| 2.143 | F | Cl | 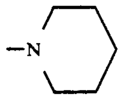 | H | 1 | $-CO-R_3$ | |
| 2.144 | F | Cl | 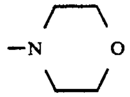 | H | 1 | $-CO-R_3$ | |
| 2.145 | F | Cl | 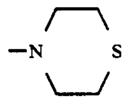 | H | 1 | $-CO-R_3$ | |
| 2.146 | F | Cl | 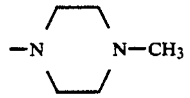 | H | 1 | $-CO-R_3$ | |
| 2.147 | F | Cl | 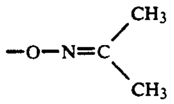 | H | 1 | $-CO-R_3$ | |
| 2.148 | F | Cl | $-O-CH_2-CH_2-Cl$ | H | 1 | $-CO-R_3$ | |
| 2.149 | F | Cl | $-O-CH_2-CN$ | H | 1 | $-CO-R_3$ | |

TABLE 2-continued

Compounds of formula I wherein W is $W_2$, $Y_3$ is oxygen and $R_{14}$ is hydrogen:

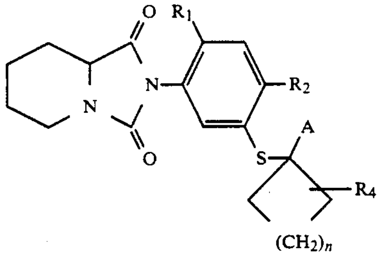

(I)

| Comp. No. | $R_1$ | $R_2$ | $R_3$ | $R_4$ | n | A | m.p. [°C.] |
|---|---|---|---|---|---|---|---|
| 2.150 | F | Cl | $-O-CH(CH_3)-CN$ | H | 1 | $-CO-R_3$ | |
| 2.151 | F | Cl | $-O-CH_2-CH=CH_2$ | H | 1 | $-CO-R_3$ | |
| 2.152 | F | Cl | $-O-CH_2-CH=CHCl$ | H | 1 | $-CO-R_3$ | |
| 2.153 | F | Cl | $-O-CH_2-C(Cl)=CH_2$ | H | 1 | $-CO-R_3$ | |
| 2.154 | F | Cl | $-O-CH_2=C\equiv CH$ | H | 1 | $-CO-R_3$ | |
| 2.155 | F | Cl | $-O-CH(CH_3)-C\equiv CH$ | H | 1 | $-CO-R_3$ | |
| 2.156 | F | Cl | —O— 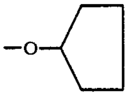 | H | 1 | $-CO-R_3$ | |
| 2.157 | F | Cl | —O— 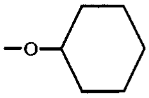 | H | 1 | $-CO-R_3$ | |
| 2.158 | F | Cl | $-O-CH_2-$ 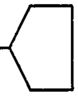 | H | 1 | $-CO-R_3$ | |
| 2.159 | F | Cl | $-O-CH_2-$ 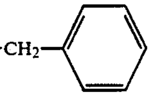 | H | 1 | $-CO-R_3$ | |
| 2.160 | F | Cl | $-O-CH_2-$ 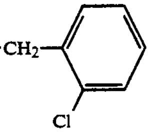 | H | 1 | $-CO-R_3$ | |
| 2.161 | F | Cl | $-O-CH_2-$ 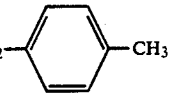 | H | 1 | $-CO-R_3$ | |
| 2.162 | F | Cl | $-S-CH_3$ | H | 1 | $-CO-R_3$ | |
| 2.163 | F | Cl | $-S-C_2H_5$ | H | 1 | $-CO-R_3$ | |
| 2.164 | F | Cl | $-S-C_3H_7$ | H | 1 | $-CO-R_3$ | |
| 2.165 | F | Cl | $-S-CH_2-CH=CH_2$ | H | 1 | $-CO-R_3$ | |
| 2.166 | F | Cl | $-S-CH_2-COOCH_3$ | H | 1 | $-CO-R_3$ | |
| 2.167 | F | Cl | $-S-CH_2-COOC_2H_5$ | H | 1 | $-CO-R_3$ | |
| 2,168 | F | Cl | $-S-CH_2-COOC_5H_{11}$ | H | 1 | $-CO-R_3$ | |
| 2.169 | F | Cl | $-S-CH(CH_3)-COOCH_3$ | H | 1 | $-CO-R_3$ | |
| 2.170 | F | Cl | $-S-(CH_3)-COOC_2H_5$ | H | 1 | $-CO-R_3$ | |

TABLE 2-continued

Compounds of formula I wherein W is $W_2$, $Y_3$ is oxygen and $R_{14}$ is hydrogen:

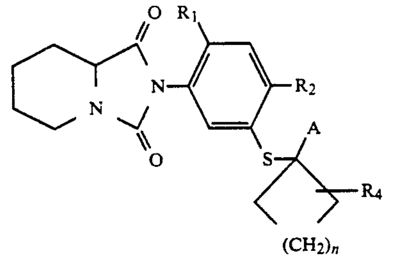

(I)

| Comp. No. | $R_1$ | $R_2$ | $R_3$ | $R_4$ | n | A | m.p. [°C.] |
|---|---|---|---|---|---|---|---|
| 2.171 | F | Cl | $-S-CH(CH_3)-COOC_3H_7$ | H | 1 | $-CO-R_3$ | |
| 2.172 | F | Cl | $-S-CH_2-CH_2-COOCH_3$ | H | 1 | $-CO-R_3$ | |
| 2.173 | F | Cl | $-S-CH_2-COOCH_2-CH_2-O-CH_3$ | H | 1 | $-CO-R_3$ | |
| 2.174 | F | Cl | $-O-CH_2-COOCH_3$ | H | 1 | $-CO-R_3$ | |
| 2.175 | F | Cl | $-O-CH(CH_3)-COOCH_3$ | H | 1 | $-CO-R_3$ | |
| 2.176 | F | Cl | $-O-CH_2-COOC_5H_{11}$ | H | 1 | $-CO-R_3$ | |
| 2.177 | F | Cl | $-O-CH_2-CH_3-Si(CH_3)_3$ | H | 1 | $-CO-R_3$ | |
| 2.178 | F | Cl | $-ONa$ | H | 1 | $-CO-R_3$ | |
| 2.179 | F | Br | $-Cl$ | H | 1 | $-CO-R_3$ | |
| 2.180 | F | Br | $-OH$ | H | 1 | $-CO-R_3$ | |
| 2.181 | F | Br | $-OCH_3$ | H | 1 | $-CO-R_3$ | |
| 2.182 | F | Br | $-OC_2H_5$ | H | 1 | $-CO-R_3$ | |
| 2.183 | F | Br | $-OC_3H_7$ | H | 1 | $-CO-R_3$ | |
| 2.184 | F | Br | 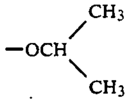 | H | 1 | $-CO-R_3$ | |
| 2.185 | F | Br | $-OC_4H_9$ | H | 1 | $-CO-R_3$ | |
| 2.186 | F | Br | $-OCH(CH_3)-CH_2-CH_3$ | H | 1 | $-CO-R_3$ | |
| 2.187 | F | Br | 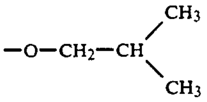 | H | 1 | $-CO-R_3$ | |
| 2.188 | F | Br | $-O-C_5H_{11}$ | H | 1 | $-CO-R_3$ | |
| 2.189 | F | Br | $-O-CH_2-CH_2-O-CH_3$ | H | 1 | $-CO-R_3$ | |
| 2.190 | F | Br | $-O-CH_2-CH_2-O-C_2H_5$ | H | 1 | $-CO-R_3$ | |
| 2.191 | F | Br | $-O-CH(CH_3)-CH_2-O-CH_3$ | H | 1 | $-CO-R_3$ | |
| 2.192 | F | Br | $-O-CH_2-CH_2-S-CH_3$ | H | 1 | $-CO-R_3$ | |
| 2.193 | F | Br | $-O-CH_2(CH_3)-S-CH_3$ | H | 1 | $-CO-R_3$ | |
| 2.194 | F | Br | $-O-CH-(CH_3)-S-C_2H_5$ | H | 1 | $-CO-R_3$ | |
| 2.195 | F | Br | $-O-CH(CH_3)-S-C_3H_7$ | H | 1 | $-CO-R_3$ | |
| 2.196 | F | Br | 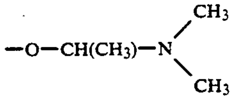 | H | 1 | $-CO-R_3$ | |
| 2.197 | F | Br | $-NH_2$ | H | 1 | $-CO-R_3$ | |
| 2.198 | F | Br | 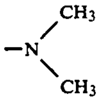 | H | 1 | $-CO-R_3$ | |
| 2.199 | F | Br | 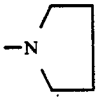 | H | 1 | $-CO-R_3$ | |
| 2.200 | F | Br | 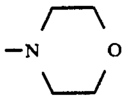 | H | 1 | $-CO-R_3$ | |

TABLE 2-continued

Compounds of formula I wherein W is $W_2$, $Y_3$ is oxygen and $R_{14}$ is hydrogen:

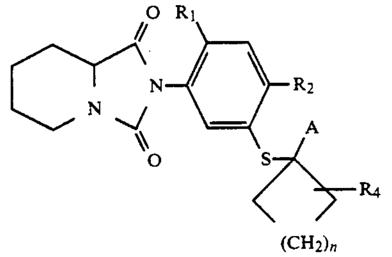

(I)

| Comp. No. | $R_1$ | $R_2$ | $R_3$ | $R_4$ | n | A | m.p. [°C.] |
|---|---|---|---|---|---|---|---|
| 2.201 | F | Br | 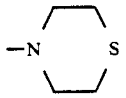 | H | 1 | $-CO-R_3$ | |
| 2.202 | F | Br | 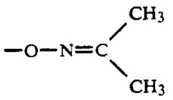 | H | 1 | $-CO-R_3$ | |
| 2.203 | F | Br | $-O-CH_2-CH_2-Cl$ | H | 1 | $-CO-R_3$ | |
| 2.204 | F | Br | $-O-CH_2-CN$ | H | 1 | $-CO-R_3$ | |
| 2.205 | F | Br | $-O-CH_2-CH=CH_2$ | H | 1 | $-CO-R_3$ | |
| 2.206 | F | Br | $-O-CH_2-C\equiv CH$ | H | 1 | $-CO-R_3$ | |
| 2.207 | F | Br | 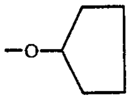 | H | 1 | $-CO-R_3$ | |
| 2.208 | F | Br | 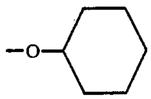 | H | 1 | $-CO-R_3$ | |
| 2.209 | F | Br | 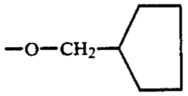 | H | 1 | $-CO-R_3$ | |
| 2.210 | F | Br | 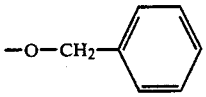 | H | 1 | $-CO-R_3$ | |
| 2.211 | F | Br | $-SCH_3$ | H | 1 | $-CO-R_3$ | |
| 2.212 | F | Br | $-S-CH_2-COOCH_3$ | H | 1 | $-CO-R_3$ | |
| 2.213 | F | Br | $-S-CH(CH_3)-COOCH_3$ | H | 1 | $-CO-R_3$ | |
| 2.214 | F | Br | $-O-CH_2-COOCH_3$ | H | 1 | $-CO-R_3$ | |
| 2.215 | F | Br | $-O-CH(CH_3)COOCH_3$ | H | 1 | $-CO-R_3$ | |
| 2.216 | F | CN | $-Cl$ | H | 1 | $-CO-R_3$ | |
| 2.217 | F | CN | $-OH$ | H | 1 | $-CO-R_3$ | |
| 2.218 | F | CN | $-OCH_3$ | H | 1 | $-CO-R_3$ | |
| 2.219 | H | Cl | $-Cl$ | H | 1 | $-CO-R_3$ | |
| 2.220 | H | Cl | $-OH$ | H | 1 | $-CO-R_3$ | |
| 2.221 | H | Cl | $-OCH_3$ | H | 1 | $-CO-R_3$ | |
| 2.222 | H | Cl | $-OC_2H_5$ | H | 1 | $-CO-R_3$ | |
| 2.223 | H | Cl | 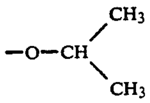 | H | 1 | $-CO-R_3$ | |
| 2.224 | H | Cl | $-O-CH_2-COOCH_3$ | H | 1 | $-CO-R_3$ | |
| 2.225 | H | Cl | $-O-CH(CH_3)COOCH_3$ | H | 1 | $-CO-R_3$ | |
| 2.226 | H | Cl | $-S-CH_2-COOCH_3$ | H | 1 | $-CO-R_3$ | |
| 2.227 | H | Cl | $-S-CH(CH_3)COOCH_3$ | H | 1 | $-CO-R_3$ | |

TABLE 2-continued

Compounds of formula I wherein W is $W_2$, $Y_3$ is oxygen and $R_{14}$ is hydrogen:

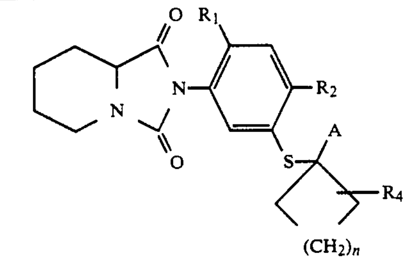

(I)

| Comp. No. | $R_1$ | $R_2$ | $R_3$ | $R_4$ | n | A | m.p. [°C.] |
|---|---|---|---|---|---|---|---|
| 2.228 | H | Cl | 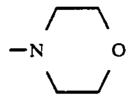 | H | 1 | —CO—$R_3$ | |
| 2.229 | F | Cl | Cl | H | 2 | —CO—$R_3$ | |
| 2.230 | F | Cl | OH | H | 2 | —CO—$R_3$ | |
| 2.231 | F | Cl | $OCH_3$ | H | 2 | —CO—$R_3$ | |
| 2.232 | F | Cl | $—OC_2H_5$ | H | 2 | —CO—$R_3$ | |
| 2.233 | F | Cl | 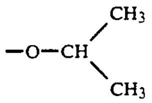 | H | 2 | —CO—$R_3$ | |
| 2.234 | F | Cl | $—O—CH_2—CH_2—CH_3$ | H | 2 | —CO—$R_3$ | |
| 2.235 | F | Cl | $—O—CH(CH_3)—CH_2—S—CH_3$ | H | 2 | —CO—$R_3$ | |
| 2.236 | F | Cl | $—O—CH_2—COOCH_3$ | H | 2 | —CO—$R_3$ | |
| 2.237 | F | Cl | $—S—CH_2—COOCH_3$ | H | 2 | —CO—$R_3$ | |
| 2.238 | F | Cl | $—CH_2—CH{=}CH_2$ | H | 2 | —CO—$R_3$ | |
| 2.239 | F | Cl | $—CH_2—C{\equiv}CH$ | H | 2 | —CO—$R_3$ | |
| 2.240 | F | Cl | Cl | H | 3 | —CO—$R_3$ | |
| 2.241 | F | Cl | OH | H | 3 | —CO—$R_3$ | |
| 2.242 | F | Cl | $OCH_3$ | H | 3 | —CO—$R_3$ | |
| 2.243 | F | Cl | $OC_2H_5$ | H | 3 | —CO—$R_3$ | |
| 2.244 | F | Ckl | 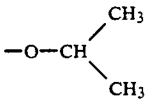 | H | 3 | —CO—$R_3$ | |
| 2.245 | F | Cl | $—O—CH_2—CH_2—O—CH$ | H | 3 | —CO—$R_3$ | |
| 2.246 | F | Cl | $—O—CH(CH_3)—CH_2—S—CH_3$ | H | 3 | —CO—$R_3$ | |
| 2.247 | F | Cl | $—O—CH_2—COOCH_3$ | H | 3 | —CO—$R_3$ | |
| 2.248 | F | Cl | $—S—CH_2—COOCH_3$ | H | 3 | —CO—$R_3$ | |
| 2.249 | F | Cl | $—O—CH_2—C{\equiv}CH$ | H | 3 | —CO—$R_3$ | |
| 2.250 | F | Cl | —Cl | Cl | 0 | —CO—$R_3$ | |
| 2.251 | F | Cl | —OH | Cl | 0 | —CO—$R_3$ | |
| 2.252 | F | Cl | $—OCH_3$ | Cl | 0 | —CO—$R_3$ | |
| 2.253 | F | Cl | $—OC_2H_5$ | Cl | 0 | —CO—$R_3$ | |
| 2.254 | F | Cl | 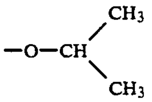 | Cl | 0 | —CO—$R_3$ | |
| 2.255 | F | Cl | $—O—CH_2—COOCH_3$ | Cl | 0 | —CO—$R_3$ | |
| 2.256 | F | Cl | $—S—CH_2—COOCH_3$ | Cl | 0 | —CO—$R_3$ | |
| 2.257 | F | Cl | $—OCH_3$ | Br | 0 | —CO—$R_3$ | |
| 2.258 | F | Cl | 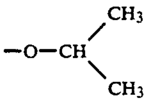 | Br | 0 | —CO—$R_3$ | |
| 2.259 | F | Cl | $—OCH_3$ | F | 0 | —CO—$R_3$ | |
| 2.260 | F | Cl | $—OCH_3$ | $CH_3$ | 0 | —CO—$R_3$ | |
| 2.261 | F | Cl | $—OC_2H_5$ | $CH_3$ | 0 | —CO—$R_3$ | |

TABLE 2-continued

Compounds of formula I wherein W is $W_2$, $Y_3$ is oxygen and $R_{14}$ is hydrogen:

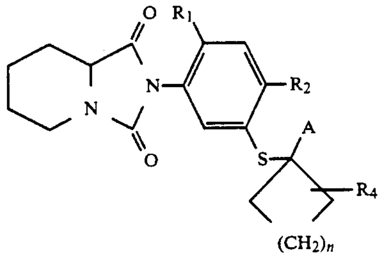

(I)

| Comp. No. | $R_1$ | $R_2$ | $R_3$ | $R_4$ | n | A | m.p. [°C.] |
|---|---|---|---|---|---|---|---|
| 2.262 | F | Cl | 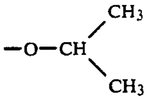 | $CH_3$ | 0 | $-CO-R_3$ | |
| 2.263 | F | Cl | $-O-CH_2-CH_2-O-CH_3$ | $CH_3$ | 0 | $-CO-R_3$ | |
| 2.264 | F | Cl | $-O-CH_2-COOCH_3$ | $CH_3$ | 0 | $-CO-R_3$ | |
| 2.265 | F | Cl | $-O-CH(CH_3)COOCH_3$ | $CH_3$ | 0 | $-CO-R_3$ | |
| 2.266 | F | Cl | $-S-CH_2-COOCH_3$ | $CH_3$ | 0 | $-CO-R_3$ | |
| 2.267 | F | Cl | $-OCH_3$ | $CF_3$ | 0 | $-CO-R_3$ | |
| 2.268 | F | Cl | $-OC_2H_5$ | $CF_3$ | 0 | $-CO-R_3$ | |
| 2.269 | F | Cl | 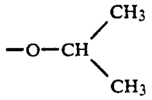 | $CF_3$ | 0 | $-CO-R_3$ | |
| 2.270 | F | Cl | $-O-CH_2-COOCH_3$ | $CF_3$ | 0 | $-CO-R_3$ | |
| 2.271 | F | Cl | $-S-CH_2-COOCH_3$ | $CF_3$ | 0 | $-CO-R_3$ | |
| 2.272 | F | Cl | — | H | 0 | $-CN$ | |
| 2.273 | F | Cl | — | H | 1 | $-CN$ | |
| 2.274 | F | Cl | — | H | 2 | $-CN$ | |
| 2.275 | F | Cl | — | H | 3 | $-CN$ | |
| 2.276 | F | Cl | — | H | 4 | $-CN$ | |

TABLE 3

Compounds of formula I wherein $W = W_3$ and $R_{14} = H$:

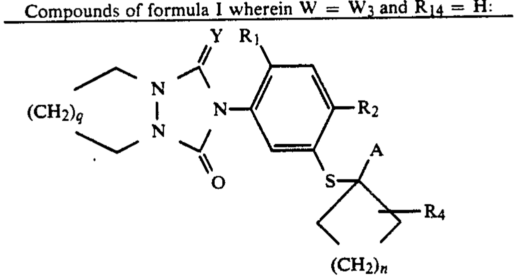

(I)

| Comp. No. | $R_1$ | $R_2$ | $R_3$ | $R_4$ | n | A | Y | q | m.p. [°C.] |
|---|---|---|---|---|---|---|---|---|---|
| 3.001 | F | Cl | $-Cl$ | H | 0 | $-CO-R_3$ | O | 1 | |
| 3.002 | F | Cl | $-OH$ | H | 0 | $-CO-R_3$ | O | 2 | |
| 3.003 | F | Cl | $-OCH_3$ | H | 0 | $-CO-R_3$ | O | 2 | |
| 3.004 | F | Cl | $-OC_2H_5$ | H | 0 | $-CO-R_3$ | O | 2 | |
| 3.005 | F | Cl | $-OC_3H_7$ | H | 0 | $-CO-R_3$ | O | 2 | |
| 3.006 | F | Cl | 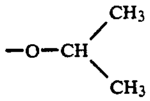 | H | 0 | $-CO-R_3$ | O | 2 | |
| 3.007 | F | Cl | $-OC_4H_9$ | H | 0 | $-CO-R_3$ | O | 2 | |
| 3.008 | F | Cl | $-O-CH(CH_3)-C_2H_5$ | H | 0 | $-CO-R_3$ | O | 2 | |
| 3.009 | F | Cl | 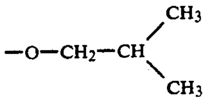 | H | 0 | $-CO-R_3$ | O | 2 | |

TABLE 3-continued

Compounds of formula I wherein W = $W_3$ and $R_{14}$ = H:

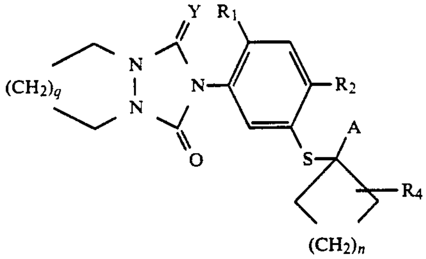

(I)

| Comp. No. | $R_1$ | $R_2$ | $R_3$ | $R_4$ | n | A | Y | q | m.p. [°C.] |
|---|---|---|---|---|---|---|---|---|---|
| 3.010 | F | Cl | $-OC_5H_{11}$ | H | 0 | $-CO-R_3$ | O | 2 | |
| 3.011 | F | Cl | $-O-CH_2-CH_2-O-CH_3$ | H | 0 | $-CO-R_3$ | O | 2 | |
| 3.012 | F | Cl | $-O-CH_2-CH_2-O-C_2H_5$ | H | 0 | $-CO-R_3$ | O | 2 | |
| 3.013 | F | Cl | $-O-CH-(CH_3)-CH_2-O-CH_3$ | H | 0 | $-CO-R_3$ | O | 2 | |
| 3.014 | F | Cl | $-O-CH_2-CH_2-S-CH_3$ | H | 0 | $-CO-R_3$ | O | 2 | |
| 3.015 | F | Cl | $-O-CH(CH_3)-CH_2-S-CH_3$ | H | 0 | $-CO-R_3$ | O | 2 | |
| 3.016 | F | Cl | $-O-CH(CH_3)-CH_2-S-C_2H_5$ | H | 0 | $-CO-R_3$ | O | 2 | |
| 3.017 | F | Cl | $-O-CH(CH_3)-CH_2-S-C_3H_7$ | H | 0 | $-CO-R_3$ | O | 2 | |
| 3.018 | F | Cl | 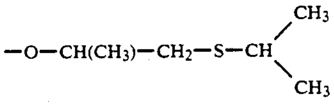 | H | 0 | $-CO-R_3$ | O | 2 | |
| 3.019 | F | Cl | $-O-CH(CH_3)-CH_2-S-C_4H_9$ | H | 0 | $-CO-R_3$ | O | 2 | |
| 3.020 | F | Cl | $-O-CH(CH_3)-CH_2-S-C_5H_{11}$ | H | 0 | $-CO-R_3$ | O | 2 | |
| 3.021 | F | Cl | 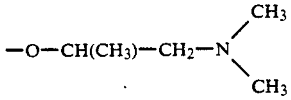 | H | 0 | $-CO-R_3$ | O | 2 | |
| 3.022 | F | Cl | 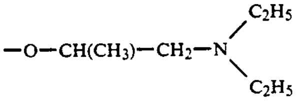 | H | 0 | $-CO-R_3$ | O | 1 | |
| 3.023 | F | Cl | $-NH_2$ | H | 0 | $-CO-R_3$ | O | 2 | |
| 3.024 | F | Cl | 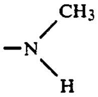 | H | 0 | $-CO-R_3$ | O | 2 | |
| 3.025 | F | Cl | 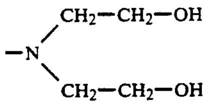 | H | 0 | $-CO-R_3$ | O | 2 | |
| 3.026 | F | Cl | $-NH-CH_2-CH=CH_2$ | H | 0 | $-CO-R_3$ | O | 2 | |
| 3.027 | F | Cl | $-N-(CH_2-CH=CH_2)_2$ | H | 0 | $-CO-R_3$ | O | 2 | |
| 3.028 | F | Cl | 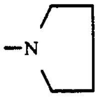 | H | 0 | $-CO-R_3$ | O | 2 | |
| 3.029 | F | Cl | 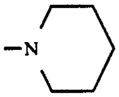 | H | 0 | $-CO-R_3$ | O | 2 | |
| 3.030 | F | Cl | 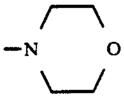 | H | 0 | $-CO-R_3$ | O | 2 | |

TABLE 3-continued

Compounds of formula I wherein W = $W_3$ and $R_{14}$ = H:

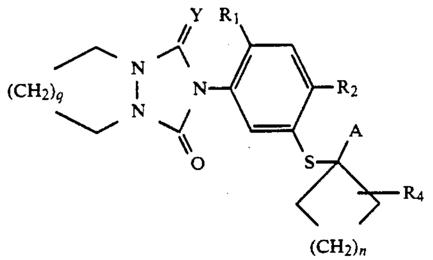

(I)

| Comp. No. | $R_1$ | $R_2$ | $R_3$ | $R_4$ | n | A | Y | q | m.p. [°C.] |
|---|---|---|---|---|---|---|---|---|---|
| 3.031 | F | Cl | 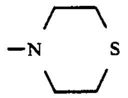 | H | 0 | $-CO-R_3$ | O | 2 | |
| 3.032 | F | Cl | 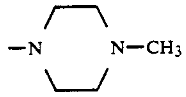 | H | 0 | $-CO-R_3$ | O | 2 | |
| 3.033 | F | Cl | $-O-N=C(CH_3)-CH_3$ | H | 0 | $-CO-R_3$ | O | 2 | |
| 3.034 | F | Cl | $-O-CH_2-CH_2-Cl$ | H | 0 | $-CO-R_3$ | O | 2 | |
| 3.035 | F | Cl | $-O-CH_2-CN$ | H | 0 | $-CO-R_3$ | O | 2 | |
| 3.036 | F | Cl | $-O-CH(CH_3)-CN$ | H | 0 | $-CO-R_3$ | O | 2 | |
| 3.037 | F | Cl | $-O-CH_2-CH=CH_2$ | H | 0 | $-CO-R_3$ | O | 2 | |
| 3.038 | F | Cl | $-O-CH_2-CH=CHCl$ | H | 0 | $-CO-R_3$ | O | 2 | |
| 3.039 | F | Cl | $-O-CH_2-C(Cl)=CH_2$ | H | 0 | $-CO-R_3$ | O | 2 | |
| 3.040 | F | Cl | $-O-CH_2=C\equiv CH$ | H | 0 | $-CO-R_3$ | O | 2 | |
| 3.041 | F | Cl | $-O-CH(CH_3)-C\equiv CH$ | H | 0 | $-CO-R_3$ | O | 2 | |
| 3.042 | F | Cl | 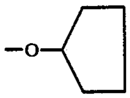 | H | 0 | $-CO-R_3$ | O | 2 | |
| 3.043 | F | Cl | 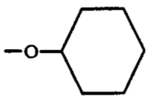 | H | 0 | $-CO-R_3$ | O | 2 | |
| 3.044 | F | Cl | 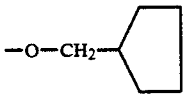 | H | 0 | $-CO-R_3$ | O | | |
| 3.045 | F | Cl | 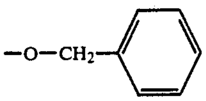 | H | 0 | $-CO-R_3$ | O | 2 | |

TABLE 3-continued

Compounds of formula I wherein W = $W_3$ and $R_{14}$ = H:

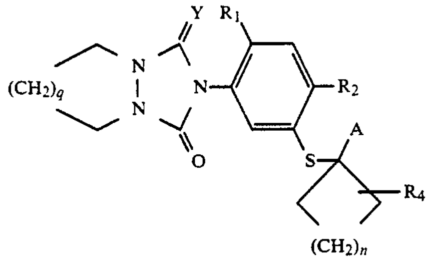

(I)

| Comp. No. | $R_1$ | $R_2$ | $R_3$ | $R_4$ | n | A | Y | q | m.p. [°C.] |
|---|---|---|---|---|---|---|---|---|---|
| 3.046 | F | Cl | 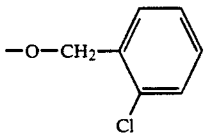 | H | 0 | $-CO-R_3$ | O | 2 | |
| 3.047 | F | Cl | 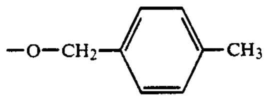 | H | 0 | $-CO-R_3$ | O | 2 | |
| 3.048 | F | Cl | $-S-CH_3$ | H | 0 | $-CO-R_3$ | O | 2 | |
| 3.049 | F | Cl | $-S-C_2H_5$ | H | 0 | $-CO-R_3$ | O | 2 | |
| 3.050 | F | Cl | $-S-C_3H_7$ | H | 0 | $-CO-R_3$ | O | 2 | |
| 3.051 | F | Cl | $-S-CH_2-CH{=}CH_2$ | H | 0 | $-CO-R_3$ | O | 2 | |
| 3.052 | F | Cl | $-S-CH_2-COOCH_3$ | H | 0 | $-CO-R_3$ | O | 2 | |
| 3.053 | F | Cl | $-S-CH_2-COOC_2H_5$ | H | 0 | $-CO-R_3$ | O | 2 | |
| 3.054 | F | Cl | $-S-CH_2-COOC_5H_{11}$ | H | 0 | $-CO-R_3$ | O | 2 | |
| 3.055 | F | Cl | $-S-CH(CH_3)-COOCH_3$ | H | 0 | $-CO-R_3$ | O | 2 | |
| 3.056 | F | Cl | $-S-(CH_3)-COOC_2H_5$ | H | 0 | $-CO-R_3$ | O | 2 | |
| 3.057 | F | Cl | $-S-CH(CH_3)-COOC_3H_7$ | H | 0 | $-CO-R_3$ | O | 2 | |
| 3.058 | F | Cl | $-S-CH_2-CH_2-COOCH_3$ | H | O | $-CO-R_3$ | O | 2 | |
| 3.059 | F | Cl | $-S-CH_2-COOCH_2-CH_2-O-CH_3$ | H | 0 | $-CO-R_3$ | O | 2 | |
| 3.060 | F | Cl | $-O-CH_2-COOCH_3$ | H | 0 | $-CO-R_3$ | O | 2 | |
| 3.061 | F | Cl | $-O-CH(CH_3)-COOCH_3$ | H | 0 | $-CO-R_3$ | O | 2 | |
| 3.062 | F | Cl | $-O-CH_2-COOC_5H_{11}$ | H | 0 | $-CO-R_3$ | O | 2 | |
| 3.063 | F | Cl | $-O-CH_2-CH_3-Si(CH_3)_3$ | H | 0 | $-CO-R_3$ | O | 2 | |
| 3.064 | F | Cl | $-ONa$ | H | 0 | $-CO-R_3$ | O | 2 | |
| 3.065 | F | Br | $-Cl$ | H | 0 | $-CO-R_3$ | O | 2 | |
| 3.066 | F | Br | $-OH$ | H | 0 | $-CO-R_3$ | O | 2 | |
| 3.067 | F | Br | $-OCH_3$ | H | 0 | $-CO-R_3$ | O | 2 | |
| 3.068 | F | Br | $-OC_2H_5$ | H | 0 | $-CO-R_3$ | O | 2 | |
| 3.069 | F | Br | $-OC_3H_7$ | H | 0 | $-CO-R_3$ | O | 2 | |
| 3.070 | F | Br | 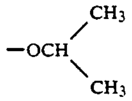 | H | 0 | $-CO-R_3$ | O | 2 | |
| 3.071 | F | Br | $-OC_4H_9$ | H | 0 | $-CO-R_3$ | O | 2 | |
| 3.072 | F | Br | $-OCH(CH_3)-CH_2-CH_3$ | H | 0 | $-CO-R_3$ | O | 2 | |
| 3.073 | F | Br | 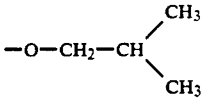 | H | 0 | $-CO-R_3$ | O | 2 | |
| 3.074 | F | Br | $-O-C_5H_{11}$ | H | 0 | $-CO-R_3$ | O | 2 | |
| 3.075 | F | Br | $-O-CH_2-CH_2-O-CH_3$ | H | 0 | $-CO-R_3$ | O | 2 | |
| 3.076 | F | Br | $-O-CH_2-CH_2-O-C_2H_5$ | H | 0 | $-CO-R_3$ | O | 2 | |
| 3.077 | F | Br | $-O-CH(CH_3)-CH_2-O-CH_3$ | H | 0 | $-CO-R_3$ | O | 2 | |
| 3.078 | F | Br | $-O-CH_2-CH_2-S-CH_3$ | H | 0 | $-CO-R_3$ | O | 2 | |
| 3.079 | F | Br | $-O-CH_2(CH_3)-S-CH_3$ | H | 0 | $-CO-R_3$ | O | 2 | |
| 3.080 | F | Br | $-O-CH-(CH_3)-S-C_2H_5$ | H | 0 | $-CO-R_3$ | O | 2 | |
| 3.081 | F | Br | $-O-CH(CH_3)-S-C_3H_7$ | H | 0 | $-CO-R_3$ | O | 2 | |
| 3.082 | F | Br | 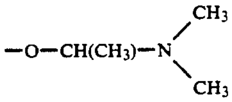 | H | 0 | $-CO-R_3$ | O | 2 | |
| 3.083 | F | Br | $-NH_2$ | H | 0 | $-CO-R_3$ | O | 2 | |

TABLE 3-continued

Compounds of formula I wherein W = $W_3$ and $R_{14}$ = H:

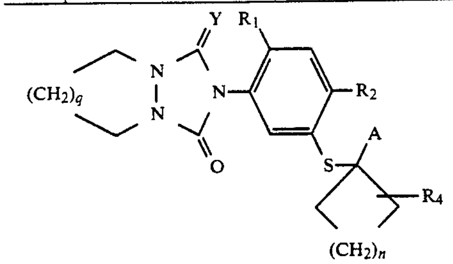

(I)

| Comp. No. | $R_1$ | $R_2$ | $R_3$ | $R_4$ | n | A | Y | q | m.p. [°C.] |
|---|---|---|---|---|---|---|---|---|---|
| 3.084 | F | Br | 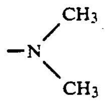 | H | 0 | $-CO-R_3$ | O | 2 | |
| 3.085 | F | Br | 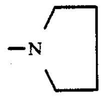 | H | 0 | $-CO-R_3$ | O | 2 | |
| 3.086 | F | Br | 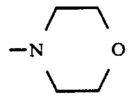 | H | 0 | $-CO-R_3$ | O | 2 | |
| 3.087 | F | Br | 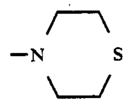 | H | 0 | $-CO-R_3$ | O | 2 | |
| 3.088 | F | Br | 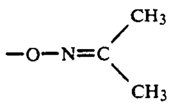 | H | 0 | $-CO-R_3$ | O | 2 | |
| 3.089 | F | Br | $-O-CH_2-CH_2-Cl$ | H | 0 | $-CO-R_3$ | O | 2 | |
| 3.090 | F | Br | $-O-CH_2-CN$ | H | 0 | $-CO-R_3$ | S | 2 | |
| 3.091 | F | Br | $-O-CH_2-CH{=}CH_2$ | H | 0 | $-CO-R_3$ | S | 2 | |
| 3.092 | F | Br | $-O-CH_2-C{\equiv}CH$ | H | 0 | $-CO-R_3$ | S | 2 | |
| 3.093 | F | Br | 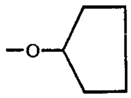 | H | 0 | $-CO-R_3$ | S | 2 | |
| 3.094 | F | Br | 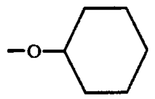 | H | 0 | $-CO-R_3$ | S | 2 | |
| 3.095 | F | Br | 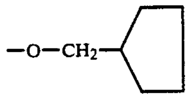 | H | 0 | $-CO-R_3$ | S | 2 | |
| 3.096 | F | Br | 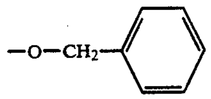 | H | 0 | $-CO-R_3$ | S | 2 | |
| 3.097 | F | Br | $-SCH_3$ | H | 0 | $-CO-R_3$ | S | 2 | |
| 3.098 | F | Br | $-S-CH_2-COOCH_3$ | H | 0 | $-CO-R_3$ | S | 2 | |
| 3.099 | F | Br | $-S-CH(CH_3)-COOCH_3$ | H | 0 | $-CO-R_3$ | S | 2 | |
| 3.100 | F | Br | $-O-CH_2-COOCH_3$ | H | 0 | $-CO-R_3$ | S | 2 | |
| 3.101 | F | Br | $-O-CH(CH_3)COOCH_3$ | H | 0 | $-CO-R_3$ | S | 2 | |
| 3.102 | F | CN | $-Cl$ | H | 0 | $-CO-R_3$ | S | 2 | |
| 3.103 | F | CN | $-OH$ | H | 0 | $-CO-R_3$ | S | 2 | |

TABLE 3-continued

Compounds of formula I wherein W = $W_3$ and $R_{14}$ = H:

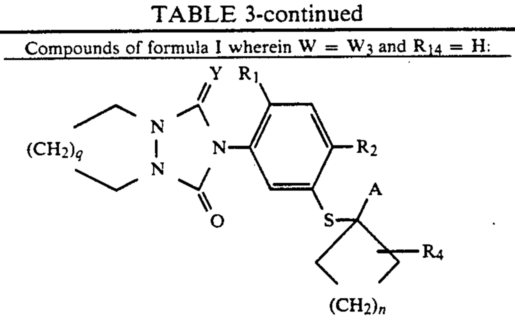

(I)

| Comp. No. | $R_1$ | $R_2$ | $R_3$ | $R_4$ | n | A | Y | q | m.p. [°C.] |
|---|---|---|---|---|---|---|---|---|---|
| 3.104 | F | CN | $-OCH_3$ | H | 0 | $-CO-R_3$ | S | 2 | |
| 3.105 | H | Cl | $-Cl$ | H | 0 | $-CO-R_3$ | S | 2 | |
| 3.106 | H | Cl | $-OH$ | H | 0 | $-CO-R_3$ | S | 2 | |
| 3.107 | H | Cl | $-OCH_3$ | H | 0 | $-CO-R_3$ | S | 2 | |
| 3.108 | H | Cl | $-OC_2H_5$ | H | 0 | $-CO-R_3$ | S | 2 | |
| 3.109 | H | Cl | 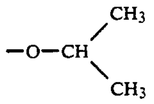 | H | 0 | $-CO-R_3$ | S | 2 | |
| 3.110 | H | Cl | $-O-CH_2-COOCH_3$ | H | 0 | $-CO-R_3$ | S | 2 | |
| 3.111 | H | Cl | $-O-CH(CH_3)COOCH_3$ | H | 0 | $-CO-R_3$ | S | 2 | |
| 3.112 | H | Cl | $-S-CH_2-COOCH_3$ | H | 0 | $-CO-R_3$ | S | 2 | |
| 3.113 | H | Cl | $-S-CH(CH_3)COOCH_3$ | H | 0 | $-CO-R_3$ | S | 2 | |
| 3.114 | H | Cl | 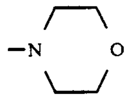 | H | 0 | $-CO-R_3$ | S | 2 | |
| 3.115 | F | Cl | $-Cl$ | H | 1 | $-CO-R_3$ | O | 2 | |
| 3.116 | F | Cl | $-OH$ | H | 1 | $-CO-R_3$ | O | 2 | |
| 3.117 | F | Cl | $-OCH_3$ | H | 1 | $-CO-R_3$ | O | 2 | |
| 3.118 | F | Cl | $-OC_2H_5$ | H | 1 | $-CO-R_3$ | O | 2 | |
| 3.119 | F | Cl | $-OC_3H_7$ | H | 1 | $-CO-R_3$ | O | 2 | |
| 3.120 | F | Cl | 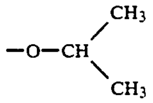 | H | 1 | $-CO-R_3$ | O | 2 | |
| 3.121 | F | Cl | $-OC_4H_9$ | H | 1 | $-CO-R_3$ | O | 2 | |
| 3.122 | F | Cl | $-O-CH(CH_3)-C_2H_5$ | H | 1 | $-CO-R_3$ | O | 2 | |
| 3.123 | F | Cl | 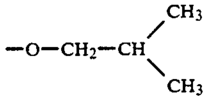 | H | 1 | $-CO-R_3$ | O | 2 | |
| 3.124 | F | Cl | $-OC_5H_{11}$ | H | 1 | $-CO-R_3$ | O | 2 | |
| 3.125 | F | Cl | $-O-CH_2-CH_2-O-CH_3$ | H | 1 | $-CO-R_3$ | O | 2 | |
| 3.126 | F | Cl | $-O-CH_2-CH_2-O-C_2H_5$ | H | 1 | $-CO-R_3$ | O | 2 | |
| 3.127 | F | Cl | $-O-CH-(CH_3)-CH_2-O-CH_3$ | H | 1 | $-CO-R_3$ | O | 2 | |
| 3.128 | F | Cl | $-O-CH_2-CH_2-S-CH_3$ | H | 1 | $-CO-R_3$ | O | 2 | |
| 3.129 | F | Cl | $-O-CH(CH_3)-CH_2-S-CH_3$ | H | 1 | $-CO-R_3$ | O | 2 | |
| 3.130 | F | Cl | $-O-CH(CH_3)-CH_2-S-C_2H_5$ | H | 1 | $-CO-R_3$ | O | 2 | |
| 3.131 | F | Cl | $-O-CH(CH_3)-CH_2-S-C_3H_7$ | H | 1 | $-CO-R_3$ | O | 2 | |
| 3.132 | F | Cl | 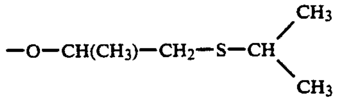 | H | 1 | $-CO-R_3$ | O | 2 | |
| 3.133 | F | Cl | $-O-CH(CH_3)-CH_2-S-C_4H_9$ | H | 1 | $-CO-R_3$ | O | 2 | |
| 3.134 | F | Cl | $-O-CH(CH_3)-CH_2-S-C_5H_{11}$ | H | 1 | $-CO-R_3$ | O | 2 | |
| 3.135 | F | Cl | 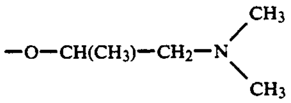 | H | 1 | $-CO-R_3$ | O | 2 | |

TABLE 3-continued
Compounds of formula I wherein W = $W_3$ and $R_{14}$ = H:
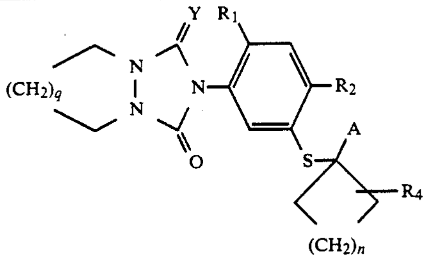
(I)
| Comp. No. | $R_1$ | $R_2$ | $R_3$ | $R_4$ | n | A | Y | q | m.p. [°C.] |
|---|---|---|---|---|---|---|---|---|---|
| 3.136 | F | Cl | 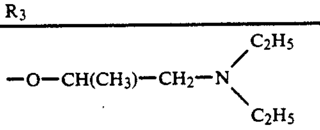 | H | 1 | $-CO-R_3$ | O | 2 | |
| 3.137 | F | Cl | $-NH_2$ | H | 1 | $-CO-R_3$ | O | 2 | |
| 3.138 | F | Cl | 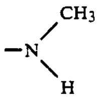 | H | 1 | $-CO-R_3$ | O | 2 | |
| 3.139 | F | Cl | 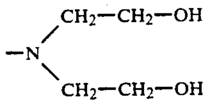 | H | 1 | $-CO-R_3$ | O | 2 | |
| 3.140 | F | Cl | $-NH-CH_2-CH=CH_2$ | H | 1 | $-CO-R_3$ | O | 2 | |
| 3.141 | F | Cl | $-N-(CH_2-CH=CH_2)_2$ | H | 1 | $-CO-R_3$ | O | 2 | |
| 3.142 | F | Cl | 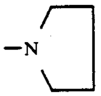 | H | 1 | $-CO-R_3$ | O | 2 | |
| 3.143 | F | Cl | 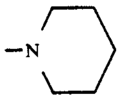 | H | 1 | $-CO-R_3$ | O | 2 | |
| 3.144 | F | Cl | 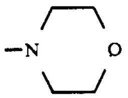 | H | 1 | $-CO-R_3$ | O | | |
| 3.145 | F | Cl | 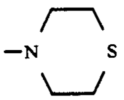 | H | 1 | $-CO-R_3$ | O | 2 | |
| 3.146 | F | Cl | 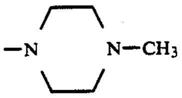 | H | 1 | $-CO-R_3$ | O | 2 | |
| 3.147 | F | Cl | 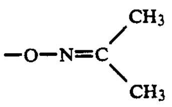 | H | 1 | $-CO-R_3$ | O | 2 | |
| 3.148 | F | Cl | $-O-CH_2-CH_2-Cl$ | H | 1 | $-CO-R_3$ | O | 2 | |
| 3.149 | F | Cl | $-O-CH_2-CN$ | H | 1 | $-CO-R_3$ | O | 2 | |
| 3.150 | F | Cl | 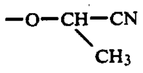 | H | 1 | $-CO-R_3$ | O | 2 | |
| 3.151 | F | Cl | $-O-CH_2-CH=CH_2$ | H | 1 | $-CO-R_3$ | O | 2 | |

TABLE 3-continued

Compounds of formula I wherein W = $W_3$ and $R_{14}$ = H:

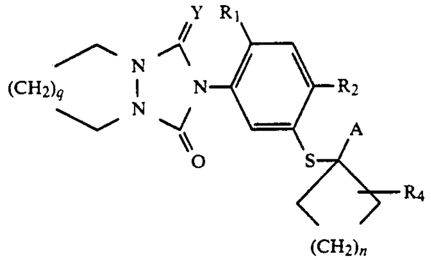

(I)

| Comp. No. | $R_1$ | $R_2$ | $R_3$ | $R_4$ | n | A | Y | q | m.p. [°C.] |
|---|---|---|---|---|---|---|---|---|---|
| 3.152 | F | Cl | $-O-CH_2-CH=CHCl$ | H | 1 | $-CO-R_3$ | O | 2 | |
| 3.153 | F | Cl | $-O-CH_2-C=CH_2$<br>Cl | H | 1 | $-CO-R_3$ | O | 2 | |
| 3.154 | F | Cl | $-O-CH_2=C\equiv CH$ | H | 1 | $-CO-R_3$ | O | 2 | |
| 3.155 | F | Cl | $-O-CH-C\equiv CH$<br>$CH_3$ | H | 1 | $-CO-R_3$ | O | 2 | |
| 3.156 | F | Cl | 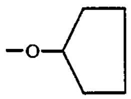 | H | 1 | $-CO-R_3$ | O | 2 | |
| 3.157 | F | Cl | 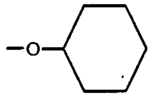 | H | 1 | $-CO-R_3$ | O | 2 | |
| 3.158 | F | Cl | 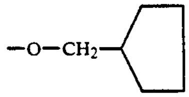 | H | 1 | $-CO-R_3$ | O | 2 | |
| 3.159 | F | Cl | 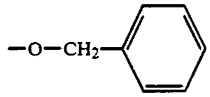 | H | 1 | $-CO-R_3$ | O | 2 | |
| 3.160 | F | Cl | 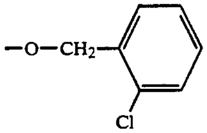 | H | 1 | $-CO-R_3$ | O | | |
| 3.161 | F | Cl | 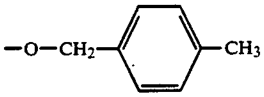 | H | 1 | $-CO-R_3$ | O | 2 | |
| 3.162 | F | Cl | $-S-CH_3$ | H | 1 | $-CO-R_3$ | O | 2 | |
| 3.163 | F | Cl | $-S-C_2H_5$ | H | 1 | $-CO-R_3$ | O | 2 | |
| 3.164 | F | Cl | $-S-C_3H_7$ | H | 1 | $-CO-R_3$ | O | 2 | |
| 3.165 | F | Cl | $-S-CH_2-CH=CH_2$ | H | 1 | $-CO-R_3$ | O | 2 | |
| 3.166 | F | Cl | $-S-CH_2-COOCH_3$ | H | 1 | $-CO-R_3$ | O | 2 | |
| 3.167 | F | Cl | $-S-CH_2-COOC_2H_5$ | H | 1 | $-CO-R_3$ | O | 2 | |
| 3.168 | F | Cl | $-S-CH_2-COOC_5H_{11}$ | H | 1 | $-CO-R_3$ | O | 2 | |
| 3.169 | F | Cl | $-S-CH(CH_3)-COOCH_3$ | H | 1 | $-CO-R_3$ | O | 2 | |
| 3.170 | F | Cl | $-S-(CH_3)-COOC_2H_5$ | H | 1 | $-CO-R_3$ | O | 2 | |
| 3.171 | F | Cl | $-S-CH(CH_3)-COOC_3H_7$ | H | 1 | $-CO-R_3$ | O | 2 | |
| 3.172 | F | Cl | $-S-CH_2-CH_2-COOCH_3$ | H | 1 | $-CO-R_3$ | O | 2 | |
| 3.173 | F | Cl | $-S-CH_2-COOCH_2-CH_2-O-CH_3$ | H | 1 | $-CO-R_3$ | O | 2 | |
| 3.174 | F | Cl | $-O-CH_2-COOCH_3$ | H | 1 | $-CO-R_3$ | O | 2 | |
| 3.175 | F | Cl | $-O-CH(CH_3)-COOCH_3$ | H | 1 | $-CO-R_3$ | O | 2 | |
| 3.176 | F | Cl | $-O-CH_2-COOC_5H_{11}$ | H | 1 | $-CO-R_3$ | O | 2 | |
| 3.177 | F | Cl | $-O-CH_2-CH_3-Si(CH_3)_3$ | H | 1 | $-CO-R_3$ | O | 2 | |

TABLE 3-continued

Compounds of formula I wherein $W = W_3$ and $R_{14} = H$:

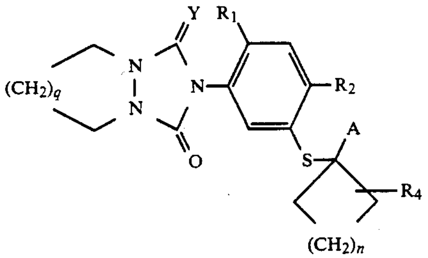

(I)

| Comp. No. | $R_1$ | $R_2$ | $R_3$ | $R_4$ | n | A | Y | q | m.p. [°C.] |
|---|---|---|---|---|---|---|---|---|---|
| 3.178 | F | Cl | $-ONa$ | H | 1 | $-CO-R_3$ | O | 2 | |
| 3.179 | F | Br | $-Cl$ | H | 1 | $-CO-R_3$ | O | 2 | |
| 3.180 | F | Br | $-OH$ | H | 1 | $-CO-R_3$ | O | 2 | |
| 3.181 | F | Br | $-OCH_3$ | H | 1 | $-CO-R_3$ | O | 2 | |
| 3.182 | F | Br | $-OC_2H_5$ | H | 1 | $-CO-R_3$ | O | 2 | |
| 3.183 | F | Br | $-OC_3H_7$ | H | 1 | $-CO-R_3$ | O | 2 | |
| 3.184 | F | Br | 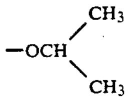 | H | 1 | $-CO-R_3$ | O | 2 | |
| 3.185 | F | Br | $-OC_4H_9$ | H | 1 | $-CO-R_3$ | O | 2 | |
| 3.186 | F | Br | $-OCH(CH_3)-CH_2-CH_3$ | H | 1 | $-CO-R_3$ | O | 2 | |
| 3.187 | F | Br | 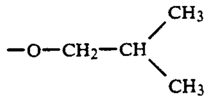 | H | 1 | $-CO-R_3$ | O | 2 | |
| 3.188 | F | Br | $-O-C_5H_{11}$ | H | 1 | $-CO-R_3$ | O | 2 | |
| 3.189 | F | Br | $-O-CH_2-CH_2-O-CH_3$ | H | 1 | $-CO-R_3$ | O | 2 | |
| 3.190 | F | Br | $-O-CH_2-CH_2-O-C_2H_5$ | H | 1 | $-CO-R_3$ | O | 2 | |
| 3.191 | F | Br | $-O-CH(CH_3)-CH_2-O-CH_3$ | H | 1 | $-CO-R_3$ | O | 2 | |
| 3.192 | F | Br | $-O-CH_2-CH_2-S-CH_3$ | H | 1 | $-CO-R_3$ | O | 2 | |
| 3.193 | F | Br | $-O-CH_2(CH_3)-S-CH_3$ | H | 1 | $-CO-R_3$ | O | 2 | |
| 3.194 | F | Br | $-O-CH-(CH_3)-S-C_2H_5$ | H | 1 | $-CO-R_3$ | O | 2 | |
| 3.195 | F | Br | $-O-CH(CH_3)-S-C_3H_7$ | H | 1 | $-CO-R_3$ | O | 2 | |
| 3.196 | F | Br | 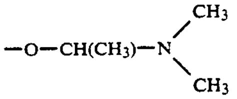 | H | 1 | $-CO-R_3$ | O | 2 | |
| 3.197 | F | Br | $-NH_2$ | H | 1 | $-CO-R_3$ | O | 2 | |
| 3.198 | F | Br | 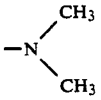 | H | 1 | $-CO-R_3$ | O | 2 | |
| 3.199 | F | Br | 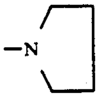 | H | 1 | $-CO-R_3$ | O | 2 | |
| 3.200 | F | Br | 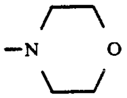 | H | 1 | $-CO-R_3$ | O | 2 | |
| 3.201 | F | Br | 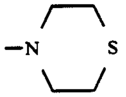 | H | 1 | $-CO-R_3$ | O | 2 | |
| 3.202 | F | Br | 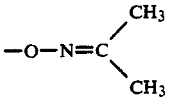 | H | 1 | $-CO-R_3$ | O | 2 | |

TABLE 3-continued

Compounds of formula I wherein W = $W_3$ and $R_{14}$ = H:

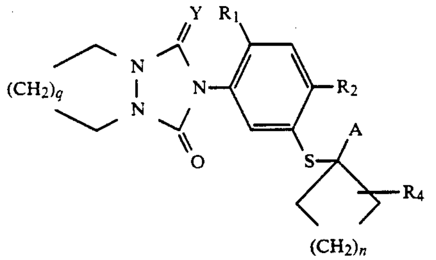

(I)

| Comp. No. | $R_1$ | $R_2$ | $R_3$ | $R_4$ | n | A | Y | q | m.p. [°C.] |
|---|---|---|---|---|---|---|---|---|---|
| 3.203 | F | Br | $-O-CH_2-CH_2-Cl$ | H | 1 | $-CO-R_3$ | O | 2 | |
| 3.204 | F | Br | $-O-CH_2-CN$ | H | 1 | $-CO-R_3$ | O | 2 | |
| 3.205 | F | Br | $-O-CH_2-CH=CH_2$ | H | 1 | $-CO-R_3$ | O | 2 | |
| 3.206 | F | Br | $-O-CH_2-C\equiv CH$ | H | 1 | $-CO-R_3$ | O | 2 | |
| 3.207 | F | Br | 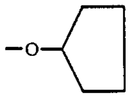 | H | 1 | $-CO-R_3$ | O | 2 | |
| 3.208 | F | Br | 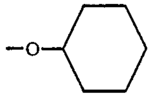 | H | 1 | $-CO-R_3$ | O | 2 | |
| 3.209 | F | Br | 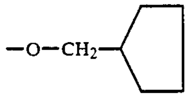 | H | 1 | $-CO-R_3$ | O | 2 | |
| 3.210 | F | Br | 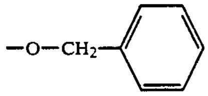 | H | 1 | $-CO-R_3$ | O | 2 | |
| 3.211 | F | Br | $-SCH_3$ | H | 1 | $-CO-R_3$ | O | 2 | |
| 3.212 | F | Br | $-S-CH_2-COOCH_3$ | H | 1 | $-CO-R_3$ | O | 2 | |
| 3.213 | F | Br | $-S-CH(CH_3)-COOCH_3$ | H | 1 | $-CO-R_3$ | O | 2 | |
| 3.214 | F | Br | $-O-CH_2-COOCH_3$ | H | 1 | $-CO-R_3$ | O | 2 | |
| 3.215 | F | Br | $-O-CH(CH_3)COOCH_3$ | H | 1 | $-CO-R_3$ | O | 2 | |
| 3.216 | F | CN | $-Cl$ | H | 1 | $-CO-R_3$ | O | 2 | |
| 3.217 | F | CN | $-OH$ | H | 1 | $-CO-R_3$ | O | 2 | |
| 3.218 | F | CN | $-OCH_3$ | H | 1 | $-CO-R_3$ | O | 2 | |
| 3.219 | H | Cl | $-Cl$ | H | 1 | $-CO-R_3$ | O | 2 | |
| 3.220 | H | Cl | $-OH$ | H | 1 | $-CO-R_3$ | O | 2 | |
| 3.221 | H | Cl | $-OCH_3$ | H | 1 | $-CO-R_3$ | O | 2 | |
| 3.222 | H | Cl | $-OC_2H_5$ | H | 1 | $-CO-R_3$ | O | 2 | |
| 3.223 | H | Cl | 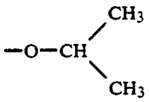 | H | 1 | $-CO-R_3$ | O | 2 | |
| 3.224 | H | Cl | $-O-CH_2-COOCH_3$ | H | 1 | $-CO-R_3$ | O | 2 | |
| 3.225 | H | Cl | $-O-CH(CH_3)COOCH_3$ | H | 1 | $-CO-R_3$ | O | 2 | |
| 3.226 | H | Cl | $-S-CH_2-COOCH_3$ | H | 1 | $-CO-R_3$ | O | 2 | |
| 3.227 | H | Cl | $-S-CH(CH_3)COOCH_3$ | H | 1 | $-CO-R_3$ | O | 2 | |
| 3.228 | H | Cl | 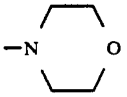 | H | 1 | $-CO-R_3$ | O | 2 | |
| 3.229 | F | Cl | Cl | H | 2 | $-CO-R_3$ | O | 2 | |
| 3.230 | F | Cl | OH | H | 2 | $-CO-R_3$ | O | 2 | |
| 3.231 | F | Cl | $OCH_3$ | H | 2 | $-CO-R_3$ | O | 2 | |
| 3.232 | F | Cl | $-OC_2H_5$ | H | 2 | $-CO-R_3$ | O | 2 | |

TABLE 3-continued

Compounds of formula I wherein W = $W_3$ and $R_{14}$ = H:

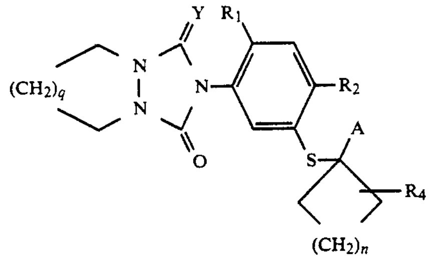

(I)

| Comp. No. | $R_1$ | $R_2$ | $R_3$ | $R_4$ | n | A | Y | q | m.p. [°C.] |
|---|---|---|---|---|---|---|---|---|---|
| 3.233 | F | Cl | 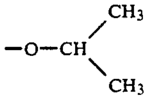 | H | 2 | $-CO-R_3$ | O | 2 | |
| 3.234 | F | Cl | $-O-CH_2-CH_2-O-CH_3$ | H | 2 | $-CO-R_3$ | O | 2 | |
| 3.235 | F | Cl | $-O-CH(CH_3)-CH_2-S-CH_3$ | H | 2 | $-CO-R_3$ | O | 2 | |
| 3.236 | F | Cl | $-O-CH_2-COOCH_3$ | H | 2 | $-CO-R_3$ | O | 2 | |
| 3.237 | F | Cl | $-S-CH_2-COOCH_3$ | H | 2 | $-CO-R_3$ | O | 2 | |
| 3.238 | F | Cl | $-CH_2-CH=CH_2$ | H | 2 | $-CO-R_3$ | O | 2 | |
| 3.239 | F | Cl | $-CH_2-C\equiv CH$ | H | 2 | $-CO-R_3$ | O | 2 | |
| 3.240 | F | Cl | Cl | H | 3 | $-CO-R_3$ | O | 2 | |
| 3.241 | F | Cl | OH | H | 3 | $-CO-R_3$ | O | 2 | |
| 3.242 | F | Cl | $OCH_3$ | H | 3 | $-CO-R_3$ | O | 2 | |
| 3.243 | F | Cl | $OC_2H_5$ | H | 3 | $-CO-R_3$ | O | 2 | |
| 3.244 | F | Cl | 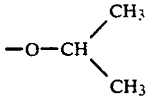 | H | 3 | $-CO-R_3$ | O | 2 | |
| 3.245 | F | Cl | $-O-CH_2-CH_2-O-CH$ | H | 3 | $-CO-R_3$ | O | 2 | |
| 3.246 | F | Cl | $-O-CH(CH_3)-CH_2-S-CH_3$ | H | 3 | $-CO-R_3$ | O | 2 | |
| 3.247 | F | Cl | $-O-CH_2-COOCH_3$ | H | 3 | $-CO-R_3$ | O | 2 | |
| 3.248 | F | Cl | $-S-CH_2-COOCH_3$ | H | 3 | $-CO-R_3$ | O | 2 | |
| 3.249 | F | Cl | $-O-CH_2-C\equiv CH$ | H | 3 | $-CO-R_3$ | O | 2 | |
| 3.250 | F | Cl | $-Cl$ | Cl | 0 | $-CO-R_3$ | O | 2 | |
| 3.251 | F | Cl | $-OH$ | Cl | 0 | $-CO-R_3$ | O | 2 | |
| 3.252 | F | Cl | $-OCH_3$ | Cl | 0 | $-CO-R_3$ | O | 2 | |
| 3.253 | F | Cl | $-OC_2H_5$ | Cl | 0 | $-CO-R_3$ | O | 2 | |
| 3.254 | F | Cl | 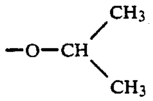 | Cl | 0 | $-CO-R_3$ | O | 2 | |
| 3.255 | F | Cl | $-O-CH_2-COOCH_3$ | Cl | 0 | $-CO-R_3$ | O | 2 | |
| 3.256 | F | Cl | $-S-CH_2-COOCH_3$ | Cl | 0 | $-CO-R_3$ | O | 2 | |
| 3.257 | F | Cl | $-OCH_3$ | Br | 0 | $-CO-R_3$ | O | 2 | |
| 3.258 | F | Cl | 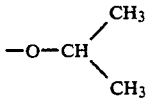 | Br | 0 | $-CO-R_3$ | O | 2 | |
| 3.259 | F | Cl | $-OCH_3$ | F | 0 | $-CO-R_3$ | O | 2 | |
| 3.260 | F | Cl | $-OCH_3$ | $CH_3$ | 0 | $-CO-R_3$ | O | 2 | |
| 3.261 | F | Cl | $-OC_2H_5$ | $CH_3$ | 0 | $-CO-R_3$ | O | 2 | |
| 3.262 | F | Cl | 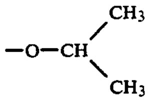 | $CH_3$ | 0 | $-CO-R_3$ | O | 2 | |
| 3.263 | F | Cl | $-O-CH_2-CH_2-O-CH_3$ | $CH_3$ | 0 | $-CO-R_3$ | O | 2 | |
| 3.264 | F | Cl | $-O-CH_2-COOCH_3$ | $CH_3$ | 0 | $-CO-R_3$ | O | 2 | |
| 3.265 | F | Cl | $-O-CH(CH_3)COOCH_3$ | $CH_3$ | 0 | $-CO-R_3$ | O | 2 | |
| 3.266 | F | Cl | $-S-CH_2-COOCH_3$ | $CH_3$ | 0 | $-CO-R_3$ | O | 2 | |
| 3.267 | F | Cl | $-OCH_3$ | $CF_3$ | 0 | $-CO-R_3$ | O | 2 | |
| 3.268 | F | Cl | $-OC_2H_5$ | $CF_3$ | 0 | $-CO-R_3$ | O | 2 | |

TABLE 3-continued

Compounds of formula I wherein W = $W_3$ and $R_{14}$ = H:

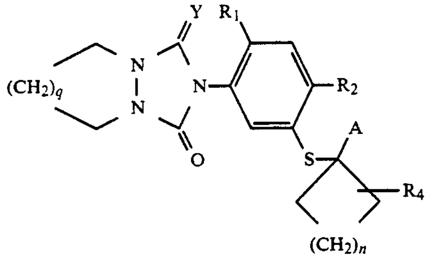

(I)

| Comp. No. | $R_1$ | $R_2$ | $R_3$ | $R_4$ | n | A | Y | q | m.p. [°C.] |
|---|---|---|---|---|---|---|---|---|---|
| 3.269 | F | Cl | $-O-CH(CH_3)_2$ | $CF_3$ | 0 | $-CO-R_3$ | O | 2 | |
| 3.270 | F | Cl | $-O-CH_2-COOCH_3$ | $CF_3$ | 0 | $-CO-R_3$ | O | 2 | |
| 3.271 | F | Cl | $-S-CH_2-COOCH_3$ | $CF_3$ | 0 | $-CO-R_3$ | O | 2 | |
| 3.272 | F | Cl | — | H | 0 | $-CN$ | O | 2 | |
| 3.273 | F | Cl | — | H | 1 | $-CN$ | O | 2 | |
| 3.274 | F | Cl | — | H | 2 | $-CN$ | O | 2 | |
| 3.275 | F | Cl | — | H | 3 | $-CN$ | O | 2 | |
| 3.276 | F | Cl | — | H | 4 | $-CN$ | O | 2 | |
| 3.277 | F | CL | $-OCH_3$ | H | 0 | $-CO-R_3$ | S | 2 | (resinous) |

TABLE 4a

Compounds of formula I wherein W = $W_4$, A = $-CO-R_3$ and $R_{14}$ = H:

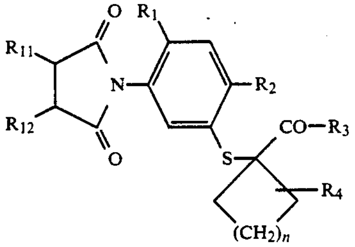

(I)

| Comp. No. | $R_1$ | $R_2$ | $R_3$ | $R_4$ | n | $R_{11}$ | $R_{12}$ | m.p. [°C.] |
|---|---|---|---|---|---|---|---|---|
| 4.001 | F | Cl | $-Cl$ | H | 0 | $-CH_3$ | $-C_2H_5$ | |
| 4.002 | F | Cl | $-OH$ | H | 0 | $-CH_3$ | $-C_2H_5$ | |
| 4.003 | F | Cl | $-OCH_3$ | H | 0 | $-CH_3$ | $-C_2H_5$ | |
| 4.004 | F | Cl | $-OC_2H_5$ | H | 0 | $-CH_3$ | $-C_2H_5$ | |
| 4.005 | F | Cl | $-OC_3H_7$ | H | 0 | $-CH_3$ | $-C_2H_5$ | |
| 4.006 | F | Cl | $-O-CH(CH_3)_2$ | H | 0 | $-CH_3$ | $-C_2H_5$ | |
| 4.007 | F | Cl | $-OC_4H_9$ | H | 0 | $-CH_3$ | $-C_2H_5$ | |
| 4.008 | F | Cl | $-O-CH(CH_3)-C_2H_5$ | H | 0 | $-CH_3$ | $-C_2H_5$ | |
| 4.009 | F | Cl | $-O-CH_2-CH(CH_3)_2$ | H | 0 | $-CH_3$ | $-C_2H_5$ | |
| 4.010 | F | Cl | $-OC_5H_{11}$ | H | 0 | $-CH_3$ | $-C_2H_5$ | |
| 4.011 | F | Cl | $-O-CH_2-CH_2-O-CH_3$ | H | 0 | $-CH_3$ | $-C_2H_5$ | |
| 4.012 | F | Cl | $-O-CH_2-CH_2-O-C_2H_5$ | H | 0 | $-CH_3$ | $-C_2H_5$ | |
| 4.013 | F | Cl | $-O-CH-(CH_3)-CH_2-O-CH_3$ | H | 0 | $-CH_3$ | $-C_2H_5$ | |
| 4.014 | F | Cl | $-O-CH_2-CH_2-S-CH_3$ | H | 0 | $-CH_3$ | $-C_2H_5$ | |
| 4.015 | F | Cl | $-O-CH(CH_3)-CH_2-S-CH_3$ | H | 0 | $-CH_3$ | $-C_2H_5$ | |
| 4.016 | F | Cl | $-O-CH(CH_3)-CH_2-S-C_2H_5$ | H | 0 | $-CH_3$ | $-C_2H_5$ | |
| 4.017 | F | Cl | $-O-CH(CH_3)-CH_2-S-C_3H_7$ | H | 0 | $-CH_3$ | $-C_2H_5$ | |

TABLE 4a-continued

Compounds of formula I wherein W = $W_4$, A = $-CO-R_3$ and $R_{14}$ = H:

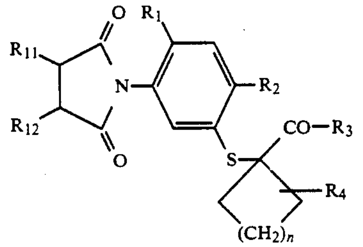

(I)

| Comp. No. | $R_1$ | $R_2$ | $R_3$ | $R_4$ | n | $R_{11}$ | $R_{12}$ | m.p. [°C.] |
|---|---|---|---|---|---|---|---|---|
| 4.018 | F | Cl | 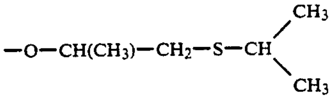 | H | 0 | $-CH_3$ | $-C_2H_5$ | |
| 4.019 | F | Cl | $-O-CH(CH_3)-CH_2-S-C_4H_9$ | H | 0 | $-CH_3$ | $-C_2H_5$ | |
| 4.020 | F | Cl | $-O-CH(CH_3)-CH_2-S-C_5H_{11}$ | H | 0 | $-CH_3$ | $-C_2H_5$ | |
| 4.021 | F | Cl | 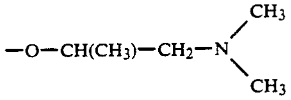 | H | 0 | $-CH_3$ | $-C_2H_5$ | |
| 4.022 | F | Cl | 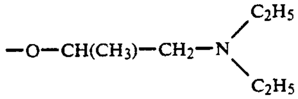 | H | 0 | $-CH_3$ | $-C_2H_5$ | |
| 4.023 | F | Cl | $-NH_2$ | H | 0 | $-CH_3$ | $-C_2H_5$ | |
| 4.024 | F | Cl | 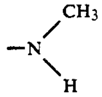 | H | 0 | $-CH_3$ | $-C_2H_5$ | |
| 4.025 | F | Cl | 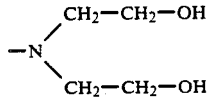 | H | 0 | $-CH_3$ | $-C_2H_5$ | |
| 4.026 | F | Cl | $-NH-CH_2-CH=CH_2$ | H | 0 | $-CH_3$ | $-C_2H_5$ | |
| 4.027 | F | Cl | $-N-(CH_2-CH=CH_2)_2$ | H | 0 | $-CH_3$ | $-C_2H_5$ | |
| 4.028 | F | Cl | 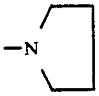 | H | 0 | $-CH_3$ | $-C_2H_5$ | |
| 4.029 | F | Cl | 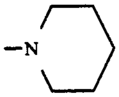 | H | 0 | $-CH_3$ | $-C_2H_5$ | |
| 4.030 | F | Cl | 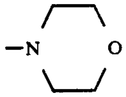 | H | 0 | $-CH_3$ | $-C_2H_5$ | |
| 4.031 | F | Cl | 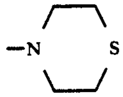 | H | 0 | $-CH_3$ | $-C_2H_5$ | |
| 4.032 | F | Cl | 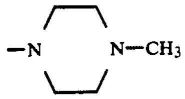 | H | 0 | $-CH_3$ | $-C_2H_5$ | |

TABLE 4a-continued

Compounds of formula I wherein W = $W_4$, A = $-CO-R_3$ and $R_{14}$ = H:

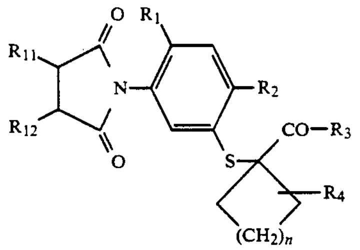

(I)

| Comp. No. | $R_1$ | $R_2$ | $R_3$ | $R_4$ | n | $R_{11}$ | $R_{12}$ | m.p. [°C.] |
|---|---|---|---|---|---|---|---|---|
| 4.033 | F | Cl | 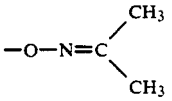 | H | 0 | $-CH_3$ | $-C_2H_5$ | |
| 4.034 | F | Cl | $-O-CH_2-CH_2-Cl$ | H | 0 | $-CH_3$ | $-C_2H_5$ | |
| 4.035 | F | Cl | $-O-CH_2-CN$ | H | 0 | $-CH_3$ | $-C_2H_5$ | |
| 4.036 | F | Cl | 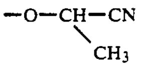 | H | 0 | $-CH_3$ | $-C_2H_5$ | |
| 4.037 | F | Cl | $-O-CH_2-CH=CH_2$ | H | 0 | $-CH_3$ | $-C_2H_5$ | |
| 4.038 | F | Cl | $-O-CH_2-CH=CHCl$ | H | 0 | $-CH_3$ | $-C_2H_5$ | |
| 4.039 | F | Cl | 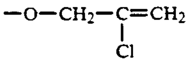 | H | 0 | $-CH_3$ | $-C_2H_5$ | |
| 4.040 | F | Cl | $-O-CH_2=C\equiv CH$ | H | 0 | $-CH_3$ | $-C_2H_5$ | |
| 4.041 | F | Cl | 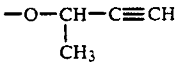 | H | 0 | $-CH_3$ | $-C_2H_5$ | |
| 4.042 | F | Cl | 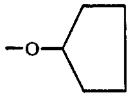 | H | 0 | $-CH_3$ | $-C_2H_5$ | |
| 4.043 | F | Cl | 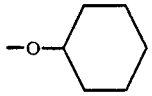 | H | 0 | $-CH_3$ | $-C_2H_5$ | |
| 4.044 | F | Cl | 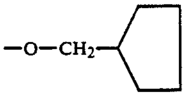 | H | 0 | $-CH_3$ | $-C_2H_5$ | |
| 4.045 | F | Cl | 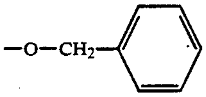 | H | 0 | $-CH_3$ | $-C_2H_5$ | |
| 4.046 | F | Cl | 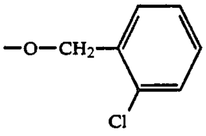 | H | 0 | $-CH_3$ | $-C_2H_5$ | |
| 4.047 | F | Cl | 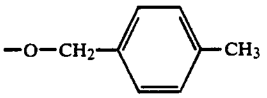 | H | 0 | $-CH_3$ | $-C_2H_5$ | |
| 4.048 | F | Cl | $-S-CH_3$ | H | 0 | $-CH_3$ | $-C_2H_5$ | |

TABLE 4a-continued

Compounds of formula I wherein W = $W_4$, A = $-CO-R_3$ and $R_{14}$ = H:

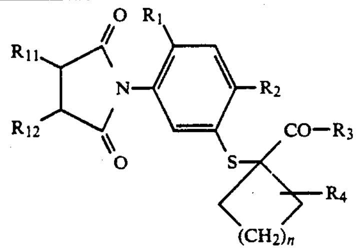

(I)

| Comp. No. | $R_1$ | $R_2$ | $R_3$ | $R_4$ | n | $R_{11}$ | $R_{12}$ | m.p. [°C.] |
|---|---|---|---|---|---|---|---|---|
| 4.049 | F | Cl | $-S-C_2H_5$ | H | 0 | $-CH_3$ | $-C_2H_5$ | |
| 4.050 | F | Cl | $-S-C_3H_7$ | H | 0 | $-CH_3$ | $-C_2H_5$ | |
| 4.051 | F | Cl | $-S-CH_2-CH=CH_2$ | H | 0 | $-CH_3$ | $-C_2H_5$ | |
| 4.052 | F | Cl | $-S-CH_2-COOCH_3$ | H | 0 | $-CH_3$ | $-C_2H_5$ | |
| 4.053 | F | Cl | $-S-CH_2-COOC_2H_5$ | H | 0 | $-CH_3$ | $-C_2H_5$ | |
| 4.054 | F | Cl | $-S-CH_2-COOC_5H_{11}$ | H | 0 | $-CH_3$ | $-C_2H_5$ | |
| 4.055 | F | Cl | $-S-CH(CH_3)-COOCH_3$ | H | 0 | $-CH_3$ | $-C_2H_5$ | |
| 4.056 | F | Cl | $-S-(CH_3)-COOC_2H_5$ | H | 0 | $-CH_3$ | $-C_2H_5$ | |
| 4.057 | F | Cl | $-S-CH(CH_3)-COOC_3H_7$ | H | 0 | $-CH_3$ | $-C_2H_5$ | |
| 4.058 | F | Cl | $-S-CH_2-CH_2-COOCH_3$ | H | 0 | $-CH_3$ | $-C_2H_5$ | |
| 4.059 | F | Cl | $-S-CH_2-COOCH_2-CH_2-O-CH_3$ | H | 0 | $-CH_3$ | $-C_2H_5$ | |
| 4.060 | F | Cl | $-O-CH_2-COOCH_3$ | H | 0 | $-CH_3$ | $-C_2H_5$ | |
| 4.061 | F | Cl | $-O-CH(CH_3)-COOCH_3$ | H | 0 | $-CH_3$ | $-C_2H_5$ | |
| 4.062 | F | Cl | $-O-CH_2-COOC_5H_{11}$ | H | 0 | $-CH_3$ | $-C_2H_5$ | |
| 4.063 | F | Cl | $-O-CH_2-CH_3-Si(CH_3)_3$ | H | 0 | $-CH_3$ | $-C_2H_5$ | |
| 4.064 | F | Cl | $-ONa$ | H | 0 | $-CH_3$ | $-C_2H_5$ | |
| 4.065 | F | Br | $-Cl$ | H | 0 | $-CH_3$ | $-C_2H_5$ | |
| 4.066 | F | Br | $-OH$ | H | 0 | $-CH_3$ | $-C_2H_5$ | |
| 4.067 | F | Br | $-OCH_3$ | H | 0 | $-CH_3$ | $-C_2H_5$ | |
| 4.068 | F | Br | $-OC_2H_5$ | H | 0 | $-CH_3$ | $-C_2H_5$ | |
| 4.069 | F | Br | $-OC_3H_7$ | H | 0 | $-CH_3$ | $-C_2H_5$ | |
| 4.070 | F | Br | 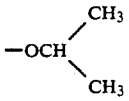 | H | 0 | $-CH_3$ | $-C_2H_5$ | |
| 4.071 | F | Br | $-OC_4H_9$ | H | 0 | $-CH_3$ | $-C_2H_5$ | |
| 4.072 | F | Br | $-OCH(CH_3)-CH_2-CH_3$ | H | 0 | $-CH_3$ | $-C_2H_5$ | |
| 4.073 | F | Br | 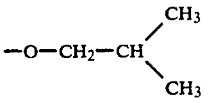 | H | 0 | $-CH_3$ | $-C_2H_5$ | |
| 4.074 | F | Br | $-O-C_5H_{11}$ | H | 0 | $-CH_3$ | $-C_2H_5$ | |
| 4.075 | F | Br | $-O-CH_2-CH_2-O-CH_3$ | H | 0 | $-CH_3$ | $-C_2H_5$ | |
| 4.076 | F | Br | $-O-CH_2-CH_2-O-C_2H_5$ | H | 0 | $-CH_3$ | $-C_2H_5$ | |
| 4.077 | F | Br | $-O-CH(CH_3)-CH_2-O-CH_3$ | H | 0 | $-CH_3$ | $-C_2H_5$ | |
| 4.078 | F | Br | $-O-CH_2-CH_2-S-CH_3$ | H | 0 | $-CH_3$ | $-C_2H_5$ | |
| 4.079 | F | Br | $-O-CH_2(CH_3)-S-CH_3$ | H | 0 | $-CH_3$ | $-C_2H_5$ | |
| 4.080 | F | Br | $-O-CH-(CH_3)-S-C_2H_5$ | H | 0 | $-CH_3$ | $-C_2H_5$ | |
| 4.081 | F | Br | $-O-CH(CH_3)-S-C_3H_7$ | H | 0 | $-CH_3$ | $-C_2H_5$ | |
| 4.082 | F | Br | 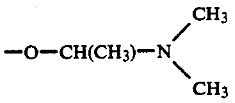 | H | 0 | $-CH_3$ | $-C_2H_5$ | |
| 4.083 | F | Br | $-NH_2$ | H | 0 | $-CH_3$ | $-C_2H_5$ | |
| 4.084 | F | Br | 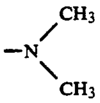 | H | 0 | $-CH_3$ | $-C_2H_5$ | |
| 4.085 | F | Br | 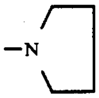 | H | 0 | $-CH_3$ | $-C_2H_5$ | |

TABLE 4a-continued

Compounds of formula I wherein $W = W_4$, $A = -CO-R_3$ and $R_{14} = H$:

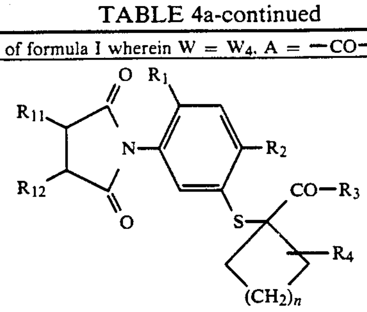

(I)

| Comp. No. | $R_1$ | $R_2$ | $R_3$ | $R_4$ | n | $R_{11}$ | $R_{12}$ | m.p. [°C.] |
|---|---|---|---|---|---|---|---|---|
| 4.086 | F | Br | 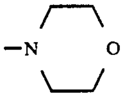 | H | 0 | $-CH_3$ | $-C_2H_5$ | |
| 4.087 | F | Br | 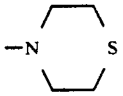 | H | 0 | $-CH_3$ | $-C_2H_5$ | |
| 4.088 | F | Br | 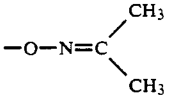 | H | 0 | $-CH_3$ | $-C_2H_5$ | |
| 4.089 | F | Br | $-O-CH_2-CH_2-Cl$ | H | 0 | $-CH_3$ | $-C_2H_5$ | |
| 4.090 | F | Br | $-O-CH_2-CN$ | H | 0 | $-CH_3$ | $-C_2H_5$ | |
| 4.091 | F | Br | $-O-CH_2-CH=CH_2$ | H | 0 | $-CH_3$ | $-C_2H_5$ | |
| 4.092 | F | Br | $-O-CH_2-C\equiv CH$ | H | 0 | $-CH_3$ | $-C_2H_5$ | |
| 4.093 | F | Br | 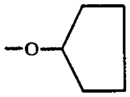 | H | 0 | $-CH_3$ | $-C_2H_5$ | |
| 4.094 | F | Br | 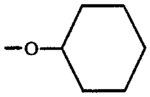 | H | 0 | $-CH_3$ | $-C_2H_5$ | |
| 4.095 | F | Br | 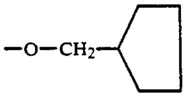 | H | 0 | $-CH_3$ | $-C_2H_5$ | |
| 4.096 | F | Br | 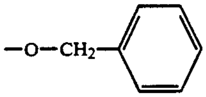 | H | 0 | $-CH_3$ | $-C_2H_5$ | |
| 4.097 | F | Br | $-SCH_3$ | H | 0 | $-CH_3$ | $-C_2H_5$ | |
| 4.098 | F | Br | $-S-CH_2-COOCH_3$ | H | 0 | $-CH_3$ | $-C_2H_5$ | |
| 4.099 | F | Br | $-S-CH(CH_3)-COOCH_3$ | H | 0 | $-CH_3$ | $-C_2H_5$ | |
| 4.100 | F | Br | $-O-CH_2-COOCH_3$ | H | 0 | $-CH_3$ | $-C_2H_5$ | |
| 4.101 | F | Br | $-O-CH(CH_3)COOCH_3$ | H | 0 | $-CH_3$ | $-C_2H_5$ | |
| 4.102 | F | CN | $-Cl$ | H | 0 | $-CH_3$ | $-C_2H_5$ | |
| 4.103 | F | CN | $-OH$ | H | 0 | $-CH_3$ | $-C_2H_5$ | |
| 4.104 | F | CN | $-OCH_3$ | H | 0 | $-CH_3$ | $-C_2H_5$ | |
| 4.105 | H | Cl | $-Cl$ | H | 0 | $-CH_3$ | $-C_2H_5$ | |
| 4.106 | H | Cl | $-OH$ | H | 0 | $-CH_3$ | $-C_2H_5$ | |
| 4.107 | H | Cl | $-OCH_3$ | H | 0 | $-CH_3$ | $-C_2H_5$ | |
| 4.108 | H | Cl | $-OC_2H_5$ | H | 0 | $-CH_3$ | $-C_2H_5$ | |
| 4.109 | H | Cl | 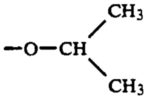 | H | 0 | $-CH_3$ | $-C_2H_5$ | |
| 4.110 | H | Cl | $-O-CH_2-COOCH_3$ | H | 0 | $-CH_3$ | $-C_2H_5$ | |

TABLE 4a-continued

Compounds of formula I wherein $W = W_4$, $A = -CO-R_3$ and $R_{14} = H$:

(I)

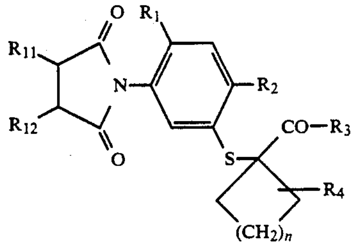

| Comp. No. | $R_1$ | $R_2$ | $R_3$ | $R_4$ | n | $R_{11}$ | $R_{12}$ | m.p. [°C.] |
|---|---|---|---|---|---|---|---|---|
| 4.111 | H | Cl | $-O-CH(CH_3)COOCH_3$ | H | 0 | $-CH_3$ | $-C_2H_5$ | |
| 4.112 | H | Cl | $-S-CH_2-COOCH_3$ | H | 0 | $-CH_3$ | $-C_2H_5$ | |
| 4.113 | H | Cl | $-S-CH(CH_3)COOCH_3$ | H | 0 | $-CH_3$ | $-C_2H_5$ | |
| 4.114 | H | Cl | 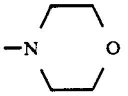 | H | 0 | $-CH_3$ | $-C_2H_5$ | |
| 4.115 | F | Cl | $-Cl$ | H | 1 | $-CH_3$ | $-C_2H_5$ | |
| 4.116 | F | Cl | $-OH$ | H | 1 | $-CH_3$ | $-C_2H_5$ | |
| 4.117 | F | Cl | $-OCH_3$ | H | 1 | $-CH_3$ | $-C_2H_5$ | 53-58 |
| 4.118 | F | Cl | $-OC_2H_5$ | H | 1 | $-CH_3$ | $-C_2H_5$ | |
| 4.119 | F | Cl | $-OC_3H_7$ | H | 1 | $-CH_3$ | $-C_2H_5$ | |
| 4.120 | F | Cl | 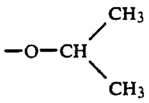 | H | 1 | $-CH_3$ | $-C_2H_5$ | |
| 4.121 | F | Cl | $-OC_4H_9$ | H | 1 | $-CH_3$ | $-C_2H_5$ | |
| 4.122 | F | Cl | $-O-CH(CH_3)-C_2H_5$ | H | 1 | $-CH_3$ | $-C_2H_5$ | |
| 4.123 | F | Cl | 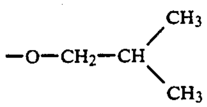 | H | 1 | $-CH_3$ | $-C_2H_5$ | |
| 4.124 | F | Cl | $-OC_5H_{11}$ | H | 1 | $-CH_3$ | $-C_2H_5$ | |
| 4.125 | F | Cl | $-O-CH_2-CH_2-O-CH_3$ | H | 1 | $-CH_3$ | $-C_2H_5$ | |
| 4.126 | F | Cl | $-O-CH_2-CH_2-O-C_2H_5$ | H | 1 | $-CH_3$ | $-C_2H_5$ | |
| 4.127 | F | Cl | $-O-CH-(CH_3)-CH_2-O-CH_3$ | H | 1 | $-CH_3$ | $-C_2H_5$ | |
| 4.128 | F | Cl | $-O-CH_2-CH_2-S-CH_3$ | H | 1 | $-CH_3$ | $-C_2H_5$ | |
| 4.129 | F | Cl | $-O-CH(CH_3)-CH_2-S-CH_3$ | H | 1 | $-CH_3$ | $-C_2H_5$ | |
| 4.130 | F | Cl | $-O-CH(CH_3)-CH_2-S-C_2H_5$ | H | 1 | $-CH_3$ | $-C_2H_5$ | |
| 4.131 | F | Cl | $-O-CH(CH_3)-CH_2-S-C_3H_7$ | H | 1 | $-CH_3$ | $-C_2H_5$ | |
| 4.132 | F | Cl | 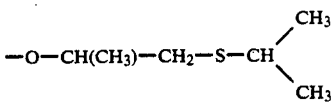 | H | 1 | $-CH_3$ | $-C_2H_5$ | |
| 4.133 | F | Cl | $-O-CH(CH_3)-CH_2-S-C_4H_9$ | H | 1 | $-CH_3$ | $-C_2H_5$ | |
| 4.134 | F | Cl | $-O-CH(CH_3)-CH_2-S-C_5H_{11}$ | H | 1 | $-CH_3$ | $-C_2H_5$ | |
| 4.135 | F | Cl | 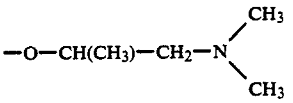 | H | 1 | $-CH_3$ | $-C_2H_5$ | |
| 4.136 | F | Cl | 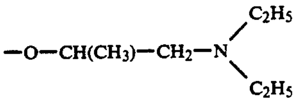 | H | 1 | $-CH_3$ | $-C_2H_5$ | |
| 4.137 | F | Cl | $-NH_2$ | H | 1 | $-CH_3$ | $-C_2H_5$ | |
| 4.138 | F | Cl | 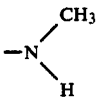 | H | 1 | $-CH_3$ | $-C_2H_5$ | |

TABLE 4a-continued

Compounds of formula I wherein W = $W_4$, A = $-CO-R_3$ and $R_{14}$ = H:

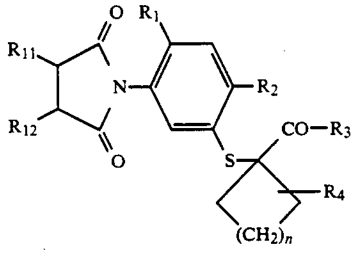

(I)

| Comp. No. | $R_1$ | $R_2$ | $R_3$ | $R_4$ | n | $R_{11}$ | $R_{12}$ | m.p. [°C.] |
|---|---|---|---|---|---|---|---|---|
| 4.139 | F | Cl | 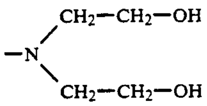 | H | 1 | $-CH_3$ | $-C_2H_5$ | |
| 4.140 | F | Cl | $-NH-CH_2-CH=CH_2$ | H | 1 | $-CH_3$ | $-C_2H_5$ | |
| 4.141 | F | Cl | $-N-(CH_2-CH=CH_2)_2$ | H | 1 | $-CH_3$ | $-C_2H_5$ | |
| 4.142 | F | Cl | 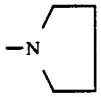 | H | 1 | $-CH_3$ | $-C_2H_5$ | |
| 4.143 | F | Cl | 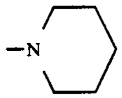 | H | 1 | $-CH_3$ | $-C_2H_5$ | |
| 4.144 | F | Cl | 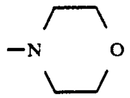 | H | 1 | $-CH_3$ | $-C_2H_5$ | |
| 4.145 | F | Cl | 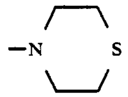 | H | 1 | $-CH_3$ | $-C_2H_5$ | |
| 4.146 | F | Cl | 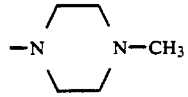 | H | 1 | $-CH_3$ | $-C_2H_5$ | |
| 4.147 | F | Cl | 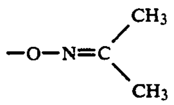 | H | 1 | $-CH_3$ | $-C_2H_5$ | |
| 4.148 | F | Cl | $-O-CH_2-CH_2-Cl$ | H | 1 | $-CH_3$ | $-C_2H_5$ | |
| 4.149 | F | Cl | $-O-CH_2-CN$ | H | 1 | $-CH_3$ | $-C_2H_5$ | |
| 4.150 | F | Cl | 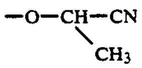 | H | 1 | $-CH_3$ | $-C_2H_5$ | |
| 4.151 | F | Cl | $-O-CH_2-CH=CH_2$ | H | 1 | $-CH_3$ | $-C_2H_5$ | |
| 4.152 | F | Cl | $-O-CH_2-CH=CHCl$ | H | 1 | $-CH_3$ | $-C_2H_5$ | |
| 4.153 | F | Cl | 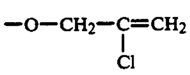 | H | 1 | $-CH_3$ | $-C_2H_5$ | |
| 4.154 | F | Cl | $-O-CH_2=C\equiv CH$ | H | 1 | $-CH_3$ | $-C_2H_5$ | |
| 4.155 | F | Cl | 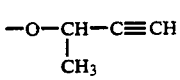 | H | 1 | $-CH_3$ | $-C_2H_5$ | |

TABLE 4a-continued

Compounds of formula I wherein W = $W_4$, A = $-CO-R_3$ and $R_{14}$ = H:

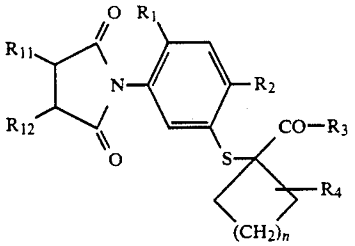

(I)

| Comp. No. | $R_1$ | $R_2$ | $R_3$ | $R_4$ | n | $R_{11}$ | $R_{12}$ | m.p. [°C.] |
|---|---|---|---|---|---|---|---|---|
| 4.156 | F | Cl | 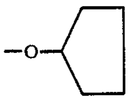 | H | 1 | $-CH_3$ | $-C_2H_5$ | |
| 4.157 | F | Cl | 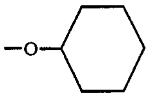 | H | 1 | $-CH_3$ | $-C_2H_5$ | |
| 4.158 | F | Cl | 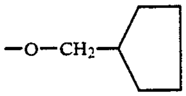 | H | 1 | $-CH_3$ | $-C_2H_5$ | |
| 4.159 | F | Cl | 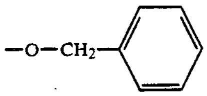 | H | 1 | $-CH_3$ | $-C_2H_5$ | |
| 4.160 | F | Cl | 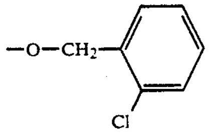 | H | 1 | $-CH_3$ | $-C_2H_5$ | |
| 4.161 | F | Cl | 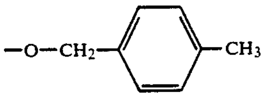 | H | 1 | $-CH_3$ | $-C_2H_5$ | |
| 4.162 | F | Cl | $-S-CH_3$ | H | 1 | $-CH_3$ | $-C_2H_5$ | |
| 4.163 | F | Cl | $-S-C_2H_5$ | H | 1 | $-CH_3$ | $-C_2H_5$ | |
| 4.164 | F | Cl | $-S-C_3H_7$ | H | 1 | $-CH_3$ | $-C_2H_5$ | |
| 4.165 | F | Cl | $-S-CH_2-CH=CH_2$ | H | 1 | $-CH_3$ | $-C_2H_5$ | |
| 4.166 | F | Cl | $-S-CH_2-COOCH_3$ | H | 1 | $-CH_3$ | $-C_2H_5$ | |
| 4.167 | F | Cl | $-S-CH_2-COOC_2H_5$ | H | 1 | $-CH_3$ | $-C_2H_5$ | |
| 4.168 | F | Cl | $-S-CH_2-COOC_5H_{11}$ | H | 1 | $-CH_3$ | $-C_2H_5$ | |
| 4.169 | F | Cl | $-S-CH(CH_3)-COOCH_3$ | H | 1 | $-CH_3$ | $-C_2H_5$ | |
| 4.170 | F | Cl | $-S-(CH_3)-COOC_2H_5$ | H | 1 | $-CH_3$ | $-C_2H_5$ | |
| 4.171 | F | Cl | $-S-CH(CH_3)-COOC_3H_7$ | H | 1 | $-CH_3$ | $-C_2H_5$ | |
| 4.172 | F | Cl | $-S-CH_2-CH_2-COOCH_3$ | H | 1 | $-CH_3$ | $-C_2H_5$ | |
| 4.173 | F | Cl | $-S-CH_2-COOCH_2-CH_2-O-CH_3$ | H | 1 | $-CH_3$ | $-C_2H_5$ | |
| 4.174 | F | Cl | $-O-CH_2-COOCH_3$ | H | 1 | $-CH_3$ | $-C_2H_5$ | |
| 4.175 | F | Cl | $-O-CH(CH_3)-COOCH_3$ | H | 1 | $-CH_3$ | $-C_2H_5$ | |
| 4.176 | F | Cl | $-O-CH_2-COOC_5H_{11}$ | H | 1 | $-CH_3$ | $-C_2H_5$ | |
| 4.177 | F | Cl | $-O-CH_2-CH_3-Si(CH_3)_3$ | H | 1 | $-CH_3$ | $-C_2H_5$ | |
| 4.178 | F | Cl | $-ONa$ | H | 1 | $-CH_3$ | $-C_2H_5$ | |
| 4.179 | F | Br | $-Cl$ | H | 1 | $-CH_3$ | $-C_2H_5$ | |
| 4.180 | F | Br | $-OH$ | H | 1 | $-CH_3$ | $-C_2H_5$ | |
| 4.181 | F | Br | $-OCH_3$ | H | 1 | $-CH_3$ | $-C_2H_5$ | |
| 4.182 | F | Br | $-OC_2H_5$ | H | 1 | $-CH_3$ | $-C_2H_5$ | |
| 4.183 | F | Br | $-OC_3H_7$ | H | 1 | $-CH_3$ | $-C_2H_5$ | |

TABLE 4a-continued

Compounds of formula I wherein W = $W_4$, A = $-CO-R_3$ and $R_{14}$ = H:

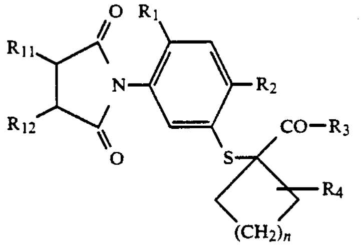

(I)

| Comp. No. | $R_1$ | $R_2$ | $R_3$ | $R_4$ | n | $R_{11}$ | $R_{12}$ | m.p. [°C.] |
|---|---|---|---|---|---|---|---|---|
| 4.184 | F | Br | 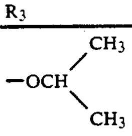 | H | 1 | $-CH_3$ | $-C_2H_5$ | |
| 4.185 | F | Br | $-OC_4H_9$ | H | 1 | $-CH_3$ | $-C_2H_5$ | |
| 4.186 | F | Br | $-OCH(CH_3)-CH_2-CH_3$ | H | 1 | $-CH_3$ | $-C_2H_5$ | |
| 4.187 | F | Br | 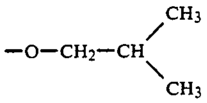 | H | 1 | $-CH_3$ | $-C_2H_5$ | |
| 4.188 | F | Br | $-O-C_5H_{11}$ | H | 1 | $-CH_3$ | $-C_2H_5$ | |
| 4.189 | F | Br | $-O-CH_2-CH_2-O-CH_3$ | H | 1 | $-CH_3$ | $-C_2H_5$ | |
| 4.190 | F | Br | $-O-CH_2-CH_2-O-C_2H_5$ | H | 1 | $-CH_3$ | $-C_2H_5$ | |
| 4.191 | F | Br | $-O-CH(CH_3)-CH_2-O-CH_3$ | H | 1 | $-CH_3$ | $-C_2H_5$ | |
| 4.192 | F | Br | $-O-CH_2-CH_2-S-CH_3$ | H | 1 | $-CH_3$ | $-C_2H_5$ | |
| 4.193 | F | Br | $-O-CH_2(CH_3)-S-CH_3$ | H | 1 | $-CH_3$ | $-C_2H_5$ | |
| 4.194 | F | Br | $-O-CH-(CH_3)-S-C_2H_5$ | H | 1 | $-CH_3$ | $-C_2H_5$ | |
| 4.195 | F | Br | $-O-CH(CH_3)-S-C_3H_7$ | H | 1 | $-CH_3$ | $-C_2H_5$ | |
| 4.196 | F | Br | 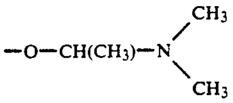 | H | 1 | $-CH_3$ | $-C_2H_5$ | |
| 4.197 | F | Br | $-NH_2$ | H | 1 | $-CH_3$ | $-C_2H_5$ | |
| 4.198 | F | Br | 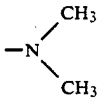 | H | 1 | $-CH_3$ | $-C_2H_5$ | |
| 4.199 | F | Br | 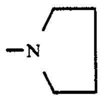 | H | 1 | $-CH_3$ | $-C_2H_5$ | |
| 4.200 | F | Br | 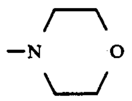 | H | 1 | $-CH_3$ | $-C_2H_5$ | |
| 4.201 | F | Br | 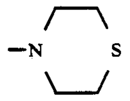 | H | 1 | $-CH_3$ | $-C_2H_5$ | |
| 4.202 | F | Br | 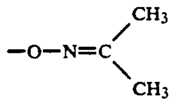 | H | 1 | $-CH_3$ | $-C_2H_5$ | |
| 4.203 | F | Br | $-O-CH_2-CH_2-Cl$ | H | 1 | $-CH_3$ | $-C_2H_5$ | |
| 4.204 | F | Br | $-O-CH_2-CN$ | H | 1 | $-CH_3$ | $-C_2H_5$ | |
| 4.205 | F | Br | $-O-CH_2-CH=CH_2$ | H | 1 | $-CH_3$ | $-C_2H_5$ | |
| 4.206 | F | Br | $-O-CH_2-C\equiv CH$ | | | | | |

TABLE 4a-continued

Compounds of formula I wherein $W = W_4$. $A = -CO-R_3$ and $R_{14} = H$:

(I)

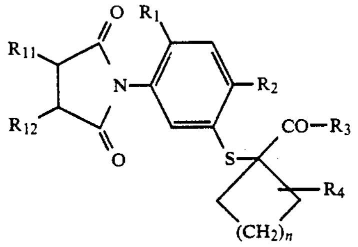

| Comp. No. | $R_1$ | $R_2$ | $R_3$ | $R_4$ | n | $R_{11}$ | $R_{12}$ | m.p. [°C.] |
|---|---|---|---|---|---|---|---|---|
| 4.207 | F | Br | 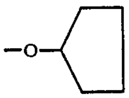 | H | 1 | $-CH_3$ | $-C_2H_5$ | |
| 4.208 | F | Br | 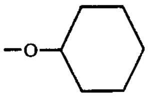 | H | 1 | $-CH_3$ | $-C_2H_5$ | |
| 4.209 | F | Br | 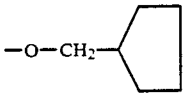 | H | 1 | $-CH_3$ | $-C_2H_5$ | |
| 4.210 | F | Br | 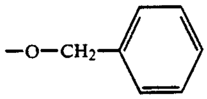 | H | 1 | $-CH_3$ | $-C_2H_5$ | |
| 4.211 | F | Br | $-SCH_3$ | H | 1 | $-CH_3$ | $-C_2H_5$ | |
| 4.212 | F | Br | $-S-CH_2-COOCH_3$ | H | 1 | $-CH_3$ | $-C_2H_5$ | |
| 4.213 | F | Br | $-S-CH(CH_3)-COOCH_3$ | H | 1 | $-CH_3$ | $-C_2H_5$ | |
| 4.214 | F | Br | $-O-CH_2-COOCH_3$ | H | 1 | $-CH_3$ | $-C_2H_5$ | |
| 4.215 | F | Br | $-O-CH(CH_3)COOCH_3$ | H | 1 | $-CH_3$ | $-C_2H_5$ | |
| 4.216 | F | CN | $-Cl$ | H | 1 | $-CH_3$ | $-C_2H_5$ | |
| 4.217 | F | CN | $-OH$ | H | 1 | $-CH_3$ | $-C_2H_5$ | |
| 4.218 | F | CN | $-OCH_3$ | H | 1 | $-CH_3$ | $-C_2H_5$ | |
| 4.219 | H | Cl | $-Cl$ | H | 1 | $-CH_3$ | $-C_2H_5$ | |
| 4.220 | H | Cl | $-OH$ | H | 1 | $-CH_3$ | $-C_2H_5$ | |
| 4.221 | H | Cl | $-OCH_3$ | H | 1 | $-CH_3$ | $-C_2H_5$ | |
| 4.222 | H | Cl | $-OC_2H_5$ | H | 1 | $-CH_3$ | $-C_2H_5$ | |
| 4.223 | H | Cl | 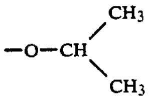 | H | 1 | $-CH_3$ | $-C_2H_5$ | |
| 4.224 | H | Cl | $-O-CH_2-COOCH_3$ | H | 1 | $-CH_3$ | $-C_2H_5$ | |
| 4.225 | H | Cl | $-O-CH(CH_3)COOCH_3$ | H | 1 | $-CH_3$ | $-C_2H_5$ | |
| 4.226 | H | Cl | $-S-CH_2-COOCH_3$ | H | 1 | $-CH_3$ | $-C_2H_5$ | |
| 4.227 | H | Cl | $-S-CH(CH_3)COOCH_3$ | H | 1 | $-CH_3$ | $-C_2H_5$ | |
| 4.228 | H | Cl | 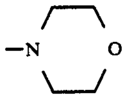 | H | 1 | $-CH_3$ | $-C_2H_5$ | |
| 4.229 | F | Cl | Cl | H | 2 | $-CH_3$ | $-C_2H_5$ | |
| 4.230 | F | Cl | OH | H | 2 | $-CH_3$ | $-C_2H_5$ | |
| 4.231 | F | Cl | $OCH_3$ | H | 2 | $-CH_3$ | $-C_2H_5$ | |
| 4.232 | F | Cl | $-OC_2H_5$ | H | 2 | $-CH_3$ | $-C_2H_5$ | |
| 4.233 | F | Cl | 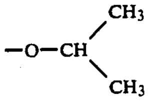 | H | 2 | $-CH_3$ | $-C_2H_5$ | |
| 4.234 | F | Cl | $-O-CH_2-CH_2-O-CH_3$ | H | 2 | $-CH_3$ | $-C_2H_5$ | |
| 4.235 | F | Cl | $-O-CH(CH_3)-CH_2-S-CH_3$ | H | 2 | $-CH_3$ | $-C_2H_5$ | |

TABLE 4a-continued

Compounds of formula I wherein W = $W_4$, A = $-CO-R_3$ and $R_{14}$ = H:

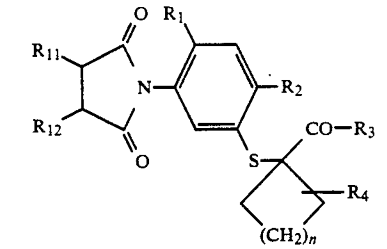

(I)

| Comp. No. | $R_1$ | $R_2$ | $R_3$ | $R_4$ | n | $R_{11}$ | $R_{12}$ | m.p. [°C.] |
|---|---|---|---|---|---|---|---|---|
| 4.236 | F | Cl | $-O-CH_2-COOCH_3$ | H | 2 | $-CH_3$ | $-C_2H_5$ | |
| 4.237 | F | Cl | $-S-CH_2-COOCH_3$ | H | 2 | $-CH_3$ | $-C_2H_5$ | |
| 4.238 | F | Cl | $-CH_2-CH=CH_2$ | H | 2 | $-CH_3$ | $-C_2H_5$ | |
| 4.239 | F | Cl | $-CH_2-C\equiv CH$ | H | 2 | $-CH_3$ | $-C_2H_5$ | |
| 4.240 | F | Cl | Cl | H | 3 | $-CH_3$ | $-C_2H_5$ | |
| 4.241 | F | Cl | OH | H | 3 | $-CH_3$ | $-C_2H_5$ | |
| 4.242 | F | Cl | $OCH_3$ | H | 3 | $-CH_3$ | $-C_2H_5$ | |
| 4.243 | F | Cl | $OC_2H_5$ | H | 3 | $-CH_3$ | $-C_2H_5$ | |
| 4.244 | F | Cl | 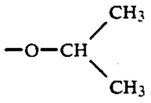 | H | 3 | $-CH_3$ | $-C_2H_5$ | |
| 4.245 | F | Cl | $-O-CH_2-CH_2-O-CH$ | H | 3 | $-CH_3$ | $-C_2H_5$ | |
| 4.246 | F | Cl | $-O-CH(CH_3)-CH_2-S-CH_3$ | H | 3 | $-CH_3$ | $-C_2H_5$ | |
| 4.247 | F | Cl | $-O-CH_2-COOCH_3$ | H | 3 | $-CH_3$ | $-C_2H_5$ | |
| 4.248 | F | Cl | $-S-CH_2-COOCH_3$ | H | 3 | $-CH_3$ | $-C_2H_5$ | |
| 4.249 | F | Cl | $-O-CH_2-C\equiv CH$ | H | 3 | $-CH_3$ | $-C_2H_5$ | |
| 4.250 | F | Cl | $-Cl$ | Cl | 0 | $-CH_3$ | $-C_2H_5$ | |
| 4.251 | F | Cl | $-OH$ | Cl | 0 | $-CH_3$ | $-C_2H_5$ | |
| 4.252 | F | Cl | $-OCH_3$ | Cl | 0 | $-CH_3$ | $-C_2H_5$ | |
| 4.253 | F | Cl | $-OC_2H_5$ | Cl | 0 | $-CH_3$ | $-C_2H_5$ | |
| 4.254 | F | Cl | 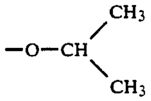 | Cl | 0 | $-CH_3$ | $-C_2H_5$ | |
| 4.255 | F | Cl | $-O-CH_2-COOCH_3$ | Cl | 0 | $-CH_3$ | $-C_2H_5$ | |
| 4.256 | F | Cl | $-S-CH_2-COOCH_3$ | Cl | 0 | $-CH_3$ | $-C_2H_5$ | |
| 4.257 | F | Cl | $-OCH_3$ | Br | 0 | $-CH_3$ | $-C_2H_5$ | |
| 4.258 | F | Cl | 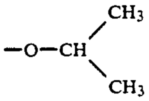 | Br | 0 | $-CH_3$ | $-C_2H_5$ | |
| 4.259 | F | Cl | $-OCH_3$ | F | 0 | $-CH_3$ | $-C_2H_5$ | |
| 4.260 | F | Cl | $-OCH_3$ | $CH_3$ | 0 | $-CH_3$ | $-C_2H_5$ | |
| 4.261 | F | Cl | $-OC_2H_5$ | $CH_3$ | 0 | $-CH_3$ | $-C_2H_5$ | |
| 4.262 | F | Cl | 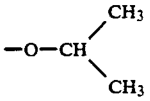 | $CH_3$ | 0 | $-CH_3$ | $-C_2H_5$ | |
| 4.263 | F | Cl | $-O-CH_2-CH_2-O-CH_3$ | $CH_3$ | 0 | $-CH_3$ | $-C_2H_5$ | |
| 4.264 | F | Cl | $-O-CH_2-COOCH_3$ | $CH_3$ | 0 | $-CH_3$ | $-C_2H_5$ | |
| 4.265 | F | Cl | $-O-CH(CH_3)COOCH_3$ | $CH_3$ | 0 | $-CH_3$ | $-C_2H_5$ | |
| 4.266 | F | Cl | $-S-CH_2-COOCH_3$ | $CH_3$ | 0 | $-CH_3$ | $-C_2H_5$ | |
| 4.267 | F | Cl | $-OCH_3$ | $CF_3$ | 0 | $-CH_3$ | $-C_2H_5$ | |
| 4.268 | F | Cl | $-OC_2H_5$ | $CF_3$ | 0 | $-CH_3$ | $-C_2H_5$ | |
| 4.269 | F | Cl | 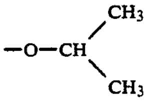 | $CF_3$ | 0 | $-CH_3$ | $-C_2H_5$ | |
| 4.270 | F | Cl | $-O-CH_2-COOCH_3$ | $CF_3$ | 0 | $-CH_3$ | $-C_2H_5$ | |
| 4.271 | F | Cl | $-S-CH_2-COOCH_3$ | $CF_3$ | 0 | $-CH_3$ | $-C_2H_5$ | |

TABLE 4b

Compounds of formula I wherein W = $W_4$, A = —CN and $R_{14}$ = H:

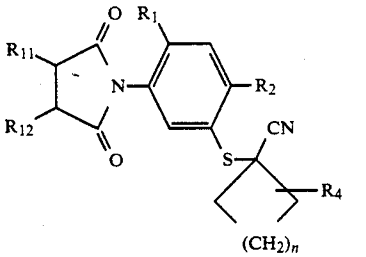

(I)

TABLE 4b-continued

| Comp. No. | $R_1$ | $R_2$ | $R_3$ | $R_4$ | n | $R_{11}$ | $R_{12}$ | m.p. [°C.] |
|---|---|---|---|---|---|---|---|---|
| 4.272 | F | Cl | — | H | 0 | $-CH_3$ | $-C_2H_5$ | |
| 4.273 | F | Cl | — | H | 1 | $-CH_3$ | $-C_2H_5$ | |
| 4.274 | F | Cl | — | H | 2 | $-CH_3$ | $-C_2H_5$ | |
| 4.275 | F | Cl | — | H | 3 | $-CH_3$ | $-C_2H_5$ | |
| 4.276 | F | Cl | — | H | 4 | $-CH_3$ | $-C_2H_5$ | |

TABLE 5a

Compounds of formula I wherein W = $W_5$, R = $-CO-R_3$ and $R_{14}$ = H:

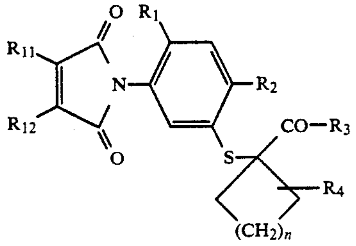

(I)

| Comp. No. | $R_1$ | $R_2$ | $R_3$ | $R_4$ | n | $R_{11}$ | $R_{12}$ | m.p. [°C.] |
|---|---|---|---|---|---|---|---|---|
| 5.001 | F | Cl | $-Cl$ | H | 0 | $-CH_3$ | $-C_2H_5$ | |
| 5.002 | F | Cl | $-OH$ | H | 0 | $-CH_3$ | $-C_2H_5$ | |
| 5.003 | F | Cl | $-OCH_3$ | H | 0 | $-CH_3$ | $-C_2H_5$ | |
| 5.004 | F | Cl | $-OC_2H_5$ | H | 0 | $-CH_3$ | $-C_2H_5$ | |
| 5.005 | F | Cl | $-OC_3H_7$ | H | 0 | $-CH_3$ | $-C_2H_5$ | |
| 5.006 | F | Cl | $-O-CH{<}^{CH_3}_{CH_3}$ | H | 0 | $-CH_3$ | $-C_2H_5$ | |
| 5.007 | F | Cl | $-OC_4H_9$ | H | 0 | $-CH_3$ | $-C_2H_5$ | |
| 5.008 | F | Cl | $-O-CH(CH_3)-C_2H_5$ | H | 0 | $-CH_3$ | $-C_2H_5$ | |
| 5.009 | F | Cl | $-O-CH_2-CH{<}^{CH_3}_{CH_3}$ | H | 0 | $-CH_3$ | $-C_2H_5$ | |
| 5.010 | F | Cl | $-OC_5H_{11}$ | H | 0 | $-CH_3$ | $-C_2H_5$ | |
| 5.011 | F | Cl | $-O-CH_2-CH_2-O-CH_3$ | H | 0 | $-CH_3$ | $-C_2H_5$ | |
| 5.012 | F | Cl | $-O-CH_2-CH_2-O-C_2H_5$ | H | 0 | $-CH_3$ | $-C_2H_5$ | |
| 5.013 | F | Cl | $-O-CH-(CH_3)-CH_2-O-CH_3$ | H | 0 | $-CH_3$ | $-C_2H_5$ | |
| 5.014 | F | Cl | $-O-CH_2-CH_2-S-CH_3$ | H | 0 | $-CH_3$ | $-C_2H_5$ | |
| 5.015 | F | Cl | $-O-CH(CH_3)-CH_2-S-CH_3$ | H | 0 | $-CH_3$ | $-C_2H_5$ | |
| 5.016 | F | Cl | $-O-CH(CH_3)-CH_2-S-C_2H_5$ | H | 0 | $-CH_3$ | $-C_2H_5$ | |
| 5.017 | F | Cl | $-O-CH(CH_3)-CH_2-S-C_3H_7$ | H | 0 | $-CH_3$ | $-C_2H_5$ | |
| 5.018 | F | Cl | $-O-CH(CH_3)-CH_2-S-CH{<}^{CH_3}_{CH_3}$ | H | 0 | $-CH_3$ | $-C_2H_5$ | |
| 5.019 | F | Cl | $-O-CH(CH_3)-CH_2-S-C_4H_9$ | H | 0 | $-CH_3$ | $-C_2H_5$ | |
| 5.020 | F | Cl | $-O-CH(CH_3)-CH_2-S-C_5H_{11}$ | H | 0 | $-CH_3$ | $-C_2H_5$ | |
| 5.021 | F | Cl | $-O-CH(CH_3)-CH_2-N{<}^{CH_3}_{CH_3}$ | H | 0 | $-CH_3$ | $-C_2H_5$ | |
| 5.022 | F | Cl | $-O-CH(CH_3)-CH_2-N{<}^{C_2H_5}_{C_2H_5}$ | H | 0 | $-CH_3$ | $-C_2H_5$ | |

TABLE 5a-continued

Compounds of formula I wherein W = $W_5$, R = $-CO-R_3$ and $R_{14}$ = H:

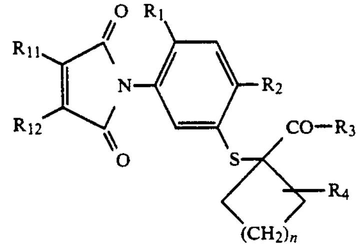

(I)

| Comp. No. | $R_1$ | $R_2$ | $R_3$ | $R_4$ | n | $R_{11}$ | $R_{12}$ | m.p. [°C.] |
|---|---|---|---|---|---|---|---|---|
| 5.023 | F | Cl | $-NH_2$ | H | 0 | $-CH_3$ | $-C_2H_5$ | |
| 5.024 | F | Cl | 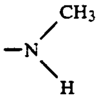 | H | 0 | $-CH_3$ | $-C_2H_5$ | |
| 5.025 | F | Cl | 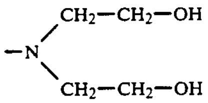 | H | 0 | $-CH_3$ | $-C_2H_5$ | |
| 5.026 | F | Cl | $-NH-CH_2-CH=CH_2$ | H | 0 | $-CH_3$ | $-C_2H_5$ | |
| 5.027 | F | Cl | $-N-(CH_2-CH=CH_2)_2$ | H | 0 | $-CH_3$ | $-C_2H_5$ | |
| 5.028 | F | Cl | 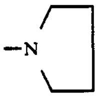 | H | 0 | $-CH_3$ | $-C_2H_5$ | |
| 5.029 | F | Cl | 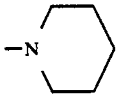 | H | 0 | $-CH_3$ | $-C_2H_5$ | |
| 5.030 | F | Cl | 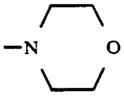 | H | 0 | $-CH_3$ | $-C_2H_5$ | |
| 5.031 | F | Cl | 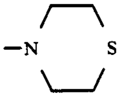 | H | 0 | $-CH_3$ | $-C_2H_5$ | |
| 5.032 | F | Cl | 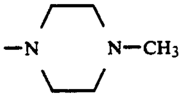 | H | 0 | $-CH_3$ | $-C_2H_5$ | |
| 5.033 | F | Cl | 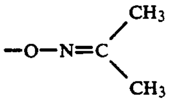 | H | 0 | $-CH_3$ | $-C_2H_5$ | |
| 5.034 | F | Cl | $-O-CH_2-CH_2-Cl$ | H | 0 | $-CH_3$ | $-C_2H_5$ | |
| 5.035 | F | Cl | $-O-CH_2-CN$ | H | 0 | $-CH_3$ | $-C_2H_5$ | |
| 5.036 | F | Cl | 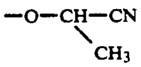 | H | 0 | $-CH_3$ | $-C_2H_5$ | |
| 5.037 | F | Cl | $-O-CH_2-CH=CH_2$ | H | 0 | $-CH_3$ | $-C_2H_5$ | |
| 5.038 | F | Cl | $-O-CH_2-CH=CHCl$ | H | 0 | $-CH_3$ | $-C_2H_5$ | |
| 5.039 | F | Cl | 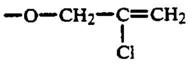 | H | 0 | $-CH_3$ | $-C_2H_5$ | |

TABLE 5a-continued

Compounds of formula I wherein W = $W_5$, R = $-CO-R_3$ and $R_{14}$ = H:

(I)

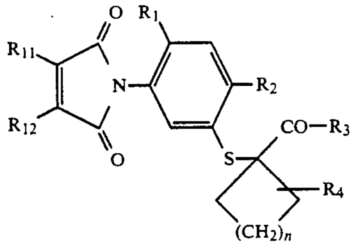

| Comp. No. | $R_1$ | $R_2$ | $R_3$ | $R_4$ | n | $R_{11}$ | $R_{12}$ | m.p. [°C.] |
|---|---|---|---|---|---|---|---|---|
| 5.040 | F | Cl | $-O-CH_2=C{\equiv}CH$ | H | 0 | $-CH_3$ | $-C_2H_5$ | |
| 5.041 | F | Cl | $-O-CH(CH_3)-C{\equiv}CH$ | H | 0 | $-CH_3$ | $-C_2H_5$ | |
| 5.042 | F | Cl | 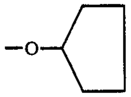 | H | 0 | $-CH_3$ | $-C_2H_5$ | |
| 5.043 | F | Cl | 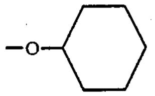 | H | 0 | $-CH_3$ | $-C_2H_5$ | |
| 5.044 | F | Cl | 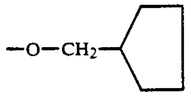 | H | 0 | $-CH_3$ | $-C_2H_5$ | |
| 5.045 | F | Cl | 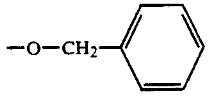 | H | 0 | $-CH_3$ | $-C_2H_5$ | |
| 5.046 | F | Cl | 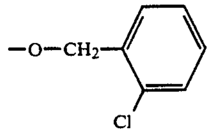 | H | 0 | $-CH_3$ | $-C_2H_5$ | |
| 5.047 | F | Cl | 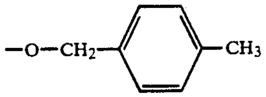 | H | 0 | $-CH_3$ | $-C_2H_5$ | |
| 5.048 | F | Cl | $-S-CH_3$ | H | 0 | $-CH_3$ | $-C_2H_5$ | |
| 5.049 | F | Cl | $-S-C_2H_5$ | H | 0 | $-CH_3$ | $-C_2H_5$ | |
| 5.050 | F | Cl | $-S-C_3H_7$ | H | 0 | $-CH_3$ | $-C_2H_5$ | |
| 5.051 | F | Cl | $-S-CH_2-CH=CH_2$ | H | 0 | $-CH_3$ | $-C_2H_5$ | |
| 5.052 | F | Cl | $-S-CH_2-COOCH_3$ | H | 0 | $-CH_3$ | $-C_2H_5$ | |
| 5.053 | F | Cl | $-S-CH_2-COOC_2H_5$ | H | 0 | $-CH_3$ | $-C_2H_5$ | |
| 5.054 | F | Cl | $-S-CH_2-COOC_5H_{11}$ | H | 0 | $-CH_3$ | $-C_2H_5$ | |
| 5.055 | F | Cl | $-S-CH(CH_3)-COOCH_3$ | H | 0 | $-CH_3$ | $-C_2H_5$ | |
| 5.056 | F | Cl | $-S-(CH_3)-COOC_2H_5$ | H | 0 | $-CH_3$ | $-C_2H_5$ | |
| 5.057 | F | Cl | $-S-CH(CH_3)-COOC_3H_7$ | H | 0 | $-CH_3$ | $-C_2H_5$ | |
| 5.058 | F | Cl | $-S-CH_2-CH_2-COOCH_3$ | H | 0 | $-CH_3$ | $-C_2H_5$ | |
| 5.059 | F | Cl | $-S-CH_2-COOCH_2-CH_2-O-CH_3$ | H | 0 | $-CH_3$ | $-C_2H_5$ | |
| 5.060 | F | Cl | $-O-CH_2-COOCH_3$ | H | 0 | $-CH_3$ | $-C_2H_5$ | |
| 5.061 | F | Cl | $-O-CH(CH_3)-COOCH_3$ | H | 0 | $-CH_3$ | $-C_2H_5$ | |
| 5.062 | F | Cl | $-O-CH_2-COOC_5H_{11}$ | H | 0 | $-CH_3$ | $-C_2H_5$ | |
| 5.063 | F | Cl | $-O-CH_2-CH_3-Si(CH_3)_3$ | H | 0 | $-CH_3$ | $-C_2H_5$ | |
| 5.064 | F | Cl | $-ONa$ | H | 0 | $-CH_3$ | $-C_2H_5$ | |
| 5.065 | F | Br | $-Cl$ | H | 0 | $-CH_3$ | $-C_2H_5$ | |
| 5.066 | F | Br | $-OH$ | H | 0 | $-CH_3$ | $-C_2H_5$ | |
| 5.067 | F | Br | $-OCH_3$ | H | 0 | $-CH_3$ | $-C_2H_5$ | |
| 5.068 | F | Br | $-OC_2H_5$ | H | 0 | $-CH_3$ | $-C_2H_5$ | |

TABLE 5a-continued

Compounds of formula I wherein W = $W_5$, R = $-CO-R_3$ and $R_{14}$ = H:

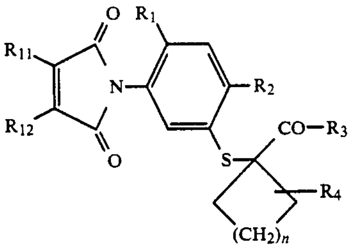

(I)

| Comp. No. | $R_1$ | $R_2$ | $R_3$ | $R_4$ | n | $R_{11}$ | $R_{12}$ | m.p. [°C.] |
|---|---|---|---|---|---|---|---|---|
| 5.069 | F | Br | $-OC_3H_7$ | H | 0 | $-CH_3$ | $-C_2H_5$ | |
| 5.070 | F | Br | 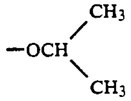 | H | 0 | $-CH_3$ | $-C_2H_5$ | |
| 5.071 | F | Br | $-OC_4H_9$ | H | 0 | $-CH_3$ | $-C_2H_5$ | |
| 5.072 | F | Br | $-OCH(CH_3)-CH_2-CH_3$ | H | 0 | $-CH_3$ | $-C_2H_5$ | |
| 5.073 | F | Br | 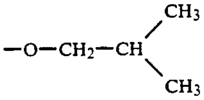 | H | 0 | $-CH_3$ | $-C_2H_5$ | |
| 5.074 | F | Br | $-O-C_5H_{11}$ | H | 0 | $-CH_3$ | $-C_2H_5$ | |
| 5.075 | F | Br | $-O-CH_2-CH_2-O-CH_3$ | H | 0 | $-CH_3$ | $-C_2H_5$ | |
| 5.076 | F | Br | $-O-CH_2-CH_2-O-C_2H_5$ | H | 0 | $-CH_3$ | $-C_2H_5$ | |
| 5.077 | F | Br | $-O-CH(CH_3)-CH_2-O-CH_3$ | H | 0 | $-CH_3$ | $-C_2H_5$ | |
| 5.078 | F | Br | $-O-CH_2-CH_2-S-CH_3$ | H | 0 | $-CH_3$ | $-C_2H_5$ | |
| 5.079 | F | Br | $-O-CH_2(CH_3)-S-CH_3$ | H | 0 | $-CH_3$ | $-C_2H_5$ | |
| 5.080 | F | Br | $-O-CH-(CH_3)-S-C_2H_5$ | H | 0 | $-CH_3$ | $-C_2H_5$ | |
| 5.081 | F | Br | $-O-CH(CH_3)-S-C_3H_7$ | H | 0 | $-CH_3$ | $-C_2H_5$ | |
| 5.082 | F | Br | 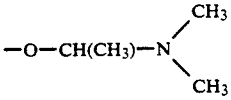 | H | 0 | $-CH_3$ | $-C_2H_5$ | |
| 5.083 | F | Br | $-NH_2$ | H | 0 | $-CH_3$ | $-C_2H_5$ | |
| 5.084 | F | Br | 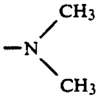 | H | 0 | $-CH_3$ | $-C_2H_5$ | |
| 5.085 | F | Br | 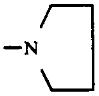 | H | 0 | $-CH_3$ | $-C_2H_5$ | |
| 5.086 | F | Br | 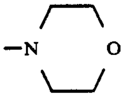 | H | 0 | $-CH_3$ | $-C_2H_5$ | |
| 5.087 | F | Br | 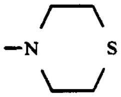 | H | 0 | $-CH_3$ | $-C_2H_5$ | |
| 5.088 | F | Br | 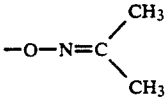 | H | 0 | $-CH_3$ | $-C_2H_5$ | |
| 5.089 | F | Br | $-O-CH_2-CH_2-Cl$ | H | 0 | $-CH_3$ | $-C_2H_5$ | |
| 5.090 | F | Br | $-O-CH_2-CN$ | H | 0 | $-CH_3$ | $-C_2H_5$ | |
| 5.091 | F | Br | $-O-CH_2-CH=CH_2$ | H | 0 | $-CH_3$ | $-C_2H_5$ | |

TABLE 5a-continued

Compounds of formula I wherein W = $W_5$, R = $-CO-R_3$ and $R_{14}$ = H:

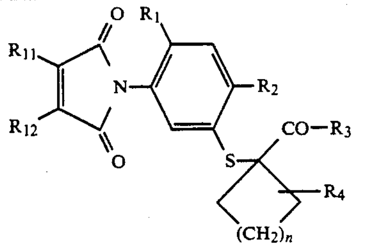

(I)

| Comp. No. | $R_1$ | $R_2$ | $R_3$ | $R_4$ | n | $R_{11}$ | $R_{12}$ | m.p. [°C.] |
|---|---|---|---|---|---|---|---|---|
| 5.092 | F | Br | $-O-CH_2-C\equiv CH$ | H | 0 | $-CH_3$ | $-C_2H_5$ | |
| 5.093 | F | Br | 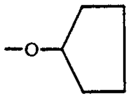 | H | 0 | $-CH_3$ | $-C_2H_5$ | |
| 5.094 | F | Br | 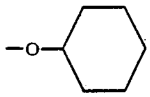 | H | 0 | $-CH_3$ | $-C_2H_5$ | |
| 5.095 | F | Br | 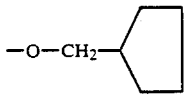 | H | 0 | $-CH_3$ | $-C_2H_5$ | |
| 5.096 | F | Br | 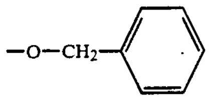 | H | 0 | $-CH_3$ | $-C_2H_5$ | |
| 5.097 | F | Br | $-SCH_3$ | H | 0 | $-CH_3$ | $-C_2H_5$ | |
| 5.098 | F | Br | $-S-CH_2-COOCH_3$ | H | 0 | $-CH_3$ | $-C_2H_5$ | |
| 5.099 | F | Br | $-S-CH(CH_3)-COOCH_3$ | H | 0 | $-CH_3$ | $-C_2H_5$ | |
| 5.100 | F | Br | $-O-CH_2-COOCH_3$ | H | 0 | $-CH_3$ | $-C_2H_5$ | |
| 5.101 | F | Br | $-O-CH(CH_3)COOCH_3$ | H | 0 | $-CH_3$ | $-C_2H_5$ | |
| 5.102 | F | CN | $-Cl$ | H | 0 | $-CH_3$ | $-C_2H_5$ | |
| 5.103 | F | CN | $-OH$ | H | 0 | $-CH_3$ | $-C_2H_5$ | |
| 5.104 | F | CN | $-OCH_3$ | H | 0 | $-CH_3$ | $-C_2H_5$ | |
| 5.105 | H | Cl | $-Cl$ | H | 0 | $-CH_3$ | $-C_2H_5$ | |
| 5.106 | H | Cl | $-OH$ | H | 0 | $-CH_3$ | $-C_2H_5$ | |
| 5.107 | H | Cl | $-OCH_3$ | H | 0 | $-CH_3$ | $-C_2H_5$ | |
| 5.108 | H | Cl | $-OC_2H_5$ | H | 0 | $-CH_3$ | $-C_2H_5$ | |
| 5.109 | H | Cl | 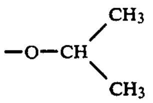 | H | 0 | $-CH_3$ | $-C_2H_5$ | |
| 5.110 | H | Cl | $-O-CH_2-COOCH_3$ | H | 0 | $-CH_3$ | $-C_2H_5$ | |
| 5.111 | H | Cl | $-O-CH(CH_3)COOCH_3$ | H | 0 | $-CH_3$ | $-C_2H_5$ | |
| 5.112 | H | Cl | $-S-CH_2-COOCH_3$ | H | 0 | $-CH_3$ | $-C_2H_5$ | |
| 5.113 | H | Cl | $-S-CH(CH_3)COOCH_3$ | H | 0 | $-CH_3$ | $-C_2H_5$ | |
| 5.114 | H | Cl | 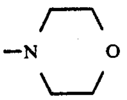 | H | 0 | $-CH_3$ | $-C_2H_5$ | |
| 5.115 | F | Cl | $-Cl$ | H | 1 | $-CH_3$ | $-C_2H_5$ | |
| 5.116 | F | Cl | $-OH$ | H | 1 | $-CH_3$ | $-C_2H_5$ | |
| 5.117 | F | Cl | $-OCH_3$ | H | 1 | $-CH_3$ | $-C_2H_5$ | |
| 5.118 | F | Cl | $-OC_2H_5$ | H | 1 | $-CH_3$ | $-C_2H_5$ | |
| 5.119 | F | Cl | $-OC_3H_7$ | H | 1 | $-CH_3$ | $-C_2H_5$ | |
| 5.120 | F | Cl | 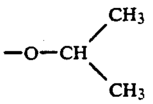 | H | 1 | $-CH_3$ | $-C_2H_5$ | |

TABLE 5a-continued

Compounds of formula I wherein W = $W_5$, R = $-CO-R_3$ and $R_{14}$ = H:

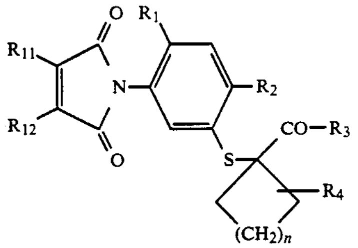

(I)

| Comp. No. | $R_1$ | $R_2$ | $R_3$ | $R_4$ | n | $R_{11}$ | $R_{12}$ | m.p. [°C.] |
|---|---|---|---|---|---|---|---|---|
| 5.121 | F | Cl | $-OC_4H_9$ | H | 1 | $-CH_3$ | $-C_2H_5$ | |
| 5.122 | F | Cl | $-O-CH(CH_3)-C_2H_5$ | H | 1 | $-CH_3$ | $-C_2H_5$ | |
| 5.123 | F | Cl | 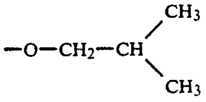 | H | 1 | $-CH_3$ | $-C_2H_5$ | |
| 5.124 | F | Cl | $-OC_5H_{11}$ | H | 1 | $-CH_3$ | $-C_2H_5$ | |
| 5.125 | F | Cl | $-O-CH_2-CH_2-O-CH_3$ | H | 1 | $-CH_3$ | $-C_2H_5$ | |
| 5.126 | F | Cl | $-O-CH_2-CH_2-O-C_2H_5$ | H | 1 | $-CH_3$ | $-C_2H_5$ | |
| 5.127 | F | Cl | $-O-CH-(CH_3)-CH_2-O-CH_3$ | H | 1 | $-CH_3$ | $-C_2H_5$ | |
| 5.128 | F | Cl | $-O-CH_2-CH_2-S-CH_3$ | H | 1 | $-CH_3$ | $-C_2H_5$ | |
| 5.129 | F | Cl | $-O-CH(CH_3)-CH_2-S-CH_3$ | H | 1 | $-CH_3$ | $-C_2H_5$ | |
| 5.130 | F | Cl | $-O-CH(CH_3)-CH_2-S-C_2H_5$ | H | 1 | $-CH_3$ | $-C_2H_5$ | |
| 5.131 | F | Cl | $-O-CH(CH_3)-CH_2-S-C_3H_7$ | H | 1 | $-CH_3$ | $-C_2H_5$ | |
| 5.132 | F | Cl | 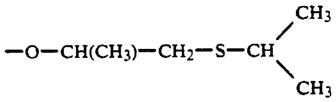 | H | 1 | $-CH_3$ | $-C_2H_5$ | |
| 5.133 | F | Cl | $-O-CH(CH_3)-CH_2-S-C_4H_9$ | H | 1 | $-CH_3$ | $-C_2H_5$ | |
| 5.134 | F | Cl | $-O-CH(CH_3)-CH_2-S-C_5H_{11}$ | H | 1 | $-CH_3$ | $-C_2H_5$ | |
| 5.135 | F | Cl | 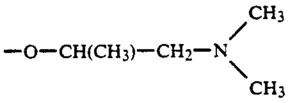 | H | 1 | $-CH_3$ | $-C_2H_5$ | |
| 5.136 | F | Cl | 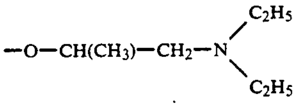 | H | 1 | $-CH_3$ | $-C_2H_5$ | |
| 5.137 | F | Cl | $-NH_2$ | H | 1 | $-CH_3$ | $-C_2H_5$ | |
| 5.138 | F | Cl | 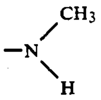 | H | 1 | $-CH_3$ | $-C_2H_5$ | |
| 5.139 | F | Cl | 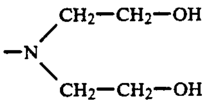 | H | 1 | $-CH_3$ | $-C_2H_5$ | |
| 5.140 | F | Cl | $-NH-CH_2-CH=CH_2$ | H | 1 | $-CH_3$ | $-C_2H_5$ | |
| 5.141 | F | Cl | $-N-(CH_2-CH=CH_2)_2$ | H | 1 | $-CH_3$ | $-C_2H_5$ | |
| 5.142 | F | Cl | 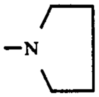 | H | 1 | $-CH_3$ | $-C_2H_5$ | |
| 5.143 | F | Cl | 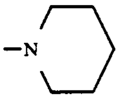 | H | 1 | $-CH_3$ | $-C_2H_5$ | |

TABLE 5a-continued

Compounds of formula I wherein W = $W_5$, R = $-CO-R_3$ and $R_{14}$ = H:

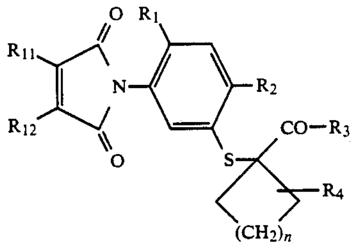

(I)

| Comp. No. | $R_1$ | $R_2$ | $R_3$ | $R_4$ | n | $R_{11}$ | $R_{12}$ | m.p. [°C.] |
|---|---|---|---|---|---|---|---|---|
| 5.144 | F | Cl | 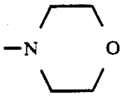 | H | 1 | $-CH_3$ | $-C_2H_5$ | |
| 5.145 | F | Cl | 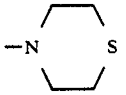 | H | 1 | $-CH_3$ | $-C_2H_5$ | |
| 5.146 | F | Cl | 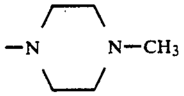 | H | 1 | $-CH_3$ | $-C_2H_5$ | |
| 5.147 | F | Cl | 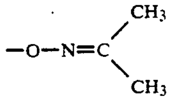 | H | 1 | $-CH_3$ | $-C_2H_5$ | |
| 5.148 | F | Cl | $-O-CH_2-CH_2-Cl$ | H | 1 | $-CH_3$ | $-C_2H_5$ | |
| 5.149 | F | Cl | $-O-CH_2-CN$ | H | 1 | $-CH_3$ | $-C_2H_5$ | |
| 5.150 | F | Cl | 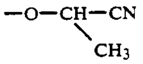 | H | 1 | $-CH_3$ | $-C_2H_5$ | |
| 5.151 | F | Cl | $-O-CH_2-CH=CH_2$ | H | 1 | $-CH_3$ | $-C_2H_5$ | |
| 5.152 | F | Cl | $-O-CH_2-CH=CHCl$ | H | 1 | $-CH_3$ | $-C_2H_5$ | |
| 5.153 | F | Cl | 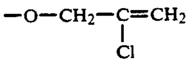 | H | 1 | $-CH_3$ | $-C_2H_5$ | |
| 5.154 | F | Cl | $-O-CH_2=C\equiv CH$ | H | 1 | $-CH_3$ | $-C_2H_5$ | |
| 5.155 | F | Cl | 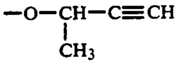 | H | 1 | $-CH_3$ | $-C_2H_5$ | |
| 5.156 | F | Cl | 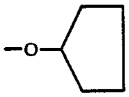 | H | 1 | $-CH_3$ | $-C_2H_5$ | |
| 5.157 | F | Cl | 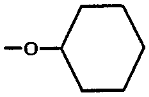 | H | 1 | $-CH_3$ | $-C_2H_5$ | |
| 5.158 | F | Cl | 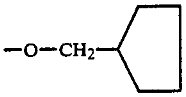 | H | 1 | $-CH_3$ | $-C_2H_5$ | |

TABLE 5a-continued

Compounds of formula I wherein W = $W_5$, R = $-CO-R_3$ and $R_{14}$ = H:

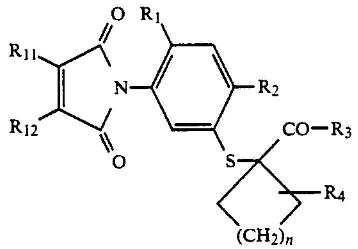

(I)

| Comp. No. | $R_1$ | $R_2$ | $R_3$ | $R_4$ | n | $R_{11}$ | $R_{12}$ | m.p. [°C.] |
|---|---|---|---|---|---|---|---|---|
| 5.159 | F | Cl | 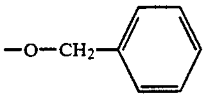 | H | 1 | $-CH_3$ | $-C_2H_5$ | |
| 5.160 | F | Cl | 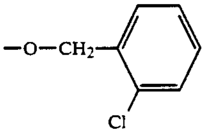 | H | 1 | $-CH_3$ | $-C_2H_5$ | |
| 5.161 | F | Cl | 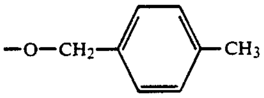 | H | 1 | $-CH_3$ | $-C_2H_5$ | |
| 5.162 | F | Cl | $-S-CH_3$ | H | 1 | $-CH_3$ | $-C_2H_5$ | |
| 5.163 | F | Cl | $-S-C_2H_5$ | H | 1 | $-CH_3$ | $-C_2H_5$ | |
| 5.164 | F | Cl | $-S-C_3H_7$ | H | 1 | $-CH_3$ | $-C_2H_5$ | |
| 5.165 | F | Cl | $-S-CH_2-CH=CH_2$ | H | 1 | $-CH_3$ | $-C_2H_5$ | |
| 5.166 | F | Cl | $-S-CH_2-COOCH_3$ | H | 1 | $-CH_3$ | $-C_2H_5$ | |
| 5.167 | F | Cl | $-S-CH_2-COOC_2H_5$ | H | 1 | $-CH_3$ | $-C_2H_5$ | |
| 5.168 | F | Cl | $-S-CH_2-COOC_5H_{11}$ | H | 1 | $-CH_3$ | $-C_2H_5$ | |
| 5.169 | F | Cl | $-S-CH(CH_3)-COOCH_3$ | H | 1 | $-CH_3$ | $-C_2H_5$ | |
| 5.170 | F | Cl | $-S-(CH_3)-COOC_2H_5$ | H | 1 | $-CH_3$ | $-C_2H_5$ | |
| 5.171 | F | Cl | $-S-CH(CH_3)-COOC_3H_7$ | H | 1 | $-CH_3$ | $-C_2H_5$ | |
| 5.172 | F | Cl | $-S-CH_2-CH_2-COOCH_3$ | H | 1 | $-CH_3$ | $-C_2H_5$ | |
| 5.173 | F | Cl | $-S-CH_2-COOCH_2-CH_2-O-CH_3$ | H | 1 | $-CH_3$ | $-C_2H_5$ | |
| 5.174 | F | Cl | $-O-CH_2-COOCH_3$ | H | 1 | $-CH_3$ | $-C_2H_5$ | |
| 5.175 | F | Cl | $-O-CH(CH_3)-COOCH_3$ | H | 1 | $-CH_3$ | $-C_2H_5$ | |
| 5.176 | F | Cl | $-O-CH_2-COOC_5H_{11}$ | H | 1 | $-CH_3$ | $-C_2H_5$ | |
| 5.177 | F | Cl | $-O-CH_2-CH_3-Si(CH_3)_3$ | H | 1 | $-CH_3$ | $-C_2H_5$ | |
| 5.178 | F | Cl | $-ONa$ | H | 1 | $-CH_3$ | $-C_2H_5$ | |
| 5.179 | F | Br | $-Cl$ | H | 1 | $-CH_3$ | $-C_2H_5$ | |
| 5.180 | F | Br | $-OH$ | H | 1 | $-CH_3$ | $-C_2H_5$ | |
| 5.181 | F | Br | $-OCH_3$ | H | 1 | $-CH_3$ | $-C_2H_5$ | |
| 5.182 | F | Br | $-OC_2H_5$ | H | 1 | $-CH_3$ | $-C_2H_5$ | |
| 5.183 | F | Br | $-OC_3H_7$ | H | 1 | $-CH_3$ | $-C_2H_5$ | |
| 5.184 | F | Br | 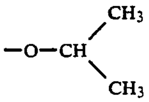 | H | 1 | $-CH_3$ | $-C_2H_5$ | |
| 5.185 | F | Br | $-OC_4H_9$ | H | 1 | $-CH_3$ | $-C_2H_5$ | |
| 5.186 | F | Br | $-OCH(CH_3)-CH_2-CH_3$ | H | 1 | $-CH_3$ | $-C_2H_5$ | |
| 5.187 | F | Br | 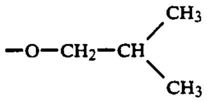 | H | 1 | $-CH_3$ | $-C_2H_5$ | |
| 5.188 | F | Br | $-O-C_5H_{11}$ | H | 1 | $-CH_3$ | $-C_2H_5$ | |
| 5.189 | F | Br | $-O-CH_2-CH_2-O-CH_3$ | H | 1 | $-CH_3$ | $-C_2H_5$ | |
| 5.190 | F | Br | $-O-CH_2-CH_2-O-C_2H_5$ | H | 1 | $-CH_3$ | $-C_2H_5$ | |
| 5.191 | F | Br | $-O-CH(CH_3)-CH_2-O-CH_3$ | H | 1 | $-CH_3$ | $-C_2H_5$ | |
| 5.192 | F | Br | $-O-CH_2-CH_2-S-CH_3$ | H | 1 | $-CH_3$ | $-C_2H_5$ | |
| 5.193 | F | Br | $-O-CH_2(CH_3)-S-CH_3$ | H | 1 | $-CH_3$ | $-C_2H_5$ | |
| 5.194 | F | Br | $-O-CH-(CH_3)-S-C_2H_5$ | H | 1 | $-CH_3$ | $-C_2H_5$ | |
| 5.195 | F | Br | $-O-CH(CH_3)-S-C_3H_7$ | H | 1 | $-CH_3$ | $-C_2H_5$ | |

TABLE 5a-continued

Compounds of formula I wherein W = $W_5$, R = $-CO-R_3$ and $R_{14}$ = H:

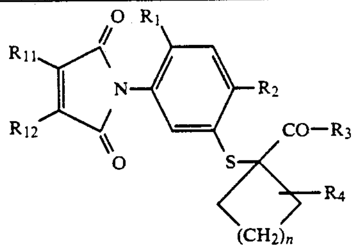

(I)

| Comp. No. | $R_1$ | $R_2$ | $R_3$ | $R_4$ | n | $R_{11}$ | $R_{12}$ | m.p. [°C.] |
|---|---|---|---|---|---|---|---|---|
| 5.196 | F | Br | 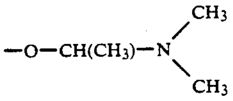 | H | 1 | $-CH_3$ | $-C_2H_5$ | |
| 5.197 | F | Br | $-NH_2$ | H | 1 | $-CH_3$ | $-C_2H_5$ | |
| 5.198 | F | Br | 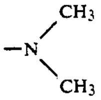 | H | 1 | $-CH_3$ | $-C_2H_5$ | |
| 5.199 | F | Br | 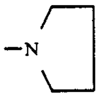 | H | 1 | $-CH_3$ | $-C_2H_5$ | |
| 5.200 | F | Br | 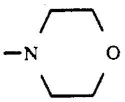 | H | 1 | $-CH_3$ | $-C_2H_5$ | |
| 5.201 | F | Br | 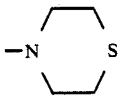 | H | 1 | $-CH_3$ | $-C_2H_5$ | |
| 5.202 | F | Br | 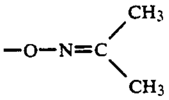 | H | 1 | $-CH_3$ | $-C_2H_5$ | |
| 5.203 | F | Br | $-O-CH_2-CH_2-Cl$ | H | 1 | $-CH_3$ | $-C_2H_5$ | |
| 5.204 | F | Br | $-O-CH_2-CN$ | H | 1 | $-CH_3$ | $-C_2H_5$ | |
| 5.205 | F | Br | $-O-CH_2-CH{=}CH_2$ | H | 1 | $-CH_3$ | $-C_2H_5$ | |
| 5.206 | F | Br | $-O-CH_2-C{\equiv}CH$ | | | | | |
| 5.207 | F | Br | 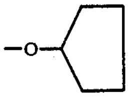 | H | 1 | $-CH_3$ | $-C_2H_5$ | |
| 5.208 | F | Br | 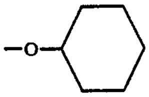 | H | 1 | $-CH_3$ | $-C_2H_5$ | |
| 5.209 | F | Br | 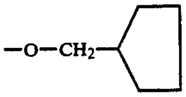 | H | 1 | $-CH_3$ | $-C_2H_5$ | |
| 5.210 | F | Br | 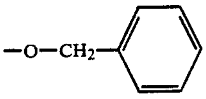 | H | 1 | $-CH_3$ | $-C_2H_5$ | |

TABLE 5a-continued

Compounds of formula I wherein $W = W_5$, $R = -CO-R_3$ and $R_{14} = H$:

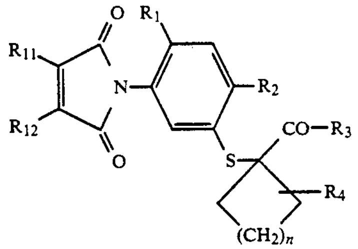

(I)

| Comp. No. | $R_1$ | $R_2$ | $R_3$ | $R_4$ | n | $R_{11}$ | $R_{12}$ | m.p. [°C.] |
|---|---|---|---|---|---|---|---|---|
| 5.211 | F | Br | $-SCH_3$ | H | 1 | $-CH_3$ | $-C_2H_5$ | |
| 5.212 | F | Br | $-S-CH_2-COOCH_3$ | H | 1 | $-CH_3$ | $-C_2H_5$ | |
| 5.213 | F | Br | $-S-CH(CH_3)-COOCH_3$ | H | 1 | $-CH_3$ | $-C_2H_5$ | |
| 5.214 | F | Br | $-O-CH_2-COOCH_3$ | H | 1 | $-CH_3$ | $-C_2H_5$ | |
| 5.215 | F | Br | $-O-CH(CH_3)COOCH_3$ | H | 1 | $-CH_3$ | $-C_2H_5$ | |
| 5.216 | F | CN | $-Cl$ | H | 1 | $-CH_3$ | $-C_2H_5$ | |
| 5.217 | F | CN | $-OH$ | H | 1 | $-CH_3$ | $-C_2H_5$ | |
| 5.218 | F | CN | $-OCH_3$ | H | 1 | $-CH_3$ | $-C_2H_5$ | |
| 5.219 | H | Cl | $-Cl$ | H | 1 | $-CH_3$ | $-C_2H_5$ | |
| 5.220 | H | Cl | $-OH$ | H | 1 | $-CH_3$ | $-C_2H_5$ | |
| 5.221 | H | Cl | $-OCH_3$ | H | 1 | $-CH_3$ | $-C_2H_5$ | |
| 5.222 | H | Cl | $-OC_2H_5$ | H | 1 | $-CH_3$ | $-C_2H_5$ | |
| 5.223 | H | Cl | 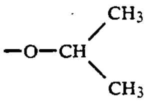 | H | 1 | $-CH_3$ | $-C_2H_5$ | |
| 5.224 | H | Cl | $-O-CH_2-COOCH_3$ | H | 1 | $-CH_3$ | $-C_2H_5$ | |
| 5.225 | H | Cl | $-O-CH(CH_3)COOCH_3$ | H | 1 | $-CH_3$ | $-C_2H_5$ | |
| 5.226 | H | Cl | $-S-CH_2-COOCH_3$ | H | 1 | $-CH_3$ | $-C_2H_5$ | |
| 5.227 | H | Cl | $-S-CH(CH_3)COOCH_3$ | H | 1 | $-CH_3$ | $-C_2H_5$ | |
| 5.228 | H | Cl | 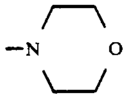 | H | 1 | $-CH_3$ | $-C_2H_5$ | |
| 5.229 | F | Cl | Cl | H | 2 | $-CH_3$ | $-C_2H_5$ | |
| 5.230 | F | Cl | OH | H | 2 | $-CH_3$ | $-C_2H_5$ | |
| 5.231 | F | Cl | $OCH_3$ | H | 2 | $-CH_3$ | $-C_2H_5$ | |
| 5.232 | F | Cl | $-OC_2H_5$ | H | 2 | $-CH_3$ | $-C_2H_5$ | |
| 5.233 | F | Cl | 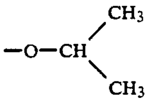 | H | 2 | $-CH_3$ | $-C_2H_5$ | |
| 5.234 | F | Cl | $-O-CH_2-CH_2-O-CH_3$ | H | 2 | $-CH_3$ | $-C_2H_5$ | |
| 5.235 | F | Cl | $-O-CH(CH_3)-CH_2-S-CH_3$ | H | 2 | $-CH_3$ | $-C_2H_5$ | |
| 5.236 | F | Cl | $-O-CH_2-COOCH_3$ | H | 2 | $-CH_3$ | $-C_2H_5$ | |
| 5.237 | F | Cl | $-S-CH_2-COOCH_3$ | H | 2 | $-CH_3$ | $-C_2H_5$ | |
| 5.238 | F | Cl | $-CH_2-CH=CH_2$ | H | 2 | $-CH_3$ | $-C_2H_5$ | |
| 5.239 | F | Cl | $-CH_2-C\equiv CH$ | H | 2 | $-CH_3$ | $-C_2H_5$ | |
| 5.240 | F | Cl | Cl | H | 3 | $-CH_3$ | $-C_2H_5$ | |
| 5.241 | F | Cl | OH | H | 3 | $-CH_3$ | $-C_2H_5$ | |
| 5.242 | F | Cl | $OCH_3$ | H | 3 | $-CH_3$ | $-C_2H_5$ | |
| 5.243 | F | Cl | $OC_2H_5$ | H | 3 | $-CH_3$ | $-C_2H_5$ | |
| 5.244 | F | Cl | 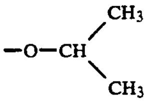 | H | 3 | $-CH_3$ | $-C_2H_5$ | |
| 5.245 | F | Cl | $-O-CH_2-CH_2-O-CH$ | H | 3 | $-CH_3$ | $-C_2H_5$ | |
| 5.246 | F | Cl | $-O-CH(CH_3)-CH_2-S-CH_3$ | H | 3 | $-CH_3$ | $-C_2H_5$ | |
| 5.247 | F | Cl | $-O-CH_2-COOCH_3$ | H | 3 | $-CH_3$ | $-C_2H_5$ | |
| 5.248 | F | Cl | $-S-CH_2-COOCH_3$ | H | 3 | $-CH_3$ | $-C_2H_5$ | |
| 5.249 | F | Cl | $-O-CH_2-C\equiv CH$ | H | 3 | $-CH_3$ | $-C_2H_5$ | |
| 5.250 | F | Cl | $-Cl$ | Cl | 0 | $-CH_3$ | $-C_2H_5$ | |
| 5.251 | F | Cl | $-OH$ | Cl | 0 | $-CH_3$ | $-C_2H_5$ | |
| 5.252 | F | Cl | $-OCH_3$ | Cl | 0 | $-CH_3$ | $-C_2H_5$ | |
| 5.253 | F | Cl | $-OC_2H_5$ | Cl | 0 | $-CH_3$ | $-C_2H_5$ | |

TABLE 5a-continued

Compounds of formula I wherein W = $W_5$, R = $-CO-R_3$ and $R_{14}$ = H:

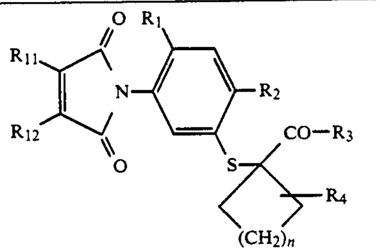
(I)

| Comp. No. | $R_1$ | $R_2$ | $R_3$ | $R_4$ | n | $R_{11}$ | $R_{12}$ | m.p. [°C.] |
|---|---|---|---|---|---|---|---|---|
| 5.254 | F | Cl | 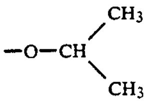 | Cl | 0 | $-CH_3$ | $-C_2H_5$ | |
| 5.255 | F | Cl | $-O-CH_2-COOCH_3$ | Cl | 0 | $-CH_3$ | $-C_2H_5$ | |
| 5.256 | F | Cl | $-S-CH_2-COOCH_3$ | Cl | 0 | $-CH_3$ | $-C_2H_5$ | |
| 5.257 | F | Cl | $-OCH_3$ | Br | 0 | $-CH_3$ | $-C_2H_5$ | |
| 5.258 | F | Cl | 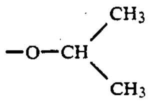 | Br | 0 | $-CH_3$ | $-C_2H_5$ | |
| 5.259 | F | Cl | $-OCH_3$ | F | 0 | $-CH_3$ | $-C_2H_5$ | |
| 5.260 | F | Cl | $-OCH_3$ | $CH_3$ | 0 | $-CH_3$ | $-C_2H_5$ | |
| 5.261 | F | Cl | $-OC_2H_5$ | $CH_3$ | 0 | $-CH_3$ | $-C_2H_5$ | |
| 5.262 | F | Cl | 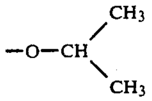 | $CH_3$ | 0 | $-CH_3$ | $-C_2H_5$ | |
| 5.263 | F | Cl | $-O-CH_2-CH_2-O-CH_3$ | $CH_3$ | 0 | $-CH_3$ | $-C_2H_5$ | |
| 5.264 | F | Cl | $-O-CH_2-COOCH_3$ | $CH_3$ | 0 | $-CH_3$ | $-C_2H_5$ | |
| 5.265 | F | Cl | $-O-CH(CH_3)COOCH_3$ | $CH_3$ | 0 | $-CH_3$ | $-C_2H_5$ | |
| 5.266 | F | Cl | $-S-CH_2-COOCH_3$ | $CH_3$ | 0 | $-CH_3$ | $-C_2H_5$ | |
| 5.267 | F | Cl | $-OCH_3$ | $CF_3$ | 0 | $-CH_3$ | $-C_2H_5$ | |
| 5.268 | F | Cl | $-OC_2H_5$ | $CF_3$ | 0 | $-CH_3$ | $-C_2H_5$ | |
| 5.269 | F | Cl | 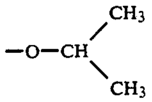 | $CF_3$ | 0 | $-CH_3$ | $-C_2H_5$ | |
| 5.270 | F | Cl | $-O-CH_2-COOCH_3$ | $CF_3$ | 0 | $-CH_3$ | $-C_2H_5$ | |
| 5.271 | F | Cl | $-S-CH_2-COOCH_3$ | $CF_3$ | 0 | $-CH_3$ | $-C_2H_5$ | |

TABLE 5b

Compounds of formula I wherein W = $W_5$, R = $-CN$ and $R_{14}$ = H:

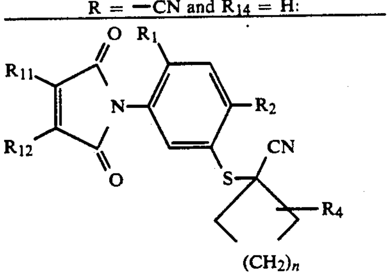
(I)

TABLE 5b-continued

| Comp. No. | $R_1$ | $R_2$ | $R_3$ | $R_4$ | n | $R_{11}$ | $R_{12}$ | m.p. [°C.] |
|---|---|---|---|---|---|---|---|---|
| 5.272 | F | Cl | — | H | 0 | $-CH_3$ | $-C_2H_5$ | |
| 5.273 | F | Cl | — | H | 1 | $-CH_3$ | $-C_2H_5$ | |
| 5.274 | F | Cl | — | H | 2 | $-CH_3$ | $-C_2H_5$ | |
| 5.275 | F | Cl | — | H | 3 | $-CH_3$ | $-C_2H_5$ | |
| 5.276 | F | Cl | — | H | 4 | $-CH_3$ | $-C_2H_5$ | |

TABLE 6a

Compounds of formula I wherein W = $W_6$, A = $-CO-R_3$ and $R_{14}$ = H:

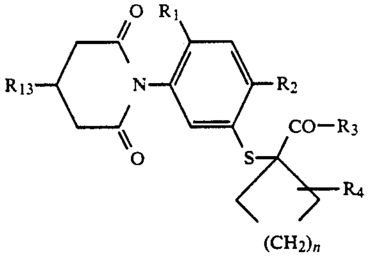

(I)

| Comp. No. | $R_1$ | $R_2$ | $R_3$ | $R_4$ | n | $R_{13}$ | m.p. [°C.] |
|---|---|---|---|---|---|---|---|
| 6.001 | F | Cl | $-Cl$ | H | 0 | $CF_3$ | |
| 6.002 | F | Cl | $-OH$ | H | 0 | $CF_3$ | |
| 6.003 | F | Cl | $-OCH_3$ | H | 0 | $CF_3$ | |
| 6.004 | F | Cl | $-OC_2H_5$ | H | 0 | $CF_3$ | |
| 6.005 | F | Cl | $-OC_3H_7$ | H | 0 | $CF_3$ | |
| 6.006 | F | Cl | 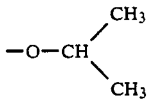 | H | 0 | $CF_3$ | |
| 6.007 | F | Cl | $-OC_4H_9$ | H | 0 | $CF_3$ | |
| 6.008 | F | Cl | $-O-CH(CH_3)-C_2H_5$ | H | 0 | $CF_3$ | |
| 6.009 | F | Cl | 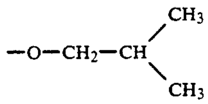 | H | 0 | $CF_3$ | |
| 6.010 | F | Cl | $-OC_5H_{11}$ | H | 0 | $CF_3$ | |
| 6.011 | F | Cl | $-O-CH_2-CH_2-O-CH_3$ | H | 0 | $CF_3$ | |
| 6.012 | F | Cl | $-O-CH_2-CH_2-O-C_2H_5$ | H | 0 | $CF_3$ | |
| 6.013 | F | Cl | $-O-CH-(CH_3)-CH_2-O-CH_3$ | H | 0 | $CF_3$ | |
| 6.014 | F | Cl | $-O-CH_2-CH_2-S-CH_3$ | H | 0 | $CF_3$ | |
| 6.015 | F | Cl | $-O-CH(CH_3)-CH_2-S-CH_3$ | H | 0 | $CF_3$ | |
| 6.016 | F | Cl | $-O-CH(CH_3)-CH_2-S-C_2H_5$ | H | 0 | $CF_3$ | |
| 6.017 | F | Cl | $-O-CH(CH_3)-CH_2-S-C_3H_7$ | H | 0 | $CF_3$ | |
| 6.018 | F | Cl | 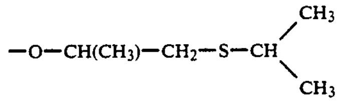 | H | 0 | $CF_3$ | |
| 6.019 | F | Cl | $-O-CH(CH_3)-CH_2-S-C_4H_9$ | H | 0 | $CF_3$ | |
| 6.020 | F | Cl | $-O-CH(CH_3)-CH_2-S-C_5H_{11}$ | H | 0 | $CF_3$ | |
| 6.021 | F | Cl | 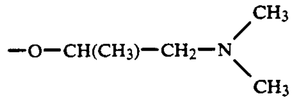 | H | 0 | $CF_3$ | |
| 6.022 | F | Cl | 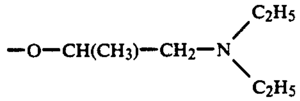 | H | 0 | $CF_3$ | |
| 6.023 | F | Cl | $-NH_2$ | H | 0 | $CF_3$ | |
| 6.024 | F | Cl | 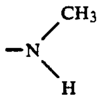 | H | 0 | $CF_3$ | |
| 6.025 | F | Cl | 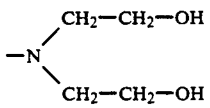 | H | 0 | $CF_3$ | |
| 6.026 | F | Cl | $-NH-CH_2-CH=CH_2$ | H | 0 | $CF_3$ | |
| 6.027 | F | Cl | $-N-(CH_2-CH=CH_2)_2$ | H | 0 | $CF_3$ | |

TABLE 6a-continued
Compounds of formula I wherein W = $W_6$, A = $-CO-R_3$ and $R_{14}$ = H:
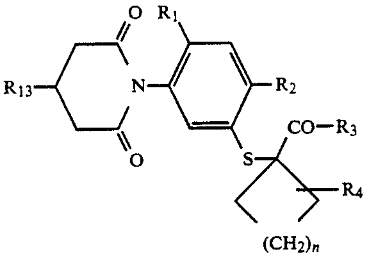
(I)
| Comp. No. | $R_1$ | $R_2$ | $R_3$ | $R_4$ | n | $R_{13}$ | m.p. [°C.] |
|---|---|---|---|---|---|---|---|
| 6.028 | F | Cl | 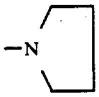 | H | 0 | $CF_3$ | |
| 6.029 | F | Cl | 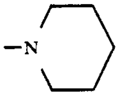 | H | 0 | $CF_3$ | |
| 6.030 | F | Cl | 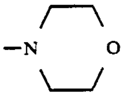 | H | 0 | $CF_3$ | |
| 6.031 | F | Cl | 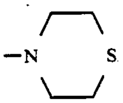 | H | 0 | $CF_3$ | |
| 6.032 | F | Cl | 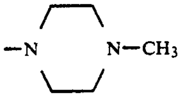 | H | 0 | $CF_3$ | |
| 6.033 | F | Cl | 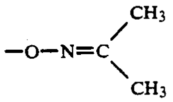 | H | 0 | $CF_3$ | |
| 6.034 | F | Cl | $-O-CH_2-CH_2-Cl$ | H | 0 | $CF_3$ | |
| 6.035 | F | Cl | $-O-CH_2-CN$ | H | 0 | $CF_3$ | |
| 6.036 | F | Cl | 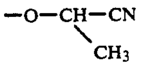 | H | 0 | $CF_3$ | |
| 6.037 | F | Cl | $-O-CH_2-CH=CH_2$ | H | 0 | $CF_3$ | |
| 6.038 | F | Cl | $-O-CH_2-CH=CHCl$ | H | 0 | $CF_3$ | |
| 6.039 | F | Cl | 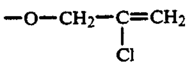 | H | 0 | $CF_3$ | |
| 6.040 | F | Cl | $-O-CH_2=C\equiv CH$ | H | 0 | $CF_3$ | |
| 6.041 | F | Cl | 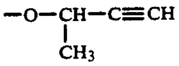 | H | 0 | $CF_3$ | |
| 6.042 | F | Cl | 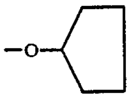 | H | 0 | $CF_3$ | |

TABLE 6a-continued

Compounds of formula I wherein W = $W_6$, A = $-CO-R_3$ and $R_{14}$ = H:

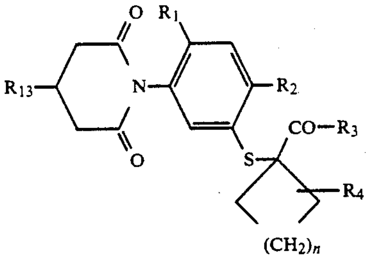

(I)

| Comp. No. | $R_1$ | $R_2$ | $R_3$ | $R_4$ | n | $R_{13}$ | m.p. [°C.] |
|---|---|---|---|---|---|---|---|
| 6.043 | F | Cl | 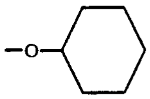 | H | 0 | $CF_3$ | |
| 6.044 | F | Cl | 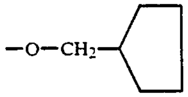 | H | 0 | $CF_3$ | |
| 6.045 | F | Cl | 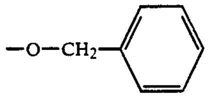 | H | 0 | $CF_3$ | |
| 6.046 | F | Cl | 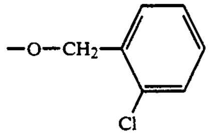 | H | 0 | $CF_3$ | |
| 6.047 | F | Cl | 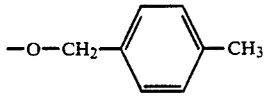 | H | 0 | $CF_3$ | |
| 6.048 | F | Cl | $-S-CH_3$ | H | 0 | $CF_3$ | |
| 6.049 | F | Cl | $-S-C_2H_5$ | H | 0 | $CF_3$ | |
| 6.050 | F | Cl | $-S-C_3H_7$ | H | 0 | $CF_3$ | |
| 6.051 | F | Cl | $-S-CH_2-CH=CH_2$ | H | 0 | $CF_3$ | |
| 6.052 | F | Cl | $-S-CH_2-COOCH_3$ | H | 0 | $CF_3$ | |
| 6.053 | F | Cl | $-S-CH_2-COOC_2H_5$ | H | 0 | $CF_3$ | |
| 6.054 | F | Cl | $-S-CH_2-COOC_5H_{11}$ | H | 0 | $CF_3$ | |
| 6.055 | F | Cl | $-S-CH(CH_3)-COOCH_3$ | H | 0 | $CF_3$ | |
| 6.056 | F | Cl | $-S-(CH_3)-COOC_2H_5$ | H | 0 | $CF_3$ | |
| 6.057 | F | Cl | $-S-CH(CH_3)-COOC_3H_7$ | H | 0 | $CF_3$ | |
| 6.058 | F | Cl | $-S-CH_2-CH_2-COOCH_3$ | H | 0 | $CF_3$ | |
| 6.059 | F | Cl | $-S-CH_2-COOCH_2-CH_2-O-CH_3$ | H | 0 | $CF_3$ | |
| 6.060 | F | Cl | $-O-CH_2-COOCH_3$ | H | 0 | $CF_3$ | |
| 6.061 | F | Cl | $-O-CH(CH_3)-COOCH_3$ | H | 0 | $CF_3$ | |
| 6.062 | F | Cl | $-O-CH_2-COOC_5H_{11}$ | H | 0 | $CF_3$ | |
| 6.063 | F | Cl | $-O-CH_2-CH_3-Si(CH_3)_3$ | H | 0 | $CF_3$ | |
| 6.064 | F | Cl | $-ONa$ | H | 0 | $CF_3$ | |
| 6.065 | F | Br | $-Cl$ | H | 0 | $CF_3$ | |
| 6.066 | F | Br | $-OH$ | H | 0 | $CF_3$ | |
| 6.067 | F | Br | $-OCH_3$ | H | 0 | $CF_3$ | |
| 6.068 | F | Br | $-OC_2H_5$ | H | 0 | $CF_3$ | |
| 6.069 | F | Br | $-OC_3H_7$ | H | 0 | $CF_3$ | |
| 6.070 | F | Br | 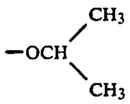 | H | 0 | $CF_3$ | |
| 6.071 | F | Br | $-OC_4H_9$ | H | 0 | $CF_3$ | |
| 6.072 | F | Br | $-OCH(CH_3)-CH_2-CH_3$ | H | 0 | $CF_3$ | |

TABLE 6a-continued

Compounds of formula I wherein W = $W_6$, A = $-CO-R_3$ and $R_{14}$ = H:

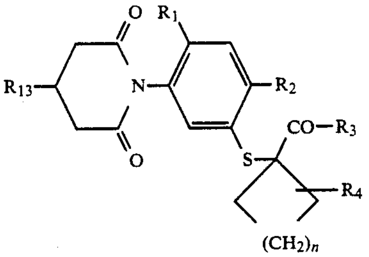

(I)

| Comp. No. | $R_1$ | $R_2$ | $R_3$ | $R_4$ | n | $R_{13}$ | m.p. [°C.] |
|---|---|---|---|---|---|---|---|
| 6.073 | F | Br | 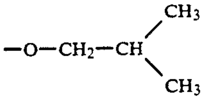 | H | 0 | $CF_3$ | |
| 6.074 | F | Br | $-O-C_5H_{11}$ | H | 0 | $CF_3$ | |
| 6.075 | F | Br | $-O-CH_2-CH_2-O-CH_3$ | H | 0 | $CF_3$ | |
| 6.076 | F | Br | $-O-CH_2-CH_2-O-C_2H_5$ | H | 0 | $CF_3$ | |
| 6.077 | F | Br | $-O-CH(CH_3)-CH_2-O-CH_3$ | H | 0 | $CF_3$ | |
| 6.078 | F | Br | $-O-CH_2-CH_2-S-CH_3$ | H | 0 | $CF_3$ | |
| 6.079 | F | Br | $-O-CH_2(CH_3)-S-CH_3$ | H | 0 | $CF_3$ | |
| 6.080 | F | Br | $-O-CH-(CH_3)-S-C_2H_5$ | H | 0 | $CF_3$ | |
| 6.081 | F | Br | $-O-CH(CH_3)-S-C_3H_7$ | H | 0 | $CF_3$ | |
| 6.082 | F | Br | 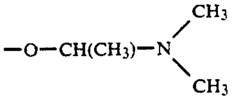 | H | 0 | $CF_3$ | |
| 6.083 | F | Br | $-NH_2$ | H | 0 | $CF_3$ | |
| 6.084 | F | Br | 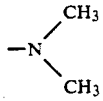 | H | 0 | $CF_3$ | |
| 6.085 | F | Br | 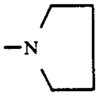 | H | 0 | $CF_3$ | |
| 6.086 | F | Br | 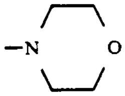 | H | 0 | $CF_3$ | |
| 6.087 | F | Br | 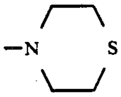 | H | 0 | $CF_3$ | |
| 6.088 | F | Br | 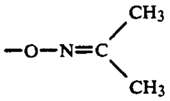 | H | 0 | $CF_3$ | |
| 6.089 | F | Br | $-O-CH_2-CH_2-Cl$ | H | 0 | $CF_3$ | |
| 6.090 | F | Br | $-O-CH_2-CN$ | H | 0 | $CF_3$ | |
| 6.091 | F | Br | $-O-CH_2-CH=CH_2$ | H | 0 | $CF_3$ | |
| 6.092 | F | Br | $-O-CH_2-C\equiv CH$ | H | 0 | $CF_3$ | |
| 6.093 | F | Br | 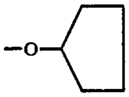 | H | 0 | $CF_3$ | |

TABLE 6a-continued

Compounds of formula I wherein W = $W_6$, A = $-CO-R_3$ and $R_{14}$ = H:

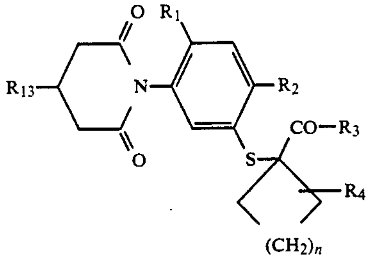

(I)

| Comp. No. | $R_1$ | $R_2$ | $R_3$ | $R_4$ | n | $R_{13}$ | m.p. [°C.] |
|---|---|---|---|---|---|---|---|
| 6.094 | F | Br | 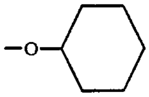 | H | 0 | $CF_3$ | |
| 6.095 | F | Br | 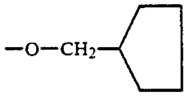 | H | 0 | $CF_3$ | |
| 6.096 | F | Br | 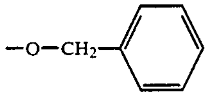 | H | 0 | $CF_3$ | |
| 6.097 | F | Br | $-SCH_3$ | H | 0 | $CF_3$ | |
| 6.098 | F | Br | $-S-CH_2-COOCH_3$ | H | 0 | $CF_3$ | |
| 6.099 | F | Br | $-S-CH(CH_3)-COOCH_3$ | H | 0 | $CF_3$ | |
| 6.100 | F | Br | $-O-CH_2-COOCH_3$ | H | 0 | $CF_3$ | |
| 6.101 | F | Br | $-O-CH(CH_3)COOCH_3$ | H | 0 | $CF_3$ | |
| 6.102 | F | CN | $-Cl$ | H | 0 | $CF_3$ | |
| 6.103 | F | CN | $-OH$ | H | 0 | $CF_3$ | |
| 6.104 | F | CN | $-OCH_3$ | H | 0 | $CF_3$ | |
| 6.105 | H | Cl | $-Cl$ | H | 0 | $CF_3$ | |
| 6.106 | H | Cl | $-OH$ | H | 0 | $CF_3$ | |
| 6.107 | H | Cl | $-OCH_3$ | H | 0 | $CF_3$ | |
| 6.108 | H | Cl | $-OC_2H_5$ | H | 0 | $CF_3$ | |
| 6.109 | H | Cl | 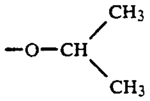 | H | 0 | $CF_3$ | |
| 6.110 | H | Cl | $-O-CH_2-COOCH_3$ | H | 0 | $CF_3$ | |
| 6.111 | H | Cl | $-O-CH(CH_3)COOCH_3$ | H | 0 | $CF_3$ | |
| 6.112 | H | Cl | $-S-CH_2-COOCH_3$ | H | 0 | $CF_3$ | |
| 6.113 | H | Cl | $-S-CH(CH_3)COOCH_3$ | H | 0 | $CF_3$ | |
| 6.114 | H | Cl | 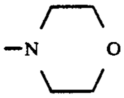 | H | 0 | $CF_3$ | |
| 6.115 | F | Cl | $-Cl$ | H | 1 | $CF_3$ | |
| 6.116 | F | Cl | $-OH$ | H | 1 | $CF_3$ | |
| 6.117 | F | Cl | $-OCH_3$ | H | 1 | $CF_3$ | 115-117 |
| 6.118 | F | Cl | $-OC_2H_5$ | H | 1 | $CF_3$ | |
| 6.119 | F | Cl | $-OC_3H_7$ | H | 1 | $CF_3$ | |
| 6.120 | F | Cl | 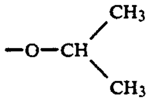 | H | 1 | $CF_3$ | |
| 6.121 | F | Cl | $-OC_4H_9$ | H | 1 | $CF_3$ | |
| 6.122 | F | Cl | $-O-CH(CH_3)-C_2H_5$ | H | 1 | $CF_3$ | |

TABLE 6a-continued

Compounds of formula I wherein W = $W_6$, A = $-CO-R_3$ and $R_{14}$ = H:

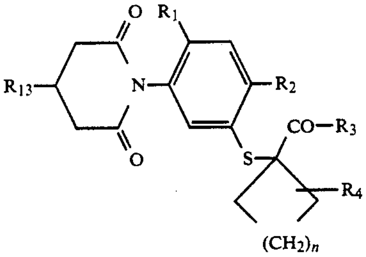

(I)

| Comp. No. | $R_1$ | $R_2$ | $R_3$ | $R_4$ | n | $R_{13}$ | m.p. [°C.] |
|---|---|---|---|---|---|---|---|
| 6.123 | F | Cl | 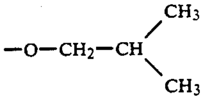 | H | 1 | $CF_3$ | |
| 6.124 | F | Cl | $-OC_5H_{11}$ | H | 1 | $CF_3$ | |
| 6.125 | F | Cl | $-O-CH_2-CH_2-O-CH_3$ | H | 1 | $CF_3$ | |
| 6.126 | F | Cl | $-O-CH_2-CH_2-O-C_2H_5$ | H | 1 | $CF_3$ | |
| 6.127 | F | Cl | $-O-CH-(CH_3)-CH_2-O-CH_3$ | H | 1 | $CF_3$ | |
| 6.128 | F | Cl | $-O-CH_2-CH_2-S-CH_3$ | H | 1 | $CF_3$ | |
| 6.129 | F | Cl | $-O-CH(CH_3)-CH_2-S-CH_3$ | H | 1 | $CF_3$ | |
| 6.130 | F | Cl | $-O-CH(CH_3)-CH_2-S-C_2H_5$ | H | 1 | $CF_3$ | |
| 6.131 | F | Cl | $-O-CH(CH_3)-CH_2-S-C_3H_7$ | H | 1 | $CF_3$ | |
| 6.132 | F | Cl | 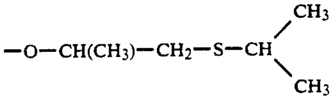 | H | 1 | $CF_3$ | |
| 6.133 | F | Cl | $-O-CH(CH_3)-CH_2-S-C_4H_9$ | H | 1 | $CF_3$ | |
| 6.134 | F | Cl | $-O-CH(CH_3)-CH_2-S-C_5H_{11}$ | H | 1 | $CF_3$ | |
| 6.135 | F | Cl | 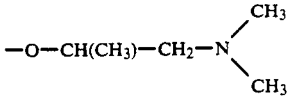 | H | 1 | $CF_3$ | |
| 6.136 | F | Cl | 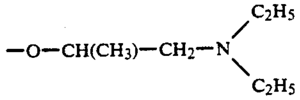 | H | 1 | $CF_3$ | |
| 6.137 | F | Cl | $-NH_2$ | H | 1 | $CF_3$ | |
| 6.138 | F | Cl | 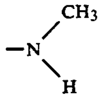 | H | 1 | $CF_3$ | |
| 6.139 | F | Cl | 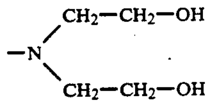 | H | 1 | $CF_3$ | |
| 6.140 | F | Cl | $-NH-CH_2-CH=CH_2$ | H | 1 | $CF_3$ | |
| 6.141 | F | Cl | $-N-(CH_2-CH=CH_2)_2$ | H | 1 | $CF_3$ | |
| 6.142 | F | Cl | 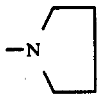 | H | 1 | $CF_3$ | |
| 6.143 | F | Cl | 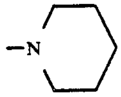 | H | 1 | $CF_3$ | |

TABLE 6a-continued
Compounds of formula I wherein $W = W_6$, $A = -CO-R_3$ and $R_{14} = H$:
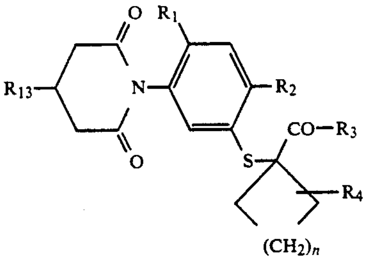
(I)
| Comp. No. | $R_1$ | $R_2$ | $R_3$ | $R_4$ | n | $R_{13}$ | m.p. [°C.] |
|---|---|---|---|---|---|---|---|
| 6.144 | F | Cl | 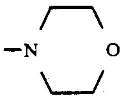 | H | 1 | $CF_3$ | |
| 6.145 | F | Cl | 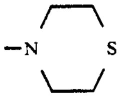 | H | 1 | $CF_3$ | |
| 6.146 | F | Cl | 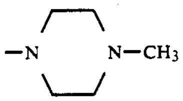 | H | 1 | $CF_3$ | |
| 6.147 | F | Cl | 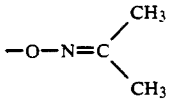 | H | 1 | $CF_3$ | |
| 6.148 | F | Cl | $-O-CH_2-CH_2-Cl$ | H | 1 | $CF_3$ | |
| 6.149 | F | Cl | $-O-CH_2-CN$ | H | 1 | $CF_3$ | |
| 6.150 | F | Cl | 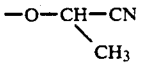 | H | 1 | $CF_3$ | |
| 6.151 | F | Cl | $-O-CH_2-CH{=}CH_2$ | H | 1 | $CF_3$ | |
| 6.152 | F | Cl | $-O-CH_2-CH{=}CHCl$ | H | 1 | $CF_3$ | |
| 6.153 | F | Cl | 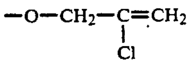 | H | 1 | $CF_3$ | |
| 6.154 | F | Cl | $-O-CH_2{=}C{\equiv}CH$ | H | 1 | $CF_3$ | |
| 6.155 | F | Cl | 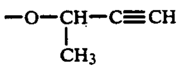 | H | 1 | $CF_3$ | |
| 6.156 | F | Cl | 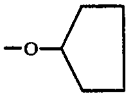 | H | 1 | $CF_3$ | |
| 6.157 | F | Cl | 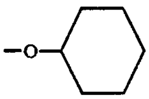 | H | 1 | $CF_3$ | |
| 6.158 | F | Cl | 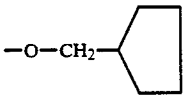 | H | 1 | $CF_3$ | |

TABLE 6a-continued

Compounds of formula I wherein W = $W_6$, A = $-CO-R_3$ and $R_{14}$ = H:

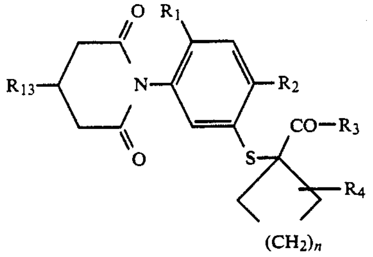

(I)

| Comp. No. | $R_1$ | $R_2$ | $R_3$ | $R_4$ | n | $R_{13}$ | m.p. [°C.] |
| --- | --- | --- | --- | --- | --- | --- | --- |
| 6.159 | F | Cl | 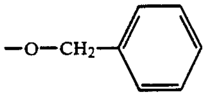 | H | 1 | $CF_3$ | |
| 6.160 | F | Cl | 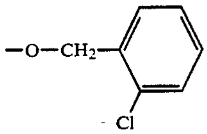 | H | 1 | $CF_3$ | |
| 6.161 | F | Cl | 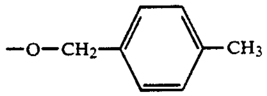 | H | 1 | $CF_3$ | |
| 6.162 | F | Cl | $-S-CH_3$ | H | 1 | $CF_3$ | |
| 6.163 | F | Cl | $-S-C_2H_5$ | H | 1 | $CF_3$ | |
| 6.164 | F | Cl | $-S-C_3H_7$ | H | 1 | $CF_3$ | |
| 6.165 | F | Cl | $-S-CH_2-CH=CH_2$ | H | 1 | $CF_3$ | |
| 6.166 | F | Cl | $-S-CH_2-COOCH_3$ | H | 1 | $CF_3$ | |
| 6.167 | F | Cl | $-S-CH_2-COOC_2H_5$ | H | 1 | $CF_3$ | |
| 6.168 | F | Cl | $-S-CH_2-COOC_5H_{11}$ | H | 1 | $CF_3$ | |
| 6.169 | F | Cl | $-S-CH(CH_3)-COOCH_3$ | H | 1 | $CF_3$ | |
| 6.170 | F | Cl | $-S-(CH_3)-COOC_2H_5$ | H | 1 | $CF_3$ | |
| 6.171 | F | Cl | $-S-CH(CH_3)-COOC_3H_7$ | H | 1 | $CF_3$ | |
| 6.172 | F | Cl | $-S-CH_2-CH_2-COOCH_3$ | H | 1 | $CF_3$ | |
| 6.173 | F | Cl | $-S-CH_2-COOCH_2-CH_2-O-CH_3$ | H | 1 | $CF_3$ | |
| 6.174 | F | Cl | $-O-CH_2-COOCH_3$ | H | 1 | $CF_3$ | |
| 6.175 | F | Cl | $-O-CH(CH_3)-COOCH_3$ | H | 1 | $CF_3$ | |
| 6.176 | F | Cl | $-O-CH_2-COOC_5H_{11}$ | H | 1 | $CF_3$ | |
| 6.177 | F | Cl | $-O-CH_2-CH_3-Si(CH_3)_3$ | H | 1 | $CF_3$ | |
| 6.178 | F | Cl | $-ONa$ | H | 1 | $CF_3$ | |
| 6.179 | F | Br | $-Cl$ | H | 1 | $CF_3$ | |
| 6.180 | F | Br | $-OH$ | H | 1 | $CF_3$ | |
| 6.181 | F | Br | $-OCH_3$ | H | 1 | $CF_3$ | |
| 6.182 | F | Br | $-OC_2H_5$ | H | 1 | $CF_3$ | |
| 6.183 | F | Br | $-OC_3H_7$ | H | 1 | $CF_3$ | |
| 6.184 | F | Br | 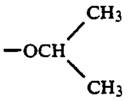 | H | 1 | $CF_3$ | |
| 6.185 | F | Br | $-OC_4H_9$ | H | 1 | $CF_3$ | |
| 6.186 | F | Br | $-OCH(CH_3)-CH_2-CH_3$ | H | 1 | $CF_3$ | |
| 6.187 | F | Br | 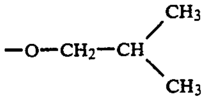 | H | 1 | $CF_3$ | |
| 6.188 | F | Br | $-O-C_5H_{11}$ | H | 1 | $CF_3$ | |
| 6.189 | F | Br | $-O-CH_2-CH_2-O-CH_3$ | H | 1 | $CF_3$ | |
| 6.190 | F | Br | $-O-CH_2-CH_2-O-C_2H_5$ | H | 1 | $CF_3$ | |
| 6.191 | F | Br | $-O-CH(CH_3)-CH_2-O-CH_3$ | H | 1 | $CF_3$ | |
| 6.192 | F | Br | $-O-CH_2-CH_2-S-CH_3$ | H | 1 | $CF_3$ | |
| 6.193 | F | Br | $-O-CH_2(CH_3)-S-CH_3$ | H | 1 | $CF_3$ | |
| 6.194 | F | Br | $-O-CH-(CH_3)-S-C_2H_5$ | H | 1 | $CF_3$ | |
| 6.195 | F | Br | $-O-CH(CH_3)-S-C_3H_7$ | H | 1 | $CF_3$ | |

TABLE 6a-continued
Compounds of formula I wherein W = $W_6$, A = $-CO-R_3$ and $R_{14}$ = H:
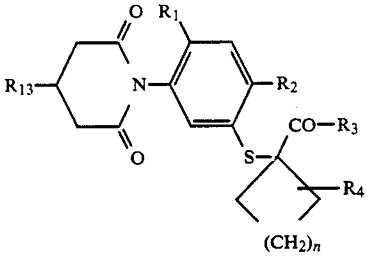
(I)
| Comp. No. | $R_1$ | $R_2$ | $R_3$ | $R_4$ | n | $R_{13}$ | m.p. [°C.] |
|---|---|---|---|---|---|---|---|
| 6.196 | F | Br | 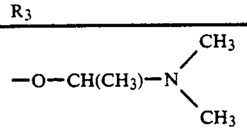 | H | 1 | $CF_3$ | |
| 6.197 | F | Br | $-NH_2$ | H | 1 | $CF_3$ | |
| 6.198 | F | Br | 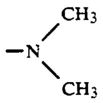 | H | 1 | $CF_3$ | |
| 6.199 | F | Br | 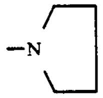 | H | 1 | $CF_3$ | |
| 6.200 | F | Br | 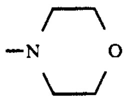 | H | 1 | $CF_3$ | |
| 6.201 | F | Br | 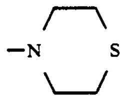 | H | 1 | $CF_3$ | |
| 6.202 | F | Br | 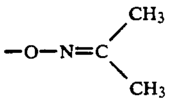 | H | 1 | $CF_3$ | |
| 6.203 | F | Br | $-O-CH_2-CH_2-Cl$ | H | 1 | $CF_3$ | |
| 6.204 | F | Br | $-O-CH_2-CN$ | H | 1 | $CF_3$ | |
| 6.205 | F | Br | $-O-CH_2-CH=CH_2$ | H | 1 | $CF_3$ | |
| 6.206 | F | Br | $-O-CH_2-C\equiv CH$ | H | 1 | $CF_3$ | |
| 6.207 | F | Br | 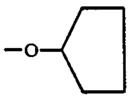 | H | 1 | $CF_3$ | |
| 6.208 | F | Br | 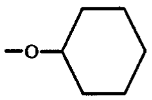 | H | 1 | $CF_3$ | |
| 6.209 | F | Br | 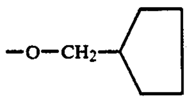 | H | 1 | $CF_3$ | |
| 6.210 | F | Br | 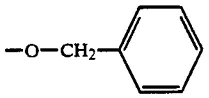 | H | 1 | $CF_3$ | |

TABLE 6a-continued

Compounds of formula I wherein W = $W_6$, A = $-CO-R_3$ and $R_{14}$ = H:

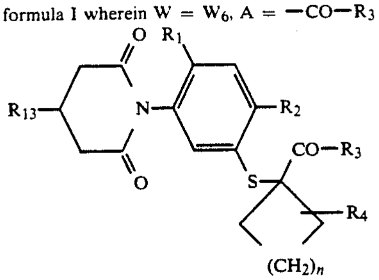

(I)

| Comp. No. | $R_1$ | $R_2$ | $R_3$ | $R_4$ | n | $R_{13}$ | m.p. [°C.] |
|---|---|---|---|---|---|---|---|
| 6.211 | F | Br | $-SCH_3$ | H | 1 | $CF_3$ | |
| 6.212 | F | Br | $-S-CH_2-COOCH_3$ | H | 1 | $CF_3$ | |
| 6.213 | F | Br | $-S-CH(CH_3)-COOCH_3$ | H | 1 | $CF_3$ | |
| 6.214 | F | Br | $-O-CH_2-COOCH_3$ | H | 1 | $CF_3$ | |
| 6.215 | F | Br | $-O-CH(CH_3)COOCH_3$ | H | 1 | $CF_3$ | |
| 6.216 | F | CN | $-Cl$ | H | 1 | $CF_3$ | |
| 6.217 | F | CN | $-OH$ | H | 1 | $CF_3$ | |
| 6.218 | F | CN | $-OCH_3$ | H | 1 | $CF_3$ | |
| 6.219 | H | Cl | $-Cl$ | H | 1 | $CF_3$ | |
| 6.220 | H | Cl | $-OH$ | H | 1 | $CF_3$ | |
| 6.221 | H | Cl | $-OCH_3$ | H | 1 | $CF_3$ | |
| 6.222 | H | Cl | $-OC_2H_5$ | H | 1 | $CF_3$ | |
| 6.223 | H | Cl | 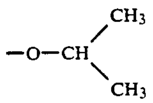 | H | 1 | $CF_3$ | |
| 6.224 | H | Cl | $-O-CH_2-COOCH_3$ | H | 1 | $CF_3$ | |
| 6.225 | H | Cl | $-O-CH(CH_3)COOCH_3$ | H | 1 | $CF_3$ | |
| 6.226 | H | Cl | $-S-CH_2-COOCH_3$ | H | 1 | $CF_3$ | |
| 6.227 | H | Cl | $-S-CH(CH_3)COOCH_3$ | H | 1 | $CF_3$ | |
| 6.228 | H | Cl | 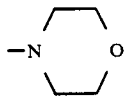 | H | 1 | $CF_3$ | |
| 6.229 | F | Cl | Cl | H | 2 | $CF_3$ | |
| 6.230 | F | Cl | OH | H | 2 | $CF_3$ | |
| 6.231 | F | Cl | $OCH_3$ | H | 2 | $CF_3$ | |
| 6.232 | F | Cl | $-OC_2H_5$ | H | 2 | $CF_3$ | |
| 6.233 | F | Cl | 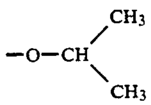 | H | 2 | $CF_3$ | |
| 6.234 | F | Cl | $-O-CH_2-CH_2-O-CH_3$ | H | 2 | $CF_3$ | |
| 6.235 | F | Cl | $-O-CH(CH_3)-CH_2-S-CH_3$ | H | 2 | $CF_3$ | |
| 6.236 | F | Cl | $-O-CH_2-COOCH_3$ | H | 2 | $CF_3$ | |
| 6.237 | F | Cl | $-S-CH_2-COOCH_3$ | H | 2 | $CF_3$ | |
| 6.238 | F | Cl | $-CH_2-CH=CH_2$ | H | 2 | $CF_3$ | |
| 6.239 | F | Cl | $-CH_2-C\equiv CH$ | H | 2 | $CF_3$ | |
| 6.240 | F | Cl | Cl | H | 3 | $CF_3$ | |
| 6.241 | F | Cl | OH | H | 3 | $CF_3$ | |
| 6.242 | F | Cl | $OCH_3$ | H | 3 | $CF_3$ | |
| 6.243 | F | Cl | $OC_2H_5$ | H | 3 | $CF_3$ | |
| 6.244 | F | Cl | 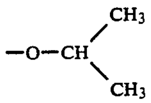 | H | 3 | $CF_3$ | |
| 6.245 | F | Cl | $-O-CH_2-CH_2-O-CH$ | H | 3 | $CF_3$ | |
| 6.246 | F | Cl | $-O-CH(CH_3)-CH_2-S-CH_3$ | H | 3 | $CF_3$ | |
| 6.247 | F | Cl | $-O-CH_2-COOCH_3$ | H | 3 | $CF_3$ | |
| 6.248 | F | Cl | $-S-CH_2-COOCH_3$ | H | 3 | $CF_3$ | |
| 6.249 | F | Cl | $-O-CH_2-C\equiv CH$ | H | 3 | $CF_3$ | |
| 6.250 | F | Cl | $-Cl$ | Cl | 0 | $CF_3$ | |
| 6.251 | F | Cl | $-OH$ | Cl | 0 | $CF_3$ | |
| 6.252 | F | Cl | $-OCH_3$ | Cl | 0 | $CF_3$ | |
| 6.253 | F | Cl | $-OC_2H_5$ | Cl | 0 | $CF_3$ | |

TABLE 6a-continued

Compounds of formula I wherein W = $W_6$, A = $-CO-R_3$ and $R_{14}$ = H:

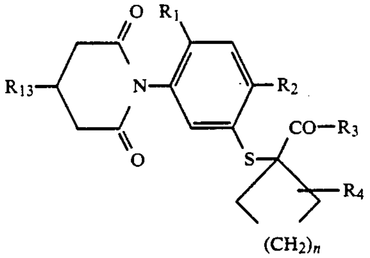

(I)

| Comp. No. | $R_1$ | $R_2$ | $R_3$ | $R_4$ | n | $R_{13}$ | m.p. [°C.] |
|---|---|---|---|---|---|---|---|
| 6.254 | F | Cl | $CH_3$<br>/<br>$-O-CH$<br>\<br>$CH_3$ | Cl | 0 | $CF_3$ | |
| 6.255 | F | Cl | $-O-CH_2-COOCH_3$ | Cl | 0 | $CF_3$ | |
| 6.256 | F | Cl | $-S-CH_2-COOCH_3$ | Cl | 0 | $CF_3$ | |
| 6.257 | F | Cl | $-OCH_3$ | Br | 0 | $CF_3$ | |
| 6.258 | F | Cl | $CH_3$<br>/<br>$-O-CH$<br>\<br>$CH_3$ | Br | 0 | $CF_3$ | |
| 6.259 | F | Cl | $-OCH_3$ | F | 0 | $CF_3$ | |
| 6.260 | F | Cl | $-OCH_3$ | $CH_3$ | 0 | $CF_3$ | |
| 6.261 | F | Cl | $-OC_2H_5$ | $CH_3$ | 0 | $CF_3$ | |
| 6.262 | F | Cl | $CH_3$<br>/<br>$-O-CH$<br>\<br>$CH_3$ | $CH_3$ | 0 | $CF_3$ | |
| 6.263 | F | Cl | $-O-CH_2-CH_2-O-CH_3$ | $CH_3$ | 0 | $CF_3$ | |
| 6.264 | F | Cl | $-O-CH_2-COOCH_3$ | $CH_3$ | 0 | $CF_3$ | |
| 6.265 | F | Cl | $-O-CH(CH_3)COOCH_3$ | $CH_3$ | 0 | $CF_3$ | |
| 6.266 | F | Cl | $-S-CH_2-COOCH_3$ | $CH_3$ | 0 | $CF_3$ | |
| 6.267 | F | Cl | $-OCH_3$ | $CF_3$ | 0 | $CF_3$ | |
| 6.268 | F | Cl | $-OC_2H_5$ | $CF_3$ | 0 | $CF_3$ | |
| 6.269 | F | Cl | $CH_3$<br>/<br>$-O-CH$<br>\<br>$CH_3$ | $CF_3$ | 0 | $CF_3$ | |
| 6.270 | F | Cl | $-O-CH_2-COOCH_3$ | $CF_3$ | 0 | $CF_3$ | |
| 6.271 | F | Cl | $-S-CH_2-COOCH_3$ | $CF_3$ | 0 | $CF_3$ | |
| 6.272 | F | Cl | $-Cl$ | H | 0 | $CH_3$ | |
| 6.273 | F | Cl | $-OH$ | H | 0 | $CH_3$ | |
| 6.274 | F | Cl | $-OCH_3$ | H | 0 | $CH_3$ | |
| 6.275 | F | Cl | $-OC_2H_5$ | H | 0 | $CH_3$ | |
| 6.276 | F | Cl | $-OC_3H_7$ | H | 0 | $CH_3$ | |
| 6.277 | F | Cl | $CH_3$<br>/<br>$-O-CH$<br>\<br>$CH_3$ | H | 0 | $CH_3$ | |
| 6.278 | F | Cl | $-OC_4H_9$ | H | 0 | $CH_3$ | |
| 6.279 | F | Cl | $-O-CH(CH_3)-C_2H_5$ | H | 0 | $CH_3$ | |
| 6.280 | F | Cl | $CH_3$<br>/<br>$-O-CH_2-CH$<br>\<br>$CH_3$ | H | 0 | $CH_3$ | |
| 6.281 | F | Cl | $-OC_5H_{11}$ | H | 0 | $CH_3$ | |
| 6.282 | F | Cl | $-O-CH_2-CH_2-O-CH_3$ | H | 0 | $CH_3$ | |
| 6.283 | F | Cl | $-O-CH_2-CH_2-O-C_2H_5$ | H | 0 | $CH_3$ | |
| 6.284 | F | Cl | $-O-CH-(CH_3)-CH_2-O-CH_3$ | H | 0 | $CH_3$ | |

TABLE 6a-continued

Compounds of formula I wherein W = $W_6$, A = $-CO-R_3$ and $R_{14}$ = H:

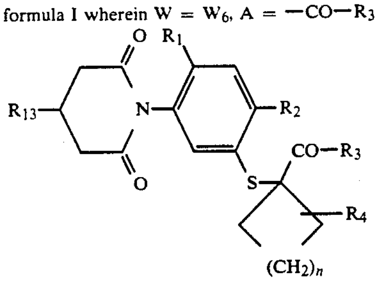

(I)

| Comp. No. | $R_1$ | $R_2$ | $R_3$ | $R_4$ | n | $R_{13}$ | m.p. [°C.] |
|---|---|---|---|---|---|---|---|
| 6.285 | F | Cl | $-O-CH_2-CH_2-S-CH_3$ | H | 0 | $CH_3$ | |
| 6.286 | F | Cl | $-O-CH(CH_3)-CH_2-S-CH_3$ | H | 0 | $CH_3$ | |
| 6.287 | F | Cl | $-O-CH(CH_3)-CH_2-S-C_2H_5$ | H | 0 | $CH_3$ | |
| 6.288 | F | Cl | $-O-CH(CH_3)-CH_2-S-C_3H_7$ | H | 0 | $CH_3$ | |
| 6.289 | F | Cl | 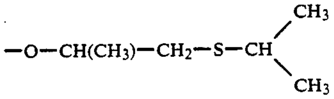 | H | 0 | $CH_3$ | |
| 6.290 | F | Cl | $-O-CH(CH_3)-CH_2-S-C_4H_9$ | H | 0 | $CH_3$ | |
| 6.291 | F | Cl | $-O-CH(CH_3)-CH_2-S-C_5H_{11}$ | H | 0 | $CH_3$ | |
| 6.292 | F | Cl | 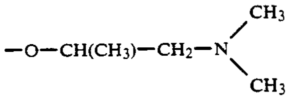 | H | 0 | $CH_3$ | |
| 6.293 | F | Cl | 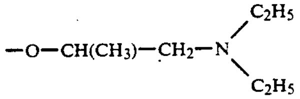 | H | 0 | $CH_3$ | |
| 6.294 | F | Cl | $-NH_2$ | H | 0 | $CH_3$ | |
| 6.295 | F | Cl | 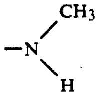 | H | 0 | $CH_3$ | |
| 6.296 | F | Cl | 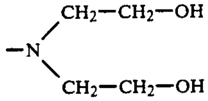 | H | 0 | $CH_3$ | |
| 6.297 | F | Cl | $-NH-CH_2-CH=CH_2$ | H | 0 | $CH_3$ | |
| 6.298 | F | Cl | $-N-(CH_2-CH=CH_2)_2$ | H | 0 | $CH_3$ | |
| 6.299 | F | Cl | 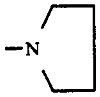 | H | 0 | $CH_3$ | |
| 6.300 | F | Cl | 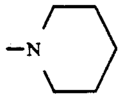 | H | 0 | $CH_3$ | |
| 6.301 | F | Cl | 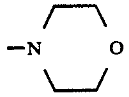 | H | 0 | $CH_3$ | |
| 6.302 | F | Cl | 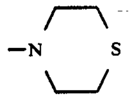 | H | 0 | $CH_3$ | |

TABLE 6a-continued
Compounds of formula I wherein W = $W_6$, A = $-CO-R_3$ and $R_{14}$ = H:
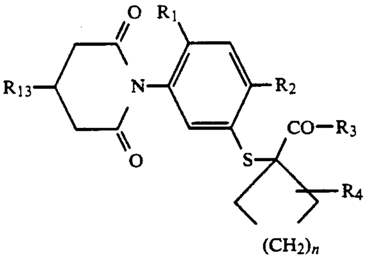
(I)
| Comp. No. | $R_1$ | $R_2$ | $R_3$ | $R_4$ | n | $R_{13}$ | m.p. [°C.] |
|---|---|---|---|---|---|---|---|
| 6.303 | F | Cl | 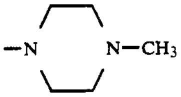 | H | 0 | $CH_3$ | |
| 6.304 | F | Cl | 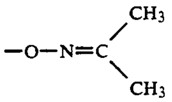 | H | 0 | $CH_3$ | |
| 6.305 | F | Cl | $-O-CH_2-CH_2-Cl$ | H | 0 | $CH_3$ | |
| 6.306 | F | Cl | $-O-CH_2-CN$ | H | 0 | $CH_3$ | |
| 6.307 | F | Cl | 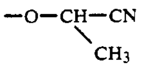 | H | 0 | $CH_3$ | |
| 6.308 | F | Cl | $-O-CH_2-CH=CH_2$ | H | 0 | $CH_3$ | |
| 6.309 | F | Cl | $-O-CH_2-CH=CHCl$ | H | 0 | $CH_3$ | |
| 6.310 | F | Cl | 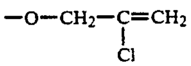 | H | 0 | $CH_3$ | |
| 6.311 | F | Cl | $-O-CH_2=C\equiv CH$ | H | 0 | $CH_3$ | |
| 6.312 | F | Cl | 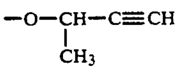 | H | 0 | $CH_3$ | |
| 6.313 | F | Cl | 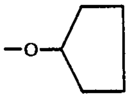 | H | 0 | $CH_3$ | |
| 6.314 | F | Cl | 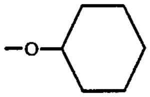 | H | 0 | $CH_3$ | |
| 6.315 | F | Cl | 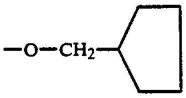 | H | 0 | $CH_3$ | |
| 6.316 | F | Cl | 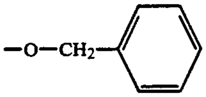 | H | 0 | $CH_3$ | |
| 6.317 | F | Cl | 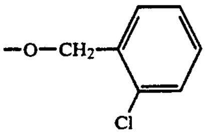 | H | 0 | $CH_3$ | |

TABLE 6a-continued

Compounds of formula I wherein W = $W_6$, A = $-CO-R_3$ and $R_{14}$ = H:

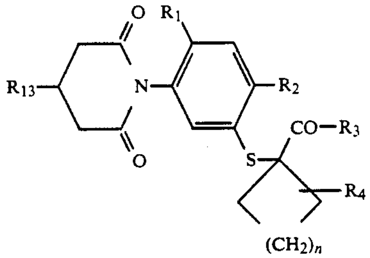

(I)

| Comp. No. | $R_1$ | $R_2$ | $R_3$ | $R_4$ | n | $R_{13}$ | m.p. [°C.] |
|---|---|---|---|---|---|---|---|
| 6.318 | F | Cl | 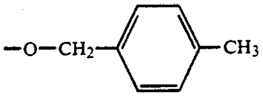 | H | 0 | $CH_3$ | |
| 6.319 | F | Cl | $-S-CH_3$ | H | 0 | $CH_3$ | |
| 6.320 | F | Cl | $-S-C_2H_5$ | H | 0 | $CH_3$ | |
| 6.321 | F | Cl | $-S-C_3H_7$ | H | 0 | $CH_3$ | |
| 6.322 | F | Cl | $-S-CH_2-CH{=}CH_2$ | H | 0 | $CH_3$ | |
| 6.323 | F | Cl | $-S-CH_2-COOCH_3$ | H | 0 | $CH_3$ | |
| 6.324 | F | Cl | $-S-CH_2-COOC_2H_5$ | H | 0 | $CH_3$ | |
| 6.325 | F | Cl | $-S-CH_2-COOC_5H_{11}$ | H | 0 | $CH_3$ | |
| 6.326 | F | Cl | $-S-CH(CH_3)-COOCH_3$ | H | 0 | $CH_3$ | |
| 6.327 | F | Cl | $-S-(CH_3)-COOC_2H_5$ | H | 0 | $CH_3$ | |
| 6.328 | F | Cl | $-S-CH(CH_3)-COOC_3H_7$ | H | 0 | $CH_3$ | |
| 6.329 | F | Cl | $-S-CH_2-CH_2-COOCH_3$ | H | 0 | $CH_3$ | |
| 6.330 | F | Cl | $-S-CH_2-COOCH_2-CH_2-O-CH_3$ | H | 0 | $CH_3$ | |
| 6.331 | F | Cl | $-O-CH_2-COOCH_3$ | H | 0 | $CH_3$ | |
| 6.332 | F | Cl | $-O-CH(CH_3)-COOCH_3$ | H | 0 | $CH_3$ | |
| 6.333 | F | Cl | $-O-CH_2-COOC_5H_{11}$ | H | 0 | $CH_3$ | |
| 6.334 | F | Cl | $-O-CH_2-CH_3-Si(CH_3)_3$ | H | 0 | $CH_3$ | |
| 6.335 | F | Cl | $-ONa$ | H | 0 | $CH_3$ | |
| 6.336 | F | Br | $-Cl$ | H | 0 | $CH_3$ | |
| 6.337 | F | Br | $-OH$ | H | 0 | $CH_3$ | |
| 6.338 | F | Br | $-OCH_3$ | H | 0 | $CH_3$ | |
| 6.339 | F | Br | $-OC_2H_5$ | H | 0 | $CH_3$ | |
| 6.340 | F | Br | $-OC_3H_7$ | H | 0 | $CH_3$ | |
| 6.341 | F | Br | 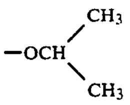 | H | 0 | $CH_3$ | |
| 6.342 | F | Br | $-OC_4H_9$ | H | 0 | $CH_3$ | |
| 6.343 | F | Br | $-OCH(CH_3)-CH_2-CH_3$ | H | 0 | $CH_3$ | |
| 6.344 | F | Br | 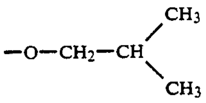 | H | 0 | $CH_3$ | |
| 6.345 | F | Br | $-O-C_5H_{11}$ | H | 0 | $CH_3$ | |
| 6.346 | F | Br | $-O-CH_2-CH_2-O-CH_3$ | H | 0 | $CH_3$ | |
| 6.347 | F | Br | $-O-CH_2-CH_2-O-C_2H_5$ | H | 0 | $CH_3$ | |
| 6.348 | F | Br | $-O-CH(CH_3)-CH_2-O-CH_3$ | H | 0 | $CH_3$ | |
| 6.349 | F | Br | $-O-CH_2-CH_2-S-CH_3$ | H | 0 | $CH_3$ | |
| 6.350 | F | Br | $-O-CH_2(CH_3)-S-CH_3$ | H | 0 | $CH_3$ | |
| 6.351 | F | Br | $-O-CH-(CH_3)-S-C_2H_5$ | H | 0 | $CH_3$ | |
| 6.352 | F | Br | $-O-CH(CH_3)-S-C_3H_7$ | H | 0 | $CH_3$ | |
| 6.353 | F | Br | 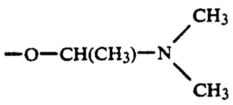 | H | 0 | $CH_3$ | |
| 6.354 | F | Br | $-NH_2$ | H | 0 | $CH_3$ | |
| 6.355 | F | Br | 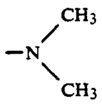 | H | 0 | $CH_3$ | |

TABLE 6a-continued

Compounds of formula I wherein W = $W_6$, A = $-CO-R_3$ and $R_{14}$ = H:

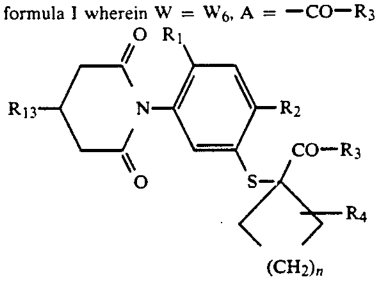

(I)

| Comp. No. | $R_1$ | $R_2$ | $R_3$ | $R_4$ | n | $R_{13}$ | m.p. [°C.] |
|---|---|---|---|---|---|---|---|
| 6.356 | F | Br | 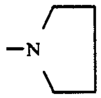 | H | 0 | $CH_3$ | |
| 6.357 | F | Br | 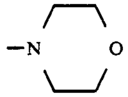 | H | 0 | $CH_3$ | |
| 6.358 | F | Br | 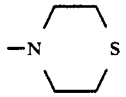 | H | 0 | $CH_3$ | |
| 6.359 | F | Br | 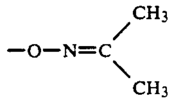 | H | 0 | $CH_3$ | |
| 6.360 | F | Br | $-O-CH_2-CH_2-Cl$ | H | 0 | $CH_3$ | |
| 6.361 | F | Br | $-O-CH_2-CN$ | H | 0 | $CH_3$ | |
| 3.362 | F | Br | $-O-CH_2-CH=CH_2$ | H | 0 | $CH_3$ | |
| 6.363 | F | Br | $-O-CH_2-C\equiv CH$ | H | 0 | $CH_3$ | |
| 6.364 | F | Br | 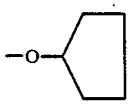 | H | 0 | $CH_3$ | |
| 3.365 | F | Br | 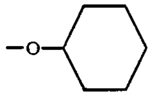 | H | 0 | $CH_3$ | |
| 3.366 | F | Br | 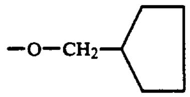 | H | 0 | $CH_3$ | |
| 3.367 | F | Br | 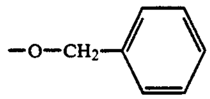 | H | 0 | $CH_3$ | |
| 3.368 | F | Br | $-SCH_3$ | H | 0 | $CH_3$ | |
| 6.369 | F | Br | $-S-CH_2-COOCH_3$ | H | 0 | $CH_3$ | |
| 6.370 | F | Br | $-S-CH(CH_3)-COOCH_3$ | H | 0 | $CH_3$ | |
| 6.371 | F | Br | $-O-CH_2-COOCH_3$ | H | 0 | $CH_3$ | |
| 6.372 | F | Br | $-O-CH(CH_3)COOCH_3$ | H | 0 | $CH_3$ | |
| 6.373 | F | CN | $-Cl$ | H | 0 | $CH_3$ | |
| 6.374 | F | CN | $-OH$ | H | 0 | $CH_3$ | |
| 6.375 | F | CN | $-OCH_3$ | H | 0 | $CH_3$ | |
| 6.376 | H | Cl | $-Cl$ | H | 0 | $CH_3$ | |
| 6.377 | H | Cl | $-OH$ | H | 0 | $CH_3$ | |
| 6.378 | H | Cl | $-OCH_3$ | H | 0 | $CH_3$ | |
| 6.379 | H | Cl | $-OC_2H_5$ | H | 0 | $CH_3$ | |

TABLE 6a-continued

Compounds of formula I wherein W = $W_6$, A = $-CO-R_3$ and $R_{14}$ = H:

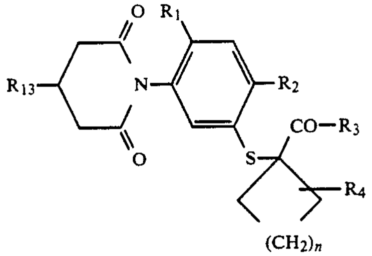

(I)

| Comp. No. | $R_1$ | $R_2$ | $R_3$ | $R_4$ | n | $R_{13}$ | m.p. [°C.] |
|---|---|---|---|---|---|---|---|
| 6.380 | H | Cl | 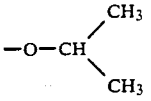 | H | 0 | $CH_3$ | |
| 6.381 | H | Cl | $-O-CH_2-COOCH_3$ | H | 0 | $CH_3$ | |
| 6.382 | H | Cl | $-O-CH(CH_3)COOCH_3$ | H | 0 | $CH_3$ | |
| 6.383 | H | Cl | $-S-CH_2-COOCH_3$ | H | 0 | $CH_3$ | |
| 6.384 | H | Cl | $-S-CH(CH_3)COOCH_3$ | H | 0 | $CH_3$ | |
| 6.385 | H | Cl | 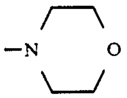 | H | 0 | $CH_3$ | |
| 6.386 | F | Cl | $-Cl$ | H | 1 | $CH_3$ | |
| 6.387 | F | Cl | $-OH$ | H | 1 | $CH_3$ | |
| 6.388 | F | Cl | $-OCH_3$ | H | 1 | $CH_3$ | |
| 6.389 | F | Cl | $-OC_2H_5$ | H | 1 | $CH_3$ | |
| 6.390 | F | Cl | $-OC_3H_7$ | H | 1 | $CH_3$ | |
| 6.391 | F | Cl | 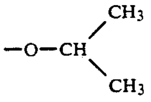 | H | 1 | $CH_3$ | |
| 6.392 | F | Cl | $-OC_4H_9$ | H | 1 | $CH_3$ | |
| 6.393 | F | Cl | $-O-CH(CH_3)-C_2H_5$ | H | 1 | $CH_3$ | |
| 6.394 | F | Cl | 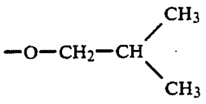 | H | 1 | $CH_3$ | |
| 6.395 | F | Cl | $-OC_5H_{11}$ | H | 1 | $CH_3$ | |
| 6.396 | F | Cl | $-O-CH_2-CH_2-O-CH_3$ | H | 1 | $CH_3$ | |
| 6.397 | F | Cl | $-O-CH_2-CH_2-O-C_2H_5$ | H | 1 | $CH_3$ | |
| 6.398 | F | Cl | $-O-CH-(CH_3)-CH_2-O-CH_3$ | H | 1 | $CH_3$ | |
| 6.399 | F | Cl | $-O-CH_2-CH_2-S-CH_3$ | H | 1 | $CH_3$ | |
| 6.400 | F | Cl | $-O-CH(CH_3)-CH_2-S-CH_3$ | H | 1 | $CH_3$ | |
| 6.401 | F | Cl | $-O-CH(CH_3)-CH_2-S-C_2H_5$ | H | 1 | $CH_3$ | |
| 6.402 | F | Cl | $-O-CH(CH_3)-CH_2-S-C_3H_7$ | H | 1 | $CH_3$ | |
| 6.403 | F | Cl | 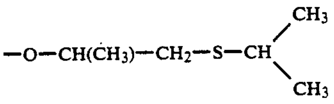 | H | 1 | $CH_3$ | |
| 6.404 | F | Cl | $-O-CH(CH_3)-CH_2-S-C_4H_9$ | H | 1 | $CH_3$ | |
| 6.405 | F | Cl | $-O-CH(CH_3)-CH_2-S-C_5H_{11}$ | H | 1 | $CH_3$ | |
| 6.406 | F | Cl | 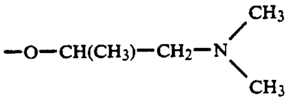 | H | 1 | $CH_3$ | |
| 6.407 | F | Cl | 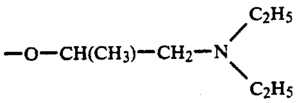 | H | 1 | $CH_3$ | |

TABLE 6a-continued
Compounds of formula I wherein W = $W_6$, A = $-CO-R_3$ and $R_{14}$ = H:
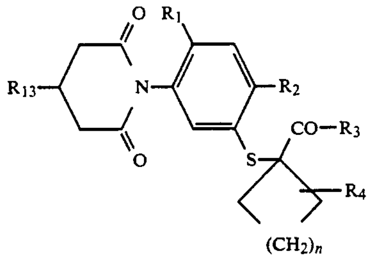
(I)
| Comp. No. | $R_1$ | $R_2$ | $R_3$ | $R_4$ | n | $R_{13}$ | m.p. [°C.] |
|---|---|---|---|---|---|---|---|
| 6.408 | F | Cl | $-NH_2$ | H | 1 | $CH_3$ | |
| 6.409 | F | Cl | 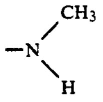 | H | 1 | $CH_3$ | |
| 6.410 | F | Cl | 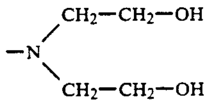 | H | 1 | $CH_3$ | |
| 6.411 | F | Cl | $-NH-CH_2-CH=CH_2$ | H | 1 | $CH_3$ | |
| 6.412 | F | Cl | $-N-(CH_2-CH=CH_2)_2$ | H | 1 | $CH_3$ | |
| 6.413 | F | Cl | 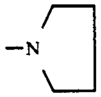 | H | 1 | $CH_3$ | |
| 6.414 | F | Cl | 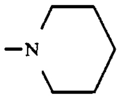 | H | 1 | $CH_3$ | |
| 6.415 | F | Cl | 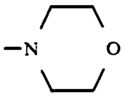 | H | 1 | $CH_3$ | |
| 6.416 | F | Cl | 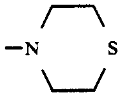 | H | 1 | $CH_3$ | |
| 6.417 | F | Cl | 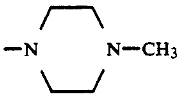 | H | 1 | $CH_3$ | |
| 6.418 | F | Cl | 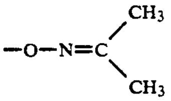 | H | 1 | $CH_3$ | |
| 6.419 | F | Cl | $-O-CH_2-CH_2-Cl$ | H | 1 | $CH_3$ | |
| 6.420 | F | Cl | $-O-CH_2-CN$ | H | 1 | $CH_3$ | |
| 6.421 | F | Cl | 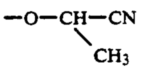 | H | 1 | $CH_3$ | |
| 6.422 | F | Cl | $-O-CH_2-CH=CH_2$ | H | 1 | $CH_3$ | |
| 6.423 | F | Cl | $-O-CH_2-CH=CHCl$ | H | 1 | $CH_3$ | |

TABLE 6a-continued

Compounds of formula I wherein W = $W_6$, A = $-CO-R_3$ and $R_{14}$ = H:

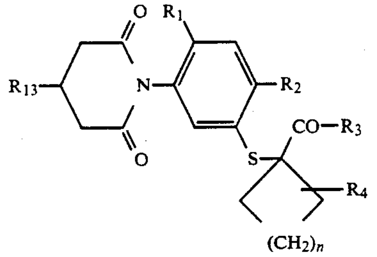

(I)

| Comp. No. | $R_1$ | $R_2$ | $R_3$ | $R_4$ | n | $R_{13}$ | m.p. [°C.] |
|---|---|---|---|---|---|---|---|
| 6.424 | F | Cl | 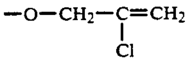 | H | 1 | $CH_3$ | |
| 6.425 | F | Cl | $-O-CH_2=C\equiv CH$ | H | 1 | $CH_3$ | |
| 6.426 | F | Cl | 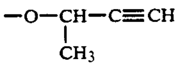 | H | 1 | $CH_3$ | |
| 6.427 | F | Cl | 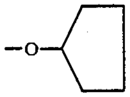 | H | 1 | $CH_3$ | |
| 6.428 | F | Cl | 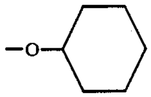 | H | 1 | $CH_3$ | |
| 6.429 | F | Cl | 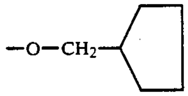 | H | 1 | $CH_3$ | |
| 6.430 | F | Cl | 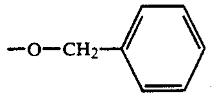 | H | 1 | $CH_3$ | |
| 6.431 | F | Cl | 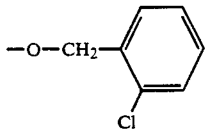 | H | 1 | $CH_3$ | |
| 6.432 | F | Cl | 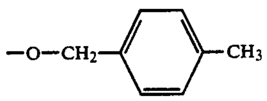 | H | 1 | $CH_3$ | |
| 6.433 | F | Cl | $-S-CH_3$ | H | 1 | $CH_3$ | |
| 6.434 | F | Cl | $-S-C_2H_5$ | H | 1 | $CH_3$ | |
| 6.435 | F | Cl | $-S-C_3H_7$ | H | 1 | $CH_3$ | |
| 6.436 | F | Cl | $-S-CH_2-CH=CH_2$ | H | 1 | $CH_3$ | |
| 6.437 | F | Cl | $-S-CH_2-COOCH_3$ | H | 1 | $CH_3$ | |
| 6.438 | F | Cl | $-S-CH_2-COOC_2H_5$ | H | 1 | $CH_3$ | |
| 6.439 | F | Cl | $-S-CH_2-COOC_5H_{11}$ | H | 1 | $CH_3$ | |
| 6.440 | F | Cl | $-S-CH(CH_3)-COOCH_3$ | H | 1 | $CH_3$ | |
| 6.441 | F | Cl | $-S-(CH_3)-COOC_2H_5$ | H | 1 | $CH_3$ | |
| 6.442 | F | Cl | $-S-CH(CH_3)-COOC_3H_7$ | H | 1 | $CH_3$ | |
| 6.443 | F | Cl | $-S-CH_2-CH_2-COOCH_3$ | H | 1 | $CH_3$ | |
| 6.444 | F | Cl | $-S-CH_2-COOCH_2-CH_2-O-CH_3$ | H | 1 | $CH_3$ | |
| 6.445 | F | Cl | $-O-CH_2-COOCH_3$ | H | 1 | $CH_3$ | |
| 6.446 | F | Cl | $-O-CH(CH_3)-COOCH_3$ | H | 1 | $CH_3$ | |
| 6.447 | F | Cl | $-O-CH_2-COOC_5H_{11}$ | H | 1 | $CH_3$ | |
| 6.448 | F | Cl | $-O-CH_2-CH_3-Si(CH_3)_3$ | H | 1 | $CH_3$ | |
| 6.449 | F | Cl | $-ONa$ | H | 1 | $CH_3$ | |

TABLE 6a-continued

Compounds of formula I wherein W = $W_6$, A = $-CO-R_3$ and $R_{14}$ = H:

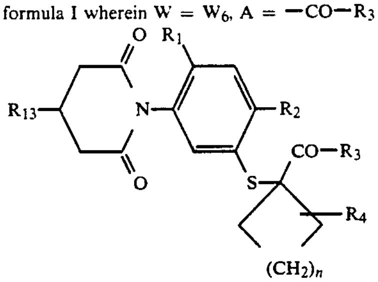

(I)

| Comp. No. | $R_1$ | $R_2$ | $R_3$ | $R_4$ | n | $R_{13}$ | m.p. [°C.] |
|---|---|---|---|---|---|---|---|
| 6.450 | F | Br | $-Cl$ | H | 1 | $CH_3$ | |
| 6.451 | F | Br | $-OH$ | H | 1 | $CH_3$ | |
| 6.452 | F | Br | $-OCH_3$ | H | 1 | $CH_3$ | |
| 6.453 | F | Br | $-OC_2H_5$ | H | 1 | $CH_3$ | |
| 6.454 | F | Br | $-OC_3H_7$ | H | 1 | $CH_3$ | |
| 6.455 | F | Br | 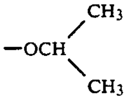 | H | 1 | $CH_3$ | |
| 6.456 | F | Br | $-OC_4H_9$ | H | 1 | $CH_3$ | |
| 6.457 | F | Br | $-OCH(CH_3)-CH_2-CH_3$ | H | 1 | $CH_3$ | |
| 6.458 | F | Br | 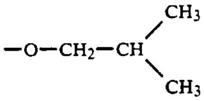 | H | 1 | $CH_3$ | |
| 6.459 | F | Br | $-O-C_5H_{11}$ | H | 1 | $CH_3$ | |
| 6.460 | F | Br | $-O-CH_2-CH_2-O-CH_3$ | H | 1 | $CH_3$ | |
| 6.461 | F | Br | $-O-CH_2-CH_2-O-C_2H_5$ | H | 1 | $CH_3$ | |
| 6.462 | F | Br | $-O-CH(CH_3)-CH_2-O-CH_3$ | H | 1 | $CH_3$ | |
| 6.463 | F | Br | $-O-CH_2-CH_2-S-CH_3$ | H | 1 | $CH_3$ | |
| 6.464 | F | Br | $-O-CH_2(CH_3)-S-CH_3$ | H | 1 | $CH_3$ | |
| 6.465 | F | Br | $-O-CH-(CH_3)-S-C_2H_5$ | H | 1 | $CH_3$ | |
| 6.466 | F | Br | $-O-CH(CH_3)-S-C_3H_7$ | H | 1 | $CH_3$ | |
| 6.467 | F | Br | 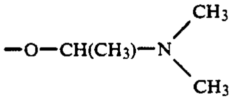 | H | 1 | $CH_3$ | |
| 6.468 | F | Br | $-NH_2$ | H | 1 | $CH_3$ | |
| 6.469 | F | Br | 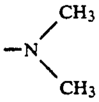 | H | 1 | $CH_3$ | |
| 6.470 | F | Br | 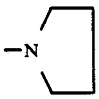 | H | 1 | $CH_3$ | |
| 6.471 | F | Br | 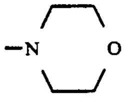 | H | 1 | $CH_3$ | |
| 6.472 | F | Br | 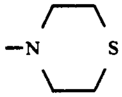 | H | 1 | $CH_3$ | |
| 6.473 | F | Br | 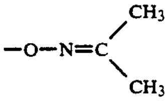 | H | 1 | $CH_3$ | |

TABLE 6a-continued

Compounds of formula I wherein W = $W_6$, A = $-CO-R_3$ and $R_{14}$ = H:

(I)

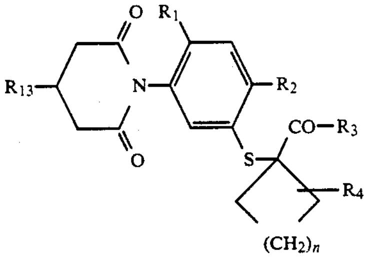

| Comp. No. | $R_1$ | $R_2$ | $R_3$ | $R_4$ | n | $R_{13}$ | m.p. [°C.] |
|---|---|---|---|---|---|---|---|
| 6.474 | F | Br | $-O-CH_2-CH_2-Cl$ | H | 1 | $CH_3$ | |
| 6.475 | F | Br | $-O-CH_2-CN$ | H | 1 | $CH_3$ | |
| 6.476 | F | Br | $-O-CH_2-CH=CH_2$ | H | 1 | $CH_3$ | |
| 6.477 | F | Br | $-O-CH_2-C\equiv CH$ | H | 1 | $CH_3$ | |
| 6.478 | F | Br | 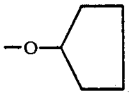 | H | 1 | $CH_3$ | |
| 6.479 | F | Br | 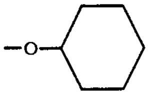 | H | 1 | $CH_3$ | |
| 6.480 | F | Br | 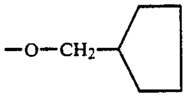 | H | 1 | $CH_3$ | |
| 6.481 | F | Br | 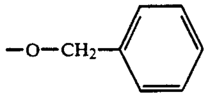 | H | 1 | $CH_3$ | |
| 6.482 | F | Br | $-SCH_3$ | H | 1 | $CH_3$ | |
| 6.483 | F | Br | $-S-CH_2-COOCH_3$ | H | 1 | $CH_3$ | |
| 6.484 | F | Br | $-S-CH(CH_3)-COOCH_3$ | H | 1 | $CH_3$ | |
| 6.485 | F | Br | $-O-CH_2-COOCH_3$ | H | 1 | $CH_3$ | |
| 6.486 | F | Br | $-O-CH(CH_3)COOCH_3$ | H | 1 | $CH_3$ | |
| 6.487 | F | CN | $-Cl$ | H | 1 | $CH_3$ | |
| 6.488 | F | CN | $-OH$ | H | 1 | $CH_3$ | |
| 6.489 | F | CN | $-OCH_3$ | H | 1 | $CH_3$ | |
| 6.490 | H | Cl | $-Cl$ | H | 1 | $CH_3$ | |
| 6.491 | H | Cl | $-OH$ | H | 1 | $CH_3$ | |
| 6.492 | H | Cl | $-OCH_3$ | H | 1 | $CH_3$ | |
| 6.493 | H | Cl | $-OC_2H_5$ | H | 1 | $CH_3$ | |
| 6.494 | H | Cl | 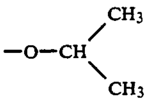 | H | 1 | $CH_3$ | |
| 6.495 | H | Cl | $-O-CH_2-COOCH_3$ | H | 1 | $CH_3$ | |
| 6.496 | H | Cl | $-O-CH(CH_3)COOCH_3$ | H | 1 | $CH_3$ | |
| 6.497 | H | Cl | $-S-CH_2-COOCH_3$ | H | 1 | $CH_3$ | |
| 6.498 | H | Cl | $-S-CH(CH_3)COOCH_3$ | H | 1 | $CH_3$ | |
| 6.499 | H | Cl | 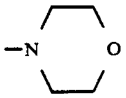 | H | 1 | $CH_3$ | |
| 6.500 | F | Cl | Cl | H | 2 | $CH_3$ | |
| 6.501 | F | Cl | OH | H | 2 | $CH_3$ | |
| 6.502 | F | Cl | $OCH_3$ | H | 2 | $CH_3$ | |
| 6.503 | F | Cl | $-OC_2H_5$ | H | 2 | $CH_3$ | |

TABLE 6a-continued

Compounds of formula I wherein W = $W_6$, A = $-CO-R_3$ and $R_{14}$ = H:

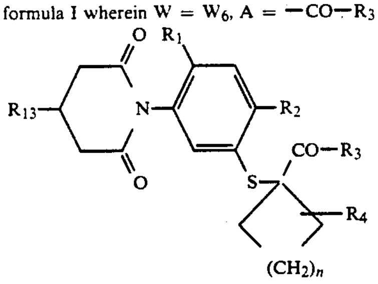

(I)

| Comp. No. | $R_1$ | $R_2$ | $R_3$ | $R_4$ | n | $R_{13}$ | m.p. [°C.] |
|---|---|---|---|---|---|---|---|
| 6.504 | F | Cl | 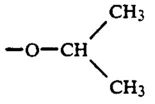 | H | 2 | $CH_3$ | |
| 6.505 | F | Cl | $-O-CH_2-CH_2-O-CH_3$ | H | 2 | $CH_3$ | |
| 6.506 | F | Cl | $-O-CH(CH_3)-CH_2-S-CH_3$ | H | 2 | $CH_3$ | |
| 6.507 | F | Cl | $-O-CH_2-COOCH_3$ | H | 2 | $CH_3$ | |
| 6.508 | F | Cl | $-S-CH_2-COOCH_3$ | H | 2 | $CH_3$ | |
| 6.509 | F | Cl | $-O-CH_2-CH=CH_2$ | H | 2 | $CH_3$ | |
| 6.510 | F | Cl | $-O-CH_2-C \equiv CH$ | H | 2 | $CH_3$ | |
| 6.511 | F | Cl | Cl | H | 3 | $CH_3$ | |
| 6.512 | F | Cl | OH | H | 3 | $CH_3$ | |
| 6.513 | F | Cl | $OCH_3$ | H | 3 | $CH_3$ | |
| 6.514 | F | Cl | $OC_2H_5$ | H | 3 | $CH_3$ | |
| 6.515 | F | Cl | 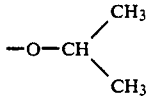 | H | 3 | $CH_3$ | |
| 6.516 | F | Cl | $-O-CH_2-CH_2-O-CH$ | H | 3 | $CH_3$ | |
| 6.517 | F | Cl | $-O-CH(CH_3)-CH_2-S-CH_3$ | H | 3 | $CH_3$ | |
| 6.518 | F | Cl | $-O-CH_2-COOCH_3$ | H | 3 | $CH_3$ | |
| 6.519 | F | Cl | $-S-CH_2-COOCH_3$ | H | 3 | $CH_3$ | |
| 6.520 | F | Cl | $-O-CH_2-C \equiv CH$ | H | 3 | $CH_3$ | |
| 6.521 | F | Cl | $-Cl$ | Cl | 0 | $CH_3$ | |
| 6.522 | F | Cl | $-OH$ | Cl | 0 | $CH_3$ | |
| 6.523 | F | Cl | $-OCH_3$ | Cl | 0 | $CH_3$ | |
| 6.524 | F | Cl | $-OC_2H_5$ | Cl | 0 | $CH_3$ | |
| 6.525 | F | Cl | 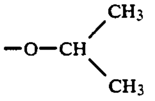 | Cl | 0 | $CH_3$ | |
| 6.526 | F | Cl | $-O-CH_2-COOCH_3$ | Cl | 0 | $CH_3$ | |
| 6.527 | F | Cl | $-S-CH_2-COOCH_3$ | Cl | 0 | $CH_3$ | |
| 6.528 | F | Cl | $-OCH_3$ | Br | 0 | $CH_3$ | |
| 6.529 | F | Cl | 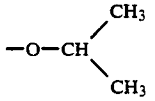 | Br | 0 | $CH_3$ | |
| 6.530 | F | Cl | $-OCH_3$ | F | 0 | $CH_3$ | |
| 6.531 | F | Cl | $-OCH_3$ | $CH_3$ | 0 | $CH_3$ | |
| 6.532 | F | Cl | $-OC_2H_5$ | $CH_3$ | 0 | $CH_3$ | |
| 6.533 | F | Cl | 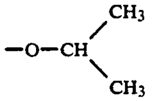 | $CH_3$ | 0 | $CH_3$ | |
| 6.534 | F | Cl | $-O-CH_2-CH_2-O-CH_3$ | $CH_3$ | 0 | $CH_3$ | |
| 6.535 | F | Cl | $-O-CH_2-COOCH_3$ | $CH_3$ | 0 | $CH_3$ | |
| 6.536 | F | Cl | $-O-CH(CH_3)COOCH_3$ | $CH_3$ | 0 | $CH_3$ | |
| 6.537 | F | Cl | $-S-CH_2-COOCH_3$ | $CH_3$ | 0 | $CH_3$ | |
| 6.538 | F | Cl | $-OCH_3$ | $CF_3$ | 0 | $CH_3$ | |
| 6.539 | F | Cl | $-OC_2H_5$ | $CF_3$ | 0 | $CH_3$ | |

TABLE 6a-continued

Compounds of formula I wherein $W = W_6$, $A = -CO-R_3$ and $R_{14} = H$:

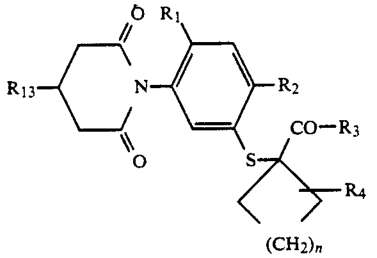

(I)

| Comp. No. | $R_1$ | $R_2$ | $R_3$ | $R_4$ | n | $R_{13}$ | m.p. [°C.] |
|---|---|---|---|---|---|---|---|
| 6.540 | F | Cl | 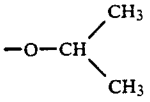 | $CF_3$ | 0 | $CH_3$ | |
| 6.541 | F | Cl | $-O-CH_2-COOCH_3$ | $CF_3$ | 0 | $CH_3$ | |
| 6.542 | F | Cl | $-S-CH_2-COOCH_3$ | $CF_3$ | 0 | $CH_3$ | |
| 6.543 | F | Cl | $-Cl$ | H | 0 | $-CH(CH_3)-CH_3$ | |
| 6.544 | F | Cl | $-OH$ | H | 0 | $-CH(CH_3)-CH_3$ | |
| 6.545 | F | Cl | $-OCH_3$ | H | 0 | $-CH(CH_3)-CH_3$ | |
| 6.546 | F | Cl | $-OC_2H_5$ | H | 0 | $-CH(CH_3)-CH_3$ | |
| 6.547 | F | Cl | $-OC_3H_7$ | H | 0 | $-CH(CH_3)-CH_3$ | |
| 6.548 | F | Cl | 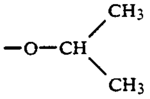 | H | 0 | $-CH(CH_3)-CH_3$ | |
| 6.549 | F | Cl | $-OC_4H_9$ | H | 0 | $-CH(CH_3)-CH_3$ | |
| 6.550 | F | Cl | $-O-CH(CH_3)-C_2H_5$ | H | 0 | $-CH(CH_3)-CH_3$ | |
| 6.551 | F | Cl | 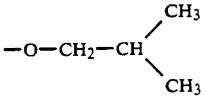 | H | 0 | $-CH(CH_3)-CH_3$ | |
| 6.552 | F | Cl | $-OC_5H_{11}$ | H | 0 | $-CH(CH_3)-CH_3$ | |
| 6.553 | F | Cl | $-O-CH_2-CH_2-O-CH_3$ | H | 0 | $-CH(CH_3)-CH_3$ | |
| 6.554 | F | Cl | $-O-CH_2-CH_2-O-C_2H_5$ | H | 0 | $-CH(CH_3)-CH_3$ | |
| 6.555 | F | Cl | $-O-CH-(CH_3)-CH_2-O-CH_3$ | H | 0 | $-CH(CH_3)-CH_3$ | |
| 6.556 | F | Cl | $-O-CH_2-CH_2-S-CH_3$ | H | 0 | $-CH(CH_3)-CH_3$ | |
| 6.557 | F | Cl | $-O-CH(CH_3)-CH_2-S-CH_3$ | H | 0 | $-CH(CH_3)-CH_3$ | |
| 6.558 | F | Cl | $-O-CH(CH_3)-CH_2-S-C_2H_5$ | H | 0 | $-CH(CH_3)-CH_3$ | |
| 6.559 | F | Cl | $-O-CH(CH_3)-CH_2-S-C_3H_7$ | H | 0 | $-CH(CH_3)-CH_3$ | |
| 6.560 | F | Cl | 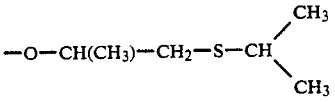 | H | 0 | $-CH(CH_3)-CH_3$ | |
| 6.561 | F | Cl | $-O-CH(CH_3)-CH_2-S-C_4H_9$ | H | 0 | $-CH(CH_3)-CH_3$ | |
| 6.562 | F | Cl | $-O-CH(CH_3)-CH_2-S-C_5H_{11}$ | H | 0 | $-CH(CH_3)-CH_3$ | |
| 6.563 | F | Cl | 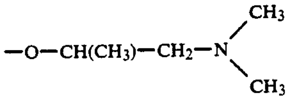 | H | 0 | $-CH(CH_3)-CH_3$ | |
| 6.564 | F | Cl | 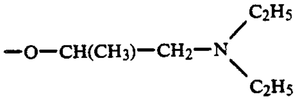 | H | 0 | $-CH(CH_3)-CH_3$ | |
| 6.565 | F | Cl | $-NH_2$ | H | 0 | $-CH(CH_3)-CH_3$ | |
| 6.566 | F | Cl | 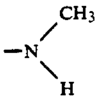 | H | 0 | $-CH(CH_3)-CH_3$ | |

TABLE 6a-continued

Compounds of formula I wherein W = $W_6$, A = $-CO-R_3$ and $R_{14}$ = H:

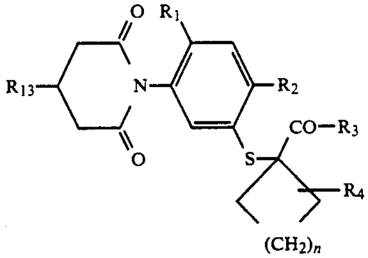

(I)

| Comp. No. | $R_1$ | $R_2$ | $R_3$ | $R_4$ | n | $R_{13}$ | m.p. [°C.] |
|---|---|---|---|---|---|---|---|
| 6.567 | F | Cl | 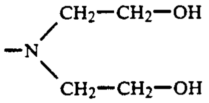 | H | 0 | $-CH(CH_3)-CH_3$ | |
| 6.568 | F | Cl | $-NH-CH_2-CH=CH_2$ | H | 0 | $-CH(CH_3)-CH_3$ | |
| 6.569 | F | Cl | $-N-(CH_2-CH=CH_2)_2$ | H | 0 | $-CH(CH_3)-CH_3$ | |
| 6.570 | F | Cl | 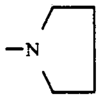 | H | 0 | $-CH(CH_3)-CH_3$ | |
| 6.571 | F | Cl | 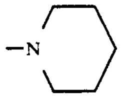 | H | 0 | $-CH(CH_3)-CH_3$ | |
| 6.572 | F | Cl | 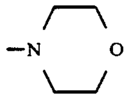 | H | 0 | $-CH(CH_3)-CH_3$ | |
| 6.573 | F | Cl | 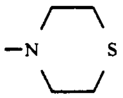 | H | 0 | $-CH(CH_3)-CH_3$ | |
| 6.574 | F | Cl | 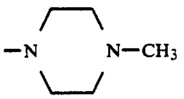 | H | 0 | $-CH(CH_3)-CH_3$ | |
| 6.575 | F | Cl | 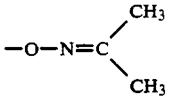 | H | 0 | $-CH(CH_3)-CH_3$ | |
| 6.576 | F | Cl | $-O-CH_2-CH_2-Cl$ | H | 0 | $-CH(CH_3)-CH_3$ | |
| 6.577 | F | Cl | $-O-CH_2-CN$ | H | 0 | $-CH(CH_3)-CH_3$ | |
| 6.578 | F | Cl | 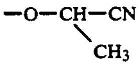 | H | 0 | $-CH(CH_3)-CH_3$ | |
| 6.579 | F | Cl | $-O-CH_2-CH=CH_2$ | H | 0 | $-CH(CH_3)-CH_3$ | |
| 6.580 | F | Cl | $-O-CH_2-CH=CHCl$ | H | 0 | $-CH(CH_3)-CH_3$ | |
| 6.581 | F | Cl | 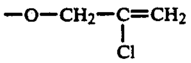 | H | 0 | $-CH(CH_3)-CH_3$ | |
| 6.582 | F | Cl | $-O-CH_2=C\equiv CH$ | H | 0 | $-CH(CH_3)-CH_3$ | |
| 6.583 | F | Cl | 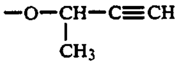 | H | 0 | $-CH(CH_3)-CH_3$ | |

TABLE 6a-continued

Compounds of formula I wherein W = $W_6$, A = $-CO-R_3$ and $R_{14}$ = H:

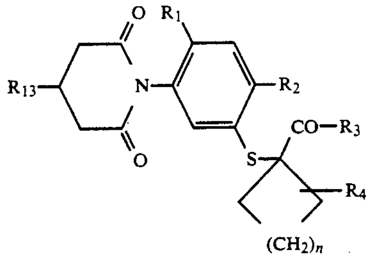

(I)

| Comp. No. | $R_1$ | $R_2$ | $R_3$ | $R_4$ | n | $R_{13}$ | m.p. [°C.] |
|---|---|---|---|---|---|---|---|
| 6.584 | F | Cl | 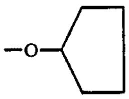 | H | 0 | $-CH(CH_3)-CH_3$ | |
| 6.585 | F | Cl | 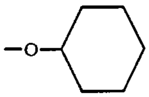 | H | 0 | $-CH(CH_3)-CH_3$ | |
| 6.586 | F | Cl | 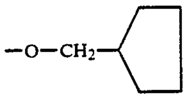 | H | 0 | $-CH(CH_3)-CH_3$ | |
| 6.587 | F | Cl | 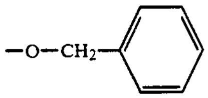 | H | 0 | $-CH(CH_3)-CH_3$ | |
| 6.588 | F | Cl | 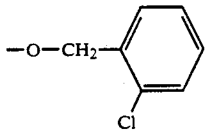 | H | 0 | $-CH(CH_3)-CH_3$ | |
| 6.589 | F | Cl | 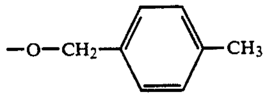 | H | 0 | $-CH(CH_3)-CH_3$ | |
| 6.590 | F | Cl | $-S-CH_3$ | H | 0 | $-CH(CH_3)-CH_3$ | |
| 6.591 | F | Cl | $-S-C_2H_5$ | H | 0 | $-CH(CH_3)-CH_3$ | |
| 6.592 | F | Cl | $-S-C_3H_7$ | H | 0 | $-CH(CH_3)-CH_3$ | |
| 6.593 | F | Cl | $-S-CH_2-CH{=}CH_2$ | H | 0 | $-CH(CH_3)-CH_3$ | |
| 6.594 | F | Cl | $-S-CH_2-COOCH_3$ | H | 0 | $-CH(CH_3)-CH_3$ | |
| 6.595 | F | Cl | $-S-CH_2-COOC_2H_5$ | H | 0 | $-CH(CH_3)-CH_3$ | |
| 6.596 | F | Cl | $-S-CH_2-COOC_5H_{11}$ | H | 0 | $-CH(CH_3)-CH_3$ | |
| 6.597 | F | Cl | $-S-CH(CH_3)-COOCH_3$ | H | 0 | $-CH(CH_3)-CH_3$ | |
| 6.598 | F | Cl | $-S-(CH_3)-COOC_2H_5$ | H | 0 | $-CH(CH_3)-CH_3$ | |
| 6.599 | F | Cl | $-S-CH(CH_3)-COOC_3H_7$ | H | 0 | $-CH(CH_3)-CH_3$ | |
| 6.600 | F | Cl | $-S-CH_2-CH_2-COOCH_3$ | H | 0 | $-CH(CH_3)-CH_3$ | |
| 6.601 | F | Cl | $-S-CH_2-COOCH_2-CH_2-O-CH_3$ | H | 0 | $-CH(CH_3)-CH_3$ | |
| 6.602 | F | Cl | $-O-CH_2-COOCH_3$ | H | 0 | $-CH(CH_3)-CH_3$ | |
| 6.603 | F | Cl | $-O-CH(CH_3)-COOCH_3$ | H | 0 | $-CH(CH_3)-CH_3$ | |
| 6.604 | F | Cl | $-O-CH_2-COOC_5H_{11}$ | H | 0 | $-CH(CH_3)-CH_3$ | |
| 6.605 | F | Cl | $-O-CH_2-CH_3-Si(CH_3)_3$ | H | 0 | $-CH(CH_3)-CH_3$ | |
| 6.606 | F | Cl | $-ONa$ | H | 0 | $-CH(CH_3)-CH_3$ | |
| 6.607 | F | Br | $-Cl$ | H | 0 | $-CH(CH_3)-CH_3$ | |
| 6.608 | F | Br | $-OH$ | H | 0 | $-CH(CH_3)-CH_3$ | |
| 6.609 | F | Br | $-OCH_3$ | H | 0 | $-CH(CH_3)-CH_3$ | |
| 6.610 | F | Br | $-OC_2H_5$ | H | 0 | $-CH(CH_3)-CH_3$ | |
| 6.611 | F | Br | $-OC_3H_7$ | H | 0 | $-CH(CH_3)-CH_3$ | |
| 6.612 | F | Br | 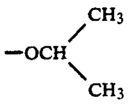 | H | 0 | $-CH(CH_3)-CH_3$ | |

TABLE 6a-continued

Compounds of formula I wherein W = $W_6$, A = $-CO-R_3$ and $R_{14}$ = H:

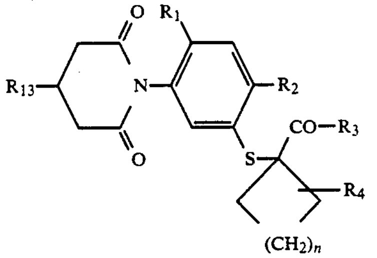

(I)

| Comp. No. | $R_1$ | $R_2$ | $R_3$ | $R_4$ | n | $R_{13}$ | m.p. [°C.] |
|---|---|---|---|---|---|---|---|
| 6.613 | F | Br | $-OC_4H_9$ | H | 0 | $-CH(CH_3)-CH_3$ | |
| 6.614 | F | Br | $-OCH(CH_3)-CH_2-CH_3$ | H | 0 | $-CH(CH_3)-CH_3$ | |
| 6.615 | F | Br | 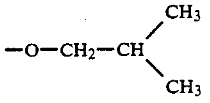 | H | 0 | $-CH(CH_3)-CH_3$ | |
| 6.616 | F | Br | $-O-C_5H_{11}$ | H | 0 | $-CH(CH_3)-CH_3$ | |
| 6.617 | F | Br | $-O-CH_2-CH_2-O-CH_3$ | H | 0 | $-CH(CH_3)-CH_3$ | |
| 6.618 | F | Br | $-O-CH_2-CH_2-O-C_2H_5$ | H | 0 | $-CH(CH_3)-CH_3$ | |
| 6.619 | F | Br | $-O-CH(CH_3)-CH_2-O-CH_3$ | H | 0 | $-CH(CH_3)-CH_3$ | |
| 6.620 | F | Br | $-O-CH_2-CH_2-S-CH_3$ | H | 0 | $-CH(CH_3)-CH_3$ | |
| 6.621 | F | Br | $-O-CH_2(CH_3)-S-CH_3$ | H | 0 | $-CH(CH_3)-CH_3$ | |
| 6.622 | F | Br | $-O-CH-(CH_3)-S-C_2H_5$ | H | 0 | $-CH(CH_3)-CH_3$ | |
| 6.623 | F | Br | $-O-CH(CH_3)-S-C_3H_7$ | H | 0 | $-CH(CH_3)-CH_3$ | |
| 6.624 | F | Br | 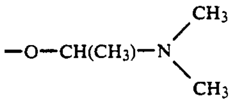 | H | 0 | $-CH(CH_3)-CH_3$ | |
| 6.625 | F | Br | $-NH_2$ | H | 0 | $-CH(CH_3)-CH_3$ | |
| 6.626 | F | Br | 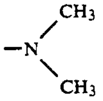 | H | 0 | $-CH(CH_3)-CH_3$ | |
| 6.627 | F | Br | 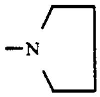 | H | 0 | $-CH(CH_3)-CH_3$ | |
| 6.628 | F | Br | 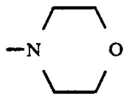 | H | 0 | $-CH(CH_3)-CH_3$ | |
| 6.629 | F | Br | 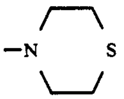 | H | 0 | $-CH(CH_3)-CH_3$ | |
| 6.630 | F | Br | 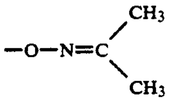 | H | 0 | $-CH(CH_3)-CH_3$ | |
| 6.631 | F | Br | $-O-CH_2-CH_2-Cl$ | H | 0 | $-CH(CH_3)-CH_3$ | |
| 6.632 | F | Br | $-O-CH_2-CN$ | H | 0 | $-CH(CH_3)-CH_3$ | |
| 6.633 | F | Br | $-O-CH_2-CH=CH_2$ | H | 0 | $-CH(CH_3)-CH_3$ | |
| 6.634 | F | Br | $-O-CH_2-C\equiv CH$ | H | 0 | $-CH(CH_3)-CH_3$ | |
| 6.635 | F | Br | 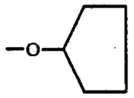 | H | 0 | $-CH(CH_3)-CH_3$ | |

TABLE 6a-continued

Compounds of formula I wherein W = $W_6$, A = $-CO-R_3$ and $R_{14}$ = H:

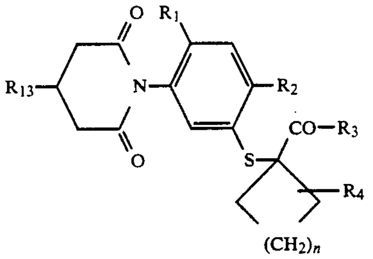

(I)

| Comp. No. | $R_1$ | $R_2$ | $R_3$ | $R_4$ | n | $R_{13}$ | m.p. [°C.] |
|---|---|---|---|---|---|---|---|
| 6.636 | F | Br | 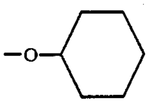 | H | 0 | $-CH(CH_3)-CH_3$ | |
| 6.637 | F | Br | 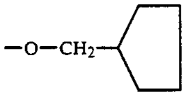 | H | 0 | $-CH(CH_3)-CH_3$ | |
| 6.638 | F | Br | 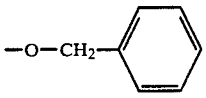 | H | 0 | $-CH(CH_3)-CH_3$ | |
| 6.639 | F | Br | $-SCH_3$ | H | 0 | $-CH(CH_3)-CH_3$ | |
| 6.640 | F | Br | $-S-CH_2-COOCH_3$ | H | 0 | $-CH(CH_3)-CH_3$ | |
| 6.641 | F | Br | $-S-CH(CH_3)-COOCH_3$ | H | 0 | $-CH(CH_3)-CH_3$ | |
| 6.642 | F | Br | $-O-CH_2-COOCH_3$ | H | 0 | $-CH(CH_3)-CH_3$ | |
| 6.643 | F | Br | $-O-CH(CH_3)COOCH_3$ | H | 0 | $-CH(CH_3)-CH_3$ | |
| 6.644 | F | CN | $-Cl$ | H | 0 | $-CH(CH_3)-CH_3$ | |
| 6.645 | F | CN | $-OH$ | H | 0 | $-CH(CH_3)-CH_3$ | |
| 6.646 | F | CN | $-OCH_3$ | H | 0 | $-CH(CH_3)-CH_3$ | |
| 6.647 | H | Cl | $-Cl$ | H | 0 | $-CH(CH_3)-CH_3$ | |
| 6.648 | H | Cl | $-OH$ | H | 0 | $-CH(CH_3)-CH_3$ | |
| 6.649 | H | Cl | $-OCH_3$ | H | 0 | $-CH(CH_3)-CH_3$ | |
| 6.650 | H | Cl | $-OC_2H_5$ | H | 0 | $-CH(CH_3)-CH_3$ | |
| 6.651 | H | Cl | 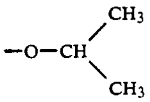 | H | 0 | $-CH(CH_3)-CH_3$ | |
| 6.652 | H | Cl | $-O-CH_2-COOCH_3$ | H | 0 | $-CH(CH_3)-CH_3$ | |
| 6.653 | H | Cl | $-O-CH(CH_3)COOCH_3$ | H | 0 | $-CH(CH_3)-CH_3$ | |
| 6.654 | H | Cl | $-S-CH_2-COOCH_3$ | H | 0 | $-CH(CH_3)-CH_3$ | |
| 6.655 | H | Cl | $-S-CH(CH_3)COOCH_3$ | H | 0 | $-CH(CH_3)-CH_3$ | |
| 6.656 | H | Cl | 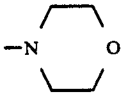 | H | 0 | $-CH(CH_3)-CH_3$ | |
| 6.657 | F | Cl | $-Cl$ | H | 1 | $-CH(CH_3)-CH_3$ | |
| 6.658 | F | Cl | $-OH$ | H | 1 | $-CH(CH_3)-CH_3$ | |
| 6.659 | F | Cl | $-OCH_3$ | H | 1 | $-CH(CH_3)-CH_3$ | |
| 6.660 | F | Cl | $-OC_2H_5$ | H | 1 | $-CH(CH_3)-CH_3$ | |
| 6.661 | F | Cl | $-OC_3H_7$ | H | 1 | $-CH(CH_3)-CH_3$ | |
| 6.662 | F | Cl | 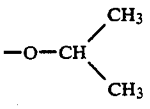 | H | 1 | $-CH(CH_3)-CH_3$ | |
| 6.663 | F | Cl | $-OC_4H_9$ | H | 1 | $-CH(CH_3)-CH_3$ | |
| 6.664 | F | Cl | $-O-CH(CH_3)-C_2H_5$ | H | 1 | $-CH(CH_3)-CH_3$ | |

TABLE 6a-continued

Compounds of formula I wherein W = $W_6$, A = $-CO-R_3$ and $R_{14}$ = H:

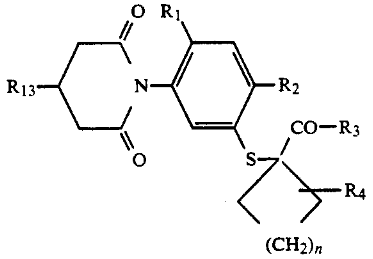

(I)

| Comp. No. | $R_1$ | $R_2$ | $R_3$ | $R_4$ | n | $R_{13}$ | m.p. [°C.] |
|---|---|---|---|---|---|---|---|
| 6.665 | F | Cl | 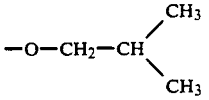 | H | 1 | $-CH(CH_3)-CH_3$ | |
| 6.666 | F | Cl | $-OC_5H_{11}$ | H | 1 | $-CH(CH_3)-CH_3$ | |
| 6.667 | F | Cl | $-O-CH_2-CH_2-O-CH_3$ | H | 1 | $-CH(CH_3)-CH_3$ | |
| 6.668 | F | Cl | $-O-CH_2-CH_2-O-C_2H_5$ | H | 1 | $-CH(CH_3)-CH_3$ | |
| 6.669 | F | Cl | $-O-CH-(CH_3)-CH_2-O-CH_3$ | H | 1 | $-CH(CH_3)-CH_3$ | |
| 6.670 | F | Cl | $-O-CH_2-CH_2-S-CH_3$ | H | 1 | $-CH(CH_3)-CH_3$ | |
| 6.671 | F | Cl | $-O-CH(CH_3)-CH_2-S-CH_3$ | H | 1 | $-CH(CH_3)-CH_3$ | |
| 6.672 | F | Cl | $-O-CH(CH_3)-CH_2-S-C_2H_5$ | H | 1 | $-CH(CH_3)-CH_3$ | |
| 6.673 | F | Cl | $-O-CH(CH_3)-CH_2-S-C_3H_7$ | H | 1 | $-CH(CH_3)-CH_3$ | |
| 6.674 | F | Cl | 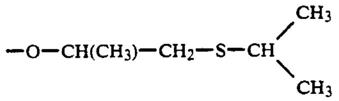 | H | 1 | $-CH(CH_3)-CH_3$ | |
| 6.675 | F | Cl | $-O-CH(CH_3)-CH_2-S-C_4H_9$ | H | 1 | $-CH(CH_3)-CH_3$ | |
| 6.676 | F | Cl | $-O-CH(CH_3)-CH_2-S-C_5H_{11}$ | H | 1 | $-CH(CH_3)-CH_3$ | |
| 6.677 | F | Cl | 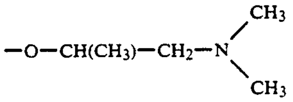 | H | 1 | $-CH(CH_3)-CH_3$ | |
| 6.678 | F | Cl | 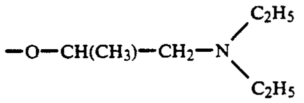 | H | 1 | $-CH(CH_3)-CH_3$ | |
| 6.679 | F | Cl | $-NH_2$ | H | 1 | $-CH(CH_3)-CH_3$ | |
| 6.680 | F | Cl | 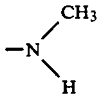 | H | 1 | $-CH(CH_3)-CH_3$ | |
| 6.681 | F | Cl | 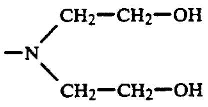 | H | 1 | $-CH(CH_3)-CH_3$ | |
| 6.682 | F | Cl | $-NH-CH_2-CH=CH_2$ | H | 1 | $-CH(CH_3)-CH_3$ | |
| 6.683 | F | Cl | $-N-(CH_2-CH=CH_2)_2$ | H | 1 | $-CH(CH_3)-CH_3$ | |
| 6.684 | F | Cl | 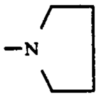 | H | 1 | $-CH(CH_3)-CH_3$ | |
| 6.685 | F | Cl | 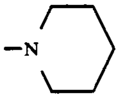 | H | 1 | $-CH(CH_3)-CH_3$ | |

TABLE 6a-continued

Compounds of formula I wherein W = $W_6$, A = $-CO-R_3$ and $R_{14}$ = H:

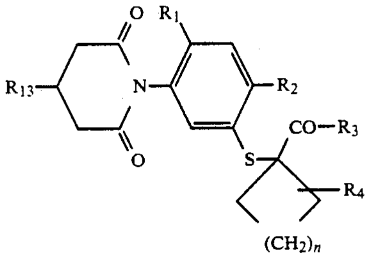

(I)

| Comp. No. | $R_1$ | $R_2$ | $R_3$ | $R_4$ | n | $R_{13}$ | m.p. [°C.] |
|---|---|---|---|---|---|---|---|
| 6.686 | F | Cl | 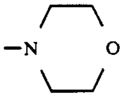 | H | 1 | $-CH(CH_3)-CH_3$ | |
| 6.687 | F | Cl | 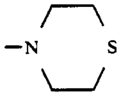 | H | 1 | $-CH(CH_3)-CH_3$ | |
| 6.688 | F | Cl | 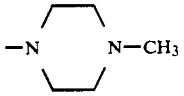 | H | 1 | $-CH(CH_3)-CH_3$ | |
| 6.689 | F | Cl | 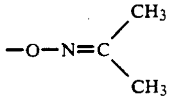 | H | 1 | $-CH(CH_3)-CH_3$ | |
| 6.690 | F | Cl | $-O-CH_2-CH_2-Cl$ | H | 1 | $-CH(CH_3)-CH_3$ | |
| 6.691 | F | Cl | $-O-CH_2-CN$ | H | 1 | $-CH(CH_3)-CH_3$ | |
| 6.692 | F | Cl | 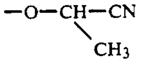 | H | 1 | $-CH(CH_3)-CH_3$ | |
| 6.693 | F | Cl | $-O-CH_2-CH=CH_2$ | H | 1 | $-CH(CH_3)-CH_3$ | |
| 6.694 | F | Cl | $-O-CH_2-CH=CHCl$ | H | 1 | $-CH(CH_3)-CH_3$ | |
| 6.695 | F | Cl | 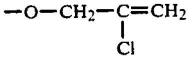 | H | 1 | $-CH(CH_3)-CH_3$ | |
| 6.696 | F | Cl | $-O-CH_2=C\equiv CH$ | H | 1 | $-CH(CH_3)-CH_3$ | |
| 6.697 | F | Cl | 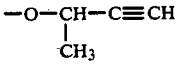 | H | 1 | $-CH(CH_3)-CH_3$ | |
| 6.698 | F | Cl | 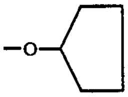 | H | 1 | $-CH(CH_3)-CH_3$ | |
| 6.699 | F | Cl | 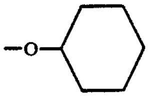 | H | 1 | $-CH(CH_3)-CH_3$ | |
| 6.700 | F | Cl | 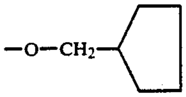 | H | 1 | $-CH(CH_3)-CH_3$ | |

TABLE 6a-continued

Compounds of formula I wherein W = $W_6$, A = $-CO-R_3$ and $R_{14}$ = H:

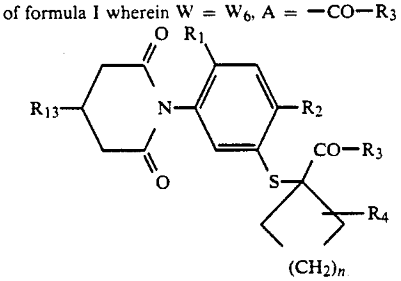

(I)

| Comp. No. | $R_1$ | $R_2$ | $R_3$ | $R_4$ | n | $R_{13}$ | m.p. [°C.] |
|---|---|---|---|---|---|---|---|
| 6.701 | F | Cl | 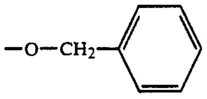 | H | 1 | $-CH(CH_3)-CH_3$ | |
| 6.702 | F | Cl | 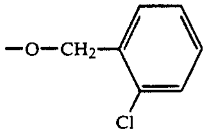 | H | 1 | $-CH(CH_3)-CH_3$ | |
| 6.703 | F | Cl | 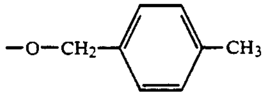 | H | 1 | $-CH(CH_3)-CH_3$ | |
| 6.704 | F | Cl | $-S-CH_3$ | H | 1 | $-CH(CH_3)-CH_3$ | |
| 6.705 | F | Cl | $-S-C_2H_5$ | H | 1 | $-CH(CH_3)-CH_3$ | |
| 6.706 | F | Cl | $-S-C_3H_7$ | H | 1 | $-CH(CH_3)-CH_3$ | |
| 6.707 | F | Cl | $-S-CH_2-CH{=}CH_2$ | H | 1 | $-CH(CH_3)-CH_3$ | |
| 6.708 | F | Cl | $-S-CH_2-COOCH_3$ | H | 1 | $-CH(CH_3)-CH_3$ | |
| 6.709 | F | Cl | $-S-CH_2-COOC_2H_5$ | H | 1 | $-CH(CH_3)-CH_3$ | |
| 6.710 | F | Cl | $-S-CH_2-COOC_5H_{11}$ | H | 1 | $-CH(CH_3)-CH_3$ | |
| 6.711 | F | Cl | $-S-CH(CH_3)-COOCH_3$ | H | 1 | $-CH(CH_3)-CH_3$ | |
| 6.712 | F | Cl | $-S-(CH_3)-COOC_2H_5$ | H | 1 | $-CH(CH_3)-CH_3$ | |
| 6.713 | F | Cl | $-S-CH(CH_3)-COOC_3H_7$ | H | 1 | $-CH(CH_3)-CH_3$ | |
| 6.714 | F | Cl | $-S-CH_2-CH_2-COOCH_3$ | H | 1 | $-CH(CH_3)-CH_3$ | |
| 6.715 | F | Cl | $-S-CH_2-COOCH_2-CH_2-O-CH_3$ | H | 1 | $-CH(CH_3)-CH_3$ | |
| 6.716 | F | Cl | $-O-CH_2-COOCH_3$ | H | 1 | $-CH(CH_3)-CH_3$ | |
| 6.717 | F | Cl | $-O-CH(CH_3)-COOCH_3$ | H | 1 | $-CH(CH_3)-CH_3$ | |
| 6.718 | F | Cl | $-O-CH_2-COOC_5H_{11}$ | H | 1 | $-CH(CH_3)-CH_3$ | |
| 6.719 | F | Cl | $-O-CH_2-CH_3-Si(CH_3)_3$ | H | 1 | $-CH(CH_3)-CH_3$ | |
| 6.720 | F | Cl | $-ONa$ | H | 1 | $-CH(CH_3)-CH_3$ | |
| 6.721 | F | Br | $-Cl$ | H | 1 | $-CH(CH_3)-CH_3$ | |
| 6.722 | F | Br | $-OH$ | H | 1 | $-CH(CH_3)-CH_3$ | |
| 6.723 | F | Br | $-OCH_3$ | H | 1 | $-CH(CH_3)-CH_3$ | |
| 6.724 | F | Br | $-OC_2H_5$ | H | 1 | $-CH(CH_3)-CH_3$ | |
| 6.725 | F | Br | $-OC_3H_7$ | H | 1 | $-CH(CH_3)-CH_3$ | |
| 6.726 | F | Br | 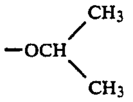 | H | 1 | $-CH(CH_3)-CH_3$ | |
| 6.727 | F | Br | $-OC_4H_9$ | H | 1 | $-CH(CH_3)-CH_3$ | |
| 6.728 | F | Br | $-OCH(CH_3)-CH_2-CH_3$ | H | 1 | $-CH(CH_3)-CH_3$ | |
| 6.729 | F | Br | 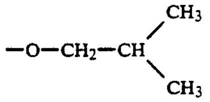 | H | 1 | $-CH(CH_3)-CH_3$ | |
| 6.730 | F | Br | $-O-C_5H_{11}$ | H | 1 | $-CH(CH_3)-CH_3$ | |
| 6.731 | F | Br | $-O-CH_2-CH_2-O-CH_3$ | H | 1 | $-CH(CH_3)-CH_3$ | |
| 6.732 | F | Br | $-O-CH_2-CH_2-O-C_2H_5$ | H | 1 | $-CH(CH_3)-CH_3$ | |
| 6.733 | F | Br | $-O-CH(CH_3)-CH_2-O-CH_3$ | H | 1 | $-CH(CH_3)-CH_3$ | |
| 6.734 | F | Br | $-O-CH_2-CH_2-S-CH_3$ | H | 1 | $-CH(CH_3)-CH_3$ | |
| 6.735 | F | Br | $-O-CH_2(CH_3)-S-CH_3$ | H | 1 | $-CH(CH_3)-CH_3$ | |
| 6.736 | F | Br | $-O-CH-(CH_3)-S-C_2H_5$ | H | 1 | $-CH(CH_3)-CH_3$ | |
| 6.737 | F | Br | $-O-CH(CH_3)-S-C_3H_7$ | H | 1 | $-CH(CH_3)-CH_3$ | |

TABLE 6a-continued

Compounds of formula I wherein W = $W_6$, A = $-CO-R_3$ and $R_{14}$ = H:

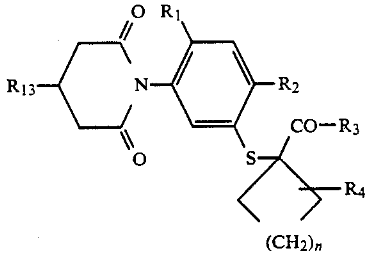

(I)

| Comp. No. | $R_1$ | $R_2$ | $R_3$ | $R_4$ | n | $R_{13}$ | m.p. [°C.] |
|---|---|---|---|---|---|---|---|
| 6.738 | F | Br | 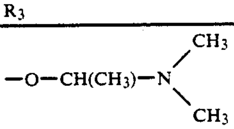 | H | 1 | $-CH(CH_3)-CH_3$ | |
| 6.739 | F | Br | $-NH_2$ | H | 1 | $-CH(CH_3)-CH_3$ | |
| 6.740 | F | Br | 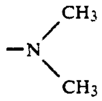 | H | 1 | $-CH(CH_3)-CH_3$ | |
| 6.741 | F | Br | 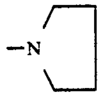 | H | 1 | $-CH(CH_3)-CH_3$ | |
| 6.742 | F | Br | 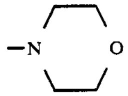 | H | 1 | $-CH(CH_3)-CH_3$ | |
| 6.743 | F | Br | 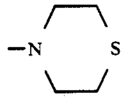 | H | 1 | $-CH(CH_3)-CH_3$ | |
| 6.744 | F | Br | 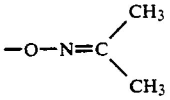 | H | 1 | $-CH(CH_3)-CH_3$ | |
| 6.745 | F | Br | $-O-CH_2-CH_2-Cl$ | H | 1 | $-CH(CH_3)-CH_3$ | |
| 6.746 | F | Br | $-O-CH_2-CN$ | H | 1 | $-CH(CH_3)-CH_3$ | |
| 6.747 | F | Br | $-O-CH_2-CH=CH_2$ | H | 1 | $-CH(CH_3)-CH_3$ | |
| 6.748 | F | Br | $-O-CH_2-C\equiv CH$ | H | 1 | $-CH(CH_3)-CH_3$ | |
| 6.749 | F | Br | 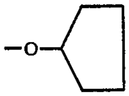 | H | 1 | $-CH(CH_3)-CH_3$ | |
| 6.750 | F | Br | 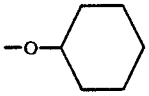 | H | 1 | $-CH(CH_3)-CH_3$ | |
| 6.751 | F | Br | 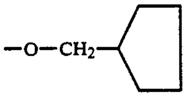 | H | 1 | $-CH(CH_3)-CH_3$ | |
| 6.752 | F | Br | 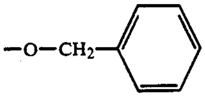 | H | 1 | $-CH(CH_3)-CH_3$ | |

TABLE 6a-continued

Compounds of formula I wherein W = $W_6$, A = $-CO-R_3$ and $R_{14}$ = H:

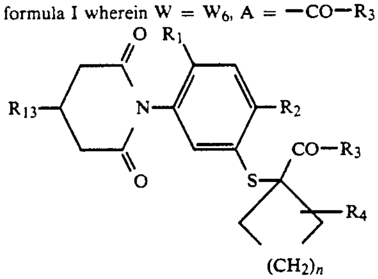

(I)

| Comp. No. | $R_1$ | $R_2$ | $R_3$ | $R_4$ | n | $R_{13}$ | m.p. [°C.] |
|---|---|---|---|---|---|---|---|
| 6.753 | F | Br | $-SCH_3$ | H | 1 | $-CH(CH_3)-CH_3$ | |
| 6.754 | F | Br | $-S-CH_2-COOCH_3$ | H | 1 | $-CH(CH_3)-CH_3$ | |
| 6.755 | F | Br | $-S-CH(CH_3)-COOCH_3$ | H | 1 | $-CH(CH_3)-CH_3$ | |
| 6.756 | F | Br | $-O-CH_2-COOCH_3$ | H | 1 | $-CH(CH_3)-CH_3$ | |
| 6.757 | F | Br | $-O-CH(CH_3)COOCH_3$ | H | 1 | $-CH(CH_3)-CH_3$ | |
| 6.758 | F | CN | $-Cl$ | H | 1 | $-CH(CH_3)-CH_3$ | |
| 6.759 | F | CN | $-OH$ | H | 1 | $-CH(CH_3)-CH_3$ | |
| 6.760 | F | CN | $-OCH_3$ | H | 1 | $-CH(CH_3)-CH_3$ | |
| 6.761 | H | Cl | $-Cl$ | H | 1 | $-CH(CH_3)-CH_3$ | |
| 6.762 | H | Cl | $-OH$ | H | 1 | $-CH(CH_3)-CH_3$ | |
| 6.763 | H | Cl | $-OCH_3$ | H | 1 | $-CH(CH_3)-CH_3$ | |
| 6.764 | H | Cl | $-OC_2H_5$ | H | 1 | $-CH(CH_3)-CH_3$ | |
| 6.765 | H | Cl | 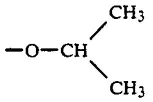 | H | 1 | $-CH(CH_3)-CH_3$ | |
| 6.766 | H | Cl | $-O-CH_2-COOCH_3$ | H | 1 | $-CH(CH_3)-CH_3$ | |
| 6.767 | H | Cl | $-O-CH(CH_3)COOCH_3$ | H | 1 | $-CH(CH_3)-CH_3$ | |
| 6.768 | H | Cl | $-S-CH_2-COOCH_3$ | H | 1 | $-CH(CH_3)-CH_3$ | |
| 6.769 | H | Cl | $-S-CH(CH_3)COOCH_3$ | H | 1 | $-CH(CH_3)-CH_3$ | |
| 6.770 | H | Cl | 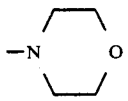 | H | 1 | $-CH(CH_3)-CH_3$ | |
| 6.771 | F | Cl | Cl | H | 2 | $-CH(CH_3)-CH_3$ | |
| 6.772 | F | Cl | OH | H | 2 | $-CH(CH_3)-CH_3$ | |
| 6.773 | F | Cl | $OCH_3$ | H | 2 | $-CH(CH_3)-CH_3$ | |
| 6.774 | F | Cl | $-OC_2H_5$ | H | 2 | $-CH(CH_3)-CH_3$ | |
| 6.775 | F | Cl | 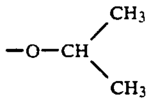 | H | 2 | $-CH(CH_3)-CH_3$ | |
| 6.776 | F | Cl | $-O-CH_2-CH_2-O-CH_3$ | H | 2 | $-CH(CH_3)-CH_3$ | |
| 6.777 | F | Cl | $-O-CH(CH_3)-CH_2-S-CH_3$ | H | 2 | $-CH(CH_3)-CH_3$ | |
| 6.778 | F | Cl | $-O-CH_2-COOCH_3$ | H | 2 | $-CH(CH_3)-CH_3$ | |
| 6.779 | F | Cl | $-S-CH_2-COOCH_3$ | H | 2 | $-CH(CH_3)-CH_3$ | |
| 6.780 | F | Cl | $-CH_2-CH=CH_2$ | H | 2 | $-CH(CH_3)-CH_3$ | |
| 6.781 | F | Cl | $-CH_2-C\equiv CH$ | H | 2 | $-CH(CH_3)-CH_3$ | |
| 6.782 | F | Cl | Cl | H | 3 | $-CH(CH_3)-CH_3$ | |
| 6.783 | F | Cl | OH | H | 3 | $-CH(CH_3)-CH_3$ | |
| 6.784 | F | Cl | $OCH_3$ | H | 3 | $-CH(CH_3)-CH_3$ | |
| 6.785 | F | Cl | $OC_2H_5$ | H | 3 | $-CH(CH_3)-CH_3$ | |
| 6.786 | F | Cl | 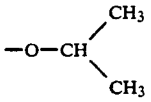 | H | 3 | $-CH(CH_3)-CH_3$ | |
| 6.787 | F | Cl | $-O-CH_2-CH_2-O-CH$ | H | 3 | $-CH(CH_3)-CH_3$ | |
| 6.788 | F | Cl | $-O-CH(CH_3)-CH_2-S-CH_3$ | H | 3 | $-CH(CH_3)-CH_3$ | |
| 6.789 | F | Cl | $-O-CH_2-COOCH_3$ | H | 3 | $-CH(CH_3)-CH_3$ | |
| 6.790 | F | Cl | $-S-CH_2-COOCH_3$ | H | 3 | $-CH(CH_3)-CH_3$ | |
| 6.791 | F | Cl | $-O-CH_2-C\equiv CH$ | H | 3 | $-CH(CH_3)-CH_3$ | |
| 6.792 | F | Cl | $-Cl$ | Cl | 0 | $-CH(CH_3)-CH_3$ | |
| 6.793 | F | Cl | $-OH$ | Cl | 0 | $-CH(CH_3)-CH_3$ | |
| 6.794 | F | Cl | $-OCH_3$ | Cl | 0 | $-CH(CH_3)-CH_3$ | |
| 6.795 | F | Cl | $-OC_2H_5$ | Cl | 0 | $-CH(CH_3)-CH_3$ | |

TABLE 6a-continued

Compounds of formula I wherein W = $W_6$, A = $-CO-R_3$ and $R_{14}$ = H:

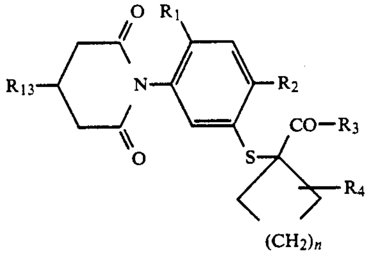

(I)

| Comp. No. | $R_1$ | $R_2$ | $R_3$ | $R_4$ | n | $R_{13}$ | m.p. [°C.] |
|---|---|---|---|---|---|---|---|
| 6.796 | F | Cl | 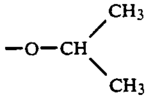 | Cl | 0 | $-CH(CH_3)-CH_3$ | |
| 6.797 | F | Cl | $-O-CH_2-COOCH_3$ | Cl | 0 | $-CH(CH_3)-CH_3$ | |
| 6.798 | F | Cl | $-S-CH_2-COOCH_3$ | Cl | 0 | $-CH(CH_3)-CH_3$ | |
| 6.799 | F | Cl | $-OCH_3$ | Br | 0 | $-CH(CH_3)-CH_3$ | |
| 6.800 | F | Cl | 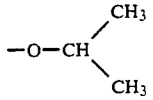 | Br | 0 | $-CH(CH_3)-CH_3$ | |
| 6.801 | F | Cl | $-OCH_3$ | F | 0 | $-CH(CH_3)-CH_3$ | |
| 6.802 | F | Cl | $-OCH_3$ | $CH_3$ | 0 | $-CH(CH_3)-CH_3$ | |
| 6.803 | F | Cl | $-OC_2H_5$ | $CH_3$ | 0 | $-CH(CH_3)-CH_3$ | |
| 6.804 | F | Cl | 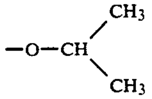 | $CH_3$ | 0 | $-CH(CH_3)-CH_3$ | |
| 6.805 | F | Cl | $-O-CH_2-CH_2-O-CH_3$ | $CH_3$ | 0 | $-CH(CH_3)-CH_3$ | |
| 6.806 | F | Cl | $-O-CH_2-COOCH_3$ | $CH_3$ | 0 | $-CH(CH_3)-CH_3$ | |
| 6.807 | F | Cl | $-O-CH(CH_3)COOCH_3$ | $CH_3$ | 0 | $-CH(CH_3)-CH_3$ | |
| 6.808 | F | Cl | $-S-CH_2-COOCH_3$ | $CH_3$ | 0 | $-CH(CH_3)-CH_3$ | |
| 6.809 | F | Cl | $-OCH_3$ | $CF_3$ | 0 | $-CH(CH_3)-CH_3$ | |
| 6.810 | F | Cl | $-OC_2H_5$ | $CF_3$ | 0 | $-CH(CH_3)-CH_3$ | |
| 6.811 | F | Cl | 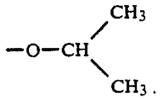 | $CF_3$ | 0 | $-CH(CH_3)-CH_3$ | |
| 6.812 | F | Cl | $-O-CH_2-COOCH_3$ | $CF_3$ | 0 | $-CH(CH_3)-CH_3$ | |
| 6.813 | F | Cl | $-S-CH_2-COOCH_3$ | $CF_3$ | 0 | $-CH(CH_3)-CH_3$ | |

TABLE 6b

Compounds of formula I wherein W = $W_6$, A = $-CN$ and $R_{14}$ = H:

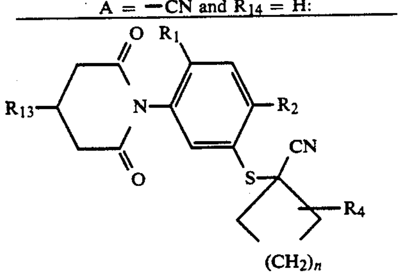

(I)

| Comp. No. | $R_1$ | $R_2$ | $R_3$ | $R_4$ | n | $R_{13}$ | m.p. [°C.] |
|---|---|---|---|---|---|---|---|
| 6.814 | F | Cl | — | H | 0 | $CF_3$ | |
| 6.815 | F | Cl | — | H | 1 | $CF_3$ | |
| 6.816 | F | Cl | — | H | 2 | $CF_3$ | |
| 6.817 | F | Cl | — | H | 3 | $CF_3$ | |

TABLE 6b-continued

Compounds of formula I wherein W = $W_6$, A = $-CN$ and $R_{14}$ = H:

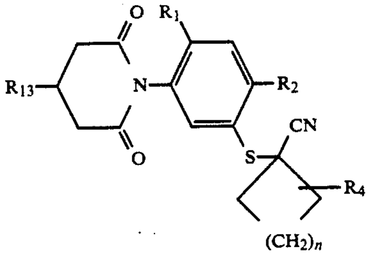

(I)

| Comp. No. | $R_1$ | $R_2$ | $R_3$ | $R_4$ | n | $R_{13}$ | m.p. [°C.] |
|---|---|---|---|---|---|---|---|
| 6.818 | F | Cl | — | H | 4 | $CF_3$ | |
| 6.819 | F | Cl | — | H | 0 | $CH_3$ | |
| 6.820 | F | Cl | — | H | 1 | $CH_3$ | |
| 6.821 | F | Cl | — | H | 2 | $CH_3$ | |

TABLE 6b-continued

Compounds of formula I wherein W = $W_6$, A = —CN and $R_{14}$ = H:

(I)

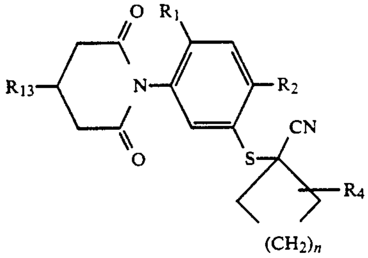

| Comp. No. | $R_1$ | $R_2$ | $R_3$ | $R_4$ | n | $R_{13}$ | m.p. [°C.] |
|---|---|---|---|---|---|---|---|
| 6.822 | F | Cl | — | H | 3 | $CH_3$ | |
| 6.823 | F | Cl | — | H | 4 | $CH_3$ | |
| 6.824 | F | Cl | — | H | 0 | —CH($CH_3$)—$CH_3$ | |
| 6.825 | F | Cl | — | H | 1 | —CH($CH_3$)—$CH_3$ | |
| 6.826 | F | Cl | — | H | 2 | —CH($CH_3$)—$CH_3$ | |
| 6.827 | F | Cl | — | H | 3 | —CH($CH_3$)—$CH_3$ | |
| 6.828 | F | Cl | — | H | 4 | —CH($CH_3$)—$CH_3$ | |

TABLE 7

Compounds of formula I wherein W is $W_7$, $Y_4$ is oxygen and $R_{14}$ is hydrogen:

(I)

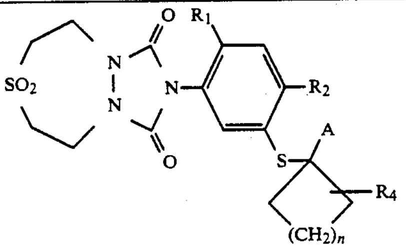

| Comp. No. | $R_1$ | $R_2$ | $R_3$ | $R_4$ | n | A | m.p. [°C.] |
|---|---|---|---|---|---|---|---|
| 7.001 | F | Cl | —Cl | H | 0 | —CO—$R_3$ | |
| 7.002 | F | Cl | —OH | H | 0 | —CO—$R_3$ | |
| 7.003 | F | Cl | —O$CH_3$ | H | 0 | —CO—$R_3$ | |
| 7.004 | F | Cl | —O$C_2H_5$ | H | 0 | —CO—$R_3$ | |
| 7.005 | F | Cl | —O$C_3H_7$ | H | 0 | —CO—$R_3$ | |
| 7.006 | F | Cl | $CH_3$<br>—O—CH<br>$CH_3$ | H | 0 | —CO—$R_3$ | |
| 7.007 | F | Cl | —O$C_4H_9$ | H | 0 | —CO—$R_3$ | |
| 7.008 | F | Cl | —O—CH($CH_3$)—$C_2H_5$ | H | 0 | —CO—$R_3$ | |
| 7.009 | F | Cl | $CH_3$<br>—O—$CH_2$—CH<br>$CH_3$ | H | 0 | —CO—$R_3$ | |
| 7.010 | F | Cl | —O$C_5H_{11}$ | H | 0 | —CO—$R_3$ | |
| 7.011 | F | Cl | —O—$CH_2$—$CH_2$—O—$CH_3$ | H | 0 | —CO—$R_3$ | |
| 7.012 | F | Cl | —O—$CH_2$—$CH_2$—O—$C_2H_5$ | H | 0 | —CO—$R_3$ | |
| 7.013 | F | Cl | —O—CH—($CH_3$)—$CH_2$—O—$CH_3$ | H | 0 | —CO—$R_3$ | |
| 7.014 | F | Cl | —O—$CH_2$—$CH_2$—S—$CH_3$ | H | 0 | —CO—$R_3$ | |
| 7.015 | F | Cl | —O—CH($CH_3$)—$CH_2$—S—$CH_3$ | H | 0 | —CO—$R_3$ | |
| 7.016 | F | Cl | —O—CH($CH_3$)—$CH_2$—S—$C_2H_5$ | H | 0 | —CO—$R_3$ | |
| 7.017 | F | Cl | —O—CH($CH_3$)—$CH_2$—S—$C_3H_7$ | H | 0 | —CO—$R_3$ | |
| 7.018 | F | Cl | $CH_3$<br>—O—CH($CH_3$)—$CH_2$—S—CH<br>$CH_3$ | H | 0 | —CO—$R_3$ | |
| 7.019 | F | Cl | —O—CH($CH_3$)—$CH_2$—S—$C_4H_9$ | H | 0 | —CO—$R_3$ | |
| 7.020 | F | Cl | —O—CH($CH_3$)—$CH_2$—S—$C_5H_{11}$ | H | 0 | —CO—$R_3$ | |
| 7.021 | F | Cl | $CH_3$<br>—O—CH($CH_3$)—$CH_2$—N<br>$CH_3$ | H | 0 | —CO—$R_3$ | |
| 7.022 | F | Cl | $C_2H_5$<br>—O—CH($CH_3$)—$CH_2$—N<br>$C_2H_5$ | H | 0 | —CO—$R_3$ | |
| 7.023 | F | Cl | —$NH_2$ | H | 0 | —CO—$R_3$ | |

TABLE 7-continued

Compounds of formula I wherein W is $W_7$, $Y_4$ is oxygen and $R_{14}$ is hydrogen:

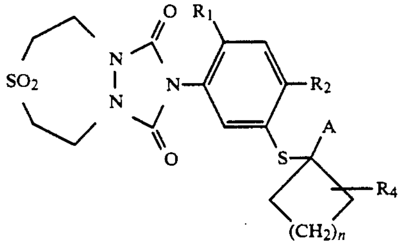

(I)

| Comp. No. | $R_1$ | $R_2$ | $R_3$ | $R_4$ | n | A | m.p. [°C.] |
|---|---|---|---|---|---|---|---|
| 7.024 | F | Cl | 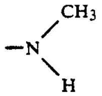 | H | 0 | $-CO-R_3$ | |
| 7.025 | F | Cl | 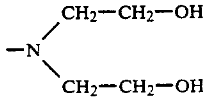 | H | 0 | $-CO-R_3$ | |
| 7.026 | F | Cl | $-NH-CH_2-CH=CH_2$ | H | 0 | $-CO-R_3$ | |
| 7.027 | F | Cl | $-N-(CH_2-CH=CH_2)_2$ | H | 0 | $-CO-R_3$ | |
| 7.028 | F | Cl | 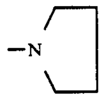 | H | 0 | $-CO-R_3$ | |
| 7.029 | F | Cl | 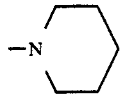 | H | 0 | $-CO-R_3$ | |
| 7.030 | F | Cl | 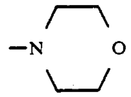 | H | 0 | $-CO-R_3$ | |
| 7.031 | F | Cl | 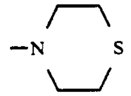 | H | 0 | $-CO-R_3$ | |
| 7.032 | F | Cl | 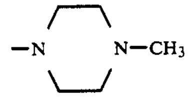 | H | 0 | $-CO-R_3$ | |
| 7.033 | F | Cl | 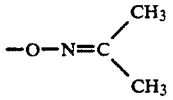 | H | 0 | $-CO-R_3$ | |
| 7.034 | F | Cl | $-O-CH_2-CH_2-Cl$ | H | 0 | $-CO-R_3$ | |
| 7.035 | F | Cl | $-O-CH_2-CN$ | H | 0 | $-CO-R_3$ | |
| 7.036 | F | Cl | 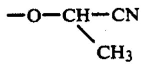 | H | 0 | $-CO-R_3$ | |
| 7.037 | F | Cl | $-O-CH_2-CH=CH_2$ | H | 0 | $-CO-R_3$ | |
| 7.038 | F | Cl | $-O-CH_2-CH=CHCl$ | H | 0 | $-CO-R_3$ | |
| 7.039 | F | Cl | 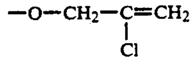 | H | 0 | $-CO-R_3$ | |
| 7.040 | F | Cl | $-O-CH_2=C\equiv CH$ | H | 0 | $-CO-R_3$ | |

TABLE 7-continued

Compounds of formula I wherein W is $W_7$, $Y_4$ is oxygen and $R_{14}$ is hydrogen:

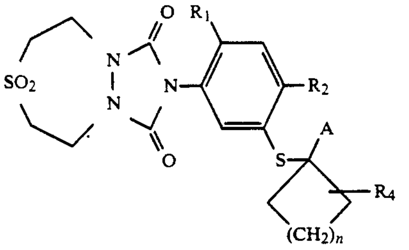

(I)

| Comp. No. | $R_1$ | $R_2$ | $R_3$ | $R_4$ | n | A | m.p. [°C.] |
|---|---|---|---|---|---|---|---|
| 7.041 | F | Cl | $-O-CH-C\equiv CH$<br>$CH_3$ | H | 0 | $-CO-R_3$ | |
| 7.042 | F | Cl | 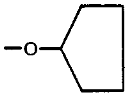 | H | 0 | $-CO-R_3$ | |
| 7.043 | F | Cl | 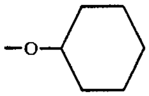 | H | 0 | $-CO-R_3$ | |
| 7.044 | F | Cl | 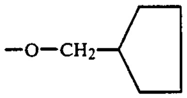 | H | 0 | $-CO-R_3$ | |
| 7.045 | F | Cl | 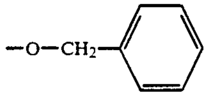 | H | 0 | $-CO-R_3$ | |
| 7.046 | F | Cl | 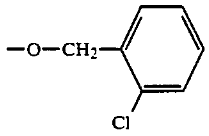 | H | 0 | $-CO-R_3$ | |
| 7.047 | F | Cl | 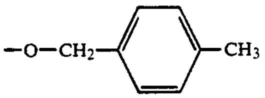 | H | 0 | $-CO-R_3$ | |
| 7.048 | F | Cl | $-S-CH_3$ | H | 0 | $-CO-R_3$ | |
| 7.049 | F | Cl | $-S-C_2H_5$ | H | 0 | $-CO-R_3$ | |
| 7.050 | F | Cl | $-S-C_3H_7$ | H | 0 | $-CO-R_3$ | |
| 7.051 | F | Cl | $-S-CH_2-CH=CH_2$ | H | 0 | $-CO-R_3$ | |
| 7.052 | F | Cl | $-S-CH_2-COOCH_3$ | H | 0 | $-CO-R_3$ | |
| 7.053 | F | Cl | $-S-CH_2-COOC_2H_5$ | H | 0 | $-CO-R_3$ | |
| 7.054 | F | Cl | $-S-CH_2-COOC_5H_{11}$ | H | 0 | $-CO-R_3$ | |
| 7.055 | F | Cl | $-S-CH(CH_3)-COOCH_3$ | H | 0 | $-CO-R_3$ | |
| 7.056 | F | Cl | $-S-(CH_3)-COOC_2H_5$ | H | 0 | $-CO-R_3$ | |
| 7.057 | F | Cl | $-S-CH(CH_3)-COOC_3H_7$ | H | 0 | $-CO-R_3$ | |
| 7.058 | F | Cl | $-S-CH_2-CH_2-COOCH_3$ | H | 0 | $-CO-R_3$ | |
| 7.059 | F | Cl | $-S-CH_2-COOCH_2-CH_2-O-CH_3$ | H | 0 | $-CO-R_3$ | |
| 7.060 | F | Cl | $-O-CH_2-COOCH_3$ | H | 0 | $-CO-R_3$ | |
| 7.061 | F | Cl | $-O-CH(CH_3)-COOCH_3$ | H | 0 | $-CO-R_3$ | |
| 7.062 | F | Cl | $-O-CH_2-COOC_5H_{11}$ | H | 0 | $-CO-R_3$ | |
| 7.063 | F | Cl | $-O-CH_2-CH_3-Si(CH_3)_3$ | H | 0 | $-CO-R_3$ | |
| 7.064 | F | Cl | $-ONa$ | H | 0 | $-CO-R_3$ | |
| 7.065 | F | Br | $-Cl$ | H | 0 | $-CO-R_3$ | |
| 7.066 | F | Br | $-OH$ | H | 0 | $-CO-R_3$ | |
| 7.067 | F | Br | $-OCH_3$ | H | 0 | $-CO-R_3$ | |
| 7.068 | F | Br | $-OC_2H_5$ | H | 0 | $-CO-R_3$ | |
| 7.069 | F | Br | $-OC_3H_7$ | H | 0 | $-CO-R_3$ | |

TABLE 7-continued

Compounds of formula I wherein W is $W_7$, $Y_4$ is oxygen and $R_{14}$ is hydrogen:

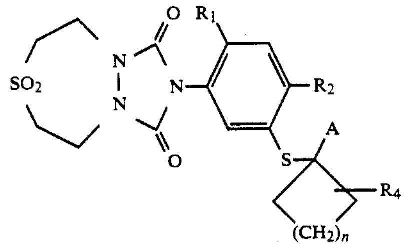

(I)

| Comp. No. | $R_1$ | $R_2$ | $R_3$ | $R_4$ | n | A | m.p. [°C.] |
|---|---|---|---|---|---|---|---|
| 7.070 | F | Br | 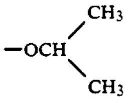 | H | 0 | $-CO-R_3$ | |
| 7.071 | F | Br | $-OC_4H_9$ | H | 0 | $-CO-R_3$ | |
| 7.072 | F | Br | $-OCH(CH_3)-CH_2-CH_3$ | H | 0 | $-CO-R_3$ | |
| 7.073 | F | Br | 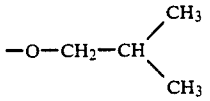 | H | 0 | $-CO-R_3$ | |
| 7.074 | F | Br | $-O-C_5H_{11}$ | H | 0 | $-CO-R_3$ | |
| 7.075 | F | Br | $-O-CH_2-CH_2-O-CH_3$ | H | 0 | $-CO-R_3$ | |
| 7.076 | F | Br | $-O-CH_2-CH_2-O-C_2H_5$ | H | 0 | $-CO-R_3$ | |
| 7.077 | F | Br | $-O-CH(CH_3)-CH_2-O-CH_3$ | H | 0 | $-CO-R_3$ | |
| 7.078 | F | Br | $-O-CH_2-CH_2-S-CH_3$ | H | 0 | $-CO-R_3$ | |
| 7.079 | F | Br | $-O-CH_2(CH_3)-S-CH_3$ | H | 0 | $-CO-R_3$ | |
| 7.080 | F | Br | $-O-CH-(CH_3)-S-C_2H_5$ | H | 0 | $-CO-R_3$ | |
| 7.081 | F | Br | $-O-CH(CH_3)-S-C_3H_7$ | H | 0 | $-CO-R_3$ | |
| 7.082 | F | Br | 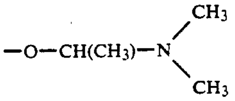 | H | 0 | $-CO-R_3$ | |
| 7.083 | F | Br | $-NH_2$ | H | 0 | $-CO-R_3$ | |
| 7.084 | F | Br | 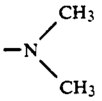 | H | 0 | $-CO-R_3$ | |
| 7.085 | F | Br | 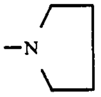 | H | 0 | $-CO-R_3$ | |
| 7.086 | F | Br | 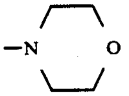 | H | 0 | $-CO-R_3$ | |
| 7.087 | F | Br | 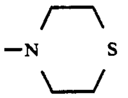 | H | 0 | $-CO-R_3$ | |
| 7.088 | F | Br | 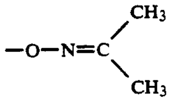 | H | 0 | $-CO-R_3$ | |
| 7.089 | F | Br | $-O-CH_2-CH_2-Cl$ | H | 0 | $-CO-R_3$ | |
| 7.090 | F | Br | $-O-CH_2-CN$ | H | 0 | $-CO-R_3$ | |
| 7.091 | F | Br | $-O-CH_2-CH=CH_2$ | H | 0 | $-CO-R_3$ | |
| 7.092 | F | Br | $-O-CH_2-C\equiv CH$ | H | 0 | $-CO-R_3$ | |

TABLE 7-continued

Compounds of formula I wherein W is $W_7$, $Y_4$ is oxygen and $R_{14}$ is hydrogen:

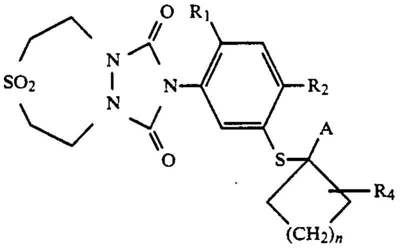

(I)

| Comp. No. | $R_1$ | $R_2$ | $R_3$ | $R_4$ | n | A | m.p. [°C.] |
|---|---|---|---|---|---|---|---|
| 7.093 | F | Br | 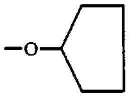 | H | 0 | $-CO-R_3$ | |
| 7.094 | F | Br | 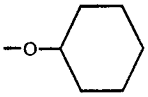 | H | 0 | $-CO-R_3$ | |
| 7.095 | F | Br | 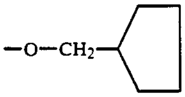 | H | 0 | $-CO-R_3$ | |
| 7.096 | F | Br | 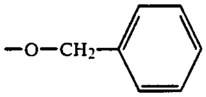 | H | 0 | $-CO-R_3$ | |
| 7.097 | F | Br | $-SCH_3$ | H | 0 | $-CO-R_3$ | |
| 7.098 | F | Br | $-S-CH_2-COOCH_3$ | H | 0 | $-CO-R_3$ | |
| 7.099 | F | Br | $-S-CH(CH_3)-COOCH_3$ | H | 0 | $-CO-R_3$ | |
| 7.100 | F | Br | $-O-CH_2-COOCH_3$ | H | 0 | $-CO-R_3$ | |
| 7.101 | F | Br | $-O-CH(CH_3)COOCH_3$ | H | 0 | $-CO-R_3$ | |
| 7.102 | F | CN | $-Cl$ | H | 0 | $-CO-R_3$ | |
| 7.103 | F | CN | $-OH$ | H | 0 | $-CO-R_3$ | |
| 7.104 | F | CN | $-OCH_3$ | H | 0 | $-CO-R_3$ | |
| 7.105 | H | Cl | $-Cl$ | H | 0 | $-CO-R_3$ | |
| 7.106 | H | Cl | $-OH$ | H | 0 | $-CO-R_3$ | |
| 7.107 | H | Cl | $-OCH_3$ | H | 0 | $-CO-R_3$ | |
| 7.108 | H | Cl | $-OC_2H_5$ | H | 0 | $-CO-R_3$ | |
| 7.109 | H | Cl | 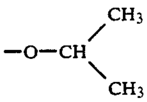 | H | 0 | $-CO-R_3$ | |
| 7.110 | H | Cl | $-O-CH_2-COOCH_3$ | H | 0 | $-CO-R_3$ | |
| 7.111 | H | Cl | $-O-CH(CH_3)COOCH_3$ | H | 0 | $-CO-R_3$ | |
| 7.112 | H | Cl | $-S-CH_2-COOCH_3$ | H | 0 | $-CO-R_3$ | |
| 7.113 | H | Cl | $-S-CH(CH_3)COOCH_3$ | H | 0 | $-CO-R_3$ | |
| 7.114 | H | Cl | 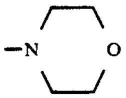 | H | 0 | $-CO-R_3$ | |
| 7.115 | F | Cl | $-Cl$ | H | 1 | $-CO-R_3$ | |
| 7.116 | F | Cl | $-OH$ | H | 1 | $-CO-R_3$ | |
| 7.117 | F | Cl | $-OCH_3$ | H | 1 | $-CO-R_3$ | |
| 7.118 | F | Cl | $-OC_2H_5$ | H | 1 | $-CO-R_3$ | |
| 7.119 | F | Cl | $-OC_3H_7$ | H | 1 | $-CO-R_3$ | |
| 7.120 | F | Cl | 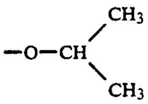 | H | 1 | $-CO-R_3$ | |
| 7.121 | F | Cl | $-OC_4H_9$ | H | 1 | $-CO-R_3$ | |

TABLE 7-continued

Compounds of formula I wherein W is $W_7$, $Y_4$ is oxygen and $R_{14}$ is hydrogen:

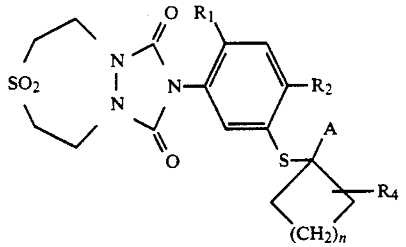

(I)

| Comp. No. | $R_1$ | $R_2$ | $R_3$ | $R_4$ | n | A | m.p. [°C.] |
|---|---|---|---|---|---|---|---|
| 7.122 | F | Cl | $-O-CH(CH_3)-C_2H_5$ | H | 1 | $-CO-R_3$ | |
| 7.123 | F | Cl | 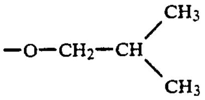 | H | 1 | $-CO-R_3$ | |
| 7.124 | F | Cl | $-OC_5H_{11}$ | H | 1 | $-CO-R_3$ | |
| 7.125 | F | Cl | $-O-CH_2-CH_2-O-CH_3$ | H | 1 | $-CO-R_3$ | |
| 7.126 | F | Cl | $-O-CH_2-CH_2-O-C_2H_5$ | H | 1 | $-CO-R_3$ | |
| 7.127 | F | Cl | $-O-CH-(CH_3)-CH_2-O-CH_3$ | H | 1 | $-CO-R_3$ | |
| 7.128 | F | Cl | $-O-CH_2-CH_2-S-CH_3$ | H | 1 | $-CO-R_3$ | |
| 7.129 | F | Cl | $-O-CH(CH_3)-CH_2-S-CH_3$ | H | 1 | $-CO-R_3$ | |
| 7.130 | F | Cl | $-O-CH(CH_3)-CH_2-S-C_2H_5$ | H | 1 | $-CO-R_3$ | |
| 7.131 | F | Cl | $-O-CH(CH_3)-CH_2-S-C_3H_7$ | H | 1 | $-CO-R_3$ | |
| 7.132 | F | Cl | 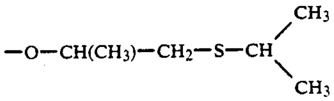 | H | 1 | $-CO-R_3$ | |
| 7.133 | F | Cl | $-O-CH(CH_3)-CH_2-S-C_4H_9$ | H | 1 | $-CO-R_3$ | |
| 7.134 | F | Cl | $-O-CH(CH_3)-CH_2-S-C_5H_{11}$ | H | 1 | $-CO-R_3$ | |
| 7.135 | F | Cl | 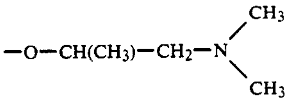 | H | 1 | $-CO-R_3$ | |
| 7.136 | F | Cl | 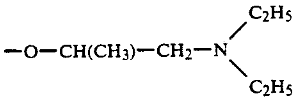 | H | 1 | $-CO-R_3$ | |
| 7.137 | F | Cl | $-NH_2$ | H | 1 | $-CO-R_3$ | |
| 7.138 | F | Cl | 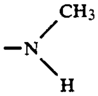 | H | 1 | $-CO-R_3$ | |
| 7.139 | F | Cl | 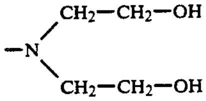 | H | 1 | $-CO-R_3$ | |
| 7.140 | F | Cl | $-NH-CH_2-CH=CH_2$ | H | 1 | $-CO-R_3$ | |
| 7.141 | F | Cl | $-N-(CH_2-CH=CH_2)_2$ | H | 1 | $-CO-R_3$ | |
| 7.142 | F | Cl | 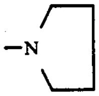 | H | 1 | $-CO-R_3$ | |
| 7.143 | F | Cl | 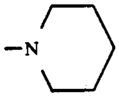 | H | 1 | $-CO-R_3$ | |

TABLE 7-continued
Compounds of formula I wherein W is $W_7$, $Y_4$ is oxygen and $R_{14}$ is hydrogen:
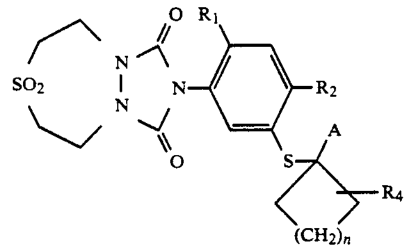
(I)
| Comp. No. | $R_1$ | $R_2$ | $R_3$ | $R_4$ | n | A | m.p. [°C.] |
|---|---|---|---|---|---|---|---|
| 7.144 | F | Cl | 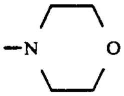 | H | 1 | $-CO-R_3$ | |
| 7.145 | F | Cl | 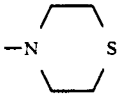 | H | 1 | $-CO-R_3$ | |
| 7.146 | F | Cl | 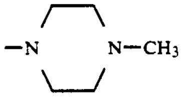 | H | 1 | $-CO-R_3$ | |
| 7.147 | F | Cl | 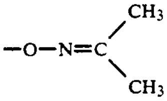 | H | 1 | $-CO-R_3$ | |
| 7.148 | F | Cl | $-O-CH_2-CH_2-Cl$ | H | 1 | $-CO-R_3$ | |
| 7.149 | F | Cl | $-O-CH_2-CN$ | H | 1 | $-CO-R_3$ | |
| 7.150 | F | Cl | 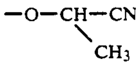 | H | 1 | $-CO-R_3$ | |
| 7.151 | F | Cl | $-O-CH_2-CH=CH_2$ | H | 1 | $-CO-R_3$ | |
| 7.152 | F | Cl | $-O-CH_2-CH=CHCl$ | H | 1 | $-CO-R_3$ | |
| 7.153 | F | Cl | 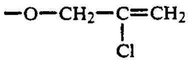 | H | 1 | $-CO-R_3$ | |
| 7.154 | F | Cl | $-O-CH_2=C\equiv CH$ | H | 1 | $-CO-R_3$ | |
| 7.155 | F | Cl | 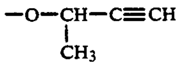 | H | 1 | $-CO-R_3$ | |
| 7.156 | F | Cl | 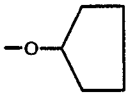 | H | 1 | $-CO-R_3$ | |
| 7.157 | F | Cl | 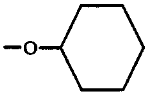 | H | 1 | $-CO-R_3$ | |
| 7.158 | F | Cl | 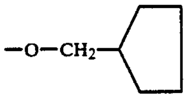 | H | 1 | $-CO-R_3$ | |

TABLE 7-continued

Compounds of formula I wherein W is $W_7$, $Y_4$ is oxygen and $R_{14}$ is hydrogen:

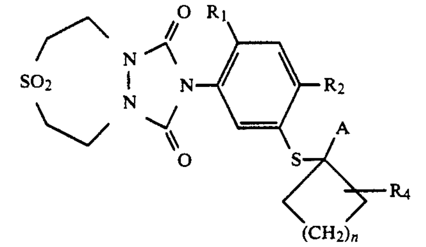

(I)

| Comp. No. | $R_1$ | $R_2$ | $R_3$ | $R_4$ | n | A | m.p. [°C.] |
|---|---|---|---|---|---|---|---|
| 7.159 | F | Cl | 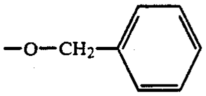 | H | 1 | $-CO-R_3$ | |
| 7.160 | F | Cl | 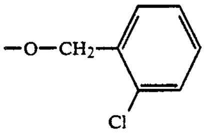 | H | 1 | $-CO-R_3$ | |
| 7.161 | F | Cl | 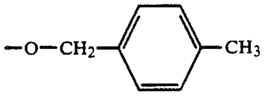 | H | 1 | $-CO-R_3$ | |
| 7.162 | F | Cl | $-S-CH_3$ | H | 1 | $-CO-R_3$ | |
| 7.163 | F | Cl | $-S-C_2H_5$ | H | 1 | $-CO-R_3$ | |
| 7.164 | F | Cl | $-S-C_3H_7$ | H | 1 | $-CO-R_3$ | |
| 7.165 | F | Cl | $-S-CH_2-CH{=}CH_2$ | H | 1 | $-CO-R_3$ | |
| 7.166 | F | Cl | $-S-CH_2-COOCH_3$ | H | 1 | $-CO-R_3$ | |
| 7.167 | F | Cl | $-S-CH_2-COOC_2H_5$ | H | 1 | $-CO-R_3$ | |
| 7.168 | F | Cl | $-S-CH_2-COOC_5H_{11}$ | H | 1 | $-CO-R_3$ | |
| 7.169 | F | Cl | $-S-CH(CH_3)-COOCH_3$ | H | 1 | $-CO-R_3$ | |
| 7.170 | F | Cl | $-S-(CH_3)-COOC_2H_5$ | H | 1 | $-CO-R_3$ | |
| 7.171 | F | Cl | $-S-CH(CH_3)-COOC_3H_7$ | H | 1 | $-CO-R_3$ | |
| 7.172 | F | Cl | $-S-CH_2-CH_2-COOCH_3$ | H | 1 | $-CO-R_3$ | |
| 7.173 | F | Cl | $-S-CH_2-COOCH_2-CH_2-O-CH_3$ | H | 1 | $-CO-R_3$ | |
| 7.174 | F | Cl | $-O-CH_2-COOCH_3$ | H | 1 | $-CO-R_3$ | |
| 7.175 | F | Cl | $-O-CH(CH_3)-COOCH_3$ | H | 1 | $-CO-R_3$ | |
| 7.176 | F | Cl | $-O-CH_2-COOC_5H_{11}$ | H | 1 | $-CO-R_3$ | |
| 7.177 | F | Cl | $-O-CH_2-CH_3-Si(CH_3)_3$ | H | 1 | $-CO-R_3$ | |
| 7.178 | F | Cl | $-ONa$ | H | 1 | $-CO-R_3$ | |
| 7.179 | F | Br | $-Cl$ | H | 1 | $-CO-R_3$ | |
| 7.180 | F | Br | $-OH$ | H | 1 | $-CO-R_3$ | |
| 7.181 | F | Br | $-OCH_3$ | H | 1 | $-CO-R_3$ | |
| 7.182 | F | Br | $-OC_2H_5$ | H | 1 | $-CO-R_3$ | |
| 7.183 | F | Br | $-OC_3H_7$ | H | 1 | $-CO-R_3$ | |
| 7.184 | F | Br | 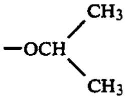 | H | 1 | $-CO-R_3$ | |
| 7.185 | F | Br | $-OC_4H_9$ | H | 1 | $-CO-R_3$ | |
| 7.186 | F | Br | $-OCH(CH_3)-CH_2-CH_3$ | H | 1 | $-CO-R_3$ | |
| 7.187 | F | Br | 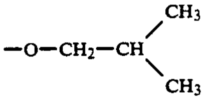 | H | 1 | $-CO-R_3$ | |
| 7.188 | F | Br | $-O-C_5H_{11}$ | H | 1 | $-CO-R_3$ | |
| 7.189 | F | Br | $-O-CH_2-CH_2-O-CH_3$ | H | 1 | $-CO-R_3$ | |
| 7.190 | F | Br | $-O-CH_2-CH_2-O-C_2H_5$ | H | 1 | $-CO-R_3$ | |
| 7.191 | F | Br | $-O-CH(CH_3)-CH_2-O-CH_3$ | H | 1 | $-CO-R_3$ | |
| 7.192 | F | Br | $-O-CH_2-CH_2-S-CH_3$ | H | 1 | $-CO-R_3$ | |
| 7.193 | F | Br | $-O-CH_2(CH_3)-S-CH_3$ | H | 1 | $-CO-R_3$ | |
| 7.194 | F | Br | $-O-CH-(CH_3)-S-C_2H_5$ | H | 1 | $-CO-R_3$ | |
| 7.195 | F | Br | $-O-CH(CH_3)-S-C_3H_7$ | H | 1 | $-CO-R_3$ | |

TABLE 7-continued
Compounds of formula I wherein W is $W_7$, $Y_4$ is oxygen and $R_{14}$ is hydrogen:
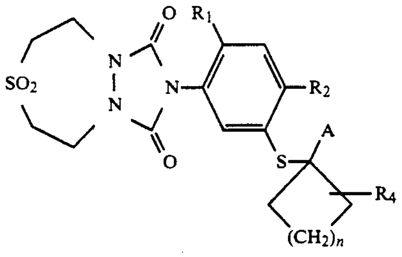
(I)
| Comp. No. | $R_1$ | $R_2$ | $R_3$ | $R_4$ | n | A | m.p. [°C.] |
|---|---|---|---|---|---|---|---|
| 7.196 | F | Br | 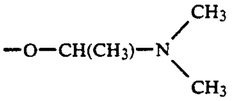 | H | 1 | $-CO-R_3$ | |
| 7.197 | F | Br | $-NH_2$ | H | 1 | $-CO-R_3$ | |
| 7.198 | F | Br | 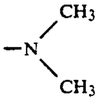 | H | 1 | $-CO-R_3$ | |
| 7.199 | F | Br | 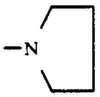 | H | 1 | $-CO-R_3$ | |
| 7.200 | F | Br | 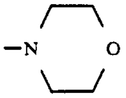 | H | 1 | $-CO-R_3$ | |
| 7.201 | F | Br | 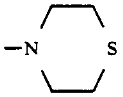 | H | 1 | $-CO-R_3$ | |
| 7.202 | F | Br | 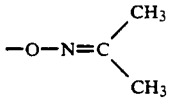 | H | 1 | $-CO-R_3$ | |
| 7.203 | F | Br | $-O-CH_2-CH_2-Cl$ | H | 1 | $-CO-R_3$ | |
| 7.204 | F | Br | $-O-CH_2-CN$ | H | 1 | $-CO-R_3$ | |
| 7.205 | F | Br | $-O-CH_2-CH=CH_2$ | H | 1 | $-CO-R_3$ | |
| 7.206 | F | Br | $-O-CH_2-C\equiv CH$ | | | | |
| 7.207 | F | Br | 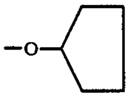 | H | 1 | $-CO-R_3$ | |
| 7.208 | F | Br | 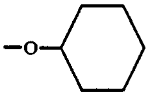 | H | 1 | $-CO-R_3$ | |
| 7.209 | F | Br | 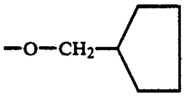 | H | 1 | $-CO-R_3$ | |
| 7.210 | F | Br | 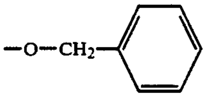 | H | 1 | $-CO-R_3$ | |

TABLE 7-continued

Compounds of formula I wherein W is $W_7$, $Y_4$ is oxygen and $R_{14}$ is hydrogen:

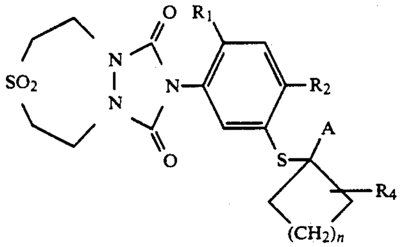

(I)

| Comp. No. | $R_1$ | $R_2$ | $R_3$ | $R_4$ | n | A | m.p. [°C.] |
|---|---|---|---|---|---|---|---|
| 7.211 | F | Br | $-SCH_3$ | H | 1 | $-CO-R_3$ | |
| 7.212 | F | Br | $-S-CH_2-COOCH_3$ | H | 1 | $-CO-R_3$ | |
| 7.213 | F | Br | $-S-CH(CH_3)-COOCH_3$ | H | 1 | $-CO-R_3$ | |
| 7.214 | F | Br | $-O-CH_2-COOCH_3$ | H | 1 | $-CO-R_3$ | |
| 7.215 | F | Br | $-O-CH(CH_3)COOCH_3$ | H | 1 | $-CO-R_3$ | |
| 7.216 | F | CN | $-Cl$ | H | 1 | $-CO-R_3$ | |
| 7.217 | F | CN | $-OH$ | H | 1 | $-CO-R_3$ | |
| 7.218 | F | CN | $-OCH_3$ | H | 1 | $-CO-R_3$ | |
| 7.219 | H | Cl | $-Cl$ | H | 1 | $-CO-R_3$ | |
| 7.220 | H | Cl | $-OH$ | H | 1 | $-CO-R_3$ | |
| 7.221 | H | Cl | $-OCH_3$ | H | 1 | $-CO-R_3$ | |
| 7.222 | H | Cl | $-OC_2H_5$ | H | 1 | $-CO-R_3$ | |
| 7.223 | H | Cl | 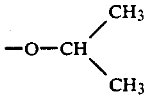 | H | 1 | $-CO-R_3$ | |
| 7.224 | H | Cl | $-O-CH_2-COOCH_3$ | H | 1 | $-CO-R_3$ | |
| 7.225 | H | Cl | $-O-CH(CH_3)COOCH_3$ | H | 1 | $-CO-R_3$ | |
| 7.226 | H | Cl | $-S-CH_2-COOCH_3$ | H | 1 | $-CO-R_3$ | |
| 7.227 | H | Cl | $-S-CH(CH_3)COOCH_3$ | H | 1 | $-CO-R_3$ | |
| 7.228 | H | Cl | 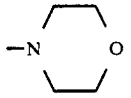 | H | 1 | $-CO-R_3$ | |
| 7.229 | F | Cl | Cl | H | 2 | $-CO-R_3$ | |
| 7.230 | F | Cl | OH | H | 2 | $-CO-R_3$ | |
| 7.231 | F | Cl | $OCH_3$ | H | 2 | $-CO-R_3$ | |
| 7.232 | F | Cl | $-OC_2H_5$ | H | 2 | $-CO-R_3$ | |
| 7.233 | F | Cl | 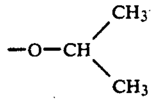 | H | 2 | $-CO-R_3$ | |
| 7.234 | F | Cl | $-O-CH_2-CH_2-O-CH_3$ | H | 2 | $-CO-R_3$ | |
| 7.235 | F | Cl | $-O-CH(CH_3)-CH_2-S-CH_3$ | H | 2 | $-CO-R_3$ | |
| 7.236 | F | Cl | $-O-CH_2-COOCH_3$ | H | 2 | $-CO-R_3$ | |
| 7.237 | F | Cl | $-S-CH_2-COOCH_3$ | H | 2 | $-CO-R_3$ | |
| 7.238 | F | Cl | $-CH_2-CH=CH_2$ | H | 2 | $-CO-R_3$ | |
| 7.239 | F | Cl | $-CH_2-C\equiv CH$ | H | 2 | $-CO-R_3$ | |
| 7.240 | F | Cl | Cl | H | 3 | $-CO-R_3$ | |
| 7.241 | F | Cl | OH | H | 3 | $-CO-R_3$ | |
| 7.242 | F | Cl | $OCH_3$ | H | 3 | $-CO-R_3$ | |
| 7.243 | F | Cl | $OC_2H_5$ | H | 3 | $-CO-R_3$ | |
| 7.244 | F | Cl | 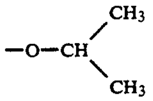 | H | 3 | $-CO-R_3$ | |
| 7.245 | F | Cl | $-O-CH_2-CH_2-O-CH$ | H | 3 | $-CO-R_3$ | |
| 7.246 | F | Cl | $-O-CH(CH_3)-CH_2-S-CH_3$ | H | 3 | $-CO-R_3$ | |
| 7.247 | F | Cl | $-O-CH_2-COOCH_3$ | H | 3 | $-CO-R_3$ | |
| 7.248 | F | Cl | $-S-CH_2-COOCH_3$ | H | 3 | $-CO-R_3$ | |
| 7.249 | F | Cl | $-O-CH_2-C\equiv CH$ | H | 3 | $-CO-R_3$ | |
| 7.250 | F | Cl | $-Cl$ | Cl | 0 | $-CO-R_3$ | |
| 7.251 | F | Cl | $-OH$ | Cl | 0 | $-CO-R_3$ | |
| 7.252 | F | Cl | $-OCH_3$ | Cl | 0 | $-CO-R_3$ | |
| 7.253 | F | Cl | $-OC_2H_5$ | Cl | 0 | $-CO-R_3$ | |

TABLE 7-continued

Compounds of formula I wherein W is $W_7$, $Y_4$ is oxygen and $R_{14}$ is hydrogen:

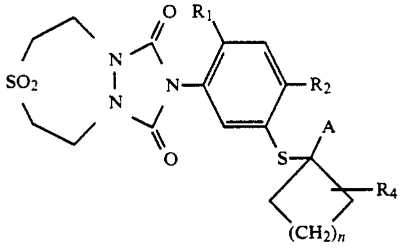

(I)

| Comp. No. | $R_1$ | $R_2$ | $R_3$ | $R_4$ | n | A | m.p. [°C.] |
|---|---|---|---|---|---|---|---|
| 7.254 | F | Cl | 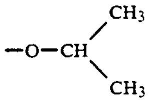 | Cl | 0 | $-CO-R_3$ | |
| 7.255 | F | Cl | $-O-CH_2-COOCH_3$ | Cl | 0 | $-CO-R_3$ | |
| 7.256 | F | Cl | $-S-CH_2-COOCH_3$ | Cl | 0 | $-CO-R_3$ | |
| 7.257 | F | Cl | $-OCH_3$ | Br | 0 | $-CO-R_3$ | |
| 7.258 | F | Cl | 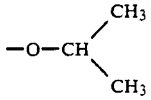 | Br | 0 | $-CO-R_3$ | |
| 7.259 | F | Cl | $-OCH_3$ | F | 0 | $-CO-R_3$ | |
| 7.260 | F | Cl | $-OCH_3$ | $CH_3$ | 0 | $-CO-R_3$ | |
| 7.261 | F | Cl | $-OC_2H_5$ | $CH_3$ | 0 | $-CO-R_3$ | |
| 7.262 | F | Cl | 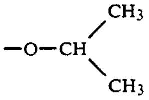 | $CH_3$ | 0 | $-CO-R_3$ | |
| 7.263 | F | Cl | $-O-CH_2-CH_2-O-CH_3$ | $CH_3$ | 0 | $-CO-R_3$ | |
| 7.264 | F | Cl | $-O-CH_2-COOCH_3$ | $CH_3$ | 0 | $-CO-R_3$ | |
| 7.265 | F | Cl | $-O-CH(CH_3)COOCH_3$ | $CH_3$ | 0 | $-CO-R_3$ | |
| 7.266 | F | Cl | $-S-CH_2-COOCH_3$ | $CH_3$ | 0 | $-CO-R_3$ | |
| 7.267 | F | Cl | $-OCH_3$ | $CF_3$ | 0 | $-CO-R_3$ | |
| 7.268 | F | Cl | $-OC_2H_5$ | $CF_3$ | 0 | $-CO-R_3$ | |
| 7.269 | F | Cl | 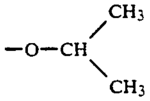 | $CF_3$ | 0 | $-CO-R_3$ | |
| 7.270 | F | Cl | $-O-CH_2-COOCH_3$ | $CF_3$ | 0 | $-CO-R_3$ | |
| 7.271 | F | Cl | $-S-CH_2-COOCH_3$ | $CF_3$ | 0 | $-CO-R_3$ | |
| 7.272 | F | Cl | — | H | 0 | —CN | |
| 7.273 | F | Cl | — | H | 1 | —CN | |
| 7.274 | F | Cl | — | H | 2 | —CN | |
| 7.275 | F | Cl | — | H | 3 | —CN | |
| 7.276 | F | Cl | — | H | 4 | —CN | |

TABLE 8

Compounds of formula I wherein W is $W_8$ and $Z_1$ is oxygen:

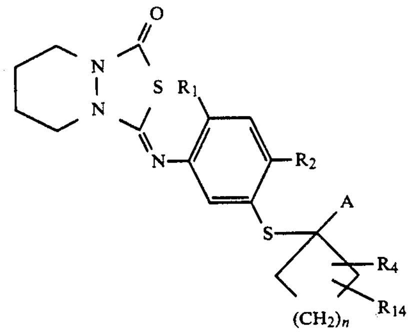

(I)

| Comp. No. | $R_1$ | $R_2$ | $R_3$ | $R_{14}$ | $R_4$ | n | A | m.p. [°C.] |
|---|---|---|---|---|---|---|---|---|
| 8.001 | F | Cl | $-Cl$ | H | H | 0 | $-CO-R_3$ | |
| 8.002 | F | Cl | $-OH$ | H | H | 0 | $-CO-R_3$ | 162-164 |
| 8.003 | F | Cl | $-OCH_3$ | H | H | 0 | $-CO-R_3$ | 149 |
| 8.004 | F | Cl | $-OC_2H_5$ | H | H | 0 | $-CO-R_3$ | 123-124 |
| 8.005 | F | Cl | $-OC_3H_7$ | H | H | 0 | $-CO-R_3$ | |
| 8.006 | F | Cl | 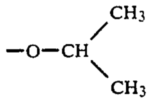 | H | H | 0 | $-CO-R_3$ | |
| 8.007 | F | Cl | $-OC_4H_9$ | H | H | 0 | $-CO-R_3$ | 75-78 |
| 8.008 | F | Cl | $-O-CH(CH_3)-C_2H_5$ | H | H | 0 | $-CO-R_3$ | |
| 8.009 | F | Cl | 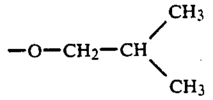 | H | H | 0 | $-CO-R_3$ | 109-111 |
| 8.010 | F | Cl | $-OC_5H_{11}$ | H | H | 0 | $-CO-R_3$ | |
| 8.011 | F | Cl | $-O-CH_2-CH_2-O-CH_3$ | H | H | 0 | $-CO-R_3$ | 89-90 |
| 8.012 | F | Cl | $-O-CH_2-CH_2-O-C_2H_5$ | H | H | 0 | $-CO-R_3$ | |
| 8.013 | F | Cl | $-O-CH-(CH_3)-CH_2-O-CH_3$ | H | H | 0 | $-CO-R_3$ | |
| 8.014 | F | Cl | $-O-CH_2-CH_2-S-CH_3$ | H | H | 0 | $-CO-R_3$ | |
| 8.015 | F | Cl | $-O-CH(CH_3)-CH_2-S-CH_3$ | H | H | 0 | $-CO-R_3$ | |
| 8.016 | F | Cl | $-O-CH(CH_3)-CH_2-S-C_2H_5$ | H | H | 0 | $-CO-R_3$ | |
| 8.017 | F | Cl | $-O-CH(CH_3)-CH_2-S-C_3H_7$ | H | H | 0 | $-CO-R_3$ | |
| 8.018 | F | Cl | 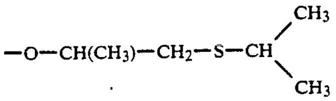 | H | H | 0 | $-CO-R_3$ | |
| 8.019 | F | Cl | $-O-CH(CH_3)-CH_2-S-C_4H_9$ | H | H | 0 | $-CO-R_3$ | |
| 8.020 | F | Cl | $-O-CH(CH_3)-CH_2-S-C_5H_{11}$ | H | H | 0 | $-CO-R_3$ | |
| 8.021 | F | Cl | 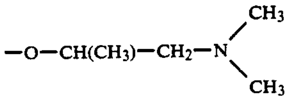 | H | H | 0 | $-CO-R_3$ | 124-126 |
| 8.022 | F | Cl | 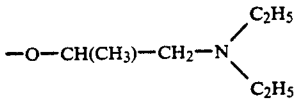 | H | H | 0 | $-CO-R_3$ | |
| 8.023 | F | Cl | $-NH_2$ | H | H | 0 | $-CO-R_3$ | |
| 8.024 | F | Cl | 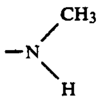 | H | H | 0 | $-CO-R_3$ | |
| 8.025 | F | Cl | 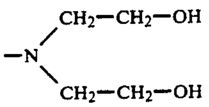 | H | H | 0 | $-CO-R_3$ | |

TABLE 8-continued

Compounds of formula I wherein W is $W_8$ and $Z_1$ is oxygen:

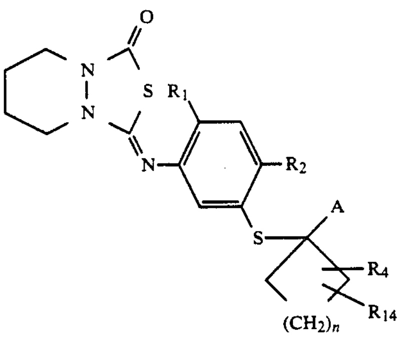

(I)

| Comp. No. | $R_1$ | $R_2$ | $R_3$ | $R_{14}$ | $R_4$ | n | A | m.p. [°C.] |
|---|---|---|---|---|---|---|---|---|
| 8.026 | F | Cl | $-NH-CH_2-CH=CH_2$ | H | H | 0 | $-CO-R_3$ | |
| 8.027 | F | Cl | $-N-(CH_2-CH=CH_2)_2$ | H | H | 0 | $-CO-R_3$ | |
| 8.028 | F | Cl | 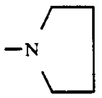 | H | H | 0 | $-CO-R_3$ | |
| 8.029 | F | Cl | 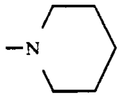 | H | H | 0 | $-CO-R_3$ | |
| 8.030 | F | Cl | 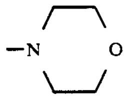 | H | H | 0 | $-CO-R_3$ | |
| 8.031 | F | Cl | 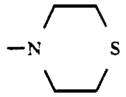 | H | H | 0 | $-CO-R_3$ | |
| 8.032 | F | Cl | 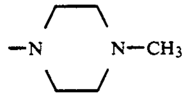 | H | H | 0 | $-CO-R_3$ | |
| 8.033 | F | Cl | $CH_3$<br>$-O-N=C$<br>$CH_3$ | H | H | 0 | $-CO-R_3$ | 149-151 |
| 8.034 | F | Cl | $-O-CH_2-CH_2-Cl$ | H | H | 0 | $-CO-R_3$ | |
| 8.035 | F | Cl | $-O-CH_2-CN$ | H | H | 0 | $-CO-R_3$ | |
| 8.036 | F | Cl | $-O-CH-CN$<br>$CH_3$ | H | H | 0 | $-CO-R_3$ | |
| 8.037 | F | Cl | $-O-CH_2-CH=CH_2$ | H | H | 0 | $-CO-R_3$ | 94-96 |
| 8.038 | F | Cl | $-O-CH_2-CH=CHCl$ | H | H | 0 | $-CO-R_3$ | 121-123 |
| 8.039 | F | Cl | $-O-CH_2-C=CH_2$<br>Cl | H | H | 0 | $-CO-R_3$ | 86-88 |
| 8.040 | F | Cl | $-O-CH_2=C\equiv CH$ | H | H | 0 | $-CO-R_3$ | 119-120 |
| 8.041 | F | Cl | $-O-CH-C\equiv CH$<br>$CH_3$ | H | H | 0 | $-CO-R_3$ | |

TABLE 8-continued

Compounds of formula I wherein W is $W_8$ and $Z_1$ is oxygen:

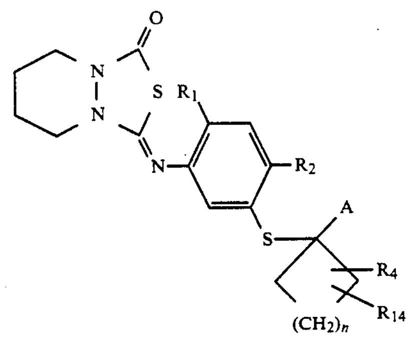

(I)

| Comp. No. | $R_1$ | $R_2$ | $R_3$ | $R_{14}$ | $R_4$ | n | A | m.p. [°C.] |
|---|---|---|---|---|---|---|---|---|
| 8.042 | F | Cl | 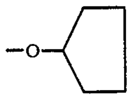 | H | H | 0 | $-CO-R_3$ | |
| 8.043 | F | Cl | 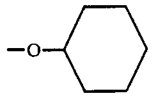 | H | H | 0 | $-CO-R_3$ | |
| 8.044 | F | Cl | 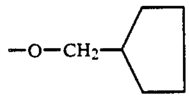 | H | H | 0 | $-CO-R_3$ | |
| 8.045 | F | Cl | 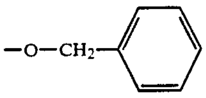 | H | H | 0 | $-CO-R_3$ | |
| 8.046 | F | Cl | 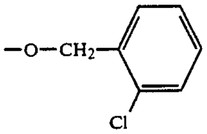 | H | | 0 | $-CO-R_3$ | |
| 8.047 | F | Cl | 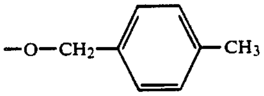 | H | H | 0 | $-CO-R_3$ | |
| 8.048 | F | Cl | $-S-CH_3$ | H | H | 0 | $-CO-R_3$ | |
| 8.049 | F | Cl | $-S-C_2H_5$ | H | H | 0 | $-CO-R_3$ | |
| 8.050 | F | Cl | $-S-C_3H_7$ | H | H | 0 | $-CO-R_3$ | |
| 8.051 | F | Cl | $-S-CH_2-CH=CH_2$ | H | H | 0 | $-CO-R_3$ | |
| 8.052 | F | Cl | $-S-CH_2-COOCH_3$ | H | H | 0 | $-CO-R_3$ | |
| 8.053 | F | Cl | $-S-CH_2-COOC_2H_5$ | H | H | 0 | $-CO-R_3$ | |
| 8.054 | F | Cl | $-S-CH_2-COOC_5H_{11}$ | H | H | 0 | $-CO-R_3$ | |
| 8.055 | F | Cl | $-S-CH(CH_3)-COOCH_3$ | H | H | 0 | $-CO-R_3$ | |
| 8.056 | F | Cl | $-S-(CH_3)-COOC_2H_5$ | H | H | 0 | $-CO-R_3$ | |
| 8.057 | F | Cl | $-S-CH(CH_3)-COOC_3H_7$ | H | H | 0 | $-CO-R_3$ | |
| 8.058 | F | Cl | $-S-CH_2-CH_2-COOCH_3$ | H | H | 0 | $-CO-R_3$ | |
| 8.059 | F | Cl | $-S-CH_2-COOCH_2-CH_2-O-CH_3$ | H | H | 0 | $-CO-R_3$ | |
| 8.060 | F | Cl | $-O-CH_2-COOCH_3$ | H | H | 0 | $-CO-R_3$ | 140-141 |
| 8.061 | F | Cl | $-O-CH(CH_3)-COOCH_3$ | H | H | 0 | $-CO-R_3$ | 122-123 |
| 8.062 | F | Cl | $-O-CH_2-COOC_5H_{11}$ | H | H | 0 | $-CO-R_3$ | |
| 8.063 | F | Cl | $-O-CH_2-CH_3-Si(CH_3)_3$ | H | H | 0 | $-CO-R_3$ | |
| 8.064 | F | Cl | $-ONa$ | H | H | 0 | $-CO-R_3$ | |
| 8.065 | F | Br | $-Cl$ | H | H | 0 | $-CO-R_3$ | |
| 8.066 | F | Br | $-OH$ | H | H | 0 | $-CO-R_3$ | |
| 8.067 | F | Br | $-OCH_3$ | H | H | 0 | $-CO-R_3$ | |
| 8.068 | F | Br | $-OC_2H_5$ | H | H | 0 | $-CO-R_3$ | |
| 8.069 | F | Br | $-OC_3H_7$ | H | H | 0 | $-CO-R_3$ | |

TABLE 8-continued

Compounds of formula I wherein W is $W_8$ and $Z_1$ is oxygen:

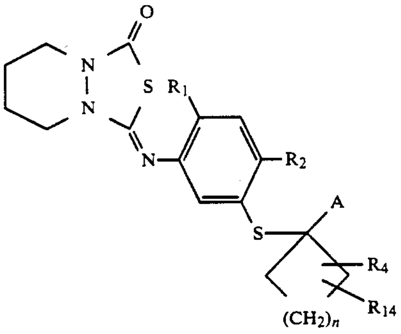

(I)

| Comp. No. | $R_1$ | $R_2$ | $R_3$ | $R_{14}$ | $R_4$ | n | A | m.p. [°C.] |
|---|---|---|---|---|---|---|---|---|
| 8.070 | F | Br | 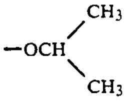 | H | H | 0 | $-CO-R_3$ | |
| 8.071 | F | Br | $-OC_4H_9$ | H | H | 0 | $-CO-R_3$ | |
| 8.072 | F | Br | $-OCH(CH_3)-CH_2-CH_3$ | H | H | 0 | $-CO-R_3$ | |
| 8.073 | F | Br | 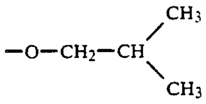 | H | H | 0 | $-CO-R_3$ | |
| 8.074 | F | Br | $-O-C_5H_{11}$ | H | H | 0 | $-CO-R_3$ | |
| 8.075 | F | Br | $-O-CH_2-CH_2-O-CH_3$ | H | H | 0 | $-CO-R_3$ | |
| 8.076 | F | Br | $-O-CH_2-CH_2-O-C_2H_5$ | H | H | 0 | $-CO-R_3$ | |
| 8.077 | F | Br | $-O-CH(CH_3)-CH_2-O-CH_3$ | H | H | 0 | $-CO-R_3$ | |
| 8.078 | F | Br | $-O-CH_2-CH_2-S-CH_3$ | H | H | 0 | $-CO-R_3$ | |
| 8.079 | F | Br | $-O-CH_2(CH_3)-S-CH_3$ | H | H | 0 | $-CO-R_3$ | |
| 8.080 | F | Br | $-O-CH-(CH_3)-S-C_2H_5$ | H | H | 0 | $-CO-R_3$ | |
| 8.081 | F | Br | $-O-CH(CH_3)-S-C_3H_7$ | H | H | 0 | $-CO-R_3$ | |
| 8.082 | F | Br | 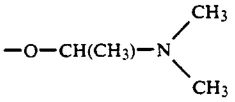 | H | H | 0 | $-CO-R_3$ | |
| 8.083 | F | Br | $-NH_2$ | H | H | 0 | $-CO-R_3$ | |
| 8.084 | F | Br | 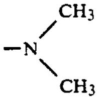 | H | H | 0 | $-CO-R_3$ | |
| 8.085 | F | Br | 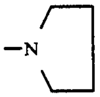 | H | H | 0 | $-CO-R_3$ | |
| 8.086 | F | Br | 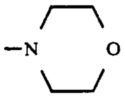 | H | H | 0 | $-CO-R_3$ | |
| 8.087 | F | Br | 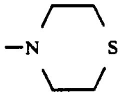 | H | H | 0 | $-CO-R_3$ | |
| 8.088 | F | Br | 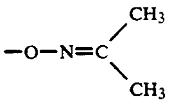 | H | H | 0 | $-CO-R_3$ | |
| 8.089 | F | Br | $-O-CH_2-CH_2-Cl$ | H | H | 0 | $-CO-R_3$ | |

TABLE 8-continued

Compounds of formula I wherein W is $W_8$ and $Z_1$ is oxygen:

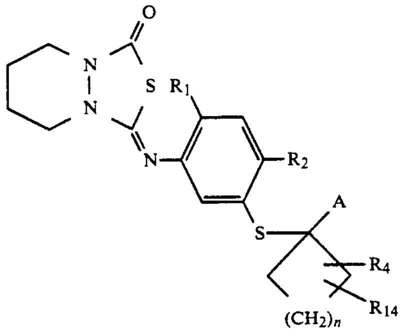

(I)

| Comp. No. | $R_1$ | $R_2$ | $R_3$ | $R_{14}$ | $R_4$ | n | A | m.p. [°C.] |
|---|---|---|---|---|---|---|---|---|
| 8.090 | F | Br | $-O-CH_2-CN$ | H | H | 0 | $-CO-R_3$ | |
| 8.091 | F | Br | $-O-CH_2-CH=CH_2$ | H | H | 0 | $-CO-R_3$ | |
| 8.092 | F | Br | $-O-CH_2-C\equiv CH$ | H | H | 0 | $-CO-R_3$ | |
| 8.093 | F | Br | 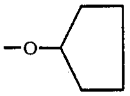 | H | H | 0 | $-CO-R_3$ | |
| 8.094 | F | Br | 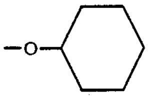 | H | H | 0 | $-CO-R_3$ | |
| 8.095 | F | Br | 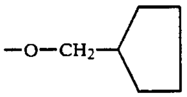 | H | H | 0 | $-CO-R_3$ | |
| 8.096 | F | Br | 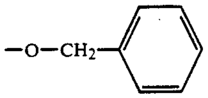 | H | H | 0 | $-CO-R_3$ | |
| 8.097 | F | Br | $-SCH_3$ | H | H | 0 | $-CO-R_3$ | |
| 8.098 | F | Br | $-S-CH_2-COOCH_3$ | H | H | 0 | $-CO-R_3$ | |
| 8.099 | F | Br | $-S-CH(CH_3)-COOCH_3$ | H | H | 0 | $-CO-R_3$ | |
| 8.100 | F | Br | $-O-CH_2-COOCH_3$ | H | H | 0 | $-CO-R_3$ | |
| 8.101 | F | Br | $-O-CH(CH_3)COOCH_3$ | H | H | 0 | $-CO-R_3$ | |
| 8.102 | F | CN | $-Cl$ | H | H | 0 | $-CO-R_3$ | |
| 8.103 | F | CN | $-OH$ | H | H | 0 | $-CO-R_3$ | |
| 8.104 | F | CN | $-OCH_3$ | H | H | 0 | $-CO-R_3$ | |
| 8.105 | H | Cl | $-Cl$ | H | H | 0 | $-CO-R_3$ | |
| 8.106 | H | Cl | $-OH$ | H | H | 0 | $-CO-R_3$ | |
| 8.107 | H | Cl | $-OCH_3$ | H | | 0 | $-CO-R_3$ | |
| 8.108 | H | Cl | $-OC_2H_5$ | H | H | 0 | $-CO-R_3$ | |
| 8.109 | H | Cl | 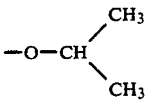 | H | H | 0 | $-CO-R_3$ | |
| 8.110 | H | Cl | $-O-CH_2-COOCH_3$ | H | H | 0 | $-CO-R_3$ | |
| 8.111 | H | Cl | $-O-CH(CH_3)COOCH_3$ | H | H | 0 | $-CO-R_3$ | |
| 8.112 | H | Cl | $-S-CH_2-COOCH_3$ | H | H | 0 | $-CO-R_3$ | |
| 8.113 | H | Cl | $-S-CH(CH_3)COOCH_3$ | H | H | 0 | $-CO-R_3$ | |
| 8.114 | H | Cl | 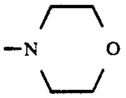 | H | H | 0 | $-CO-R_3$ | |
| 8.115 | F | Cl | $-Cl$ | H | H | 1 | $-CO-R_3$ | |
| 8.116 | F | Cl | $-OH$ | H | H | 1 | $-CO-R_3$ | |
| 8.117 | F | Cl | $-OCH_3$ | H | H | 1 | $-CO-R_3$ | $\eta_D^{22}$ 1.6010 |
| 8.118 | F | Cl | $-OC_2H_5$ | H | H | 1 | $-CO-R_3$ | |

TABLE 8-continued

Compounds of formula I wherein W is $W_8$ and $Z_1$ is oxygen:

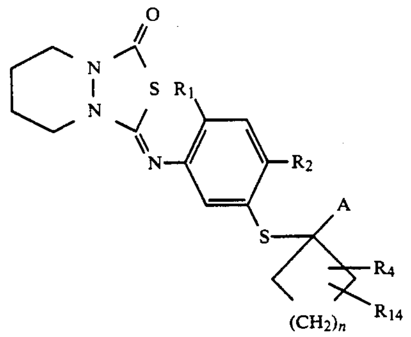

(I)

| Comp. No. | $R_1$ | $R_2$ | $R_3$ | $R_{14}$ | $R_4$ | n | A | m.p. [°C.] |
|---|---|---|---|---|---|---|---|---|
| 8.119 | F | Cl | $-OC_3H_7$ | H | H | 1 | $-CO-R_3$ | |
| 8.120 | F | Cl | $CH_3$<br>$-O-CH$<br>$CH_3$ | H | H | 1 | $-CO-R_3$ | |
| 8.121 | F | Cl | $-OC_4H_9$ | H | H | 1 | $-CO-R_3$ | |
| 8.122 | F | Cl | $-O-CH(CH_3)-C_2H_5$ | H | H | 1 | $-CO-R_3$ | |
| 8.123 | F | Cl | $CH_3$<br>$-O-CH_2-CH$<br>$CH_3$ | H | H | 1 | $-CO-R_3$ | |
| 8.124 | F | Cl | $-OC_5H_{11}$ | H | H | 1 | $-CO-R_3$ | |
| 8.125 | F | Cl | $-O-CH_2-CH_2-O-CH_3$ | H | H | 1 | $-CO-R_3$ | |
| 8.126 | F | Cl | $-O-CH_2-CH_2-O-C_2H_5$ | H | H | 1 | $-CO-R_3$ | |
| 8.127 | F | Cl | $-O-CH-(CH_3)-CH_2-O-CH_3$ | H | H | 1 | $-CO-R_3$ | |
| 8.128 | F | Cl | $-O-CH_2-CH_2-S-CH_3$ | H | H | 1 | $-CO-R_3$ | |
| 8.129 | F | Cl | $-O-CH(CH_3)-CH_2-S-CH_3$ | H | H | 1 | $-CO-R_3$ | |
| 8.130 | F | Cl | $-O-CH(CH_3)-CH_2-S-C_2H_5$ | H | H | 1 | $-CO-R_3$ | |
| 8.131 | F | Cl | $-O-CH(CH_3)-CH_2-S-C_3H_7$ | H | H | 1 | $-CO-R_3$ | |
| 8.132 | F | Cl | $CH_3$<br>$-O-CH(CH_3)-CH_2-S-CH$<br>$CH_3$ | H | H | 1 | $-CO-R_3$ | |
| 8.133 | F | Cl | $-O-CH(CH_3)-CH_2-S-C_4H_9$ | H | H | 1 | $-CO-R_3$ | |
| 8.134 | F | Cl | $-O-CH(CH_3)-CH_2-S-C_5H_{11}$ | H | H | 1 | $-CO-R_3$ | |
| 8.135 | F | Cl | $CH_3$<br>$-O-CH(CH_3)-CH_2-N$<br>$CH_3$ | H | H | 1 | $-CO-R_3$ | |
| 8.136 | F | Cl | $C_2H_5$<br>$-O-CH(CH_3)-CH_2-N$<br>$C_2H_5$ | H | H | 1 | $-CO-R_3$ | |
| 8.137 | F | Cl | $-NH_2$ | H | H | 1 | $-CO-R_3$ | |
| 8.138 | F | Cl | $CH_3$<br>$-N$<br>H | H | H | 1 | $-CO-R_3$ | |
| 8.139 | F | Cl | $CH_2-CH_2-OH$<br>$-N$<br>$CH_2-CH_2-OH$ | H | H | 1 | $-CO-R_3$ | |
| 8.140 | F | Cl | $-NH-CH_2-CH=CH_2$ | H | H | 1 | $-CO-R_3$ | |
| 8.141 | F | Cl | $-N-(CH_2-CH=CH_2)_2$ | H | H | 1 | $-CO-R_3$ | |

TABLE 8-continued
Compounds of formula I wherein W is $W_8$ and $Z_1$ is oxygen:
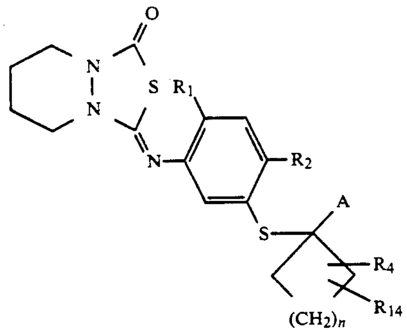
(I)
| Comp. No. | $R_1$ | $R_2$ | $R_3$ | $R_{14}$ | $R_4$ | n | A | m.p. [°C.] |
|---|---|---|---|---|---|---|---|---|
| 8.142 | F | Cl | 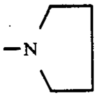 | H | H | 1 | $-CO-R_3$ | |
| 8.143 | F | Cl | 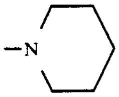 | H | H | 1 | $-CO-R_3$ | |
| 8.144 | F | Cl | 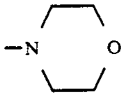 | H | H | 1 | $-CO-R_3$ | |
| 8.145 | F | Cl | 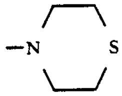 | H | H | 1 | $-CO-R_3$ | |
| 8.146 | F | Cl | 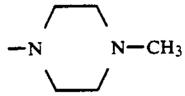 | H | H | 1 | $-CO-R_3$ | |
| 8.147 | F | Cl | 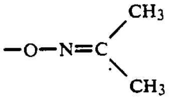 | H | H | 1 | $-CO-R_3$ | |
| 8.148 | F | Cl | $-O-CH_2-CH_2-Cl$ | H | H | 1 | $-CO-R_3$ | |
| 8.149 | F | Cl | $-O-CH_2-CN$ | H | H | 1 | $-CO-R_3$ | |
| 8.150 | F | Cl | 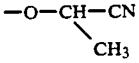 | H | H | 1 | $-CO-R_3$ | |
| 8.151 | F | Cl | $-O-CH_2-CH=CH_2$ | H | H | 1 | $-CO-R_3$ | |
| 8.152 | F | Cl | $-O-CH_2-CH=CHCl$ | H | H | 1 | $-CO-R_3$ | |
| 8.153 | F | Cl | 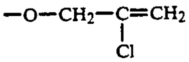 | H | H | 1 | $-CO-R_3$ | |
| 8.154 | F | Cl | $-O-CH_2=C\equiv CH$ | H | H | 1 | $-CO-R_3$ | |
| 8.155 | F | Cl | 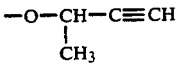 | H | H | 1 | $-CO-R_3$ | |
| 8.156 | F | Cl | 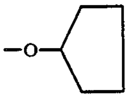 | H | H | 1 | $-CO-R_3$ | |

TABLE 8-continued

Compounds of formula I wherein W is $W_8$ and $Z_1$ is oxygen:

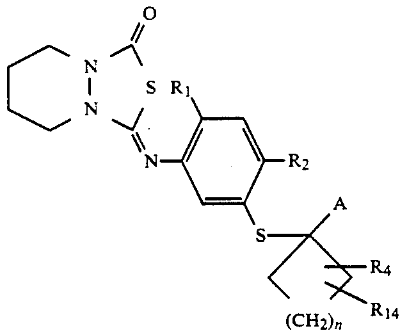

(I)

| Comp. No. | $R_1$ | $R_2$ | $R_3$ | $R_{14}$ | $R_4$ | n | A | m.p. [°C.] |
|---|---|---|---|---|---|---|---|---|
| 8.157 | F | Cl | 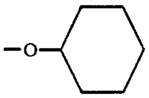 | H | H | 1 | $-CO-R_3$ | |
| 8.158 | F | Cl | 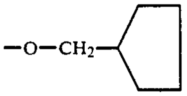 | H | H | 1 | $-CO-R_3$ | |
| 8.159 | F | Cl | 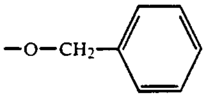 | H | H | 1 | $-CO-R_3$ | |
| 8.160 | F | Cl | 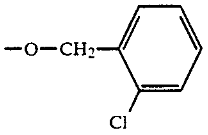 | H | H | 1 | $-CO-R_3$ | |
| 8.161 | F | Cl | 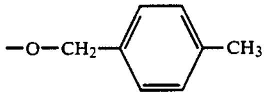 | H | H | 1 | $-CO-R_3$ | |
| 8.162 | F | Cl | $-S-CH_3$ | H | H | 1 | $-CO-R_3$ | |
| 8.163 | F | Cl | $-S-C_2H_5$ | H | H | 1 | $-CO-R_3$ | |
| 8.164 | F | Cl | $-S-C_3H_7$ | H | H | 1 | $-CO-R_3$ | |
| 8.165 | F | Cl | $-S-CH_2-CH{=}CH_2$ | H | H | 1 | $-CO-R_3$ | |
| 8.166 | F | Cl | $-S-CH_2-COOCH_3$ | H | H | 1 | $-CO-R_3$ | |
| 8.167 | F | Cl | $-S-CH_2-COOC_2H_5$ | H | H | 1 | $-CO-R_3$ | |
| 8.168 | F | Cl | $-S-CH_2-COOC_5H_{11}$ | H | H | 1 | $-CO-R_3$ | |
| 8.169 | F | Cl | $-S-CH(CH_3)-COOCH_3$ | H | H | 1 | $-CO-R_3$ | |
| 8.170 | F | Cl | $-S-(CH_3)-COOC_2H_5$ | H | H | 1 | $-CO-R_3$ | |
| 8.171 | F | Cl | $-S-CH(CH_3)-COOC_3H_7$ | H | H | 1 | $-CO-R_3$ | |
| 8.172 | F | Cl | $-S-CH_2-CH_2-COOCH_3$ | H | H | 1 | $-CO-R_3$ | |
| 8.173 | F | Cl | $-S-CH_2-COOCH_2-CH_2-O-CH_3$ | H | H | 1 | $-CO-R_3$ | |
| 8.174 | F | Cl | $-O-CH_2-COOCH_3$ | H | H | 1 | $-CO-R_3$ | |
| 8.175 | F | Cl | $-O-CH(CH_3)-COOCH_3$ | H | H | 1 | $-CO-R_3$ | |
| 8.176 | F | Cl | $-O-CH_2-COOC_5H_{11}$ | H | H | 1 | $-CO-R_3$ | |
| 8.177 | F | Cl | $-O-CH_2-CH_3-Si(CH_3)_3$ | H | H | 1 | $-CO-R_3$ | |
| 8.178 | F | Cl | $-ONa$ | H | H | 1 | $-CO-R_3$ | |
| 8.179 | F | Br | $-Cl$ | H | H | 1 | $-CO-R_3$ | |
| 8.180 | F | Br | $-OH$ | H | H | 1 | $-CO-R_3$ | |
| 8.181 | F | Br | $-OCH_3$ | H | H | 1 | $-CO-R_3$ | |
| 8.182 | F | Br | $-OC_2H_5$ | H | H | 1 | $-CO-R_3$ | |
| 8.183 | F | Br | $-OC_3H_7$ | H | H | 1 | $-CO-R_3$ | |
| 8.184 | F | Br | 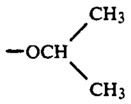 | H | H | 1 | $-CO-R_3$ | |

TABLE 8-continued

Compounds of formula I wherein W is $W_8$ and $Z_1$ is oxygen:

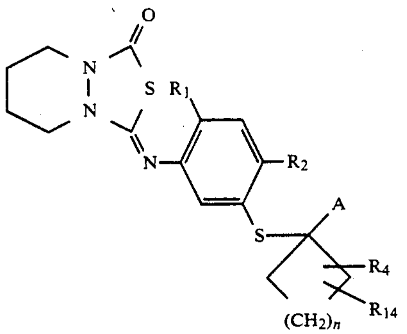

(I)

| Comp. No. | $R_1$ | $R_2$ | $R_3$ | $R_{14}$ | $R_4$ | n | A | m.p. [°C.] |
|---|---|---|---|---|---|---|---|---|
| 8.185 | F | Br | $-OC_4H_9$ | H | H | 1 | $-CO-R_3$ | |
| 8.186 | F | Br | $-OCH(CH_3)-CH_2-CH_3$ | H | H | 1 | $-CO-R_3$ | |
| 8.187 | F | Br | 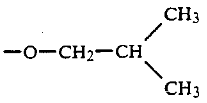 | H | H | 1 | $-CO-R_3$ | |
| 8.188 | F | Br | $-O-C_5H_{11}$ | H | H | 1 | $-CO-R_3$ | |
| 8.189 | F | Br | $-O-CH_2-CH_2-O-CH_3$ | H | H | 1 | $-CO-R_3$ | |
| 8.190 | F | Br | $-O-CH_2-CH_2-O-C_2H_5$ | H | H | 1 | $-CO-R_3$ | |
| 8.191 | F | Br | $-O-CH(CH_3)-CH_2-O-CH_3$ | H | H | 1 | $-CO-R_3$ | |
| 8.192 | F | Br | $-O-CH_2-CH_2-S-CH_3$ | H | H | 1 | $-CO-R_3$ | |
| 8.193 | F | Br | $-O-CH_2(CH_3)-S-CH_3$ | H | H | 1 | $-CO-R_3$ | |
| 8.194 | F | Br | $-O-CH-(CH_3)-S-C_2H_5$ | H | H | 1 | $-CO-R_3$ | |
| 8.195 | F | Br | $-O-CH(CH_3)-S-C_3H_7$ | H | H | 1 | $-CO-R_3$ | |
| 8.196 | F | Br | 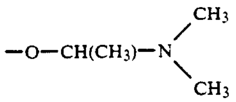 | H | H | 1 | $-CO-R_3$ | |
| 8.197 | F | Br | $-NH_2$ | H | H | 1 | $-CO-R_3$ | |
| 8.198 | F | Br | 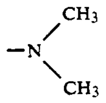 | H | H | 1 | $-CO-R_3$ | |
| 8.199 | F | Br | 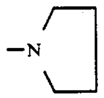 | H | H | 1 | $-CO-R_3$ | |
| 8.200 | F | Br | 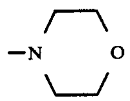 | H | H | 1 | $-CO-R_3$ | |
| 8.201 | F | Br | 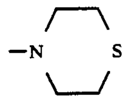 | H | H | 1 | $-CO-R_3$ | |
| 8.202 | F | Br | 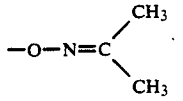 | H | H | 1 | $-CO-R_3$ | |
| 8.203 | F | Br | $-O-CH_2-CH_2-Cl$ | H | H | 1 | $-CO-R_3$ | |
| 8.204 | F | Br | $-O-CH_2-CN$ | H | H | 1 | $-CO-R_3$ | |
| 8.205 | F | Br | $-O-CH_2-CH=CH_2$ | H | H | 1 | $-CO-R_3$ | |
| 8.206 | F | Br | $-O-CH_2-C\equiv CH$ | H | H | 1 | $-CO-R_3$ | |

TABLE 8-continued

Compounds of formula I wherein W is $W_8$ and $Z_1$ is oxygen:

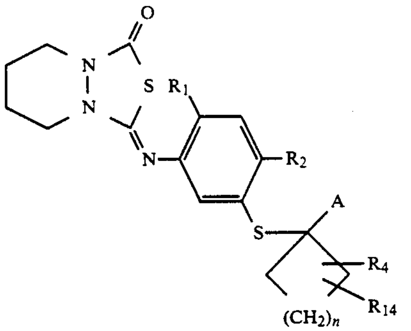

(I)

| Comp. No. | $R_1$ | $R_2$ | $R_3$ | $R_{14}$ | $R_4$ | n | A | m.p. [°C.] |
|---|---|---|---|---|---|---|---|---|
| 8.207 | F | Br | 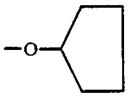 | H | H | 1 | —CO—$R_3$ | |
| 8.208 | F | Br | 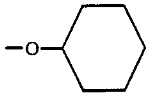 | H | H | 1 | —CO—$R_3$ | |
| 8.209 | F | Br | 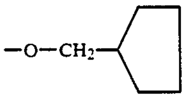 | H | H | 1 | —CO—$R_3$ | |
| 8.210 | F | Br | 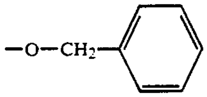 | H | H | 1 | —CO—$R_3$ | |
| 8.211 | F | Br | $-SCH_3$ | H | H | 1 | —CO—$R_3$ | |
| 8.212 | F | Br | $-S-CH_2-COOCH_3$ | H | H | 1 | —CO—$R_3$ | |
| 8.213 | F | Br | $-S-CH(CH_3)-COOCH_3$ | H | H | 1 | —CO—$R_3$ | |
| 8.214 | F | Br | $-O-CH_2-COOCH_3$ | H | H | 1 | —CO—$R_3$ | |
| 8.215 | F | Br | $-O-CH(CH_3)COOCH_3$ | H | H | 1 | —CO—$R_3$ | |
| 8.216 | F | CN | —Cl | H | H | 1 | —CO—$R_3$ | |
| 8.217 | F | CN | —OH | H | H | 1 | —CO—$R_3$ | |
| 8.218 | F | CN | $-OCH_3$ | H | H | 1 | —CO—$R_3$ | |
| 8.219 | H | Cl | —Cl | H | H | 1 | —CO—$R_3$ | |
| 8.220 | H | Cl | —OH | H | | 1 | —CO—$R_3$ | |
| 8.221 | H | Cl | $-OCH_3$ | H | H | 1 | —CO—$R_3$ | |
| 8.222 | H | Cl | $-OC_2H_5$ | H | H | 1 | —CO—$R_3$ | |
| 8.223 | H | Cl | $-O-CH(CH_3)_2$ | H | H | 1 | —CO—$R_3$ | |
| 8.224 | H | Cl | $-O-CH_2-COOCH_3$ | H | H | 1 | —CO—$R_3$ | |
| 8.225 | H | Cl | $-O-CH(CH_3)COOCH_3$ | H | H | 1 | —CO—$R_3$ | |
| 8.226 | H | Cl | $-S-CH_2-COOCH_3$ | H | H | 1 | —CO—$R_3$ | |
| 8.227 | H | Cl | $-S-CH(CH_3)COOCH_3$ | H | H | 1 | —CO—$R_3$ | |
| 8.228 | H | Cl | 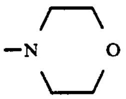 | H | H | 1 | —CO—$R_3$ | |
| 8.229 | F | Cl | Cl | H | H | 2 | —CO—$R_3$ | |
| 8.230 | F | Cl | OH | H | H | 2 | —CO—$R_3$ | |
| 8.231 | F | Cl | $OCH_3$ | H | H | 2 | —CO—$R_3$ | |
| 8.232 | F | Cl | $-OC_2H_5$ | H | H | 2 | —CO—$R_3$ | |

TABLE 8-continued

Compounds of formula I wherein W is $W_8$ and $Z_1$ is oxygen:

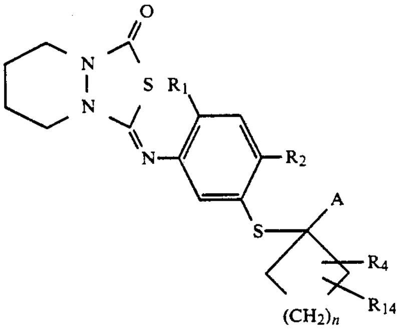

(I)

| Comp. No. | $R_1$ | $R_2$ | $R_3$ | $R_{14}$ | $R_4$ | n | A | m.p. [°C.] |
|---|---|---|---|---|---|---|---|---|
| 8.233 | F | Cl | 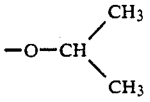 | H | H | 2 | $-CO-R_3$ | |
| 8.234 | F | Cl | $-O-CH_2-CH_2-O-CH_3$ | H | H | 2 | $-CO-R_3$ | |
| 8.235 | F | Cl | $-O-CH(CH_3)-CH_2-S-CH_3$ | H | H | 2 | $-CO-R_3$ | |
| 8.236 | F | Cl | $-O-CH_2-COOCH_3$ | H | H | 2 | $-CO-R_3$ | |
| 8.237 | F | Cl | $-S-CH_2-COOCH_3$ | H | H | 2 | $-CO-R_3$ | |
| 8.238 | F | Cl | $-CH_2-CH{=}CH_2$ | H | H | 2 | $-CO-R_3$ | |
| 8.239 | F | Cl | $-CH_2-C{\equiv}CH$ | H | H | 2 | $-CO-R_3$ | |
| 8.240 | F | Cl | Cl | H | H | 3 | $-CO-R_3$ | |
| 8.241 | F | Cl | OH | H | H | 3 | $-CO-R_3$ | |
| 8.242 | F | Cl | $OCH_3$ | H | H | 3 | $-CO-R_3$ | |
| 8.243 | F | Cl | $OC_2H_5$ | H | H | 3 | $-CO-R_3$ | |
| 8.244 | F | Cl | 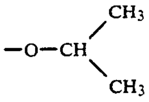 | H | H | 3 | $-CO-R_3$ | |
| 8.245 | F | Cl | $-O-CH_2-CH_2-O-CH$ | H | H | 3 | $-CO-R_3$ | |
| 8.246 | F | Cl | $-O-CH(CH_3)-CH_2-S-CH_3$ | H | H | 3 | $-CO-R_3$ | |
| 8.247 | F | Cl | $-O-CH_2-COOCH_3$ | H | H | 3 | $-CO-R_3$ | |
| 8.248 | F | Cl | $-S-CH_2-COOCH_3$ | H | H | 3 | $-CO-R_3$ | |
| 8.249 | F | Cl | $-O-CH_2-C{\equiv}CH$ | H | H | 3 | $-CO-R_3$ | |
| 8.250 | F | Cl | $-Cl$ | H | Cl | 0 | $-CO-R_3$ | |
| 8.251 | F | Cl | $-OH$ | H | Cl | 0 | $-CO-R_3$ | |
| 8.252 | F | Cl | $-OCH_3$ | H | Cl | 0 | $-CO-R_3$ | |
| 8.253 | F | Cl | $-OC_2H_5$ | H | Cl | 0 | $-CO-R_3$ | |
| 8.254 | F | Cl | 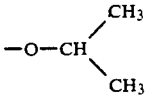 | H | Cl | 0 | $-CO-R_3$ | |
| 8.255 | F | Cl | $-O-CH_2-COOCH_3$ | H | Cl | 0 | $-CO-R_3$ | |
| 8.256 | F | Cl | $-S-CH_2-COOCH_3$ | H | Cl | 0 | $-CO-R_3$ | |
| 8.257 | F | Cl | $-OCH_3$ | H | Br | 0 | $-CO-R_3$ | |
| 8.258 | F | Cl | 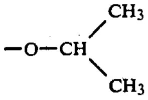 | H | Br | 0 | $-CO-R_3$ | |
| 8.259 | F | Cl | $-OCH_3$ | H | F | 0 | $-CO-R_3$ | |
| 8.260 | F | Cl | $-OCH_3$ | H | $CH_3$ | 0 | $-CO-R_3$ | |
| 8.261 | F | Cl | $-OC_2H_5$ | H | $CH_3$ | 0 | $-CO-R_3$ | |
| 8.262 | F | Cl | 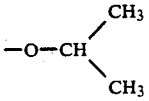 | H | $CH_3$ | 0 | $-CO-R_3$ | |
| 8.263 | F | Cl | $-O-CH_2-CH_2-O-CH_3$ | H | $CH_3$ | 0 | $-CO-R_3$ | |
| 8.264 | F | Cl | $-O-CH_2-COOCH_3$ | H | $CH_3$ | 0 | $-CO-R_3$ | |
| 8.265 | F | Cl | $-O-CH(CH_3)COOCH_3$ | H | $CH_3$ | 0 | $-CO-R_3$ | |
| 8.266 | F | Cl | $-S-CH_2-COOCH_3$ | H | $CH_3$ | 0 | $-CO-R_3$ | |

TABLE 8-continued

Compounds of formula I wherein W is $W_8$ and $Z_1$ is oxygen:

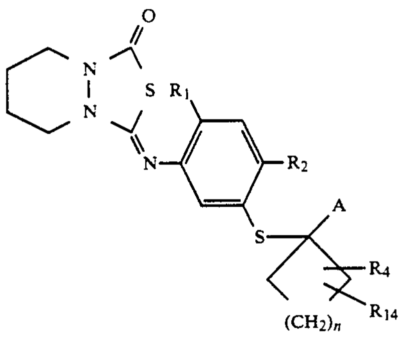

(I)

| Comp. No. | $R_1$ | $R_2$ | $R_3$ | $R_{14}$ | $R_4$ | n | A | m.p. [°C.] |
|---|---|---|---|---|---|---|---|---|
| 8.267 | F | Cl | $-OCH_3$ | H | $CF_3$ | 0 | $-CO-R_3$ | |
| 8.268 | F | Cl | $-OC_2H_5$ | H | $CF_3$ | 0 | $-CO-R_3$ | |
| 8.269 | F | Cl | 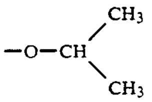 | H | $CF_3$ | 0 | $-CO-R_3$ | |
| 8.270 | F | Cl | $-O-CH_2-COOCH_3$ | H | $CF_3$ | 0 | $-CO-R_3$ | |
| 8.271 | F | Cl | $-S-CH_2-COOCH_3$ | H | $CF_3$ | 0 | $-CO-R_3$ | |
| 8.272 | F | Cl | — | H | H | 0 | $-CN$ | |
| 8.273 | F | Cl | — | H | H | 1 | $-CN$ | |
| 8.274 | F | Cl | — | H | H | 2 | $-CN$ | |
| 8.275 | F | Cl | — | H | H | 3 | $-CN$ | |
| 8.276 | F | Cl | — | H | H | 4 | $-CN$ | |
| 8.277 | F | Cl | — | 2-Cl | 2-Cl | 0 | $-CN$ | 152-153 |
| 8.278 | F | Cl | 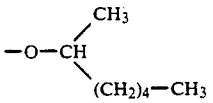 | H | H | 0 | $-CO-R_3$ | 120-121 |
| 8.279 | F | Cl | $-O-C_2H_5$ | H | H | 0 | $-CO-R_3$ | 94-96 |
| 8.280 | F | Cl | $-O-C_2H_5$ | H | H | 0 | $-CO-R_3$ | $\eta_D^{20}$ 1.6011 |
| 8.281 | F | Cl | $-O-CH_2CF_3$ | H | H | 0 | $-CO-R_3$ | 134-136 |
| 8.282 | F | Cl | 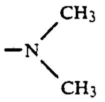 | H | H | 0 | $-CO-R_3$ | 98-100 |

TABLE 9

Compounds of formula I wherein W is $W_9$, $Z_2$ is oxygen and $R_{14}$ is hydrogen:

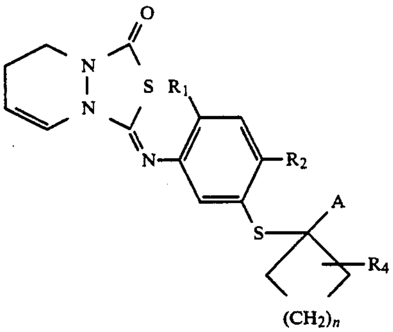

(I)

| Comp. No. | $R_1$ | $R_2$ | $R_3$ | $R_4$ | n | A | m.p. [°C.] |
|---|---|---|---|---|---|---|---|
| 9.001 | F | Cl | $-Cl$ | H | 0 | $-CO-R_3$ | |
| 9.002 | F | Cl | $-OH$ | H | 0 | $-CO-R_3$ | |
| 9.003 | F | Cl | $-OCH_3$ | H | 0 | $-CO-R_3$ | |
| 9.004 | F | Cl | $-OC_2H_5$ | H | 0 | $-CO-R_3$ | |
| 9.005 | F | Cl | $-OC_3H_7$ | H | 0 | $-CO-R_3$ | |

TABLE 9-continued

Compounds of formula I wherein W is $W_9$, $Z_2$ is oxygen and $R_{14}$ is hydrogen:

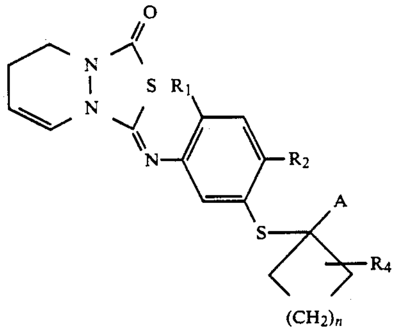

(I)

| Comp. No. | $R_1$ | $R_2$ | $R_3$ | $R_4$ | n | A | m.p. [°C.] |
|---|---|---|---|---|---|---|---|
| 9.006 | F | Cl | 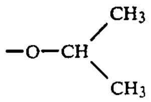 | H | 0 | $-CO-R_3$ | |
| 9.007 | F | Cl | $-OC_4H_9$ | H | 0 | $-CO-R_3$ | |
| 9.008 | F | Cl | $-O-CH(CH_3)-C_2H_5$ | H | 0 | $-CO-R_3$ | |
| 9.009 | F | Cl | 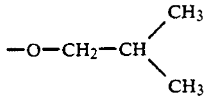 | H | 0 | $-CO-R_3$ | |
| 9.010 | F | Cl | $-OC_5H_{11}$ | H | 0 | $-CO-R_3$ | |
| 9.011 | F | Cl | $-O-CH_2-CH_2-O-CH_3$ | H | 0 | $-CO-R_3$ | |
| 9.012 | F | Cl | $-O-CH_2-CH_2-O-C_2H_5$ | H | 0 | $-CO-R_3$ | |
| 9.013 | F | Cl | $-O-CH-(CH_3)-CH_2-O-CH_3$ | H | 0 | $-CO-R_3$ | |
| 9.014 | F | Cl | $-O-CH_2-CH_2-S-CH_3$ | H | 0 | $-CO-R_3$ | |
| 9.015 | F | Cl | $-O-CH(CH_3)-CH_2-S-CH_3$ | H | 0 | $-CO-R_3$ | |
| 9.016 | F | Cl | $-O-CH(CH_3)-CH_2-S-C_2H_5$ | H | 0 | $-CO-R_3$ | |
| 9.017 | F | Cl | $-O-CH(CH_3)-CH_2-S-C_3H_7$ | H | 0 | $-CO-R_3$ | |
| 9.018 | F | Cl | 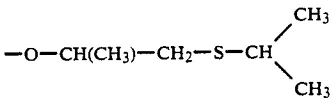 | H | 0 | $-CO-R_3$ | |
| 9.019 | F | Cl | $-O-CH(CH_3)-CH_2-S-C_4H_9$ | H | 0 | $-CO-R_3$ | |
| 9.020 | F | Cl | $-O-CH(CH_3)-CH_2-S-C_5H_{11}$ | H | 0 | $-CO-R_3$ | |
| 9.021 | F | Cl | 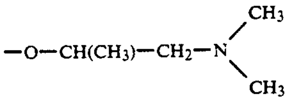 | H | 0 | $-CO-R_3$ | |
| 9.022 | F | Cl | 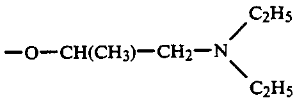 | H | 0 | $-CO-R_3$ | |
| 9.023 | F | Cl | $-NH_2$ | H | 0 | $-CO-R_3$ | |
| 9.024 | F | Cl | 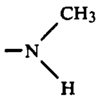 | H | 0 | $-CO-R_3$ | |
| 9.025 | F | Cl | 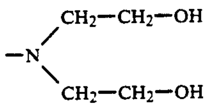 | H | 0 | $-CO-R_3$ | |
| 9.026 | F | Cl | $-NH-CH_2-CH=CH_2$ | H | 0 | $-CO-R_3$ | |
| 9.027 | F | Cl | $-N-(CH_2-CH=CH_2)_2$ | H | 0 | $-CO-R_3$ | |

TABLE 9-continued

Compounds of formula I wherein W is $W_9$, $Z_2$ is oxygen and $R_{14}$ is hydrogen:

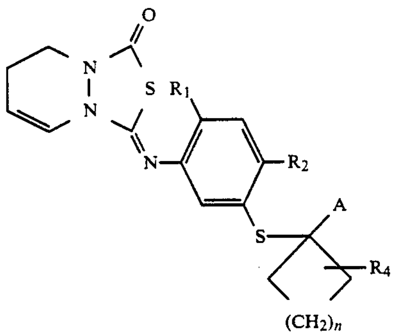

(I)

| Comp. No. | $R_1$ | $R_2$ | $R_3$ | $R_4$ | n | A | m.p. [°C.] |
|---|---|---|---|---|---|---|---|
| 9.028 | F | Cl | 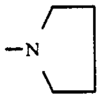 | H | 0 | $-CO-R_3$ | |
| 9.029 | F | Cl | 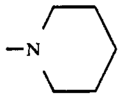 | H | 0 | $-CO-R_3$ | |
| 9.030 | F | Cl | 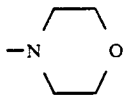 | H | 0 | $-CO-R_3$ | |
| 9.031 | F | Cl | 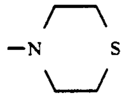 | H | 0 | $-CO-R_3$ | |
| 9.032 | F | Cl | 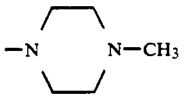 | H | 0 | $-CO-R_3$ | |
| 9.033 | F | Cl | $-O-N=C(CH_3)-CH_3$ | H | 0 | $-CO-R_3$ | |
| 9.034 | F | Cl | $-O-CH_2-CH_2-Cl$ | H | 0 | $-CO-R_3$ | |
| 9.035 | F | Cl | $-O-CH_2-CN$ | H | 0 | $-CO-R_3$ | |
| 9.036 | F | Cl | $-O-CH(CH_3)-CN$ | H | 0 | $-CO-R_3$ | |
| 9.037 | F | Cl | $-O-CH_2-CH=CH_2$ | H | 0 | $-CO-R_3$ | |
| 9.038 | F | Cl | $-O-CH_2-CH=CHCl$ | H | 0 | $-CO-R_3$ | |
| 9.039 | F | Cl | $-O-CH_2-C(Cl)=CH_2$ | H | 0 | $-CO-R_3$ | |
| 9.040 | F | Cl | $-O-CH_2=C\equiv CH$ | H | 0 | $-CO-R_3$ | |
| 9.041 | F | Cl | $-O-CH(CH_3)-C\equiv CH$ | H | 0 | $-CO-R_3$ | |
| 9.042 | F | Cl | 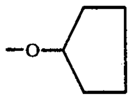 | H | 0 | $-CO-R_3$ | |

TABLE 9-continued

Compounds of formula I wherein W is $W_9$, $Z_2$ is oxygen and $R_{14}$ is hydrogen:

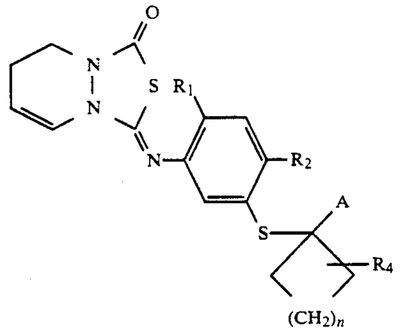

(I)

| Comp. No. | $R_1$ | $R_2$ | $R_3$ | $R_4$ | n | A | m.p. [°C.] |
|---|---|---|---|---|---|---|---|
| 9.043 | F | Cl | 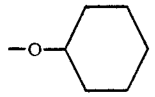 | H | 0 | $-CO-R_3$ | |
| 9.044 | F | Cl | 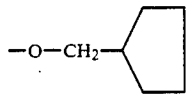 | H | 0 | $-CO-R_3$ | |
| 9.045 | F | Cl | 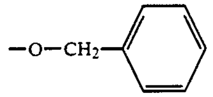 | H | 0 | $-CO-R_3$ | |
| 9.046 | F | Cl | 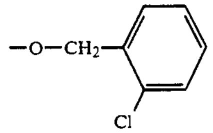 | H | 0 | $-CO-R_3$ | |
| 9.047 | F | Cl | 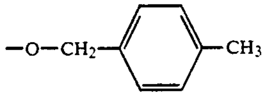 | H | 0 | $-CO-R_3$ | |
| 9.048 | F | Cl | $-S-CH_3$ | H | 0 | $-CO-R_3$ | |
| 9.049 | F | Cl | $-S-C_2H_5$ | H | 0 | $-CO-R_3$ | |
| 9.050 | F | Cl | $-S-C_3H_7$ | H | 0 | $-CO-R_3$ | |
| 9.051 | F | Cl | $-S-CH_2-CH=CH_2$ | H | 0 | $-CO-R_3$ | |
| 9.052 | F | Cl | $-S-CH_2-COOCH_3$ | H | 0 | $-CO-R_3$ | |
| 9.053 | F | Cl | $-S-CH_2-COOC_2H_5$ | H | 0 | $-CO-R_3$ | |
| 9.054 | F | Cl | $-S-CH_2-COOC_5H_{11}$ | H | 0 | $-CO-R_3$ | |
| 9.055 | F | Cl | $-S-CH(CH_3)-COOCH_3$ | H | 0 | $-CO-R_3$ | |
| 9.056 | F | Cl | $-S-(CH_3)-COOC_2H_5$ | H | 0 | $-CO-R_3$ | |
| 9.057 | F | Cl | $-S-CH(CH_3)-COOC_3H_7$ | H | 0 | $-CO-R_3$ | |
| 9.058 | F | Cl | $-S-CH_2-CH_2-COOCH_3$ | H | 0 | $-CO-R_3$ | |
| 9.059 | F | Cl | $-S-CH_2-COOCH_2-CH_2-O-CH_3$ | H | 0 | $-CO-R_3$ | |
| 9.060 | F | Cl | $-O-CH_2-COOCH_3$ | H | 0 | $-CO-R_3$ | |
| 9.061 | F | Cl | $-O-CH(CH_3)-COOCH_3$ | H | 0 | $-CO-R_3$ | |
| 9.062 | F | Cl | $-O-CH_2-COOC_5H_{11}$ | H | 0 | $-CO-R_3$ | |
| 9.063 | F | Cl | $-O-CH_2-CH_3-Si(CH_3)_3$ | H | 0 | $-CO-R_3$ | |
| 9.064 | F | Cl | $-ONa$ | H | 0 | $-CO-R_3$ | |
| 9.065 | F | Br | $-Cl$ | H | 0 | $-CO-R_3$ | |
| 9.066 | F | Br | $-OH$ | H | 0 | $-CO-R_3$ | |
| 9.067 | F | Br | $-OCH_3$ | H | 0 | $-CO-R_3$ | |
| 9.068 | F | Br | $-OC_2H_5$ | H | 0 | $-CO-R_3$ | |
| 9.069 | F | Br | $-OC_3H_7$ | H | 0 | $-CO-R_3$ | |
| 9.070 | F | Br | 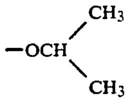 | H | 0 | $-CO-R_3$ | |

TABLE 9-continued

Compounds of formula I wherein W is $W_9$, $Z_2$ is oxygen and $R_{14}$ is hydrogen:

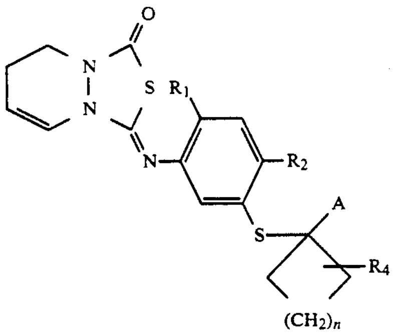

(I)

| Comp. No. | $R_1$ | $R_2$ | $R_3$ | $R_4$ | n | A | m.p. [°C.] |
|---|---|---|---|---|---|---|---|
| 9.071 | F | Br | $-OC_4H_9$ | H | 0 | $-CO-R_3$ | |
| 9.072 | F | Br | $-OCH(CH_3)-CH_2-CH_3$ | H | 0 | $-CO-R_3$ | |
| 9.073 | F | Br | 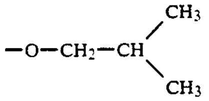 | H | 0 | $-CO-R_3$ | |
| 9.074 | F | Br | $-O-C_5H_{11}$ | H | 0 | $-CO-R_3$ | |
| 9.075 | F | Br | $-O-CH_2-CH_2-O-CH_3$ | H | 0 | $-CO-R_3$ | |
| 9.076 | F | Br | $-O-CH_2-CH_2-O-C_2H_5$ | H | 0 | $-CO-R_3$ | |
| 9.077 | F | Br | $-O-CH(CH_3)-CH_2-O-CH_3$ | H | 0 | $-CO-R_3$ | |
| 9.078 | F | Br | $-O-CH_2-CH_2-S-CH_3$ | H | 0 | $-CO-R_3$ | |
| 9.079 | F | Br | $-O-CH_2(CH_3)-S-CH_3$ | H | 0 | $-CO-R_3$ | |
| 9.080 | F | Br | $-O-CH-(CH_3)-S-C_2H_5$ | H | 0 | $-CO-R_3$ | |
| 9.081 | F | Br | $-O-CH(CH_3)-S-C_3H_7$ | H | 0 | $-CO-R_3$ | |
| 9.082 | F | Br | 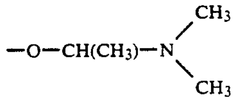 | H | 0 | $-CO-R_3$ | |
| 9.083 | F | Br | $-NH_2$ | H | 0 | $-CO-R_3$ | |
| 9.084 | F | Br | 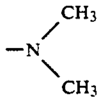 | H | 0 | $-CO-R_3$ | |
| 9.085 | F | Br | 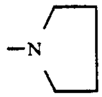 | H | 0 | $-CO-R_3$ | |
| 9.086 | F | Br | 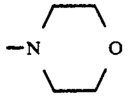 | H | 0 | $-CO-R_3$ | |
| 9.087 | F | Br | 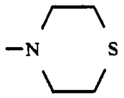 | H | 0 | $-CO-R_3$ | |
| 9.088 | F | Br | 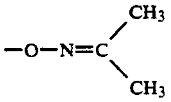 | H | 0 | $-CO-R_3$ | |
| 9.089 | F | Br | $-O-CH_2-CH_2-Cl$ | H | 0 | $-CO-R_3$ | |
| 9.090 | F | Br | $-O-CH_2-CN$ | H | 0 | $-CO-R_3$ | |
| 9.091 | F | Br | $-O-CH_2-CH=CH_2$ | H | 0 | $-CO-R_3$ | |
| 9.092 | F | Br | $-O-CH_2-C\equiv CH$ | H | 0 | $-CO-R_3$ | |

TABLE 9-continued

Compounds of formula I wherein W is $W_9$, $Z_2$ is oxygen and $R_{14}$ is hydrogen:

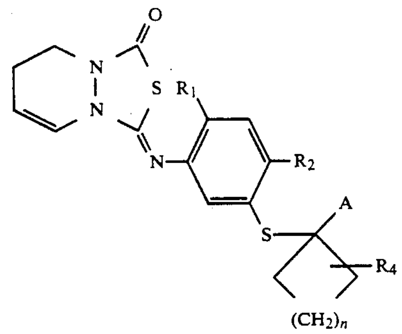

(I)

| Comp. No. | $R_1$ | $R_2$ | $R_3$ | $R_4$ | n | A | m.p. [°C.] |
|---|---|---|---|---|---|---|---|
| 9.093 | F | Br | 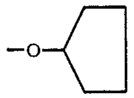 | H | 0 | $-CO-R_3$ | |
| 9.094 | F | Br | 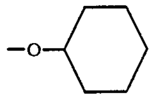 | H | 0 | $-CO-R_3$ | |
| 9.095 | F | Br | 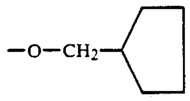 | H | 0 | $-CO-R_3$ | |
| 9.096 | F | Br | 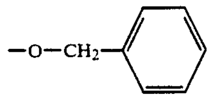 | H | 0 | $-CO-R_3$ | |
| 9.097 | F | Br | $-SCH_3$ | H | 0 | $-CO-R_3$ | |
| 9.098 | F | Br | $-S-CH_2-COOCH_3$ | H | 0 | $-CO-R_3$ | |
| 9.099 | F | Br | $-S-CH(CH_3)-COOCH_3$ | H | 0 | $-CO-R_3$ | |
| 9.100 | F | Br | $-O-CH_2-COOCH_3$ | H | 0 | $-CO-R_3$ | |
| 9.101 | F | Br | $-O-CH(CH_3)COOCH_3$ | H | 0 | $-CO-R_3$ | |
| 9.102 | F | CN | $-Cl$ | H | 0 | $-CO-R_3$ | |
| 9.103 | F | CN | $-OH$ | H | 0 | $-CO-R_3$ | |
| 9.104 | F | CN | $-OCH_3$ | H | 0 | $-CO-R_3$ | |
| 9.105 | H | Cl | $-Cl$ | H | 0 | $-CO-R_3$ | |
| 9.106 | H | Cl | $-OH$ | H | 0 | $-CO-R_3$ | |
| 9.107 | H | Cl | $-OCH_3$ | H | 0 | $-CO-R_3$ | |
| 9.108 | H | Cl | $-OC_2H_5$ | H | 0 | $-CO-R_3$ | |
| 9.109 | H | Cl | 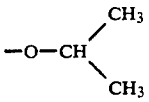 | H | 0 | $-CO-R_3$ | |
| 9.110 | H | Cl | $-O-CH_2-COOCH_3$ | H | 0 | $-CO-R_3$ | |
| 9.111 | H | Cl | $-O-CH(CH_3)COOCH_3$ | H | 0 | $-CO-R_3$ | |
| 9.112 | H | Cl | $-S-CH_2-COOCH_3$ | H | 0 | $-CO-R_3$ | |
| 9.113 | H | Cl | $-S-CH(CH_3)COOCH_3$ | H | 0 | $-CO-R_3$ | |
| 9.114 | H | Cl | 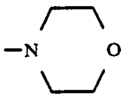 | H | 0 | $-CO-R_3$ | |
| 9.115 | F | Cl | $-Cl$ | H | 1 | $-CO-R_3$ | |
| 9.116 | F | Cl | $-OH$ | H | 1 | $-CO-R_3$ | |
| 9.117 | F | Cl | $-OCH_3$ | H | 1 | $-CO-R_3$ | |
| 9.118 | F | Cl | $-OC_2H_5$ | H | 1 | $-CO-R_3$ | |
| 9.119 | F | Cl | $-OC_3H_7$ | H | 1 | $-CO-R_3$ | |

TABLE 9-continued

Compounds of formula I wherein W is $W_9$, $Z_2$ is oxygen and $R_{14}$ is hydrogen:

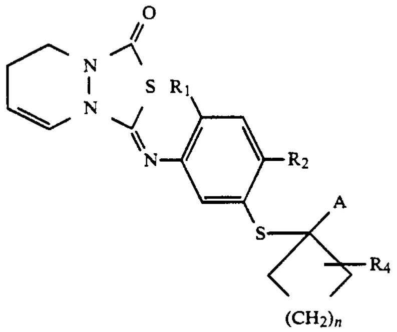

(I)

| Comp. No. | $R_1$ | $R_2$ | $R_3$ | $R_4$ | n | A | m.p. [°C.] |
|---|---|---|---|---|---|---|---|
| 9.120 | F | Cl | 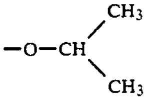 | H | 1 | $-CO-R_3$ | |
| 9.121 | F | Cl | $-OC_4H_9$ | H | 1 | $-CO-R_3$ | |
| 9.122 | F | Cl | $-O-CH(CH_3)-C_2H_5$ | H | 1 | $-CO-R_3$ | |
| 9.123 | F | Cl | 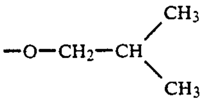 | H | 1 | $-CO-R_3$ | |
| 9.124 | F | Cl | $-OC_5H_{11}$ | H | 1 | $-CO-R_3$ | |
| 9.125 | F | Cl | $-O-CH_2-CH_2-O-CH_3$ | H | 1 | $-CO-R_3$ | |
| 9.126 | F | Cl | $-O-CH_2-CH_2-O-C_2H_5$ | H | 1 | $-CO-R_3$ | |
| 9.127 | F | Cl | $-O-CH-(CH_3)-CH_2-O-CH_3$ | H | 1 | $-CO-R_3$ | |
| 9.128 | F | Cl | $-O-CH_2-CH_2-S-CH_3$ | H | 1 | $-CO-R_3$ | |
| 9.129 | F | Cl | $-O-CH(CH_3)-CH_2-S-CH_3$ | H | 1 | $-CO-R_3$ | |
| 9.130 | F | Cl | $-O-CH(CH_3)-CH_2-S-C_2H_5$ | H | 1 | $-CO-R_3$ | |
| 9.131 | F | Cl | $-O-CH(CH_3)-CH_2-S-C_3H_7$ | H | 1 | $-CO-R_3$ | |
| 9.132 | F | Cl | 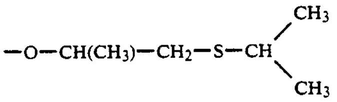 | H | 1 | $-CO-R_3$ | |
| 9.133 | F | Cl | $-O-CH(CH_3)-CH_2-S-C_4H_9$ | H | 1 | $-CO-R_3$ | |
| 9.134 | F | Cl | $-O-CH(CH_3)-CH_2-S-C_5H_{11}$ | H | 1 | $-CO-R_3$ | |
| 9.135 | F | Cl | 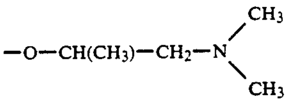 | H | 1 | $-CO-R_3$ | |
| 9.136 | F | Cl | 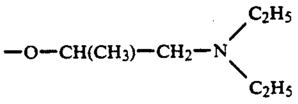 | H | 1 | $-CO-R_3$ | |
| 9.137 | F | Cl | $-NH_2$ | H | 1 | $-CO-R_3$ | |
| 9.138 | F | Cl | 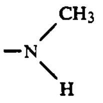 | H | 1 | $-CO-R_3$ | |
| 9.139 | F | Cl | 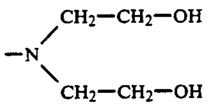 | H | 1 | $-CO-R_3$ | |
| 9.140 | F | Cl | $-NH-CH_2-CH=CH_2$ | H | 1 | $-CO-R_3$ | |
| 9.141 | F | Cl | $-N-(CH_2-CH=CH_2)_2$ | H | 1 | $-CO-R_3$ | |

TABLE 9-continued
Compounds of formula I wherein W is $W_9$, $Z_2$ is oxygen and $R_{14}$ is hydrogen:
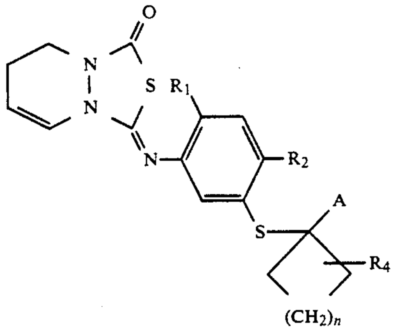
(I)
| Comp. No. | $R_1$ | $R_2$ | $R_3$ | $R_4$ | n | A | m.p. [°C.] |
|---|---|---|---|---|---|---|---|
| 9.142 | F | Cl | 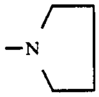 | H | 1 | $-CO-R_3$ | |
| 9.143 | F | Cl | 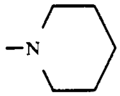 | H | 1 | $-CO-R_3$ | |
| 9.144 | F | Cl | 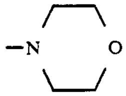 | H | 1 | $-CO-R_3$ | |
| 9.145 | F | Cl | 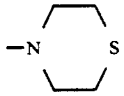 | H | 1 | $-CO-R_3$ | |
| 9.146 | F | Cl | 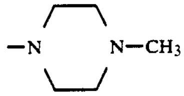 | H | 1 | $-CO-R_3$ | |
| 9.147 | F | Cl | 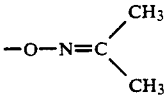 | H | 1 | $-CO-R_3$ | |
| 9.148 | F | Cl | $-O-CH_2-CH_2-Cl$ | H | 1 | $-CO-R_3$ | |
| 9.149 | F | Cl | $-O-CH_2-CN$ | H | 1 | $-CO-R_3$ | |
| 9.150 | F | Cl | 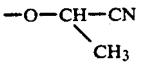 | H | 1 | $-CO-R_3$ | |
| 9.151 | F | Cl | $-O-CH_2-CH=CH_2$ | H | 1 | $-CO-R_3$ | |
| 9.152 | F | Cl | $-O-CH_2-CH=CHCl$ | H | 1 | $-CO-R_3$ | |
| 9.153 | F | Cl | 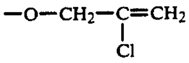 | H | 1 | $-CO-R_3$ | |
| 9.154 | F | Cl | $-O-CH_2=C\equiv CH$ | H | 1 | $-CO-R_3$ | |
| 9.155 | F | Cl | 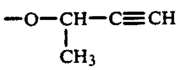 | H | 1 | $-CO-R_3$ | |
| 9.156 | F | Cl | 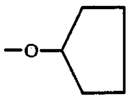 | H | 1 | $-CO-R_3$ | |

TABLE 9-continued

Compounds of formula I wherein W is $W_9$, $Z_2$ is oxygen and $R_{14}$ is hydrogen:

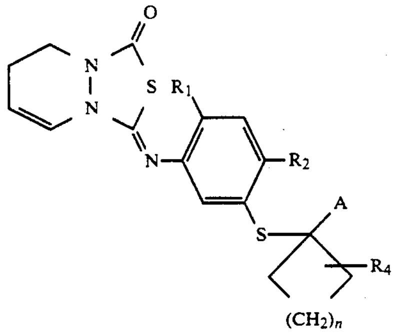

(I)

| Comp. No. | $R_1$ | $R_2$ | $R_3$ | $R_4$ | n | A | m.p. [°C.] |
|---|---|---|---|---|---|---|---|
| 9.157 | F | Cl | 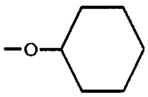 | H | 1 | $-CO-R_3$ | |
| 9.158 | F | Cl | 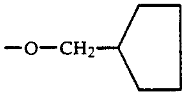 | H | 1 | $-CO-R_3$ | |
| 9.159 | F | Cl | 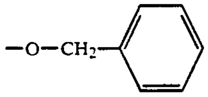 | H | 1 | $-CO-R_3$ | |
| 9.160 | F | Cl | 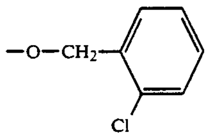 | H | 1 | $-CO-R_3$ | |
| 9.161 | F | Cl | 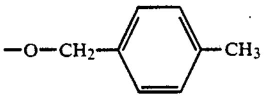 | H | 1 | $-CO-R_3$ | |
| 9.162 | F | Cl | $-S-CH_3$ | H | 1 | $-CO-R_3$ | |
| 9.163 | F | Cl | $-S-C_2H_5$ | H | 1 | $-CO-R_3$ | |
| 9.164 | F | Cl | $-S-C_3H_7$ | H | 1 | $-CO-R_3$ | |
| 9.165 | F | Cl | $-S-CH_2-CH{=}CH_2$ | H | 1 | $-CO-R_3$ | |
| 9.166 | F | Cl | $-S-CH_2-COOCH_3$ | H | 1 | $-CO-R_3$ | |
| 9.167 | F | Cl | $-S-CH_2-COOC_2H_5$ | H | 1 | $-CO-R_3$ | |
| 9.168 | F | Cl | $-S-CH_2-COOC_5H_{11}$ | H | 1 | $-CO-R_3$ | |
| 9.169 | F | Cl | $-S-CH(CH_3)-COOCH_3$ | H | 1 | $-CO-R_3$ | |
| 9.170 | F | Cl | $-S-(CH_3)-COOC_2H_5$ | H | 1 | $-CO-R_3$ | |
| 9.171 | F | Cl | $-S-CH(CH_3)-COOC_3H_7$ | H | 1 | $-CO-R_3$ | |
| 9.172 | F | Cl | $-S-CH_2-CH_2-COOCH_3$ | H | 1 | $-CO-R_3$ | |
| 9.173 | F | Cl | $-S-CH_2-COOCH_2-CH_2-O-CH_3$ | H | 1 | $-CO-R_3$ | |
| 9.174 | F | Cl | $-O-CH_2-COOCH_3$ | H | 1 | $-CO-R_3$ | |
| 9.175 | F | Cl | $-O-CH(CH_3)-COOCH_3$ | H | 1 | $-CO-R_3$ | |
| 9.176 | F | Cl | $-O-CH_2-COOC_5H_{11}$ | H | 1 | $-CO-R_3$ | |
| 9.177 | F | Cl | $-O-CH_2-CH_3-Si(CH_3)_3$ | H | 1 | $-CO-R_3$ | |
| 9.178 | F | Cl | $-ONa$ | H | 1 | $-CO-R_3$ | |
| 9.179 | F | Br | $-Cl$ | H | 1 | $-CO-R_3$ | |
| 9.180 | F | Br | $-OH$ | H | 1 | $-CO-R_3$ | |
| 9.181 | F | Br | $-OCH_3$ | H | 1 | $-CO-R_3$ | |
| 9.182 | F | Br | $-OC_2H_5$ | H | 1 | $-CO-R_3$ | |
| 9.183 | F | Br | $-OC_3H_7$ | H | 1 | $-CO-R_3$ | |
| 9.184 | F | Br | 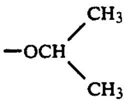 | H | 1 | $-CO-R_3$ | |

TABLE 9-continued

Compounds of formula I wherein W is $W_9$, $Z_2$ is oxygen and $R_{14}$ is hydrogen:

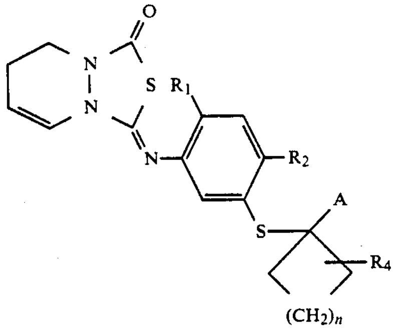

(I)

| Comp. No. | $R_1$ | $R_2$ | $R_3$ | $R_4$ | n | A | m.p. [°C.] |
|---|---|---|---|---|---|---|---|
| 9.185 | F | Br | $-OC_4H_9$ | H | 1 | $-CO-R_3$ | |
| 9.186 | F | Br | $-OCH(CH_3)-CH_2-CH_3$ | H | 1 | $-CO-R_3$ | |
| 9.187 | F | Br | 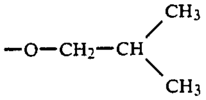 | H | 1 | $-CO-R_3$ | |
| 9.188 | F | Br | $-O-C_5H_{11}$ | H | 1 | $-CO-R_3$ | |
| 9.189 | F | Br | $-O-CH_2-CH_2-O-CH_3$ | H | 1 | $-CO-R_3$ | |
| 9.190 | F | Br | $-O-CH_2-CH_2-O-C_2H_5$ | H | 1 | $-CO-R_3$ | |
| 9.191 | F | Br | $-O-CH(CH_3)-CH_2-O-CH_3$ | H | 1 | $-CO-R_3$ | |
| 9.192 | F | Br | $-O-CH_2-CH_2-S-CH_3$ | H | 1 | $-CO-R_3$ | |
| 9.193 | F | Br | $-O-CH_2(CH_3)-S-CH_3$ | H | 1 | $-CO-R_3$ | |
| 9.194 | F | Br | $-O-CH-(CH_3)-S-C_2H_5$ | H | 1 | $-CO-R_3$ | |
| 9.195 | F | Br | $-O-CH(CH_3)-S-C_3H_7$ | H | 1 | $-CO-R_3$ | |
| 9.196 | F | Br | 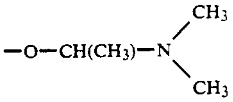 | H | 1 | $-CO-R_3$ | |
| 9.197 | F | Br | $-NH_2$ | H | 1 | $-CO-R_3$ | |
| 9.198 | F | Br | 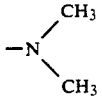 | H | 1 | $-CO-R_3$ | |
| 9.199 | F | Br | 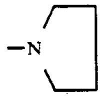 | H | 1 | $-CO-R_3$ | |
| 9.200 | F | Br | 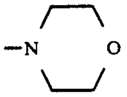 | H | 1 | $-CO-R_3$ | |
| 9.201 | F | Br | 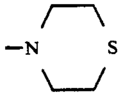 | H | 1 | $-CO-R_3$ | |
| 9.202 | F | Br | 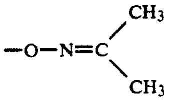 | H | 1 | $-CO-R_3$ | |
| 9.203 | F | Br | $-O-CH_2-CH_2-Cl$ | H | 1 | $-CO-R_3$ | |
| 9.204 | F | Br | $-O-CH_2-CN$ | H | 1 | $-CO-R_3$ | |
| 9.205 | F | Br | $-O-CH_2-CH=CH_2$ | H | 1 | $-CO-R_3$ | |
| 9.206 | F | Br | $-O-CH_2-C\equiv CH$ | H | 1 | $-CO-R_3$ | |

TABLE 9-continued

Compounds of formula I wherein W is $W_9$, $Z_2$ is oxygen and $R_{14}$ is hydrogen:

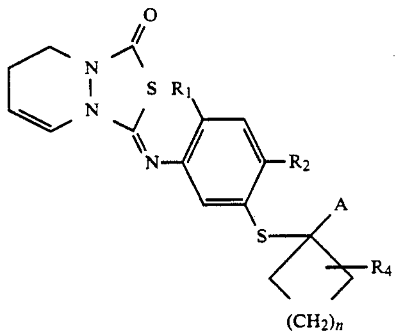

(I)

| Comp. No. | $R_1$ | $R_2$ | $R_3$ | $R_4$ | n | A | m.p. [°C.] |
|---|---|---|---|---|---|---|---|
| 9.207 | F | Br | 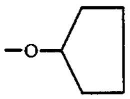 | H | 1 | $-CO-R_3$ | |
| 9.208 | F | Br | 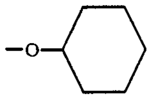 | H | 1 | $-CO-R_3$ | |
| 9.209 | F | Br | 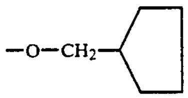 | H | 1 | $-CO-R_3$ | |
| 9.210 | F | Br | 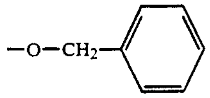 | H | 1 | $-CO-R_3$ | |
| 9.211 | F | Br | $-SCH_3$ | H | 1 | $-CO-R_3$ | |
| 9.212 | F | Br | $-S-CH_2-COOCH_3$ | H | 1 | $-CO-R_3$ | |
| 9.213 | F | Br | $-S-CH(CH_3)-COOCH_3$ | H | 1 | $-CO-R_3$ | |
| 9.214 | F | Br | $-O-CH_2-COOCH_3$ | H | 1 | $-CO-R_3$ | |
| 9.215 | F | Br | $-O-CH(CH_3)COOCH_3$ | H | 1 | $-CO-R_3$ | |
| 9.216 | F | CN | $-Cl$ | H | 1 | $-CO-R_3$ | |
| 9.217 | F | CN | $-OH$ | H | 1 | $-CO-R_3$ | |
| 9.218 | F | CN | $-OCH_3$ | H | 1 | $-CO-R_3$ | |
| 9.219 | H | Cl | $-Cl$ | H | 1 | $-CO-R_3$ | |
| 9.220 | H | Cl | $-OH$ | H | 1 | $-CO-R_3$ | |
| 9.221 | H | Cl | $-OCH_3$ | H | 1 | $-CO-R_3$ | |
| 9.222 | H | Cl | $-OC_2H_5$ | H | 1 | $-CO-R_3$ | |
| 9.223 | H | Cl | 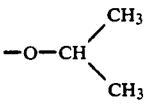 | H | 1 | $-CO-R_3$ | |
| 9.224 | H | Cl | $-O-CH_2-COOCH_3$ | H | 1 | $-CO-R_3$ | |
| 9.225 | H | Cl | $-O-CH(CH_3)COOCH_3$ | H | 1 | $-CO-R_3$ | |
| 9.226 | H | Cl | $-S-CH_2-COOCH_3$ | H | 1 | $-CO-R_3$ | |
| 9.227 | H | Cl | $-S-CH(CH_3)COOCH_3$ | H | 1 | $-CO-R_3$ | |
| 9.228 | H | Cl | 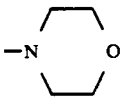 | H | 1 | $-CO-R_3$ | |
| 9.229 | F | Cl | Cl | H | 2 | $-CO-R_3$ | |
| 9.230 | F | Cl | OH | H | 2 | $-CO-R_3$ | |
| 9.231 | F | Cl | $OCH_3$ | H | 2 | $-CO-R_3$ | |
| 9.232 | F | Cl | $-OC_2H_5$ | H | 2 | $-CO-R_3$ | |

TABLE 9-continued

Compounds of formula I wherein W is $W_9$, $Z_2$ is oxygen and $R_{14}$ is hydrogen:

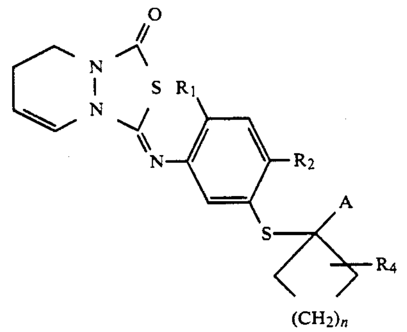

(I)

| Comp. No. | $R_1$ | $R_2$ | $R_3$ | $R_4$ | n | A | m.p. [°C.] |
|---|---|---|---|---|---|---|---|
| 9.233 | F | Cl | 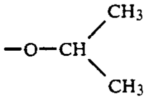 | H | 2 | $-CO-R_3$ | |
| 9.234 | F | Cl | $-O-CH_2-CH_2-O-CH_3$ | H | 2 | $-CO-R_3$ | |
| 9.235 | F | Cl | $-O-CH(CH_3)-CH_2-S-CH_3$ | H | 2 | $-CO-R_3$ | |
| 9.236 | F | Cl | $-O-CH_2-COOCH_3$ | H | 2 | $-CO-R_3$ | |
| 9.237 | F | Cl | $-S-CH_2-COOCH_3$ | H | 2 | $-CO-R_3$ | |
| 9.238 | F | Cl | $-CH_2-CH=CH_2$ | H | 2 | $-CO-R_3$ | |
| 9.239 | F | Cl | $-CH_2-C\equiv CH$ | H | 2 | $-CO-R_3$ | |
| 9.240 | F | Cl | Cl | H | 3 | $-CO-R_3$ | |
| 9.241 | F | Cl | OH | H | 3 | $-CO-R_3$ | |
| 9.242 | F | Cl | $OCH_3$ | H | 3 | $-CO-R_3$ | |
| 9.243 | F | Cl | $OC_2H_5$ | H | 3 | $-CO-R_3$ | |
| 9.244 | F | Cl | 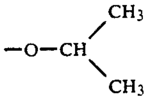 | H | 3 | $-CO-R_3$ | |
| 9.245 | F | Cl | $-O-CH_2-CH_2-O-CH$ | H | 3 | $-CO-R_3$ | |
| 9.246 | F | Cl | $-O-CH(CH_3)-CH_2-S-CH_3$ | H | 3 | $-CO-R_3$ | |
| 9.247 | F | Cl | $-O-CH_2-COOCH_3$ | H | 3 | $-CO-R_3$ | |
| 9.248 | F | Cl | $-S-CH_2-COOCH_3$ | H | 3 | $-CO-R_3$ | |
| 9.249 | F | Cl | $-O-CH_2-C\equiv CH$ | H | 3 | $-CO-R_3$ | |
| 9.250 | F | Cl | $-Cl$ | Cl | 0 | $-CO-R_3$ | |
| 9.251 | F | Cl | $-OH$ | Cl | 0 | $-CO-R_3$ | |
| 9.252 | F | Cl | $-OCH_3$ | Cl | 0 | $-CO-R_3$ | |
| 9.253 | F | Cl | $-OC_2H_5$ | Cl | 0 | $-CO-R_3$ | |
| 9.254 | F | Cl | 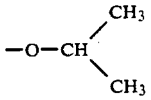 | Cl | 0 | $-CO-R_3$ | |
| 9.255 | F | Cl | $-O-CH_2-COOCH_3$ | Cl | 0 | $-CO-R_3$ | |
| 9.256 | F | Cl | $-S-CH_2-COOCH_3$ | Cl | 0 | $-CO-R_3$ | |
| 9.257 | F | Cl | $-OCH_3$ | Br | 0 | $-CO-R_3$ | |
| 9.258 | F | Cl | 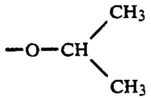 | Br | 0 | $-CO-R_3$ | |
| 9.259 | F | Cl | $-OCH_3$ | F | 0 | $-CO-R_3$ | |
| 9.260 | F | Cl | $-OCH_3$ | $CH_3$ | 0 | $-CO-R_3$ | |
| 9.261 | F | Cl | $-OC_2H_5$ | $CH_3$ | 0 | $-CO-R_3$ | |
| 9.262 | F | Cl | 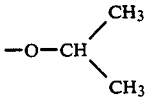 | $CH_3$ | 0 | $-CO-R_3$ | |
| 9.263 | F | Cl | $-O-CH_2-CH_2-O-CH_3$ | $CH_3$ | 0 | $-CO-R_3$ | |
| 9.264 | F | Cl | $-O-CH_2-COOCH_3$ | $CH_3$ | 0 | $-CO-R_3$ | |
| 9.265 | F | Cl | $-O-CH(CH_3)COOCH_3$ | $CH_3$ | 0 | $-CO-R_3$ | |
| 9.266 | F | Cl | $-S-CH_2-COOCH_3$ | $CH_3$ | 0 | $-CO-R_3$ | |

TABLE 9-continued

Compounds of formula I wherein W is $W_9$, $Z_2$ is oxygen and $R_{14}$ is hydrogen:

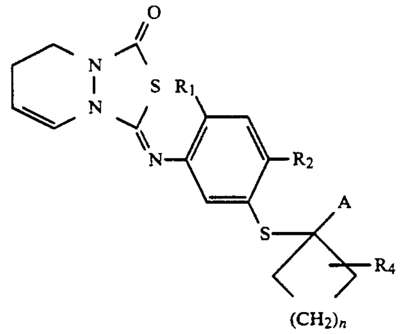

(I)

| Comp. No. | $R_1$ | $R_2$ | $R_3$ | $R_4$ | n | A | m.p. [°C.] |
|---|---|---|---|---|---|---|---|
| 9.267 | F | Cl | $-OCH_3$ | $CF_3$ | 0 | $-CO-R_3$ | |
| 9.268 | F | Cl | $-OC_2H_5$ | $CF_3$ | 0 | $-CO-R_3$ | |
| 9.269 | F | Cl | 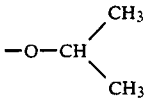 | $CF_3$ | 0 | $-CO-R_3$ | |
| 9.270 | F | Cl | $-O-CH_2-COOCH_3$ | $CF_3$ | 0 | $-CO-R_3$ | |
| 9.271 | F | Cl | $-S-CH_2-COOCH_3$ | $CF_3$ | 0 | $-CO-R_3$ | |
| 9.272 | F | Cl | — | H | 0 | $-CN$ | |
| 9.273 | F | Cl | — | H | 1 | $-CN$ | |
| 9.274 | F | Cl | — | H | 2 | $-CN$ | |
| 9.275 | F | Cl | — | H | 3 | $-CN$ | |
| 9.276 | F | Cl | — | H | 4 | $-CN$ | |

TABLE 10a

Compounds of formula I wherein W is $W_{10}$, $Y_1$ is oxygen, $Y_2$ is oxygen, $R_{14}$ is hydrogen and A is $-CO-R_3$:

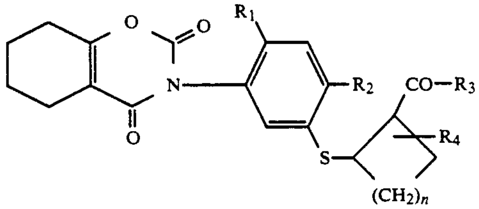

(I)

| Comp. No. | $R_1$ | $R_2$ | $R_3$ | $R_4$ | n | m.p. [°C.] |
|---|---|---|---|---|---|---|
| 10.001 | F | Cl | $-Cl$ | H | 0 | |
| 10.002 | F | Cl | $-OH$ | H | 0 | |
| 10.003 | F | Cl | $-OCH_3$ | H | 0 | |
| 10.004 | F | Cl | $-OC_2H_5$ | H | 0 | |
| 10.005 | F | Cl | $-OC_3H_7$ | H | 0 | |
| 10.006 | F | Cl | 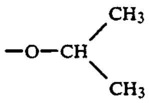 | H | 0 | |
| 10.007 | F | Cl | $-OC_4H_9$ | H | 0 | |
| 10.008 | F | Cl | $-O-CH(CH_3)-C_2H_5$ | H | 0 | |
| 10.009 | F | Cl | 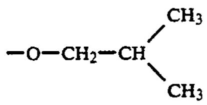 | H | 0 | |
| 10.010 | F | Cl | $-OC_5H_{11}$ | H | 0 | |
| 10.011 | F | Cl | $-O-CH_2-CH_2-O-CH_3$ | H | 0 | |
| 10.012 | F | Cl | $-O-CH_2-CH_2-O-C_2H_5$ | H | 0 | |
| 10.013 | F | Cl | $-O-CH-(CH_3)-CH_2-O-CH_3$ | H | 0 | |
| 10.014 | F | Cl | $-O-CH_2-CH_2-S-CH_3$ | H | 0 | |
| 10.015 | F | Cl | $-O-CH(CH_3)-CH_2-S-CH_3$ | H | 0 | |
| 10.016 | F | Cl | $-O-CH(CH_3)-CH_2-S-C_2H_5$ | H | 0 | |

TABLE 10a-continued
Compounds of formula I wherein W is $W_{10}$, $Y_1$ is oxygen, $Y_2$ is oxygen, $R_{14}$ is hydrogen and A is $-CO-R_3$:
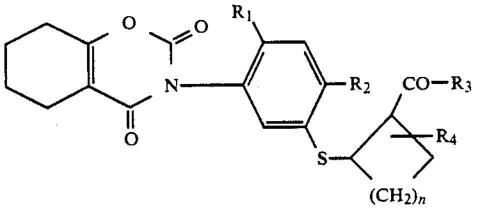
(I)
| Comp. No. | $R_1$ | $R_2$ | $R_3$ | $R_4$ | n | m.p. [°C.] |
|---|---|---|---|---|---|---|
| 10.017 | F | Cl | $-O-CH(CH_3)-CH_2-S-C_3H_7$ | H | 0 | |
| 10.018 | F | Cl | 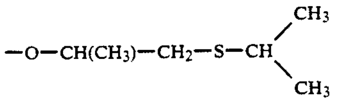 | H | 0 | |
| 10.019 | F | Cl | $-O-CH(CH_3)-CH_2-S-C_4H_9$ | H | 0 | |
| 10.020 | F | Cl | $-O-CH(CH_3)-CH_2-S-C_5H_{11}$ | H | 0 | |
| 10.021 | F | Cl | 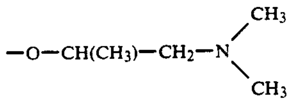 | H | 0 | |
| 10.022 | F | Cl | 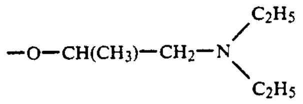 | H | 0 | |
| 10.023 | F | Cl | $-NH_2$ | H | 0 | |
| 10.024 | F | Cl | 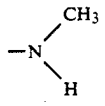 | H | 0 | |
| 10.025 | F | Cl | 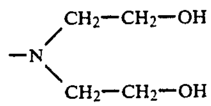 | H | 0 | |
| 10.026 | F | Cl | $-NH-CH_2-CH=CH_2$ | H | 0 | |
| 10.027 | F | Cl | $-N-(CH_2-CH=CH_2)_2$ | H | 0 | |
| 10.028 | F | Cl | 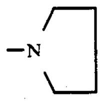 | H | 0 | |
| 10.029 | F | Cl | 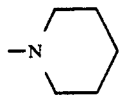 | H | 0 | |
| 10.030 | F | Cl | 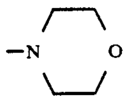 | H | 0 | |
| 10.031 | F | Cl | 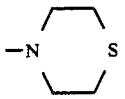 | H | 0 | |
| 10.032 | F | Cl | 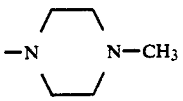 | H | 0 | |

TABLE 10a-continued
Compounds of formula I wherein W is $W_{10}$, $Y_1$ is oxygen, $Y_2$ is oxygen, $R_{14}$ is hydrogen and A is $-CO-R_3$:
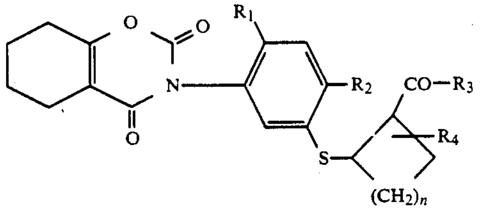
(I)
| Comp. No. | $R_1$ | $R_2$ | $R_3$ | $R_4$ | n | m.p. [°C.] |
|---|---|---|---|---|---|---|
| 10.033 | F | Cl | 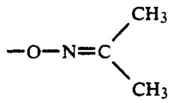 | H | 0 | |
| 10.034 | F | Cl | $-O-CH_2-CH_2-Cl$ | H | 0 | |
| 10.035 | F | Cl | $-O-CH_2-CN$ | H | 0 | |
| 10.036 | F | Cl | 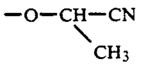 | H | 0 | |
| 10.037 | F | Cl | $-O-CH_2-CH=CH_2$ | H | 0 | |
| 10.038 | F | Cl | $-O-CH_2-CH=CHCl$ | H | 0 | |
| 10.039 | F | Cl | 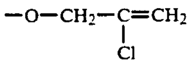 | H | 0 | |
| 10.040 | F | Cl | $-O-CH_2=C\equiv CH$ | H | 0 | |
| 10.041 | F | Cl | 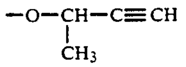 | H | 0 | |
| 10.042 | F | Cl | 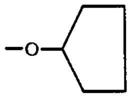 | H | 0 | |
| 10.043 | F | Cl | 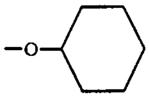 | H | 0 | |
| 10.044 | F | Cl | 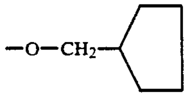 | H | 0 | |
| 10.045 | F | Cl | 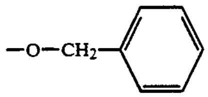 | H | 0 | |
| 10.046 | F | Cl | 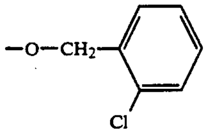 | H | 0 | |
| 10.047 | F | Cl | 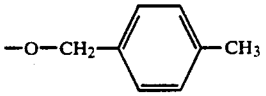 | H | 0 | |
| 10.048 | F | Cl | $-S-CH_3$ | H | 0 | |
| 10.049 | F | Cl | $-S-C_2H_5$ | H | 0 | |
| 10.050 | F | Cl | $-S-C_3H_7$ | H | 0 | |

TABLE 10a-continued

Compounds of formula I wherein W is $W_{10}$, $Y_1$ is oxygen, $Y_2$ is oxygen, $R_{14}$ is hydrogen and A is $-CO-R_3$:

(I)

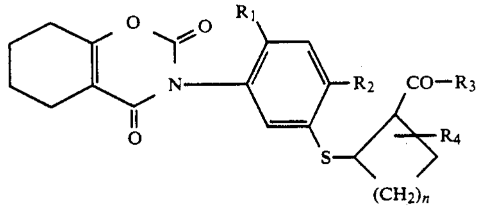

| Comp. No. | $R_1$ | $R_2$ | $R_3$ | $R_4$ | n | m.p. [°C.] |
|---|---|---|---|---|---|---|
| 10.051 | F | Cl | $-S-CH_2-CH=CH_2$ | H | 0 | |
| 10.052 | F | Cl | $-S-CH_2-COOCH_3$ | H | 0 | |
| 10.053 | F | Cl | $-S-CH_2-COOC_2H_5$ | H | 0 | |
| 10.054 | F | Cl | $-S-CH_2-COOC_5H_{11}$ | H | 0 | |
| 10.055 | F | Cl | $-S-CH(CH_3)-COOCH_3$ | H | 0 | |
| 10.056 | F | Cl | $-S-(CH_3)-COOC_2H_5$ | H | 0 | |
| 10.057 | F | Cl | $-S-CH(CH_3)-COOC_3H_7$ | H | 0 | |
| 10.058 | F | Cl | $-S-CH_2-CH_2-COOCH_3$ | H | 0 | |
| 10.059 | F | Cl | $-S-CH_2-COOCH_2-CH_2-O-CH_3$ | H | 0 | |
| 10.060 | F | Cl | $-O-CH_2-COOCH_3$ | H | 0 | |
| 10.061 | F | Cl | $-O-CH(CH_3)-COOCH_3$ | H | 0 | |
| 10.062 | F | Cl | $-O-CH_2-COOC_5H_{11}$ | H | 0 | |
| 10.063 | F | Cl | $-O-CH_2-CH_3-Si(CH_3)_3$ | H | 0 | |
| 10.064 | F | Cl | $-ONa$ | H | 0 | |
| 10.065 | F | Br | $-Cl$ | H | 0 | |
| 10.066 | F | Br | $-OH$ | H | 0 | |
| 10.067 | F | Br | $-OCH_3$ | H | 0 | |
| 10.068 | F | Br | $-OC_2H_5$ | H | 0 | |
| 10.069 | F | Br | $-OC_3H_7$ | H | 0 | |
| 10.070 | F | Br | 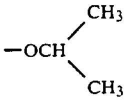 | H | 0 | |
| 10.071 | F | Br | $-OC_4H_9$ | H | 0 | |
| 10.072 | F | Br | $-OCH(CH_3)-CH_2-CH_3$ | H | 0 | |
| 10.073 | F | Br | 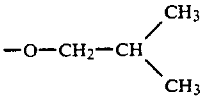 | H | 0 | |
| 10.074 | F | Br | $-O-C_5H_{11}$ | H | 0 | |
| 10.075 | F | Br | $-O-CH_2-CH_2-O-CH_3$ | H | 0 | |
| 10.076 | F | Br | $-O-CH_2-CH_2-O-C_2H_5$ | H | 0 | |
| 10.077 | F | Br | $-O-CH(CH_3)-CH_2-O-CH_3$ | H | 0 | |
| 10.078 | F | Br | $-O-CH_2-CH_2-S-CH_3$ | H | 0 | |
| 10.079 | F | Br | $-O-CH_2(CH_3)-S-CH_3$ | H | 0 | |
| 10.080 | F | Br | $-O-CH-(CH_3)-S-C_2H_5$ | H | 0 | |
| 10.081 | F | Br | $-O-CH(CH_3)-S-C_3H_7$ | H | 0 | |
| 10.082 | F | Br | 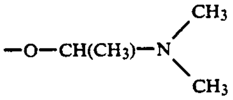 | H | 0 | |
| 10.083 | F | Br | $-NH_2$ | H | 0 | |
| 10.084 | F | Br | 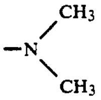 | H | 0 | |
| 10.085 | F | Br | 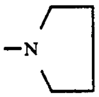 | H | 0 | |
| 10.086 | F | Br | 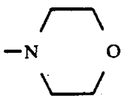 | H | 0 | |

TABLE 10a-continued

Compounds of formula I wherein W is $W_{10}$, $Y_1$ is oxygen, $Y_2$ is oxygen, $R_{14}$ is hydrogen and A is $-CO-R_3$:

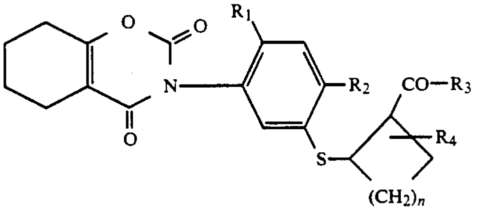

(I)

| Comp. No. | $R_1$ | $R_2$ | $R_3$ | $R_4$ | n | m.p. [°C.] |
|---|---|---|---|---|---|---|
| 10.087 | F | Br | 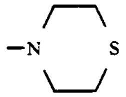 | H | 0 | |
| 10.088 | F | Br | 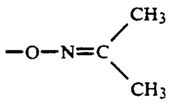 | H | 0 | |
| 10.089 | F | Br | $-O-CH_2-CH_2-Cl$ | H | 0 | |
| 10.090 | F | Br | $-O-CH_2-CN$ | H | 0 | |
| 10.091 | F | Br | $-O-CH_2-CH=CH_2$ | H | 0 | |
| 10.092 | F | Br | $-O-CH_2-C\equiv CH$ | H | 0 | |
| 10.093 | F | Br | 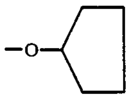 | H | 0 | |
| 10.094 | F | Br | 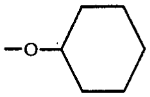 | H | 0 | |
| 10.095 | F | Br | 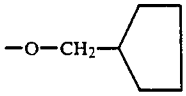 | H | 0 | |
| 10.096 | F | Br | 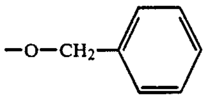 | H | 0 | |
| 10.097 | F | Br | $-SCH_3$ | H | 0 | |
| 10.098 | F | Br | $-S-CH_2-COOCH_3$ | H | 0 | |
| 10.099 | F | Br | $-S-CH(CH_3)-COOCH_3$ | H | 0 | |
| 10.100 | F | Br | $-O-CH_2-COOCH_3$ | H | 0 | |
| 10.101 | F | Br | $-O-CH(CH_3)COOCH_3$ | H | 0 | |
| 10.102 | F | CN | $-Cl$ | H | 0 | |
| 10.103 | F | CN | $-OH$ | H | 0 | |
| 10.104 | F | CN | $-OCH_3$ | H | 0 | |
| 10.105 | H | Cl | $-Cl$ | H | 0 | |
| 10.106 | H | Cl | $-OH$ | H | 0 | |
| 10.107 | H | Cl | $-OCH_3$ | H | 0 | |
| 10.108 | H | Cl | $-OC_2H_5$ | H | 0 | |
| 10.109 | H | Cl | 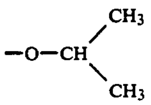 | H | 0 | |
| 10.110 | H | Cl | $-O-CH_2-COOCH_3$ | H | 0 | |
| 10.111 | H | Cl | $-O-CH(CH_3)COOCH_3$ | H | 0 | |
| 10.112 | H | Cl | $-S-CH_2-COOCH_3$ | H | 0 | |
| 10.113 | H | Cl | $-S-CH(CH_3)COOCH_3$ | H | 0 | |

TABLE 10a-continued

Compounds of formula I wherein W is $W_{10}$, $Y_1$ is oxygen, $Y_2$ is oxygen, $R_{14}$ is hydrogen and A is $-CO-R_3$:

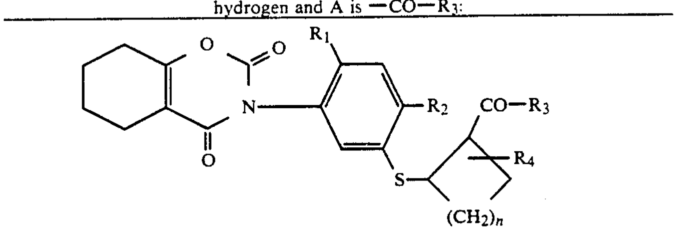

(I)

| Comp. No. | $R_1$ | $R_2$ | $R_3$ | $R_4$ | n | m.p. [°C.] |
|---|---|---|---|---|---|---|
| 10.114 | H | Cl | 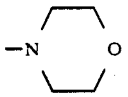 | H | 0 | |
| 10.115 | F | Cl | $-Cl$ | H | 1 | |
| 10.116 | F | Cl | $-OH$ | H | 1 | |
| 10.117 | F | Cl | $-OCH_3$ | H | 1 | 105-107 |
| 10.118 | F | Cl | $-OC_2H_5$ | H | 1 | |
| 10.119 | F | Cl | $-OC_3H_7$ | H | 1 | |
| 10.120 | F | Cl | $CH_3$<br>$-O-CH$<br>$CH_3$ | H | 1 | |
| 10.121 | F | Cl | $-OC_4H_9$ | H | 1 | |
| 10.122 | F | Cl | $-O-CH(CH_3)-C_2H_5$ | H | 1 | |
| 10.123 | F | Cl | $CH_3$<br>$-O-CH_2-CH$<br>$CH_3$ | H | 1 | |
| 10.124 | F | Cl | $-OC_5H_{11}$ | H | 1 | |
| 10.125 | F | Cl | $-O-CH_2-CH_2-O-CH_3$ | H | 1 | |
| 10.126 | F | Cl | $-O-CH_2-CH_2-O-C_2H_5$ | H | 1 | |
| 10.127 | F | Cl | $-O-CH-(CH_3)-CH_2-O-CH_3$ | H | 1 | |
| 10.128 | F | Cl | $-O-CH_2-CH_2-S-CH_3$ | H | 1 | |
| 10.129 | F | Cl | $-O-CH(CH_3)-CH_2-S-CH_3$ | H | 1 | |
| 10.130 | F | Cl | $-O-CH(CH_3)-CH_2-S-C_2H_5$ | H | 1 | |
| 10.131 | F | Cl | $-O-CH(CH_3)-CH_2-S-C_3H_7$ | H | 1 | |
| 10.132 | F | Cl | $CH_3$<br>$-O-CH(CH_3)-CH_2-S-CH$<br>$CH_3$ | H | 1 | |
| 10.133 | F | Cl | $-O-CH(CH_3)-CH_2-S-C_4H_9$ | H | 1 | |
| 10.134 | F | Cl | $-O-CH(CH_3)-CH_2-S-C_5H_{11}$ | H | 1 | |
| 10.135 | F | Cl | $CH_3$<br>$-O-CH(CH_3)-CH_2-N$<br>$CH_3$ | H | 1 | |
| 10.136 | F | Cl | $C_2H_5$<br>$-O-CH(CH_3)-CH_2-N$<br>$C_2H_5$ | H | 1 | |
| 10.137 | F | Cl | $-NH_2$ | H | 1 | |
| 10.138 | F | Cl | $CH_3$<br>$-N$<br>H | H | 1 | |
| 10.139 | F | Cl | $CH_2-CH_2-OH$<br>$-N$<br>$CH_2-CH_2-OH$ | H | 1 | |

TABLE 10a-continued

Compounds of formula I wherein W is $W_{10}$, $Y_1$ is oxygen, $Y_2$ is oxygen, $R_{14}$ is hydrogen and A is $-CO-R_3$:

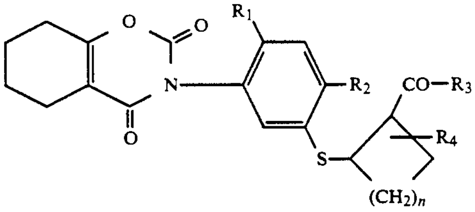

(I)

| Comp. No. | $R_1$ | $R_2$ | $R_3$ | $R_4$ | n | m.p. [°C.] |
|---|---|---|---|---|---|---|
| 10.140 | F | Cl | $-NH-CH_2-CH=CH_2$ | H | 1 | |
| 10.141 | F | Cl | $-N-(CH_2-CH=CH_2)_2$ | H | 1 | |
| 10.142 | F | Cl | 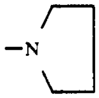 | H | 1 | |
| 10.143 | F | Cl | 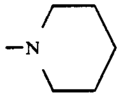 | H | 1 | |
| 10.144 | F | Cl | 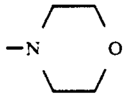 | H | 1 | |
| 10.145 | F | Cl | 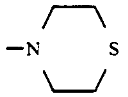 | H | 1 | |
| 10.146 | F | Cl | 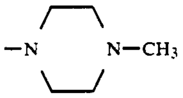 | H | 1 | |
| 10.147 | F | Cl | $CH_3$<br>$-O-N=C$<br>$CH_3$ | H | 1 | |
| 10.148 | F | Cl | $-O-CH_2-CH_2-Cl$ | H | 1 | |
| 10.149 | F | Cl | $-O-CH_2-CN$ | H | 1 | |
| 10.150 | F | Cl | $-O-CH-CN$<br>$CH_3$ | H | 1 | |
| 10.151 | F | Cl | $-O-CH_2-CH=CH_2$ | H | 1 | |
| 10.152 | F | Cl | $-O-CH_2-CH=CHCl$ | H | 1 | |
| 10.153 | F | Cl | $-O-CH_2-C=CH_2$<br>Cl | H | 1 | |
| 10.154 | F | Cl | $-O-CH_2=C\equiv CH$ | H | 1 | |
| 10.155 | F | Cl | $-O-CH-C\equiv CH$<br>$CH_3$ | H | 1 | |
| 10.156 | F | Cl | 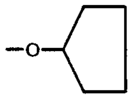 | H | 1 | |

TABLE 10a-continued

Compounds of formula I wherein W is $W_{10}$, $Y_1$ is oxygen, $Y_2$ is oxygen, $R_{14}$ is hydrogen and A is $-CO-R_3$:

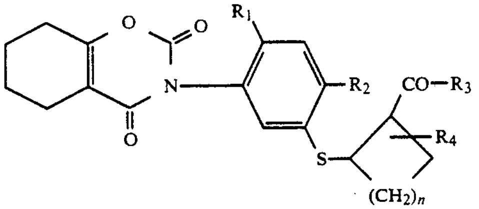

(I)

| Comp. No. | $R_1$ | $R_2$ | $R_3$ | $R_4$ | n | m.p. [°C.] |
|---|---|---|---|---|---|---|
| 10.157 | F | Cl | 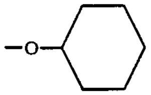 | H | 1 | |
| 10.158 | F | Cl | 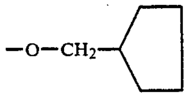 | H | 1 | |
| 10.159 | F | Cl | 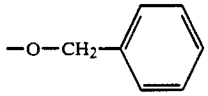 | H | 1 | |
| 10.160 | F | Cl | 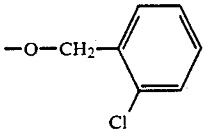 | H | 1 | |
| 10.161 | F | Cl | 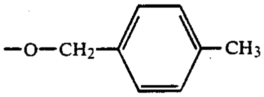 | H | 1 | |
| 10.162 | F | Cl | $-S-CH_3$ | H | 1 | |
| 10.163 | F | Cl | $-S-C_2H_5$ | H | 1 | |
| 10.164 | F | Cl | $-S-C_3H_7$ | H | 1 | |
| 10.165 | F | Cl | $-S-CH_2-CH{=}CH_2$ | H | 1 | |
| 10.166 | F | Cl | $-S-CH_2-COOCH_3$ | H | 1 | |
| 10.167 | F | Cl | $-S-CH_2-COOC_2H_5$ | H | 1 | |
| 10.168 | F | Cl | $-S-CH_2-COOC_5H_{11}$ | H | 1 | |
| 10.169 | F | Cl | $-S-CH(CH_3)-COOCH_3$ | H | 1 | |
| 10.170 | F | Cl | $-S-(CH_3)-COOC_2H_5$ | H | 1 | |
| 10.171 | F | Cl | $-S-CH(CH_3)-COOC_3H_7$ | H | 1 | |
| 10.172 | F | Cl | $-S-CH_2-CH_2-COOCH_3$ | H | 1 | |
| 10.173 | F | Cl | $-S-CH_2-COOCH_2-CH_2-O-CH_3$ | H | 1 | |
| 10.174 | F | Cl | $-O-CH_2-COOCH_3$ | H | 1 | |
| 10.175 | F | Cl | $-O-CH(CH_3)-COOCH_3$ | H | 1 | |
| 10.176 | F | Cl | $-O-CH_2-COOC_5H_{11}$ | H | 1 | |
| 10.177 | F | Cl | $-O-CH_2-CH_3-Si(CH_3)_3$ | H | 1 | |
| 10.178 | F | Cl | $-ONa$ | H | 1 | |
| 10.179 | F | Br | $-Cl$ | H | 1 | |
| 10.180 | F | Br | $-OH$ | H | 1 | |
| 10.181 | F | Br | $-OCH_3$ | H | 1 | |
| 10.182 | F | Br | $-OC_2H_5$ | H | 1 | |
| 10.183 | F | Br | $-OC_3H_7$ | H | 1 | |
| 10.184 | F | Br | 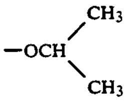 | H | 1 | |
| 10.185 | F | Br | $-OC_4H_9$ | H | 1 | |
| 10.186 | F | Br | $-OCH(CH_3)-CH_2-CH_3$ | H | 1 | |

TABLE 10a-continued

Compounds of formula I wherein W is $W_{10}$, $Y_1$ is oxygen, $Y_2$ is oxygen, $R_{14}$ is hydrogen and A is $-CO-R_3$:

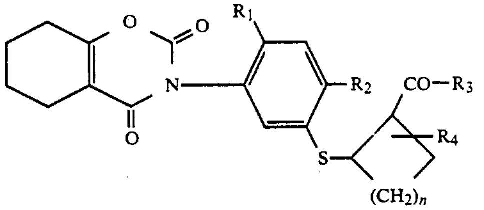

(I)

| Comp. No. | $R_1$ | $R_2$ | $R_3$ | $R_4$ | n | m.p. [°C.] |
|---|---|---|---|---|---|---|
| 10.187 | F | Br | 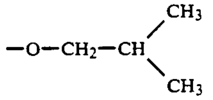 | H | 1 | |
| 10.188 | F | Br | $-O-C_5H_{11}$ | H | 1 | |
| 10.189 | F | Br | $-O-CH_2-CH_2-O-CH_3$ | H | 1 | |
| 10.190 | F | Br | $-O-CH_2-CH_2-O-C_2H_5$ | H | 1 | |
| 10.191 | F | Br | $-O-CH(CH_3)-CH_2-O-CH_3$ | H | 1 | |
| 10.192 | F | Br | $-O-CH_2-CH_2-S-CH_3$ | H | 1 | |
| 10.193 | F | Br | $-O-CH_2(CH_3)-S-CH_3$ | H | 1 | |
| 10.194 | F | Br | $-O-CH-(CH_3)-S-C_2H_5$ | H | 1 | |
| 10.195 | F | Br | $-O-CH(CH_3)-S-C_3H_7$ | H | 1 | |
| 10.196 | F | Br | 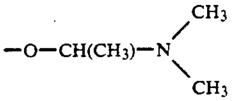 | H | 1 | |
| 10.197 | F | Br | $-NH_2$ | H | 1 | |
| 10.198 | F | Br | 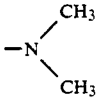 | H | 1 | |
| 10.199 | F | Br | 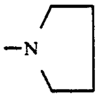 | H | 1 | |
| 10.200 | F | Br | 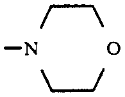 | H | 1 | |
| 10.201 | F | Br | 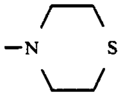 | H | 1 | |
| 10.202 | F | Br | 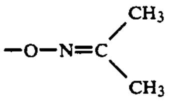 | H | 1 | |
| 10.203 | F | Br | $-O-CH_2-CH_2-Cl$ | H | 1 | |
| 10.204 | F | Br | $-O-CH_2-CN$ | H | 1 | |
| 10.205 | F | Br | $-O-CH_2-CH=CH_2$ | H | 1 | |
| 10.206 | F | Br | $-O-CH_2-C\equiv CH$ | H | 1 | |
| 10.207 | F | Br | 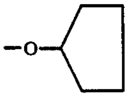 | H | 1 | |
| 10.208 | F | Br | 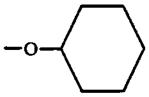 | H | 1 | |

TABLE 10a-continued

Compounds of formula I wherein W is $W_{10}$, $Y_1$ is oxygen, $Y_2$ is oxygen, $R_{14}$ is hydrogen and A is $-CO-R_3$:

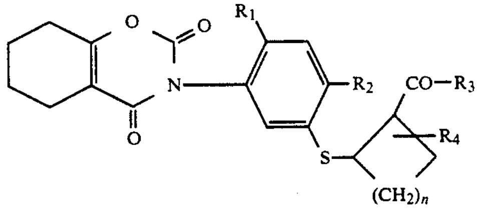
(I)

| Comp. No. | $R_1$ | $R_2$ | $R_3$ | $R_4$ | n | m.p. [°C.] |
|---|---|---|---|---|---|---|
| 10.209 | F | Br | 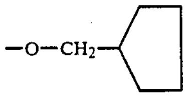 | H | 1 | |
| 10.210 | F | Br | 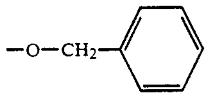 | H | 1 | |
| 10.211 | F | Br | $-SCH_3$ | H | 1 | |
| 10.212 | F | Br | $-S-CH_2-COOCH_3$ | H | 1 | |
| 10.213 | F | Br | $-S-CH(CH_3)-COOCH_3$ | H | 1 | |
| 10.214 | F | Br | $-O-CH_2-COOCH_3$ | H | 1 | |
| 10.215 | F | Br | $-O-CH(CH_3)COOCH_3$ | H | 1 | |
| 10.216 | F | CN | $-Cl$ | H | 1 | |
| 10.217 | F | CN | $-OH$ | H | 1 | |
| 10.218 | F | CN | $-OCH_3$ | H | 1 | |
| 10.219 | H | Cl | $-Cl$ | H | 1 | |
| 10.220 | H | Cl | $-OH$ | H | 1 | |
| 10.221 | H | Cl | $-OCH_3$ | H | 1 | |
| 10.222 | H | Cl | $-OC_2H_5$ | H | 1 | |
| 10.223 | H | Cl | 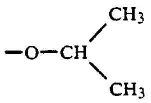 | H | 1 | |
| 10.224 | H | Cl | $-O-CH_2-COOCH_3$ | H | 1 | |
| 10.225 | H | Cl | $-O-CH(CH_3)COOCH_3$ | H | 1 | |
| 10.226 | H | Cl | $-S-CH_2-COOCH_3$ | H | 1 | |
| 10.227 | H | Cl | $-S-CH(CH_3)COOCH_3$ | H | 1 | |
| 10.228 | H | Cl | 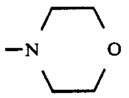 | H | 1 | |
| 10.229 | F | Cl | Cl | H | 2 | |
| 10.230 | F | Cl | OH | H | 2 | |
| 10.231 | F | Cl | $OCH_3$ | H | 2 | |
| 10.232 | F | Cl | $-OC_2H_5$ | H | 2 | |
| 10.233 | F | Cl | 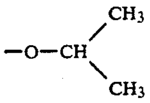 | H | 2 | |
| 10.234 | F | Cl | $-OCH_2-CH_2-O-CH_3$ | H | 2 | |
| 10.235 | F | Cl | $-O-CH(CH_3)-CH_2-S-CH_3$ | H | 2 | |
| 10.236 | F | Cl | $-O-CH_2-COOCH_3$ | H | 2 | |
| 10.237 | F | Cl | $-S-CH_2-COOCH_3$ | H | 2 | |
| 10.238 | F | Cl | $-CH_2-CH=CH_2$ | H | 2 | |
| 10.239 | F | Cl | $-CH_2-C\equiv CH$ | H | 2 | |
| 10.240 | F | Cl | Cl | H | 3 | |
| 10.241 | F | Cl | OH | H | 3 | |
| 10.242 | F | Cl | $OCH_3$ | H | 3 | |
| 10.243 | F | Cl | $OC_2H_5$ | H | 3 | |

TABLE 10a-continued

Compounds of formula I wherein W is $W_{10}$, $Y_1$ is oxygen, $Y_2$ is oxygen, $R_{14}$ is hydrogen and A is —CO—$R_3$:

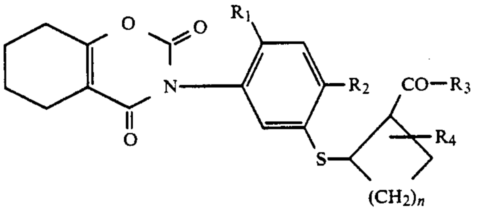

(I)

| Comp. No. | $R_1$ | $R_2$ | $R_3$ | $R_4$ | n | m.p. [°C.] |
|---|---|---|---|---|---|---|
| 10.244 | F | Cl | 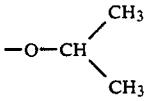 | H | 3 | |
| 10.245 | F | Cl | $-O-CH_2-CH_2-O-CH$ | H | 3 | |
| 10.246 | F | Cl | $-O-CH(CH_3)-CH_2-S-CH_3$ | H | 3 | |
| 10.247 | F | Cl | $-O-CH_2-COOCH_3$ | H | 3 | |
| 10.248 | F | Cl | $-S-CH_2-COOCH_3$ | H | 3 | |
| 10.249 | F | Cl | $-O-CH_2-C{\equiv}CH$ | H | 3 | |
| 10.250 | F | Cl | $-Cl$ | Cl | 0 | |
| 10.251 | F | Cl | $-OH$ | Cl | 0 | |
| 10.252 | F | Cl | $-OCH_3$ | Cl | 0 | |
| 10.253 | F | Cl | $-OC_2H_5$ | Cl | 0 | |
| 10.254 | F | Cl | 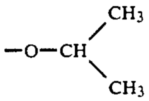 | Cl | 0 | |
| 10.255 | F | Cl | $-O-CH_2-COOCH_3$ | Cl | 0 | |
| 10.256 | F | Cl | $-S-CH_2-COOCH_3$ | Cl | 0 | |
| 10.257 | F | Cl | $-OCH_3$ | Br | 0 | |
| 10.258 | F | Cl | 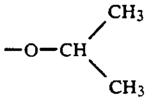 | Br | 0 | |
| 10.259 | F | Cl | $-OCH_3$ | F | 0 | |
| 10.260 | F | Cl | $-OCH_3$ | $CH_3$ | 0 | |
| 10.261 | F | Cl | $-OC_2H_5$ | $CH_3$ | 0 | |
| 10.262 | F | Cl | 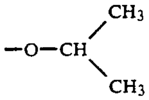 | $CH_3$ | 0 | |
| 10.263 | F | Cl | $-O-CH_2-CH_2-O-CH_3$ | $CH_3$ | 0 | |
| 10.264 | F | Cl | $-O-CH_2-COOCH_3$ | $CH_3$ | 0 | |
| 10.265 | F | Cl | $-O-CH(CH_3)COOCH_3$ | $CH_3$ | 0 | |
| 10.266 | F | Cl | $-S-CH_2-COOCH_3$ | $CH_3$ | 0 | |
| 10.267 | F | Cl | $-OCH_3$ | $CF_3$ | 0 | |
| 10.268 | F | Cl | $-OC_2H_5$ | $CF_3$ | 0 | |
| 10.269 | F | Cl | 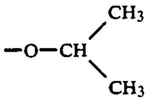 | $CF_3$ | 0 | |
| 10.270 | F | Cl | $-O-CH_2-COOCH_3$ | $CF_3$ | 0 | |
| 10.271 | F | Cl | $-S-CH_2-COOCH_3$ | $CF_3$ | 0 | |

TABLE 10b

Compounds of formula I wherein W is $W_{10}$, $Y_1$ is oxygen, $Y_2$ is oxygen, $R_{14}$ is hydrogen and A is —CN:

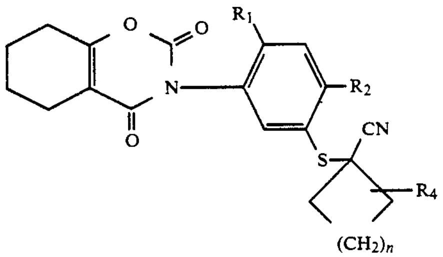

(I)

TABLE 10b-continued

| Comp. No. | $R_1$ | $R_2$ | $R_3$ | $R_4$ | n | m.p.[°C.] |
|---|---|---|---|---|---|---|
| 10.272 | F | Cl | — | H | 0 | |
| 10.273 | F | Cl | — | H | 1 | |
| 10.274 | F | Cl | — | H | 2 | |
| 10.275 | F | Cl | — | H | 3 | |
| 10.276 | F | Cl | — | H | 4 | |

TABLE 11

Intermediates of formula III wherein $R_{14}$ is hydrogen:

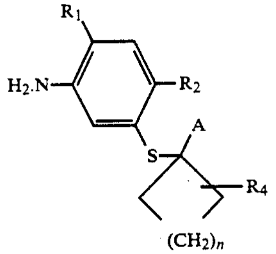

(III)

| Comp. No. | $R_1$ | $R_2$ | $R_3$ | $R_4$ | n | A | m.p.[°C.] |
|---|---|---|---|---|---|---|---|
| 11.001 | F | Cl | OH | H | 0 | $-CO-R_3$ | 227-229 |
| 11.002 | F | Cl | $OCH_3$ | H | 0 | $-CO-R_3$ | 223-224 |
| 11.003 | F | Cl | $OC_2H_5$ | H | 0 | $-CO-R_3$ | 96-99 |
| 11.004 | F | Cl | 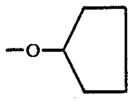 | H | 0 | $-CO-R_3$ | |
| 11.005 | F | Cl | $-O-CH_2-CH_2-O-CH_3$ | H | 0 | $-CO-R_3$ | |
| 11.006 | F | Cl | —OH | H | 1 | $-CO-R_3$ | |
| 11.007 | F | Cl | $OCH_3$ | H | 1 | $-CO-R_3$ | 89-90 |
| 11.008 | F | Cl | $OC_2H_5$ | H | 1 | $-CO-R_3$ | $\eta_D^{22}$1.5711 |
| 11.009 | F | Cl | 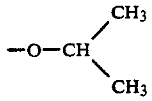 | H | 1 | $-CO-R_3$ | |
| 11.010 | F | Cl | —OH | H | 2 | $-CO-R_3$ | |
| 11.011 | F | Cl | $-OCH_3$ | H | 2 | $-CO-R_3$ | |
| 11.012 | F | Cl | $-OCH_3$ | H | 3 | $-CO-R_3$ | |
| 11.013 | H | Cl | OH | H | 0 | $-CO-R_3$ | |
| 11.014 | H | Cl | $OCH_3$ | H | 0 | $-CO-R_3$ | |
| 11.015 | H | Cl | 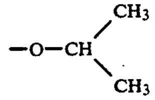 | H | 0 | $-CO-R_3$ | |
| 11.016 | H | Cl | —OH | H | 1 | $-CO-R_3$ | |
| 11.017 | H | Cl | $-OCH_3$ | H | 1 | $-CO-R_3$ | |
| 11.018 | F | Br | —OH | H | 0 | $-CO-R_3$ | |
| 11.019 | F | Br | $-OCH_3$ | H | 0 | $-CO-R_3$ | |
| 11.020 | F | Br | $-OC_3H_5$ | H | 0 | $-CO-R_3$ | |
| 11.021 | F | Cl | OH | Cl | 0 | $-CO-R_3$ | 173-174 |
| 11.022 | F | Cl | $OCH_3$ | Cl | 0 | $-CO-R_3$ | |
| 11.023 | F | Cl | $O_2H_5$ | Cl | 0 | $-CO-R_3$ | |

TABLE 11-continued

Intermediates of formula III wherein $R_{14}$ is hydrogen:

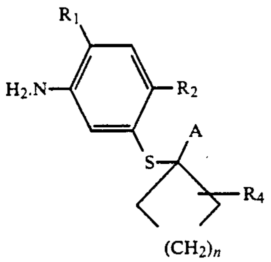

(III)

| Comp. No. | $R_1$ | $R_2$ | $R_3$ | $R_4$ | n | A | m.p.[°C.] |
|---|---|---|---|---|---|---|---|
| 11.024 | F | Cl | —OH | Cl | 1 | —CO—$R_3$ | |
| 11.025 | F | Cl | —$OCH_3$ | Cl | 1 | —CO—$R_3$ | |
| 11.026 | F | Cl | —$OC_2H_5$ | Cl | 1 | —CO—$R_3$ | |
| 11.027 | F | Cl | —OH | F | 0 | —CO—$R_3$ | |
| 11.028 | F | Cl | —$OCH_3$ | F | 0 | —CO—$R_3$ | |
| 11.029 | F | Cl | —$OCH_3$ | $CH_3$ | 0 | —CO—$R_3$ | |
| 11.030 | F | Cl | —$OCH_3$ | $CF_3$ | 0 | —CO—$R_3$ | |
| 11.031 | F | Cl | — | H | 0 | —CN | |
| 11.032 | F | Cl | — | H | 1 | —CN | |
| 11.033 | F | Cl | — | H | 2 | —CN | |
| 11.034 | H | Cl | — | H | 0 | —CN | |

TABLE 12

Intermediates of formula VII wherein $R_{14}$ is hydrogen:

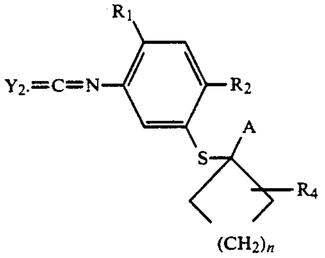

(VII)

| Comp. No. | $R_1$ | $R_2$ | $R_3$ | $R_4$ | n | A | $Y_2$ | m.p.[°C.] |
|---|---|---|---|---|---|---|---|---|
| 12.001 | F | Cl | OH | H | 0 | —CO—$R_3$ | S | 181-183 |
| 12.002 | F | Cl | $OCH_3$ | H | 0 | —CO—$R_3$ | S | 100-101 |
| 12.003 | F | Cl | $OC_2H_5$ | H | 0 | —CO—$R_3$ | S | 68-71 |
| 12.004 | F | Cl | 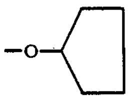 | H | 0 | —CO—$R_3$ | S | |
| 12.005 | F | Cl | —O—$CH_2$—$CH_2$—O—$CH_3$ | H | 0 | —CO—$R_3$ | S | |
| 12.006 | F | Cl | —OH | H | 1 | —CO—$R_3$ | S | |
| 12.007 | F | Cl | $OCH_3$ | H | 1 | —CO—$R_3$ | S | |
| 12.008 | F | Cl | $OC_2H_5$ | H | 1 | —CO—$R_3$ | S | |
| 12.009 | F | Cl | 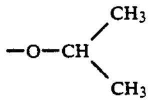 | H | 1 | —CO—$R_3$ | S | |
| 12.010 | F | Cl | —OH | H | 2 | —CO—$R_3$ | S | |
| 12.011 | F | Cl | —$OCH_3$ | H | 2 | —CO—$R_3$ | S | |
| 12.012 | F | Cl | —$OCH_3$ | H | 3 | —CO—$R_3$ | S | |
| 12.013 | H | Cl | OH | H | 0 | —CO—$R_3$ | S | |
| 12.014 | H | Cl | $OCH_3$ | H | 0 | —CO—$R_3$ | S | |
| 12.015 | H | Cl | 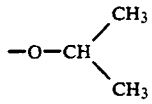 | H | 0 | —CO—$R_3$ | S | |

TABLE 12-continued

Intermediates of formula VII wherein $R_{14}$ is hydrogen:

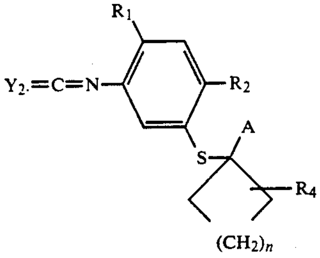

(VII)

| Comp. No. | $R_1$ | $R_2$ | $R_3$ | $R_4$ | n | A | $Y_2$ | m.p.[°C.] |
|---|---|---|---|---|---|---|---|---|
| 12.016 | H | Cl | $-OH$ | H | 1 | $-CO-R_3$ | S | |
| 12.017 | H | Cl | $-OCH_3$ | H | 1 | $-CO-R_3$ | S | |
| 12.018 | F | Br | $-OH$ | H | 0 | $-CO-R_3$ | S | |
| 12.019 | F | Br | $-OCH_3$ | H | 0 | $-CO-R_3$ | S | |
| 12.020 | F | Br | $-OC_3H_5$ | H | 0 | $-CO-R_3$ | S | |
| 12.021 | F | Cl | OH | Cl | 0 | $-CO-R_3$ | S | |
| 12.022 | F | Cl | $OCH_3$ | Cl | 0 | $-CO-R_3$ | S | |
| 12.023 | F | Cl | $O_2H_5$ | Cl | 0 | $-CO-R_3$ | S | |
| 12.024 | F | Cl | $-OH$ | Cl | 1 | $-CO-R_3$ | S | |
| 12.025 | F | Cl | $-OCH_3$ | Cl | 1 | $-CO-R_3$ | S | |
| 12.026 | F | Cl | $-OC_2H_5$ | Cl | 1 | $-CO-R_3$ | S | |
| 12.027 | F | Cl | $-OH$ | F | 0 | $-CO-R_3$ | S | |
| 12.028 | F | Cl | $-OCH_3$ | F | 0 | $-CO-R_3$ | S | |
| 12.029 | F | Cl | $-OCH_3$ | $CH_3$ | 0 | $-CO-R_3$ | S | |
| 12.030 | F | Cl | $-OCH_3$ | $CF_3$ | 0 | $-CO-R_3$ | S | |
| 12.031 | F | Cl | — | H | 0 | $-CN$ | S | |
| 12.032 | F | Cl | — | H | 1 | $-CN$ | S | |
| 12.033 | F | Cl | — | H | 2 | $-CN$ | S | |
| 12.034 | H | Cl | — | H | 0 | $-CN$ | S | |
| 12.035 | F | Cl | OH | H | 0 | $-CO-R_3$ | O | |
| 12.036 | F | Cl | $OCH_3$ | H | 0 | $-CO-R_3$ | O | |
| 12.037 | F | Cl | $OC_2H_5$ | H | 0 | $-CO-R_3$ | O | |
| 12.038 | F | Cl | 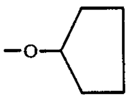 | H | 0 | $-CO-R_3$ | O | |
| 12.039 | F | Cl | $-O-CH_2-CH_2-O-CH_3$ | H | 0 | $-CO-R_3$ | O | |
| 12.040 | F | Cl | $-OH$ | H | 1 | $-CO-R_3$ | O | |
| 12.041 | F | Cl | $OCH_3$ | H | 1 | $-CO-R_3$ | O | |
| 12.042 | F | Cl | $OC_2H_5$ | H | 1 | $-CO-R_3$ | O | |
| 12.043 | F | Cl | 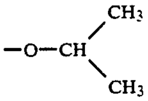 | H | 1 | $-CO-R_3$ | O | |
| 12.044 | F | Cl | $-OH$ | H | 2 | $-CO-R_3$ | O | |
| 12.045 | F | Cl | $-OCH_3$ | H | 2 | $-CO-R_3$ | O | |
| 12.046 | F | Cl | $-OCH_3$ | H | 3 | $-CO-R_3$ | O | |
| 12.047 | H | Cl | OH | H | 0 | $-CO-R_3$ | O | |
| 12.048 | H | Cl | $OCH_3$ | H | 0 | $-CO-R_3$ | O | |
| 12.049 | H | Cl | 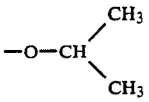 | H | 0 | $-CO-R_3$ | O | |
| 12.050 | H | Cl | $-OH$ | H | 1 | $-CO-R_3$ | O | |
| 12.051 | H | Cl | $-OCH_3$ | H | 1 | $-CO-R_3$ | O | |
| 12.052 | F | Br | $-OH$ | H | 0 | $-CO-R_3$ | O | |
| 12.053 | F | Br | $-OCH_3$ | H | 0 | $-CO-R_3$ | O | |
| 12.054 | F | Br | $-OC_3H_5$ | H | 0 | $-CO-R_3$ | O | |
| 12.055 | F | Cl | OH | Cl | 0 | $-CO-R_3$ | O | |
| 12.056 | F | Cl | $OCH_3$ | Cl | 0 | $-CO-R_3$ | O | |
| 12.057 | F | Cl | $O_2H_5$ | Cl | 0 | $-CO-R_3$ | O | |
| 12.058 | F | Cl | $-OH$ | Cl | 1 | $-CO-R_3$ | O | |
| 12.059 | F | Cl | $-OCH_3$ | Cl | 1 | $-CO-R_3$ | O | |
| 12.060 | F | Cl | $-OC_2H_5$ | Cl | 1 | $-CO-R_3$ | O | |
| 12.061 | F | Cl | $-OH$ | F | 0 | $-CO-R_3$ | O | |

TABLE 12-continued

Intermediates of formula VII wherein $R_{14}$ is hydrogen:

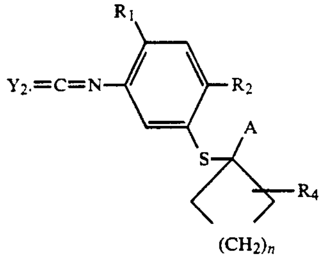

(VII)

| Comp. No. | $R_1$ | $R_2$ | $R_3$ | $R_4$ | n | A | $Y_2$ | m.p.[°C.] |
|---|---|---|---|---|---|---|---|---|
| 12.062 | F | Cl | $-OCH_3$ | F | 0 | $-CO-R_3$ | O | |
| 12.063 | F | Cl | $-OCH_3$ | $CH_3$ | 0 | $-CO-R_3$ | O | |
| 12.064 | F | Cl | $-OCH_3$ | $CF_3$ | 0 | $-CO-R_3$ | O | |
| 12.065 | F | Cl | — | H | 0 | $-CN$ | O | |
| 12.065 | F | Cl | — | H | 0 | $-CN$ | O | |
| 12.066 | F | Cl | — | H | 1 | $-CN$ | O | |
| 12.067 | F | Cl | — | H | 2 | $-CN$ | O | |
| 12.068 | F | Cl | — | H | 0 | $-CN$ | O | |

The compounds of formula I are generally used successfully at rates of application of from 0.001 to 4 kg/ha, especially from 0.005 to 1 kg/ha. The concentration required to achieve the desired effect can be determined by experiment. It is dependent on the mode of action, the stage of development of the cultivated plant and of the weed, and also on the application (place, time, method) and, in dependence on those parameters, can vary within wide limits.

When used at relatively low rates of application, the compounds of formula I are distinguished by growth inhibiting and herbicidal properties, which render them excellently suitable for use in crops of useful plants, especially in cereals, cotton, soybeans, rape, maize and rice, their use in maize crops being very especially preferred.

The invention relates also to herbicidal and plant growth regulating compositions comprising a novel compound of formula I, and to methods of inhibiting plant growth.

Plant growth regulators are substances that bring about agronomically desirable biochemical and/or physiological and/or morphological changes in/to the plant.

The active ingredients that the compositions according to the invention comprise influence plant growth in different ways depending on the time of application, the concentration, the mode of application and the environmental conditions. Plant growth regulators of formula I can, for example, inhibit the vegetative growth of plants. This type of action is valuable in the case of lawn areas, in the cultivation of ornamentals, in fruit plantations, in the case of roadside embankments and in sports fields and industrial sites, but also in the specific inhibition of side-shoots, as in the case of tobacco. In agriculture, inhibition of the vegetative growth of cereals leads, owing to strengthening of the stalk, to reduced lodging, and similar agronomic effects are achieved in rape, sunflowers, maize and other cultivated plants. Moreover, by inhibiting the vegetative growth it is possible to increase the number of plants per unit area. Another field of application for growth inhibitors is the selective control of cover plants in plantations or widely spaced crops by greatly inhibiting the growth of the cover crops without killing them, so that competition with the main crop is eliminated but the agronomically positive effects, such as prevention of erosion, fixing of nitrogen and loose soil structure, are preserved.

A method of inhibiting plant growth is to be understood as being a method of controlling a plant's natural development without changing its life-cycle, as determined by genetic characteristics, in the sense of a mutation. The method of regulating growth is applied at a time in the plant's development that has to be determined for each individual case. The compounds of formula I can be applied pre- or post-emergence, for example to the seeds or seedlings, to roots, tubers, stalks, leaves, blossoms or other parts of the plant. This can be done, for example, by applying the compound as such or in the form of a composition to the plants, and/or by treating the plant's nutrient medium (soil).

Various methods and techniques are suitable for the use of the compounds of formula I or of compositions comprising them for regulating plant growth, for example the following:

i) Seed dressing a) Dressing the seeds with an active ingredient formulated as a wettable powder, by shaking in a container until the formulation is uniformly distributed over the surface of the seeds (dry dressing). Up to 4 g of compound of formula I (in the case of a 50% formulation: up to 8.0 g of wettable powder) are used per 1 kg of seed.

b) Dressing the seeds with an emulsifiable concentrate of the active ingredient or with an aqueous solution of the compound of formula I formulated as a wettable powder according to method a) (wet dressing).

c) Dressing by soaking the seeds for a period of from 1 to 72 hours in a mixture comprising up to 1000 ppm of compound of formula I and, if desired, subsequently drying the seeds (seed soaking).

Seed dressing or treatment of the germinated seedling are naturally the preferred methods of application because the treatment with the active ingredient is then directed wholly at the target crop. From 0.001 g to 4.0 g of active ingredient are normally used per 1 kg of seed, although, depending on the method employed, which also allows the addition of other active ingredients or micronutrients, amounts that exceed or fall short of the specified concentration limits may be employed (repeat dressing).

ii) Controlled release of active ingredient

A solution of the active ingredient is applied to mineral granulated carriers or polymerised granules (urea/-formaldehyde) and allowed to dry. If required, a coating may be applied (coated granules), which allows the active ingredient to be released in metered amounts over a specific period of time.

The compounds of formula I are used in unmodified form, as obtainable from the synthesis, or, preferably, together with the adjuvants conventionally employed in formulation technology, and are therefore formulated in known manner e.g. into emulsifiable concentrates, directly sprayable or dilutable solutions, dilute emulsions, wettable powders, soluble powders, dusts, granules, and also encapsulations in e.g. polymer substances. As with the nature of the compositions, the methods of application, such as spraying, atomising, dusting, wetting, scattering or pouring, are chosen in accordance with the intended objectives and the prevailing circumstances.

The formulations, i.e. the compositions, preparations or mixtures comprising the compound (active ingredient) of formula I and, where appropriate, one or more solid or liquid adjuvants, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, such as mixtures of alkyl benzenes, e.g. xylene mixtures or alkylated naphthalenes; aliphatic and cycloaliphatic hydrocarbons such as paraffins, cyclohexane or tetrahydronaphthalene; alcohols, such as ethanol, propanol or butanol; glycols and their ethers and esters, such as propylene glycol or dipropylene glycol ether; ketones such as cyclohexanone, isophorone or diacetone alcohol, strongly polar solvents such as N-methyl-2-pyrrolidone, dimethyl sulfoxide or water; vegetable oils and their esters, such as rape oil, castor oil or soybean oil; and, where appropriate, silicone oils.

The solid carriers used, e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are, for example, calcite or sand. In addition, a great number of pregranulated materials of inorganic or organic nature can be used, e.g. especially dolomite or pulverised plant residues.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty alcohol sulfonates, fatty alcohol sulfates, sulfonated benzimidazole derivatives or alkylarylsulfonates.

The fatty alcohol sulfonates or sulfates are usually in the form of alkali metal salts, alkaline earth metal salts or unsubstituted or substituted ammonium salts and contain a $C_8$–$C_{22}$alkyl radical, which also includes the alkyl moiety of acyl radicals, e.g. the sodium or calcium salt of lignosulfonic acid, of dodecyl sulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyethylene glycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methyl sulfates or ethyl sulfates, e.g. stearyltrimethylammonium chloride or benzyldi(2-chloroethyl)ethylammonium bromide.

The surfactants customarily employed in formulation technology are described inter alia in the following publications:

"McCutcheon's Detergents and Emulsifiers Annual", Mc Publishing Corp., Glen Rock, N.J., 1988;

M. and J. Ash, "Encyclopedia of Surfactants", Vol. I-III, Chemical Publishing Co., N.Y., 1980-1981;

Dr. Helmut Stache, "Tensid-Taschenbuch", Carl Hanser Verlag, Munich/Vienna, 1981.

The herbicidal compositions generally comprise 0.1 to 99%, preferably 0.1 to 95%, of a compound of formula I, 1 to 99% of a solid or liquid adjuvant and 0 to 25%, preferably 0.1 to 25%, of a surfactant.

Whereas commercial products will preferably be formulated as concentrates, the end user will normally employ dilute formulations.

The compositions may also comprise further adjuvants such as stabilisers, for example vegetable oils and epoxidised vegetable oils (epoxidised coconut oil, rape oil or soybean oil), antifoams, for example silicone oil, preservatives, viscosity regulators, binders, tackifiers as well as fertilisers or other active ingredients for obtaining special effects.

Preferred formulations are composed in particular of the following constituents (throughout, percentages are by weight):

| | |
|---|---|
| Emulsifiable concentrates: | |
| active ingredient: | 1 to 90%, preferably 5 to 20% |
| surfactant: | 1 to 30%, preferably 10 to 20% |
| liquid carrier: | 50 to 94%, preferably 70 to 85 % |
| Dusts: | |
| active ingredient: | 0.1 to 10%, preferably 0.1 to 1% |
| solid carrier: | 99.9 to 90%, preferably 99.9 to 99% |
| Suspension concentrates: | |
| active ingredient: | 5 to 75%, preferably 10 to 50% |
| water: | 94 to 24%, preferably 88 to 30% |
| surfactant: | 1 to 40%, preferably 2 to 30% |
| Wettable powders: | |
| active ingredient: | 0.5 to 90%, preferably 1 to 80% |
| surfactant: | 0.5 to 20%, preferably 1 to 15% |
| solid carrier: | 5 to 95%, preferably 15 to 90% |
| Granules: | |
| active ingredient: | 0.5 to 30%, preferably 3 to 15% |
| solid carrier: | 99.5 to 70%, preferably 97 to 85% |

FORMULATION EXAMPLES FOR LIQUID ACTIVE INGREDIENTS OF FORMULA I (THROUGHOUT, PERCENTAGES ARE BY WEIGHT)

| 1. Emulsifiable concentrates | a) | b) | c) |
|---|---|---|---|
| compound of Tables 1-10 | 25% | 40% | 50% |
| calcium dodecylbenzene sulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any required concentration can be obtained from these concentrates by dilution with water.

| 2. Solutions | a) | b) | c) | d) |
|---|---|---|---|---|
| compound of Tables 1-10 | 80% | 10% | 5% | 95% |
| propylene glycol monomethyl ether | 20% | — | — | — |
| polyethylene glycol mol. wt. 400 | — | 70% | — | — |
| N-methyl-2-pyrrolidone | — | 20% | — | — |
| epoxidised coconut oil | — | — | 1% | 5% |
| petroleum fraction (boiling range 160-190° C.) | — | — | 94% | — |

The solutions are suitable for use in the form of microdrops.

| 3. Granules | a) | b) | c) | d) |
|---|---|---|---|---|
| compound of Tables 1-10 | 5% | 10% | 8% | 21% |
| kaolin | 94% | — | 79% | 54% |
| highly dispersed silicic acid | 1% | — | 13% | 7% |
| atapulgite | — | 90% | — | 18% |

The active ingredient is dissolved in methylene chloride and sprayed onto the carrier, and the solvent is then evaporated off in vacuo.

| 4. Dusts | a) | b) |
|---|---|---|
| compound of Tables 1-10 | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

FORMULATION EXAMPLES FOR SOLID ACTIVE INGREDIENTS OF FORMULA I (THROUGHOUT, PERCENTAGES ARE BY WEIGHT)

| 5. Wettable powders | a) | b) | c) |
|---|---|---|---|
| compound of Tables 1-10 | 25% | 50% | 75% |
| sodium lignosulfonate | 5% | 5% | — |
| sodium laurylsulfate | 3% | — | 5% |
| sodium diisobutylnaphthalene-sulfonate | — | 6% | 10% |
| octylphenol polyethylene glycol ether (7-8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| 6. Emulsifiable concentrate | |
|---|---|
| compound of Tables 1-10 | 10% |
| octylphenol polyethylene glycol ether (4-5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| 7. Dusts | a) | b) |
|---|---|---|
| compound of Tables 1-10 | 5% | 8% |
| talcum | 95% | — |
| kaolin | — | 92% |

Ready-for-use dusts are obtained by mixing the active ingredient with the carriers and grinding the mixture in a suitable mill.

| 8. Extruder granules | |
|---|---|
| compound of Tables 1-10 | 10% |
| sodium lignosulfonate | 2% |
| carboxymethylcellulose | 1% |
| kaolin | 87% |

The active ingredient is mixed and ground with the adjuvants, and the mixture is moistened with water. The mixture is extruded and then dried in a stream of air.

| 9. Coated granules | |
|---|---|
| compound of Tables 1-10 | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granules are obtained in this manner.

| 10. Suspension concentrate | |
|---|---|
| compound of Tables 1-10 | 40% |
| propylene glycol | 10% |
| nonylphenol polyethylene glycol ether (15 moles of ethylene oxide) | 6% |
| sodium lignosulfonate | 10% |
| carboxymethylcellulose | 1% |
| silicone oil in the form of a 75% aqueous emulsion | 1% |
| water | 32% |

The finely ground active ingredient is intimately mixed with the adjuvants, giving a suspension concentrate from which suspensions of any desired concentration can be obtained by dilution with water. The compounds of formula I are used in unmodified form or, preferably, in the form of compositions together with the adjuvants customarily employed in formulation technology, and are therefore formulated in known manner e.g. into emulsifiable concentrates, directly sprayable or dilutable solutions, dilute emulsions, wettable powders, soluble powders, dusts, granules, and also encapsulations in e.g. polymer substances. As with the nature of the compositions, the methods of application, such as spraying, atomising, dusting, scattering or pouring, are chosen in accordance with the intended objectives and the prevailing circumstances.

BIOLOGICAL EXAMPLES

Example B1

Preemergence herbicidal action

In a greenhouse, immediately after the test plants have been sown in seed trays, the surface of the soil is treated with an aqueous spray mixture in an amount corresponding to a rate of application of 4 kg of test compound/hectare. The seed trays are kept in the greenhouse at 22°-25° C. and 50-70% humidity.

After 3 weeks, the herbicidal action is evaluated according to a scale of nine ratings (1=total damage, 9=no action) in comparison with an untreated control group.

Ratings of from 1 to 4 (especially from 1 to 3) indicate good to very good herbicidal action. Ratings of from 6 to 9 (especially from 7 to 9) indicate good tolerance (especially in cultivated plants).

The compounds of Table 1 exhibit pronounced herbicidal activity in this test.

Example B2

Postemergence herbicidal action (contact herbicide)

A number of weeds, both mono- and dicotyledonous, are sprayed postemergence (in the 4- to 6-leaf stage) with an aqueous active ingredient dispersion at a rate of 250-1000 g of test compound per hectare and kept at 24°-26° C. and 45-60% relative humidity. 15 days after the treatment the herbicidal action is evaluated according to a scale of nine ratings (1= total damage, 9=no action) in comparison with an untreated control group. Individual results are listed in Tables B1 and B2:

TABLE B1

Herbicidal action of compound no. 1.117

| Plant | rate of application [g/ha] 1000 | 500 | 250 |
|---|---|---|---|
| Abutilon | 1 | 1 | 1 |
| *Sida spinosa* | 1 | 1 | 1 |
| Xanthium Sp. | 1 | 1 | 1 |
| *Amaranthus ret.* | 1 | 1 | 1 |
| Chenopodium Sp. | 1 | 1 | 1 |
| Ipomoea | 1 | 1 | 1 |
| Sinapis | 1 | 1 | 1 |
| Stellaria | 2 | 2 | 2 |
| *Chrysanthe. leuc.* | 1 | 1 | 1 |
| *Galium aparine* | 1 | 1 | 1 |
| *Viola tricolor* | 1 | 1 | 1 |
| Veronica Sp. | 1 | 1 | 3 |
| *Solanum nigrum* | 1 | 1 | 1 |

TABLE B2

Herbicidal action of compound no. 1.118

| Plant | rate of application [g/ha] 1000 | 500 | 250 |
|---|---|---|---|
| Abutilon | 1 | 1 | 1 |
| *Sida spinosa* | 1 | 1 | 1 |
| Xanthium Sp. | 1 | 1 | 1 |
| *Amaranthus ret.* | 1 | 1 | 1 |
| Chenopodium Sp. | 1 | 1 | 1 |
| Ipomoea | 1 | 1 | 1 |
| Sinapis | 1 | 1 | 1 |
| Stellaria | 3 | 4 | 4 |
| *Chrysanthe. leuc.* | 1 | 1 | 2 |
| *Galium aparine* | 1 | 1 | 2 |
| *Viola tricolor* | 1 | 1 | 1 |
| Veronica Sp. | 1 | 1 | 3 |
| *Solanum nigrum* | 1 | 1 | 1 |

Example B3

Herbicidal action in wild rice (paddy rice)

The weeds *Echinochloa crus galli* and *Monocharia vag.*, which occur in water, are sown in plastic beakers (surface: 60 $cm^2$; volume: 500 ml). After sowing, the beakers are filled with water up to the surface of the soil. 3 days after sowing, the water level is increased to slightly above the soil surface (3-5 mm). Application is effected 3 days after sowing by spraying the beakers with the test compounds. The rate of application corresponds to a concentration of 2 kg of active ingredient per hectare. The beakers are then kept in the greenhouse under optimum growth conditions for rice weeds, i.e. at 25°-30° C. and at high humidity.

The evaluation of the tests takes place 3 weeks after application. The compounds of Table 1 damage the weeds but not the rice.

Example B4

Growth inhibition of tropical cover crops

The test plants *Centrosema pubescens* and *Psophocarpus palustris* are propagated by means of cuttings in 4 cm peat pots containing earth (45%), peat (45%) and Zonolite (10%). The cuttings are raised in a greenhouse at a day temperature of 27° C. and a night temperature of 23° C. The plants are illuminated for at least 14 hours/day with an intensity of at least 7000 lux.

About 50 days after the cuttings were taken, they are transplanted into 13 cm pots, 4–5 plants/pot. After a further 60 days, the plants are cut back to a height of about 15 cm and treated by spraying with an aqueous spray mixture at a concentration of 0.1 to 300 g of active ingredient/ha (usually as a 25% formulation). The amount of water applied is about 200 l/ha.

4 weeks after application, the weight of the new growth is determined and expressed as a percentage of the average of the untreated controls. The necrotic damage is given as a percentage of the total leaf area.

The new growth on the treated plants is markedly less than that on the untreated controls.

Example B5

Growth regulation of soybeans

Test plants of the Williams variety are sown in 11 cm clay pots containing earth (45%), peat (45%) and Zonolite (10%) and are raised in a climatic chamber at a day temperature of 24° C. and a night temperature of 19° C. The plants are illuminated for 16 hours per day with an intensity of about 350 micro-Einsteins.

About 24 days after sowing, the plants are transplanted into 18 cm pots, 2 plants/pot. After a further 12 days, when the plants are in the 5–6 trefoil leaf stage, the test compound is applied at a concentration of 0.1 to 300 g of active ingredient/ha, usually as a 25% formulation and in an aqueous spray mixture. The amount of water applied is about 200 l/ha.

Evaluation is made about 4 weeks after application. The height of the new growth is measured and expressed as a percentage of the average of the untreated controls. The necrotic damage is given as a percentage of the total leaf area.

The treated plants exhibit markedly less new growth than do the untreated controls.

Example B6

Growth inhibition of cereals

Test plants (summer barley of the Iban variety) are sown in 15 cm plastic pots containing sterile earth and are raised in a climatic chamber at a day temperature of 10°–15° C. and a night temperature of 5°–10° C. The plants are illuminated for 13.5 hours per day with an intensity of about 25,000 lux.

About 34 days after sowing, and after the plants have been thinned out to 4 plants/pot, the test compound is applied at a concentration of 0.1 to 300 g of active ingredient/ha, usually as a 25% formulation and in an aqueous spray mixture. The amount of water applied is about 500 l/ha. After application, the plants are placed in a greenhouse at a day temperature of at least 10° C. They are illuminated for at least 13.5 hours/day.

Evaluation is made about 28 days after the treatment. The height of the new growth is expressed as a percentage of the average of the untreated controls. The necrotic damage is given as a percentage of the total leaf area.

The treated plants exhibit a reduction in new growth in comparison with untreated controls.

Example B7

Growth inhibition of grasses

A mixture of grasses (e.g. Poa, Festuca, Lolium, Bromus, Cynosurus) and clover (*Trifolium pratense/repens*) is sown in 15 cm plastic pots containing sterile earth and the plants are raised in a greenhouse at a day temperature of 21° C. and a night temperature of 17° C. The plants are illuminated for 13.5 hours/day with an intensity of at least 7000 lux. The emergent plants are cut back weekly to a height of about 6 cm. About 42 days after sowing and 1 day after the last cut, the test compound is applied at a concentration of 0.1 to 300 g of active ingredient/ha, usually as a 25% formulation and in an aqueous spray mixture. The amount of water applied is about 500 l/ha.

Evaluation is made about 3 weeks after treatment. The height of the new growth is measured and expressed as a percentage of the average of the untreated controls. The necrotic damage is given as a percentage of the total leaf area.

The tested compounds of Table 1 effect a reduction in new growth in comparison with untreated controls.

What is claimed is:

1. A cycloalkanecarboxylic acid compound of the formula I

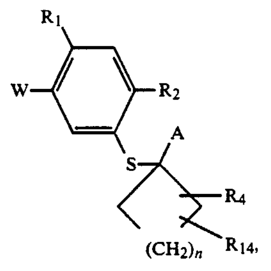

(I)

wherein W is

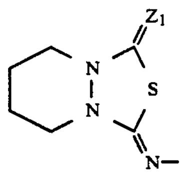

($W_8$)

or

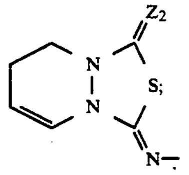

($W_9$)

and

A is CO—$R_3$ or CN;

$R_1$ is hydrogen or fluorine;

$R_2$ is halogen or cyano;

$R_3$ is chlorine, X—$R_5$, amino, $C_1$–$C_4$alkylamino, di-$C_1$–$C_4$alkylamino, $C_2$–$C_4$haloalkylamino, di-$C_2$–$C_4$haloalkylamino, $C_1$–$C_4$hydroxyalkylamino, di-$C_1$–$C_4$hydroxyalkylamino, $C_3$–$C_4$alkenylamino, diallylamino, —N-pyrrolidino, —N-piperidino, —N-morpholino, —N-thiomorpholino, —N-piperidazino, the group —O—N═C—($R_9$)$R_{10}$ or the group —N—$R_6$($OR_6$); each of $R_4$ and $R_{14}$, independently of the other, is hydrogen, fluorine, chlorine, bromine, $C_1$–$C_4$alkyl or trifluoromethyl;

$R_5$ is hydrogen, $C_1$–$C_{10}$alkyl, $C_1$–$C_4$alkoxy-$C_1$–$C_4$alkyl, halo-$C_1$–$C_8$alkyl, $C_1$–$C_{10}$alkylthio-$C_1$–$C_4$alkyl, di-$C_{1/-C4}$alkylamino-$C_1$–$C_4$alkyl, cyano-$C_1$–$C_8$alkyl, $C_3$–$C_8$alkenyl, halo-$C_3$–$C_8$alkenyl, $C_3$–$C_8$alkynyl, $C_3$–$C_7$cycloalkyl, $C_3$–$C_7$cycloalkyl-$C_1$–$C_4$alkyl or halo-$C_3$–$C_7$cycloalkyl, or benzyl which is unsubstituted or substituted at the phenyl ring by up to three identical or different substituents selected from the group consisting of halogen, $C_1$–$C_4$alkyl, halo-$C_1$–$C_4$alkyl, halo-$C_1$–$C_4$alkoxy and $C_1$–$C_4$alkoxy, or is an alkali metal ion, an alkaline earth metal ion or an ammonium ion, the group —$CHR_6$—$(CH_2)_m$—$COOR_7$, or the group —$CHR_6$—$(CH_2)_t$—$Si(R_8)_3$;

$R_6$ is hydrogen or $C_1$–$C_4$alkyl;

$R_7$ is hydrogen, $C_1$–$C_6$alkyl, $C_3$–$C_8$alkenyl, $C_3$–$C_8$alkynyl, $C_1$–$C_8$alkoxy-$C_2$–$C_8$alkyl, $C_1$–$C_8$alkylthio-$C_2$–$C_8$alkyl or $C_3$–$C_7$cycloalkyl;

$R_8$ is $C_1$–$C_4$alkyl;

$R_9$ is $C_1$–$C_4$alkyl;

$R_{10}$ is $C_1$–$C_4$alkyl or phenyl;

or $R_9$ and $R_{10}$, together with the carbon atom to which they are bonded, form a cyclohexane ring;

$R_{11}$ is $C_1$–$C_8$alkyl;

$R_{12}$ is hydrogen or $C_1$–$C_8$alkyl;

$R_{13}$ is hydrogen, $C_1$–$C_6$alkyl, $C_3$–$C_7$cycloalkyl, $C_1$–$C_4$alkoxy-$C_1$–$C_4$alkyl, $C_1$–$C_4$alkylthio-$C_1$–$C_4$alkyl, halo-$C_1$–$C_7$alkyl, $C_3$–$C_7$alkenyl or $C_3$–$C_7$alkynyl;

X is oxygen or sulfur;

$Z_1$ is oxygen or sulfur;

$Z_2$ is oxygen or sulfur;

n is 0, 1, 2, 3 or 4;

m is 0, 1, 2, 3 or 4;

q is 1 or 2; and t is 0, 1, 2, 3 or 4, or an agriculturally acceptable salt thereof.

2. A cycloalkanecarboxylic acid derivative of formula I according to claim 1 wherein $R_{14}$ is hydrogen.

3. A cycloalkanecarboxylic acid derivative of formula I according to claim 1 wherein $R_1$ is fluorine.

4. A cycloalkanecarboxylic acid derivative of formula I according to claim 1 wherein $R_1$ is fluorine and $R_2$ is chlorine.

5. A cycloalkanecarboxylic acid derivative of formula I according to claim 1 wherein A is CO—$R_3$ and $R_3$ is X—$R_5$.

6. A cycloalkanecarboxylic acid derivative of formula I according to claim 1 wherein A is CO—$R_3$ and $R_3$ is X—$R_5$ and $R_5$ is $C_1$–$C_{10}$alkyl.

7. A cycloalkanecarboxylic acid derivative of formula I according to claim 1 wherein A is CO—$R_3$ and $R_1$ is fluorine.

8. A cycloalkanecarboxylic acid derivative of formula I according to claim 1 wherein A is CO—$R_3$ and $R_1$ is fluorine and $R_2$ is chlorine.

9. A cycloalkanecarboxylic acid derivative of formula I according to claim 1 wherein A is CO—$R_3$ and $R_1$ is fluorine, $R_2$ is chlorine, $R_3$ is X—$R_5$, and $R_5$ is $C_1$–$C_{10}$alkyl.

10. A cycloalkanecarboxylic acid derivative of formula I according to claim 1 wherein A is CO—$R_3$ and $R_4$ is hydrogen.

11. A cycloalkanecarboxylic acid derivative of formula I according to claim 9 wherein X is oxygen and $R_5$ is $C_1$–$C_4$alkyl.

12. A cycloalkanecarboxylic acid derivative of formula I according to claim 9 wherein X is oxygen and $R_5$ is $C_1$–$C_4$alkyl, and n is the number 1.

13. 9-[4-chloro-2-fluoro-5-methoxycarbonylcyclobutylthio)-phenylimino]-8-thia-1,6-diazabicyclo[4.3.0]nonan-7-one.

14. 9-[4-chloro-2-fluoro-5-(1-methoxycarbonylcyclopropylthio)phenylimino]-8-thia-1,6-diazabicyclo[4.3.0]nonan-7-one.

15. A herbicidal and plant growth inhibiting composition comprising at least a herbicidal and plant growth inhibitingly effective amount of a cycloalkanecarboxylic acid derivative of formula I according to claim 1 and an agriculturally acceptable carrier.

16. A composition according to claim 15 comprising from 0.1% to 95% of said compound of formula I.

17. A method of controlling undesirable plant growth, which comprises applying to the plants or to the locus thereof a herbicidally effective amount of a compound of formula I, according to claim 1, or of a composition comprising such a compound.

18. A method according to claim 17, which comprises applying an active ingredient in an amount of from 0.001 to 2 kg per hectare.

19. A method of inhibiting plant growth, which comprises applying to the plants or to the locus thereof a growth-regulatingly effective amount of a compound of formula I, according to claim 1, or of a composition comprising such a compound.

20. A method according to claim 17 for the selective control of weeds in crops of useful plants.

* * * * *